US011780843B2

(12) United States Patent
Schrøder Glad et al.

(10) Patent No.: US 11,780,843 B2
(45) Date of Patent: Oct. 10, 2023

(54) COMPOUNDS ACTIVE TOWARDS NUCLEAR RECEPTORS

(71) Applicant: NUEVOLUTION A/S, Copenhagen (DK)

(72) Inventors: Sanne Schrøder Glad, Copenhagen (DK); Ian Sarvary, Copenhagen (DK); Alex Haahr Gouliaev, Copenhagen (DK); Thomas Franch, Copenhagen (DK); Luigi Piero Stasi, Copenhagen (DK); Montserrat Erra Solà, Sant Feliu de Llobregat (ES); Joan Taltavull Moll, Sant Feliu de Llobregat (ES); Paul Robert Eastwood, Sant Feliu de Llobregat (ES)

(73) Assignee: NUEVOLUTION A/S, Copenhagen (DK)

( * ) Notice: Subject to any disclaimer, the term of this patent is extended or adjusted under 35 U.S.C. 154(b) by 190 days.

(21) Appl. No.: 17/218,543

(22) Filed: Mar. 31, 2021

(65) Prior Publication Data
US 2022/0363683 A1    Nov. 17, 2022

Related U.S. Application Data

(60) Provisional application No. 63/002,648, filed on Mar. 31, 2020.

(51) Int. Cl.
*A61P 37/06* (2006.01)
*C07D 487/04* (2006.01)
*C07D 473/34* (2006.01)

(52) U.S. Cl.
CPC .......... *C07D 473/34* (2013.01); *A61P 37/06* (2018.01); *C07D 487/04* (2013.01)

(58) Field of Classification Search
CPC .................................................. C07D 487/04
See application file for complete search history.

(56) References Cited

U.S. PATENT DOCUMENTS

| | | | |
|---|---|---|---|
| 4,298,602 A | 11/1981 | Pawloski | |
| 5,463,071 A | 10/1995 | Himmelsbach et al. | |
| 5,530,129 A | 6/1996 | Gallenkamp et al. | |
| 7,931,909 B2 | 4/2011 | Hughes et al. | |
| 8,338,439 B2 | 12/2012 | Singh et al. | |
| 10,683,293 B2 | 6/2020 | Glad et al. | |
| 10,683,393 B2 | 6/2020 | Boydston et al. | |
| 10,689,383 B2 | 6/2020 | Glad et al. | |
| 2003/0191121 A1 | 10/2003 | Miller et al. | |
| 2004/0054173 A1 | 3/2004 | Kimura et al. | |
| 2004/0087577 A1 | 5/2004 | Pratt et al. | |
| 2004/0097492 A1 | 5/2004 | Pratt et al. | |
| 2004/0180906 A1 | 9/2004 | Flynn et al. | |
| 2005/0124623 A1 | 6/2005 | Bender et al. | |
| 2005/0153989 A1 | 7/2005 | Grotzfeld et al. | |
| 2005/0182045 A1 | 8/2005 | Nagase et al. | |
| 2005/0245536 A1 | 11/2005 | Hao et al. | |
| 2005/0288286 A1 | 12/2005 | Flynn et al. | |
| 2006/0004018 A1 | 1/2006 | Xue et al. | |
| 2006/0052374 A1 | 3/2006 | Carroll et al. | |
| 2006/0069093 A1 | 3/2006 | Scarborough et al. | |
| 2006/0199821 A1 | 9/2006 | Tester et al. | |
| 2006/0235017 A1 | 10/2006 | Cirillo et al. | |
| 2006/0241104 A1 | 10/2006 | Borzilleri et al. | |
| 2006/0281712 A1 | 12/2006 | Yen et al. | |
| 2008/0021063 A1 | 1/2008 | Kazantsev | |
| 2008/0070319 A1 | 3/2008 | Makino | |
| 2009/0018112 A1 | 1/2009 | Chapdelaine et al. | |
| 2009/0018116 A1 | 1/2009 | Jin et al. | |
| 2009/0018134 A1 | 1/2009 | Pike et al. | |
| 2009/0018166 A1 | 1/2009 | Amin et al. | |
| 2009/0029994 A1 | 1/2009 | Nakamura et al. | |
| 2009/0036434 A1 | 2/2009 | Jones et al. | |
| 2009/0069559 A1 | 3/2009 | Kazantsev | |
| 2009/0143302 A1 | 6/2009 | Yen et al. | |
| 2009/0163545 A1 | 6/2009 | Goldfarb | |
| 2010/0152445 A1 | 6/2010 | Bolin et al. | |
| 2010/0249153 A1 | 9/2010 | Tandon et al. | |
| 2011/0135604 A1 | 6/2011 | Casarez et al. | |
| 2011/0281842 A1 | 11/2011 | Michaelides et al. | |
| 2012/0142714 A1 | 6/2012 | Yasuma et al. | |
| 2012/0214762 A1 | 8/2012 | Staben et al. | |
| 2012/0264798 A1 | 10/2012 | Sinha et al. | |
| 2013/0040855 A1 | 2/2013 | Takayama et al. | |
| 2013/0158031 A1 | 6/2013 | Cai et al. | |
| 2013/0190249 A1 | 7/2013 | Lemieux et al. | |
| 2013/0231519 A1 | 9/2013 | Heinrich et al. | |
| 2014/0018361 A1 | 1/2014 | Harriman et al. | |

(Continued)

FOREIGN PATENT DOCUMENTS

| | | |
|---|---|---|
| CL | 201700271 | 10/2017 |
| CL | 201700287 | 11/2017 |

(Continued)

OTHER PUBLICATIONS

Huang. Journal of Organic Chemistry, 1991, 56(21), 6007-6018 (Year: 1991).*
Miossec et al., Targeting IL-17 and TH17 cells in chronic inflammation, Nature Rev. Drug Disc, 11:763-776 (2012).
Montebugnoli et al., Traceless solid-phase synthesis of 2,4,6-chlorodiamino and triaminopyrimidines, Tetrahedron, 59:7147-7156 (2003).
Mordenti et al., Intraocular pharmacokinetics and safety of a humanized monoclonal antibody in rabbits after intravitreal administration of a solution or a PLGA microsphere formulation, Toxicol. Sci., 52(1):101-6 (1999).
Muller et al., Chiral Pyrrolo[2,3d]pyrimidine and pyrimido[4,5-b]indole derivatives: structure-activity relationships of potent, highly stereoselective A1-adenosine receptor antagonists, J. Med. Chem., 39:2482-2491 (1996).

(Continued)

*Primary Examiner* — Noble E Jarrell
(74) *Attorney, Agent, or Firm* — MARSHALL, GERSTEIN & BORUN LLP

(57) ABSTRACT

Disclosed are compounds active towards nuclear receptors, pharmaceutical compositions containing the compounds and use of the compounds in therapy.

20 Claims, No Drawings

(56) References Cited

U.S. PATENT DOCUMENTS

| | | |
|---|---|---|
| 2020/0392140 A1 | 12/2020 | Schrøder Glad et al. |
| 2021/0188807 A1 | 6/2021 | Schrøder Glad et al. |
| 2021/0188828 A1 | 6/2021 | Schrøder Glad et al. |

FOREIGN PATENT DOCUMENTS

| | | |
|---|---|---|
| CL | 201701288 | 12/2017 |
| CL | 201701289 | 3/2018 |
| CN | 102786512 A | 11/2012 |
| CN | 103588795 A | 2/2014 |
| DE | 3737748 A1 | 5/1989 |
| DE | 4124942 A1 | 1/1993 |
| DE | 10108480 A1 | 9/2002 |
| EP | 0384244 A1 | 8/1990 |
| EP | 0419831 A2 | 4/1991 |
| EP | 0434341 A1 | 6/1991 |
| EP | 1396489 A1 | 3/2004 |
| FR | 2870541 A1 | 11/2005 |
| FR | 2926556 A1 | 7/2009 |
| JP | 04-348326 A | 12/1992 |
| JP | 06-220059 A | 8/1994 |
| JP | 10-251255 A | 9/1998 |
| JP | 2000-086663 A | 3/2000 |
| JP | 2002-284779 A | 10/2002 |
| JP | 2007-507529 A | 3/2007 |
| JP | 2007-119450 A | 5/2007 |
| JP | 2007-126551 A | 5/2007 |
| JP | 2007-186580 A | 7/2007 |
| JP | 2008-501698 A | 1/2008 |
| JP | 2008-051696 A | 3/2008 |
| JP | 2012-519005 A | 8/2012 |
| JP | 2013-517809 A | 5/2013 |
| WO | 1993/14082 A1 | 7/1993 |
| WO | 1993/22311 A1 | 11/1993 |
| WO | 1996/40142 A1 | 12/1996 |
| WO | 1997/12878 A1 | 4/1997 |
| WO | 1997/44038 A1 | 11/1997 |
| WO | 1998/23613 A1 | 6/1998 |
| WO | 2001/12601 A1 | 2/2001 |
| WO | 2001/030778 A1 | 5/2001 |
| WO | 2001/047921 A1 | 7/2001 |
| WO | 2001/57038 A1 | 8/2001 |
| WO | 2002/22584 A1 | 3/2002 |
| WO | 2003/11836 A1 | 2/2003 |
| WO | 2003/45941 A1 | 6/2003 |
| WO | 2003/66604 A2 | 8/2003 |
| WO | 2003/75828 A2 | 9/2003 |
| WO | 2003/94918 A1 | 11/2003 |
| WO | 2003/101959 A1 | 12/2003 |
| WO | 2004/000843 A1 | 12/2003 |
| WO | 2004/014384 A2 | 2/2004 |
| WO | 2004/039785 A1 | 5/2004 |
| WO | 2004/039786 A1 | 5/2004 |
| WO | 2004/039788 A1 | 5/2004 |
| WO | 2004/054987 A1 | 7/2004 |
| WO | 2004/060305 A2 | 7/2004 |
| WO | 2004/060306 A2 | 7/2004 |
| WO | 2004/083174 A2 | 9/2004 |
| WO | 2004/083185 A2 | 9/2004 |
| WO | 2004/101557 A1 | 11/2004 |
| WO | 2004/110350 A2 | 12/2004 |
| WO | 2005/033072 A2 | 4/2005 |
| WO | 2005/040119 A1 | 5/2005 |
| WO | 2005/067546 A2 | 7/2005 |
| WO | 2005/068457 A1 | 7/2005 |
| WO | 2005/084667 A1 | 9/2005 |
| WO | 2005/111003 A1 | 11/2005 |
| WO | 2005/117909 A2 | 12/2005 |
| WO | 2005/121121 A2 | 12/2005 |
| WO | 2005/123731 A2 | 12/2005 |
| WO | 2006/004741 A2 | 1/2006 |
| WO | 2006/022773 A1 | 3/2006 |
| WO | 2006/045828 A1 | 5/2006 |
| WO | 2006/074057 A2 | 7/2006 |
| WO | 2006/076706 A1 | 7/2006 |
| WO | 2006/091963 A1 | 8/2006 |
| WO | 2006/122773 A1 | 11/2006 |
| WO | 2007/012661 A1 | 2/2007 |
| WO | 2007/021941 A2 | 2/2007 |
| WO | 2007/030574 A2 | 3/2007 |
| WO | 2007/068418 A1 | 6/2007 |
| WO | 2007/072163 A2 | 6/2007 |
| WO | 2007/072201 A2 | 6/2007 |
| WO | 2007/080382 A1 | 7/2007 |
| WO | 2007/088277 A1 | 8/2007 |
| WO | 2007/107545 A1 | 9/2007 |
| WO | 2007/121280 A1 | 10/2007 |
| WO | 2008/005368 A2 | 1/2008 |
| WO | 2008/005538 A2 | 1/2008 |
| WO | 2008/011476 A2 | 1/2008 |
| WO | 2008/023159 A2 | 2/2008 |
| WO | 2008/023180 A1 | 2/2008 |
| WO | 2008/074982 A1 | 6/2008 |
| WO | 2008/104077 A1 | 9/2008 |
| WO | 2008/115973 A2 | 9/2008 |
| WO | 2008/152093 A2 | 12/2008 |
| WO | 2009/007749 A2 | 1/2009 |
| WO | 2009/007750 A1 | 1/2009 |
| WO | 2009/007751 A2 | 1/2009 |
| WO | 2009/017664 A1 | 2/2009 |
| WO | 2009/055331 A2 | 4/2009 |
| WO | 2009/079683 A1 | 7/2009 |
| WO | 2009/099193 A1 | 8/2009 |
| WO | 2009/102736 A1 | 8/2009 |
| WO | 2009/103432 A2 | 8/2009 |
| WO | 2009/123221 A1 | 10/2009 |
| WO | 2009/128661 A2 | 10/2009 |
| WO | 2009/134384 A1 | 11/2009 |
| WO | 2009/149188 A1 | 12/2009 |
| WO | 2009/156484 A2 | 12/2009 |
| WO | 2010/012442 A2 | 2/2010 |
| WO | 2010/020432 A2 | 2/2010 |
| WO | 2010/022121 A1 | 2/2010 |
| WO | 2010/022125 A1 | 2/2010 |
| WO | 2010/022128 A1 | 2/2010 |
| WO | 2010/036316 A1 | 4/2010 |
| WO | 2010/048207 A2 | 4/2010 |
| WO | 2010/052569 A2 | 5/2010 |
| WO | 2010/080996 A1 | 7/2010 |
| WO | 2010/100127 A1 | 9/2010 |
| WO | 2010/114957 A1 | 10/2010 |
| WO | 2010/120994 A2 | 10/2010 |
| WO | 2010/129053 A2 | 11/2010 |
| WO | 2010/129242 A2 | 11/2010 |
| WO | 2010/135470 A1 | 11/2010 |
| WO | 2011/017513 A1 | 2/2011 |
| WO | 2011/022440 A2 | 2/2011 |
| WO | 2011/029043 A1 | 3/2011 |
| WO | 2011/029046 A1 | 3/2011 |
| WO | 2011/049946 A1 | 4/2011 |
| WO | 2011/055911 A1 | 5/2011 |
| WO | 2011/075684 A1 | 6/2011 |
| WO | 2011/078143 A1 | 6/2011 |
| WO | 2011/105572 A1 | 9/2011 |
| WO | 2011/115940 A1 | 9/2011 |
| WO | 2011/143129 A1 | 11/2011 |
| WO | 2011/153553 A2 | 12/2011 |
| WO | 2012/037226 A1 | 3/2012 |
| WO | 2012/041872 A1 | 4/2012 |
| WO | 2012/041873 A1 | 4/2012 |
| WO | 2012/046869 A1 | 4/2012 |
| WO | 2012/074022 A1 | 6/2012 |
| WO | 2012/103295 A2 | 8/2012 |
| WO | 2012/147516 A1 | 11/2012 |
| WO | 2012/147890 A1 | 11/2012 |
| WO | 2012/163773 A1 | 12/2012 |
| WO | 2012/166716 A2 | 12/2012 |
| WO | 2013/017461 A1 | 2/2013 |
| WO | 2013/019824 A2 | 2/2013 |
| WO | 2013/022766 A1 | 2/2013 |
| WO | 2013/036912 A2 | 3/2013 |
| WO | 2013/052526 A1 | 4/2013 |
| WO | 2013/068306 A1 | 5/2013 |
| WO | 2013/090912 A1 | 6/2013 |

(56) References Cited

FOREIGN PATENT DOCUMENTS

| | | |
|---|---|---|
| WO | 2013/117649 A1 | 8/2013 |
| WO | 2013/134467 A1 | 9/2013 |
| WO | 2013/157022 A1 | 10/2013 |
| WO | 2013/178075 A1 | 12/2013 |
| WO | 2013/183673 A1 | 12/2013 |
| WO | 2014/005129 A1 | 1/2014 |
| WO | 2014/015523 A1 | 1/2014 |
| WO | 2014/015675 A1 | 1/2014 |
| WO | 2014/015830 A1 | 1/2014 |
| WO | 2014/015936 A1 | 1/2014 |
| WO | 2014/017513 A1 | 1/2014 |
| WO | 2014/019908 A2 | 2/2014 |
| WO | 2014/185358 A1 | 11/2014 |
| WO | 2015/033558 A1 | 3/2015 |
| WO | 2015/129263 A1 | 9/2015 |
| WO | 2016/020288 A1 | 2/2016 |
| WO | 2016/020295 A1 | 2/2016 |
| WO | 2016/020320 A1 | 2/2016 |
| WO | 2016/081670 A2 | 5/2016 |
| WO | 2016/081918 A1 | 5/2016 |
| WO | 2017/024018 A1 | 2/2017 |

OTHER PUBLICATIONS

Nogrady, Medicinal chemistry a biochemical approach, Oxford University Press, New York, 388-392 (1985).

Pandya et al., Combating Autoimmune Diseases With Retinoic Acid Receptor-Related Orphan Receptor- γ (RORγ or RORc) Inhibitors: Hits and Misses, J. Med. Chem., 61(24):10976-10995 (2018).

Pryde et al., The discovery of a novel prototype small molecule TLR7 agonist for the treatment of hepatitis C virus infection, Med. Chem. Commun., 2:185-189(2011).

PUBCHEM (National Center for Biotechnology Information. PUBCHEM Compound Database; CID=3236972, https://pubchem.ncbi.nlm.nih gov/compound/3236972 (accessed Sep. 15, 2018), created Aug. 16, 2005, pp. 1-13).

Search Report for Swedish Patent Application No. 1450920-2, dated Feb. 17, 2015.

Search Report for Swedish Patent Application No. 1451406-1, dated May 29, 2015.

Serafini et al., Detection of ectopic b-cell follicles with germinal centers in the meninges of patients with secondary progressive multiple sclerosis. Brain Pathol., 14(2):164-174 (2004).

Shedden et al., Efficacy and tolerability of timolol maleate ophthalmic gel-forming solution versus timolol ophthalmic solution in adults with open-angle glaucoma or ocular hypertension: a six-month, double-masked, multicenter study, Clin. Ther., 23(3):440-50 (2001).

Solt et al., Action of RORs and their ligands in (patho) physiology, Trends in Endocrinology and Metabolism, 23(12):619-627 (2012).

Traverso et al., The syntheses and pharmacological activities of amide, sulfamide, and urea derivatives of 4,6-diaminopyrimidines, J. Med. Pharm. Chem., 91:808-15 (1962).

Tyukavkina et al., Bioorganicheskaya himiya, moskva, Drofa., 83-85 (2005) with partial English translation.

Upadhyaya et al., Identification of adducts formed in the reactions of 5'-acetoxy-N'-nitrosonornicotine with deoxyadenosine, thymidine, and DNA, Chem. Res. Toxicol., 21:2164-2171 (2008).

Wu et al., Discovery of aminoheterocycles as potent and brain penetrant prolylcarboxypeptidase inhibitors, Bioorganic & Medicinal Chemistry Letters, 22:1727-1730 (2012).

Yang et al., Discovery of Tertiary Amine and Indole Derivatives as Potent RORγ Inverse Agonists, ACS Medical Chemistry Letters, 5:65-68 (2014).

Yang et al., Targeting Th17 cells in autoimmune diseases, Trends Pharmacol Sci., 35(10):493-500 (2014).

Yoo et al., Synthesis of mono-, Di-, and triaminosubstituted-Pyrimidine derivatives, Korean J. Med. Chem., 9:83-86 (1999).

33 Substances CAS Registry Nos. 1515972-57-2; 357614-47-2; 1537342-62-3; 357614-41-6; 1509319-43-0; 357614-39-2; 1508163-79-8; 1543241-09-3; 1507549-73-6; 1539058-95-1; 1504736-18-8; 1538881-49-0; 1502546-73-7; 537342-62-3; 1502393-44-3; 1536916-94-5; 1501684-14-5; 1536417-79-4; 1500313-42-7; 1529040-93-4; 1499708-15-4; 1526739-06-9; 1020711-29-8; 1526652-58-3; 1020711-25-4; 1522387-54-7; 403668-62-2; 1522083-19-7; 357614-51-8; 1521680-88-5; 357614-49-4; 1519623-48-3; 357614-48-3 (2014).

Alm et al., Effects of topically applied PGF2 alpha and its isopropylester on normal and glaucomatous human eyes, Prog. Clin. Biol. Res., 312:447-58 (1989).

Aloisi et al., Lymphoid neogenesis in chronic inflammatory diseases, Nat. Rev. Immunol., 6:205-217 (2006).

Barnes, Immunology of asthma and chronic obstructive pulmonary disease, Nat. Rev. Immunol., 8(3):183-192 (2008).

Bronner et al., ROR γ antagonists and inverse agonists: a patent review, Expert Opinion on Therapeutics Patents, 27(1):101-112 (2017).

Caira, Crystalline Polymorphism of Organic Compounds, Topics in Current Chemistry, 198:163-208 (1998).

Cas Reg No. 929970-65-0, STN Entry Date: Apr. 13, 2007; 7H-Pyrrolo[2,3-d]pyrimidin-4-amine,5,6-dimethyl-7-(phenylmethyl)-N-(4-pyridinylmethyl)- [2].

Cas Reg. No. 1539496-16-6, STN Entry Date: Feb. 9, 2014; 4,6-Pyrimidinediamine, N6-ethyl-N4-methyl-5-(1-methylethyl)-N4-[(1-methyl-1 H-pyrazol-4-yl)methyl- ]-.

Cas Reg. No. 1540192-80-0, STN Entry Date: Feb. 10, 2014; 4,6-Pyrimidinediamine, N4,N6-diethyl-2,5-dimethyl-N4-(2-thienylmethyl)-.

Cas Reg. No. 1542543-24-7, STN Entry Date: Feb. 14, 2014; 4,6-Pyrimidinediamine, N4-[(4-chlorophenyl)methyl]-N4,5-dimethyl-N6 propyl-.

Cas Reg. No. 1543250-40-3, STN Entry Date: Feb. 14, 2014; 4,6-Pyrimidinediamine, 5- methoxy-N4-methyl-N6-propyl-N4-[(tetrahydro-2H-pyran-3-yl)methyl]-.

Cas Reg. No. 1544786-92-6, STN Entry Date: Feb. 16, 2014; 4,6-Pyrimidinediamine, N6- ethyl-N4,2-dimethyl-N4-[(5-methyl-2-furanyl)methyl]-.

Cas Reg.No.1101785-73-2, STN Entry Date: Feb. 6, 2009; L-Alanine, N-[7-(2-furanylmethyl)-5,6-dimethyl-7H-pyrrolo[2,3-d]pyrimidin-4-yl]- [2].

Castro et al., RORγt and RORa signature genes in human Th17 cells, PlosOne, 12(8):e0181868 (2017).

Chang et al., Pharmacologic Repression of Retinoic Acid Receptor—Related Orphan Nuclear Receptor γ Is Therapeutic in the Collagen-Induced Arthritis Experimental Model, Arthritis & Rheumatism, 66(3):579-588 (2014).

Chang et al., RORs in autoimmune disease, sphingosine-1-phosphate signaling in immunology and infectious diseases, Curr. Topics in Microb. Immun., 378:171-182 (2014).

Cook et al., Retinoic Acid-Related Orphan Receptors (RORs): Regulatory Functions in Immunity, Development, Circadian Rhythm, and Metabolism, Nuclear Receptor Research, 2, Article ID 101185:1-24 (2015).

Cyr et al., Recent progress on nuclear receptor RORγ modulators, Bioorganic & Medicinal Chemistry Letters, 26(18):4387-4393 (2016).

Database Registry,2013, RN 1445611-7, 1424439 [03, 2006.01, 01, 1, 1423758 - [35, 2006.01, 74] 3, 13118835, 1281111-22-5, 1281111-13-4; Retrieved from STN international [online] ;retrieved on Apr. 12, 2019.

Fa et al., Synthesis, structure, and fullerene-complexing property of azacalix[6]aromatics, J. Org. Chem., 79:3559-3571 (2014).

Fan et al., Retinoic Acid Receptor-Related Orphan Receptors: Critical Roles in Tumorigenesis, Frontiers in Immunology, 1187:1-10 (2018).

Fauber et al., Modulators of the nuclear receptor retinoic acid receptor-related orphan receptor-γ (RORγ or RORc), J. Med. Chem., 57(14):5871-92 (2014).

Fingl et al., The pharmacological basis of therapeutics, Ch. 1 (1975).

Gaffen et al., The IL-23-IL-17 immune axis: from mechanisms to therapeutic testing, Nat. Rev. Immunol., 14(9):585-600 (2014).

Han et al., Efficient and library-friendly synthesis of furo- and thienol[2,3-d] pyrimidin-4-amine derivatives by microwave irradiation, Tetrahedron Letters, 51: 629-632 (2010).

(56) References Cited

OTHER PUBLICATIONS

Huh et al., Small molecule inhibitors of RORγt: Targeting Th17 cells and other applications, NIH public access author manuscript, Eur. J. Immunol., 42(9):2232-2237 (2012).
International Application No. PCT/EP2015/067692, International Search Report and Written Opinion, dated Sep. 21, 2015.
International Application No. PCT/EP2015/067713, International Preliminary Report on Patentability, dated Feb. 16, 2017.
International Application No. PCT/EP2015/067713, International Search Report and Written Opinion, dated Sep. 22, 2015.
International Application No. PCT/IB2021/052701, International Search Report and Written Opinion, dated Jun. 17, 2021.
International Application No. PCT/IB2021/052702, International Search Report and Written Opinion, dated Jun. 17, 2021.
International Preliminary Report on Patentability for corresponding International Application No. PCT/EP2015/067692, dated Feb. 16, 2017.
Isono et al., Inhibiting RORγt/Th17 axis for autoimmune disorders, Drug Disc. Today, 18:1205-11 (2014).
IUPAC-IUB [International Union of Pure and Applied Chemistry-International Union of Biochemistry] Commission of Biochemical Nomenclature. Abbreviated nomenclature of synthetic polypeptides (polymerized amino acids). Revised recommendations (1971), Biochem., 11(5):942-944 (1972).
Jäger et al., Th1, Th17, and Th9 effector cells induce experimental autoimmune encephalomyelitis with different pathological phenotypes, J. Immunol., 183(11):7169-7177 (2009).
Jetten, Retinoid-related orphan receptors (RORs): critical roles in development, immunity, circadian rhythm, and cellular metabolism, Nucl. Recept. Signal., 7:e003 (2009).
Joshi, Microparticulates for ophthalmic drug delivery, J. Ocul. Pharmacol., 10(1):29-45 (1994).
Kamenecka et al., Synthetic modulators of the retinoic acid receptor-related orphan receptors, Med. Chem. Commun., 4:764-776 (2013).
Kim et al., Substituted pyrimidines as cannabinoid CB1 receptor ligands, Bioorganic & Medicinal Chemistry Letters, 19:4692-4697 (2009).
Klecka et al., Direct C—H borylation and C—H arylation of pyrrolo[2,3d]pyrimidines: synthesis of 6,8-disubstituted7-deazapurines, Org. Biomol. Chem., 7:866-868 (2009).
Kojetin et al., REV-ERB and ROR nuclear receptors as drug targets, Nature Rev. Drug Disc., 13:197-216 (2014).
Kosary et al., Preparation of pyrimidine derivatives with potential cardiotonic activity, Acta. Pharmacetical Hungarica., 56(6):241-247 (abstract CA 112:216531), Retrieved from Chemical Abstracts (1989).
Krueger et al., Interleukin-17 alters the biology of many cell types involved in the genesis of psoriasis, systemic inflammation and associated comorbidities, Exp. Dermatol., 27(2):115-123 (2018).
Lai et al., Mesenchymal stem cell exosomes, Seminars in Cell & Development Biology, 40:82-8 (2015).
Ma et al., Combinatorial synthesis of substituted biaryls and heterocyclic arylamines, J. Comb. Chem., 6(3):426-430 (2004).
Magliozzi et al., Meningeal B-cell follicles in secondary progressive multiple sclerosis associate with early onset of disease and severe cortical pathology, Brain, 130:1089-1104 (2007).
Marquet et al., New series of purine analogs with antimitotic action, Structure activity relations, Chimica. Therapeutica., 6(6):427-38 (1971).
Mashkovskiy, Lekarstvennie sredstva, Moscow, Medicina., part 1:8 (1993) with partial English translation.
Mayer et al., Efficacy of a novel hydrogel formulation in human volunteers, Ophthalmologica, 210(2):101-3 (1996).
Meier et al., Ectopic lymphoid-organ development occurs through interleukin 7-mediated enhanced survival of lymphoid-tissue-inducer cells, Immunity, 26(5):643-654 (2007).

* cited by examiner

COMPOUNDS ACTIVE TOWARDS NUCLEAR RECEPTORS

FIELD

Aspects and embodiments described herein relate to compounds active towards nuclear receptors, pharmaceutical compositions comprising the compounds, and methods of treating inflammatory, metabolic, oncologic and autoimmune diseases or disorders using the compounds.

BACKGROUND

Nuclear receptors are a family of transcription factors involved in the regulation of physiological functions, such as cell differentiation, embryonic development, and organ physiology. Nuclear receptors have also been identified as important pathological regulators in diseases such as cancer, diabetes, and autoimmune disorders.

Examples of nuclear receptors include the nuclear retinoic acid receptor-related orphan receptors (RORs). RORs contain four principal domains: an N-terminal A/B domain, a DNA-binding domain, a hinge domain and a ligand binding domain. Binding of ligands to the ligand-binding domain is believed to cause conformational changes in the domain resulting in downstream actions. Different isoforms exist and these isoforms differ in their N-terminal A/B domain only (Jetten, 2009, Nuclear Receptor Signaling).

RORs consist of three members, namely ROR alpha (RORα or RORa), ROR beta (RORβ or RORb) and ROR gamma (RORγ or RORc).

RORα is expressed in many tissues such as cerebellar Purkinje cells, the liver, thymus, skeletal muscle, skin, lung, adipose tissue and kidney. RORα regulates neuronal cell development, bone metabolism, and arteriosclerosis (Jetten, 2009, Nuclear Receptor Signaling). Additionally, RORα plays a role in the immune responses, such as in the regulation interleukin (IL) 17A expression in T helper (Th) 17 cells and the function of T regulatory (Treg) cells (Castro PLOS 2017; Malhotra 2018).

RORβ exhibits a restriction pattern of expression limited to certain regions of brain (cerebral cortex, thalamus, hypothalamus and pineal gland) as well as retina (Jetten, 2009, Nuclear Receptor Signaling). RORβ has been related to epilepsy and together with RORα also to bipolar disease (Rudolf 2016; Lai 2015).

RORγ shows a broad expression pattern and was the most recently discovered of the three members. To date two different protein isoforms have been recorded: RORγ1 and RORγ2 (RORγ2 is also known as RORγt). Generally RORγ is used to describe RORγ1 and/or RORγt. RORγ1 is expressed in many tissues and is predominantly expressed in the kidneys, liver, and skeletal muscle. In contrast, expression of RORγt is restricted to some cell types of the immune system and to lymphoid organs such as the thymus and secondary lymphoid tissues (Hirose 1994; Jetten, 2009, Nuclear Receptor Signaling).

RORγt has been identified as a key regulator of Th17 cell differentiation and IL-17 production by γδ T cells, Th17 cells, T cytotoxic (Tc) 17 cells and innate lymphoid cells type 3 (ILC3) cells (Gaffen 2014). Th17 cells are a subset of T helper cells which preferentially produce the cytokines IL-17A, IL-17F, IL-21 and IL-22 (Castro PLOS 2017). T cells lacking RORγt failed to differentiate into Th17 cells even under Th17-polarizing culture conditions, while overexpression of RORγt in naïve CD4+ T cells was sufficient to accelerate the expression of Th17-related cytokines and chemokines (Gaffen 2014, Nat Rev Immunol; Yang 2014, Trend Pharmacol Sci). IL-23 is a vital checkpoint in the generation, maintenance and activation of pathogenic Th17 cells. In response to IL-23 signals, RORγt cooperates with a network of transcription factors (STAT3, IRF4 and BATF) to initiate the complete differentiation program of Th17 cells (Gaffen 2014, Nat Rev Immunol).

Th17 cells and IL-17 immune response have been shown to be associated with the pathology of many human inflammatory and autoimmune disorders. Therapeutic strategies targeting the IL-23-IL-17 axis are being developed in many autoimmune diseases, and some of them have already demonstrated to provide clinical efficacy some diseases (Patel 2015; Krueger 2018 Exp Dermatol).

There is thus evidence that RORα, RORβ and RORγ play a role in the pathogenesis of many diseases.

It would be desirable to provide compounds that modulate the activity of RORα and/or RORγ for use in treating inflammatory, metabolic and autoimmune diseases.

WO2016020288 and WO2016020295 describe compounds that modulate the activity or RORgamma receptors. However, a need still exists for potent RORgamma modulators having improved physicho-chemical properties.

SUMMARY

In one aspect provided herein are compounds of Formula (I)

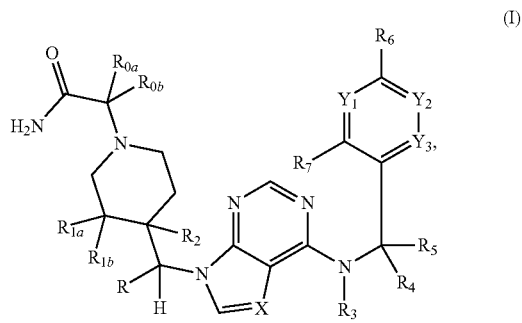

a stereoisomer thereof, or a pharmaceutically acceptable salt of the compound or stereoisomer, wherein:

$Y_1$, $Y_2$ and $Y_3$ are independently —N— or —$CR_8$—;

X is —$CR_9$—, or —N—;

$R_{0a}$ and $R_{0b}$ independently are selected from the group consisting of hydrogen, $C_{1-4}$ alkyl, $C_{1-4}$ hydroxyalkyl, and $C_{1-4}$ haloalkyl;

R is selected from the group consisting of hydrogen, $C_{1-6}$ alkyl and $C_{1-4}$ hydroxyalkyl;

$R_{1a}$ and $R_{1b}$ are independently selected from the group consisting of hydrogen, hydroxyl, halogen, amino, $C_{1-4}$ alkyl, $C_{1-4}$ hydroxyalkyl, and $C_{1-4}$ haloalkyl;

$R_2$ is selected from the group consisting of hydrogen, hydroxyl, amino, cyano, halogen, $C_{1-4}$ alkyl, $C_{1-4}$ haloalkyl, $C_{1-4}$ hydroxyalkyl, —C(=O)$NH_2$, —C(=O)OH, —C(=O)O—$C_{1-4}$ alkyl, and substituted or unsubstituted heteroaryl;

$R_3$ is selected from the group consisting of $C_{1-4}$ alkyl, $C_{1-4}$ alkenyl, $C_{1-4}$ haloalkyl, $C_{1-4}$ hydroxyalkyl, $C_{3-7}$ cycloalkyl, and $C_{3-7}$ cycloalkenyl; or $R_3$ and $R_4$ are taken together with the atoms to which they are attached to form a 4-6 membered heteroalicyclic ring system optionally substituted with one to three substituents selected from halogen, hydroxyl, and $C_{1-4}$ alkyl;

$R_4$ is hydrogen or $C_{1-4}$ alkyl, provided $R_3$ and $R_4$ are not taken together with the atoms to which they are attached to form a 4-6 membered heteroalicyclic ring system; or $R_4$ and $R_5$ are taken together with the carbon atom to which they are attached to form a $C_{3-4}$ cycloalkyl;

$R_5$ is absent, hydrogen or $C_{1-4}$ alkyl, provided $R_4$ and $R_5$ are not taken together with the carbon atom to which they are attached to form a $C_{3-4}$ cycloalkyl;

$R_6$ is selected from the group consisting of hydrogen, —CN, halogen, $C_{1-4}$ alkyl, $C_{1-4}$ hydroxyalkyl, $C_{1-4}$ haloalkyl, $C_{1-6}$ hydroxyhaloalkyl, $C_{1-4}$ alkoxy, $C_{1-4}$ haloalkoxy, and 5-6 membered heteroaryl, wherein 5-6 membered heteroaryl is optionally substituted with $C_{1-4}$ alkyl;

$R_7$ is selected from the group consisting of hydrogen, hydroxyl, —CN, halogen, $C_{1-4}$ alkyl, $C_{1-4}$ haloalkyl, $C_{1-4}$ hydroxyalkyl, $C_{1-4}$ alkoxy, and $C_{1-4}$ haloalkoxy;

each $R_8$ is independently selected from the group consisting of hydrogen, hydroxyl, —CN, halogen, $C_{1-4}$ alkyl, $C_{1-4}$ haloalkyl, $C_{1-4}$ alkoxy, and $C_{1-4}$ haloalkoxy; and whenever $R_7$ is hydrogen and each $R_8$ present is hydrogen, then $R_6$ is selected from the group consisting of —CN, halogen, $C_{1-4}$ alkyl, $C_{1-4}$ haloalkyl, $C_{1-6}$ hydroxyhaloalkyl, $C_{1-4}$ hydroxyalkyl, $C_{1-4}$ alkoxy, $C_{1-4}$ haloalkoxy, and 5-6 membered heteroaryl, wherein 5-6 membered heteroaryl is optionally substituted with $C_{1-4}$ alkyl;

$R_9$ is selected from the group consisting of hydrogen, halogen, cyano, and $C_{1-4}$ alkyl.

In one aspect provided herein are pharmaceutical compositions comprising a compound of Formula (I) or a stereoisomer thereof, or a pharmaceutically acceptable salt of the compound or stereoisomer of Formula (I) and at least one pharmaceutical acceptable excipient.

In one aspect provided herein are compounds of Formula (I) or a stereoisomer thereof, or a pharmaceutically acceptable salt of the compound or stereoisomer of Formula (I), or pharmaceutical compositions thereof for use in treatment and/or prevention of a disease or disorder or a symptom thereof selected from the group consisting of asthma, acne, chronic obstructive pulmonary disease (COPD), bronchitis, atherosclerosis, *Helicobacter pylori* infection, allergic diseases including allergic rhinitis, allergic conjunctivitis and uveitis, sprue and food allergy, atopic dermatitis, lichen planus, cystic fibrosis, lung allograph rejection, multiple sclerosis, rheumatoid arthritis, juvenile idiopathic arthritis, osteoarthritis, ankylosing spondylitis, psoriasis, psoriatic arthritis, ichthyoses, bullous diseases, hidradenitis suppurativa, steatosis, steatohepatitis, non-alcoholic fatty liver disease (NAFLD), non-alcoholic steatohepatitis (NASH), lupus erythematosus, Hashimoto's disease, pancreatitis, autoimmune diabetes, autoimmune ocular disease, ulcerative colitis, colitis, Crohn's disease, inflammatory bowel disease (IBD), inflammatory bowel syndrome (IBS), Sjogren's syndrome, optic neuritis, type I diabetes, neuromyelitis optica, Myastehnia Gravis, Guillain-Barre syndrome, Graves' disease, scleritis, obesity, obesity-induced insulin resistance, type II diabetes, and cancer.

Further, advantageous features of various embodiments are defined in the dependent claims and within the detailed description below.

DETAILED DESCRIPTION OF PREFERRED EMBODIMENTS

Definitions

Unless defined otherwise, all technical and scientific terms used herein have the same meaning as is commonly understood by one of ordinary skill in the art. All patents, applications, published applications and other publications referenced herein are incorporated by reference in their entirety. In the event that there are a plurality of definitions for a term herein, those in this section prevail unless stated otherwise.

As used herein, any "R" group(s) such as, without limitation, $R_1$, $R_2$, $R_3$, $R_4$, $R_5$, $R_6$, $R_7$, $R_8$, $R_9$, and Rio, represent substituents that can be attached to the indicated atom. Examples of R groups includes but is not limited to hydrogen, hydroxy, alkyl, alkenyl, alkynyl, alkoxy, cycloalkyl, cycloalkenyl, cycloalkynyl, aryl, heteroaryl, and heteroalicyclyl. If two "R" groups are covalently bonded to the same atom or to adjacent atoms, then they may be "taken together" or "combined" as defined herein to form a cycloalkyl, aryl, heteroaryl or heteroalicyclyl group. For example, without limitation, if $R_a$ and $R_b$ of an $NR_aR_b$ group are indicated to be "taken together" or "combined", it means that they are covalently bonded to one another at their terminal atoms to form a ring that includes the nitrogen:

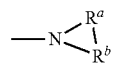

As readily recognized by the skilled person, any given group disclosed herein may comprise further hydrogen(s) than the one(s) provided by a R-group, being hydrogen, attached to the group.

Whenever a group is described as being "unsubstituted or substituted," if substituted, the substituent(s) (which may be present one or more times, such as 1, 2, 3 or 4 times) are independently selected from alkyl, alkenyl, alkynyl, cycloalkyl, cycloalkenyl, cycloalkynyl, aryl, heteroaryl, heteroalicyclyl, aralkyl, heteroaralkyl, (heteroalicyclyl)alkyl, hydroxy, oxo, alkoxy, aryloxy, acyl, ester, O-carboxy, mercapto, alkylthio, arylthio, cyano, halogen, carbonyl, thiocarbonyl, C-amido, N-amido, S-sulfonamido, N-sulfonamido, nitro, silyl, sulfenyl, sulfinyl, sulfonyl, haloalkyl, hydroxyalkyl, hydroxyhaloalkyl, haloalkoxy, trihalomethanesulfonyl, trihalomethanesulfonamido, and amino, including mono- and di-substituted amino groups, and the protected derivatives thereof. When a substituent on a group is deemed to be "substituted," the substituent itself is substituted with one or more of the indicated substituents. When the referenced substituent is substituted, it is meant that one or more hydrogen atoms on the referenced substituent may be replaced with a group(s) individually and independently selected from alkyl, alkenyl, alkynyl, cycloalkyl, cycloalkenyl, cycloalkynyl, aryl, heteroaryl, heteroalicyclyl, aralkyl, heteroaralkyl, (heteroalicyclyl)alkyl, hydroxy, oxo, alkoxy, aryloxy, acyl, ester, O-carboxy, mercapto, alkylthio, arylthio, cyano, halogen, carbonyl, thiocarbonyl, C-amido, N-amido, S-sulfonamido, N-sulfonamido, nitro, silyl, sulfenyl, sulfinyl, sulfonyl, haloalkyl, hydroxyalkyl, hydroxyhaloalkyl, haloalkoxy, trihalomethanesulfonyl, trihalomethanesulfonamido, and amino, including mono- and di-substituted amino groups, and the protected derivatives thereof. The protecting groups that may form the protective derivatives of the above substituents are known to those of skill in the art and may be found in references Greene and Wuts, Protective Groups in Organic Synthesis, $3^{rd}$ Ed., John Wiley & Sons, New York, N.Y., 1999, which is hereby incorporated by reference in its entirety.

As used herein, "$C_m$ to $C_n$," "$C_m$-$C_n$," or "$C_{m-n}$" in which "m" and "n" are integers refers to the number of carbon atoms in the relevant group. That is, the group can contain from "m" to "n", inclusive, carbon atoms. Thus, for example, a "$C_1$ to $C_6$ alkyl" group refers to all alkyl groups having from 1 to 6 carbons, that is, $CH_3$—, $CH_3CH_2$—, $CH_3CH_2CH_2$—, $(CH_3)_2CH$—, $CH_3CH_2CH_2CH_2$—, $CH_3CH_2CH(CH_3)$—, $CH_3CH(CH)_3CH_2$—, $CH_3CH(CH)_3CH_2$— and $(CH_3)_3C$—. If no "m" and "n" are designated with regard to a group, the broadest range described in these definitions is to be assumed.

As used herein, "alkyl" refers to a straight or branched hydrocarbon chain group that is fully saturated (no double or triple bonds). The alkyl group may have 1 to 20 carbon atoms (whenever it appears herein, a numerical range such as "1 to 20" refers to each integer in the given range; e.g., "1 to 20 carbon atoms" means that the alkyl group may consist of 1 carbon atom, 2 carbon atoms, 3 carbon atoms, etc., up to and including 20 carbon atoms, although the present definition also covers the occurrence of the term "alkyl" where no numerical range is designated). The alkyl group may also be an alkyl having 1 to 10 carbon atoms, such as "$C_1$-6". The alkyl group could also be a lower alkyl having 1 to 4 carbon atoms. The alkyl group of the compounds may be designated as "$C_1$-$C_4$ alkyl," "$C_{1-4}$ alkyl" or similar designations. By way of example only, "$C_1$-$C_4$ alkyl" or "$C_{1-4}$ alkyl" indicates that there are one to four carbon atoms in the alkyl chain, i.e., the alkyl chain is selected from the group consisting of methyl, ethyl, propyl, isopropyl, n-butyl, iso-butyl, sec-butyl, and t-butyl. Typical alkyl groups include, but are in no way limited to, methyl, ethyl, propyl, isopropyl, butyl, isobutyl, tertiary butyl, pentyl, hexyl, and the like. When substituted, the substituent group(s) is(are) one or more group(s) individually and independently selected from alkenyl, alkynyl, cycloalkyl, cycloalkenyl, cycloalkynyl, aryl, heteroaryl, heteroalicyclyl, aralkyl, heteroaralkyl, (heteroalicyclyl)alkyl, hydroxy, oxo, alkoxy, aryloxy, acyl, ester, O-carboxy, mercapto, alkylthio, arylthio, cyano, halogen, carbonyl, thiocarbonyl, C-amido, N-amido, S-sulfonamido, N-sulfonamido, nitro, silyl, sulfenyl, sulfinyl, sulfonyl, haloalkyl, hydroxyalkyl, hydroxyhaloalkyl, haloalkoxy, trihalomethanesulfonyl, trihalomethanesulfonamido, and amino, including mono- and di-substituted amino groups, and the protected derivatives thereof.

As used herein, "alkenyl" refers to an alkyl group that contains in the straight or branched hydrocarbon chain one or more double bonds. If more than one double bond is present, the double bonds may be conjugated or not conjugated. The alkenyl group may have 2 to 20 carbon atoms (whenever it appears herein, a numerical range such as "2 to 20" refers to each integer in the given range; e.g., "2 to 20 carbon atoms" means that the alkenyl group may consist of 2 carbon atoms, 3 carbon atoms, 4 carbon atoms, etc., up to and including 20 carbon atoms, although the present definition also covers the occurrence of the term "alkenyl" where no numerical range is designated). When substituted, the substituent group(s) is(are) one or more group(s) individually and independently selected from alkyl, alkenyl, alkynyl, cycloalkyl, cycloalkenyl, cycloalkynyl, aryl, heteroaryl, heteroalicyclyl, aralkyl, heteroaralkyl, (heteroalicyclyl)alkyl, hydroxy, oxo, alkoxy, mercapto, alkylthio, cyano, halogen, nitro, haloalkyl, hydroxyalkyl, hydroxyhaloalkyl, haloalkoxy, and amino, including mono- and di-substituted amino groups, and the protected derivatives thereof.

As used herein, "alkynyl" refers to an alkyl group that contains in the straight or branched hydrocarbon chain one or more triple bonds. The alkynyl group may have 2 to 20 carbon atoms (whenever it appears herein, a numerical range such as "2 to 20" refers to each integer in the given range; e.g., "2 to 20 carbon atoms" means that the alkynyl group may consist of 2 carbon atoms, 3 carbon atoms, 4 carbon atoms, etc., up to and including 20 carbon atoms, although the present definition also covers the occurrence of the term "alkynyl" where no numerical range is designated). An alkynyl group may be unsubstituted or substituted. When substituted, the substituent(s) may be selected from the same groups disclosed above with regard to alkenyl group substitution.

As used herein, "hetero" may be attached to a group and refers to one or more carbon atom(s) and the associated hydrogen atom(s) in the attached group have been independently replaced with the same or different heteroatoms selected from nitrogen, oxygen, phosphorus and sulfur.

As used herein, "heteroalkyl," by itself or in combination with another term, refers to a straight or branched alkyl group consisting of the stated number of carbon atoms, where one or more carbon atom(s), such as 1, 2, 3 or 4 carbon atom(s), and the associated hydrogen atom(s) have been independently replaced with the same or different heteroatoms selected from nitrogen, oxygen and sulfur. The carbon atom(s) being replaced may be in the middle or at the end of the alkyl group. Examples of heteroalkyl include $C_{1-6}$ heteroalkyl wherein one or more of the carbon atom(s) has been replaced by a heteroatom selected from the group consisting of nitrogen, oxygen and sulfur, examples are, —S-alkyl, —O-alkyl, —NH-alkyl, -alkylene-O-alkyl, etc. A heteroalkyl may be substituted.

As used herein, "aryl" refers to a carbocyclic (all carbon) ring or two or more fused rings (rings that share two adjacent carbon atoms) that have a fully delocalized pi-electron system. In some embodiments described herein the aryl group is a $C_{1-10}$ aryl, which may be substituted or unsubstituted. Examples of aryl groups include, but are not limited to, benzene, naphthalene and azulene. An aryl group may be substituted. When substituted, hydrogen atoms are replaced by substituent group(s) that is(are) one or more group(s) independently selected from alkyl, alkenyl, alkynyl, cycloalkyl, cycloalkenyl, cycloalkynyl, aryl, heteroaryl, heteroalicyclyl, aralkyl, heteroaralkyl, (heteroalicyclyl)alkyl, hydroxy, oxo, alkoxy, aryloxy, acyl, ester, O-carboxy, mercapto, alkylthio, arylthio, cyano, halogen, carbonyl, thiocarbonyl, C-amido, N-amido, S-sulfonamido, N-sulfonamido, nitro, silyl, sulfenyl, sulfinyl, sulfonyl, haloalkyl, hydroxyalkyl, hydroxyhaloalkyl, haloalkoxy, trihalomethanesulfonyl, trihalomethanesulfonamido, and amino, including mono- and di-substituted amino groups, and the protected derivatives thereof. When substituted, substituents on an aryl group may form a non-aromatic ring fused to the aryl group, including a cycloalkyl, cycloalkenyl, cycloalkynyl, and heterocyclyl.

As used herein, "heteroaryl" refers to a monocyclic or multicyclic aromatic ring system (a ring system with fully delocalized pi-electron system), in which at least one of the atoms in the ring system is a heteroatom, that is, an element other than carbon, including but not limited to, nitrogen, oxygen and sulfur. In some embodiments described herein the heteroaryl includes, but is not limited to, $C_{6-10}$ heteroaryl, wherein one to four carbon atoms is/are replaced by one to four heteroatoms independently selected from the group consisting of nitrogen, oxygen and sulfur. Examples of monocyclic "heteroaryl" include, but are not limited to, furan, thiophene, phthalazine, pyrrole, oxazole, oxadiazole, thiazole, imidazole, pyrazole, isoxazole, isothiazole, triazole, thiadiazole, pyridine, pyridazine, pyrimidine, pyrazine, tetrazole, and triazine. Examples of multicyclic "heteroaryl" include, but are not limited to, quinoline, isoquinoline, quinazoline, quinoxaline, indole, purines, benzofuran, benzothiophene, benzopyranones (e.g. coumarin, chromone, and isocoumarin). A heteroaryl may be substituted. When substituted, hydrogen atoms are replaced by substituent group(s) that is(are) one or more group(s) independently selected from alkyl, alkenyl, alkynyl, cycloalkyl, cycloalkenyl, cycloalkynyl, aryl, heteroaryl, heteroalicyclyl, aralkyl, heteroaralkyl, (heteroalicyclyl)alkyl, hydroxy, oxo, alkoxy, aryloxy, acyl, ester, O-carboxy, mercapto, alkylthio, arylthio, cyano, halogen, carbonyl, thiocarbonyl, C-amido, N-amido, S-sulfonamido, N-sulfonamido, nitro, silyl, sulfenyl, sulfinyl, sulfonyl, haloalkyl, hydroxyalkyl, hydroxyhaloalkyl, haloalkoxy, trihalomethanesulfonyl, trihalomethanesulfonamido, and amino, including mono- and di-substituted amino groups, and the protected derivatives thereof. When substituted, substituents on a heteroayl group may form a non-aromatic ring fused to the aryl group, including a cycloalkyl, cycloalkenyl, cycloalkynyl, and heterocyclyl.

An "aralkyl" or "arylalkyl" is an aryl group connected, as a substituent, via an alkylene group. The alkylene and aryl group of an aralkyl may be substituted. Examples include but are not limited to benzyl, substituted benzyl, 2-phenylethyl, 3-phenylpropyl, and naphthylalkyl. In some cases, the alkylene group is a lower alkylene group.

A "heteroaralkyl" or "heteroarylalkyl" is heteroaryl group connected, as a substituent, via an alkylene group. The alkylene and heteroaryl group of heteroaralkyl may be substituted. Examples include but are not limited to 2-thienylmethyl, 3-thienylmethyl, furylmethyl, thienylethyl, pyrrolylalkyl, pyridylalkyl, isoxazolylalkyl, pyrazolylalkyl and imidazolylalkyl, and their substituted as well as benzo-fused analogs. In some cases, the alkylene group is a lower alkylene group.

An "alkylene" is a straight-chained tethering group, forming bonds to connect molecular fragments via their terminal carbon atoms. The alkylene may have 1 to 20 carbon atoms. The alkylene may also be a, alkylene having 1 to 10 carbon atoms, such as "$C_1$-6". The alkylene could also be a lower alkylene having 1 to 4 carbon atoms. The alkylene may be designated as "$C_1$-$C_4$ alkylene", "$C_{1-4}$ alkylene" or similar designations. Non-limiting examples include, methylene (—$CH_2$—), ethylene (—$CH_2CH_2$—), propylene (—$CH_2CH_2CH_2$—), and butylene (—$(CH_2)_4$—) groups. In the case of methylene, the two connected fragments are connected to the same carbon atom. A lower alkylene group may be substituted.

As used herein, "heteroalkylene" by itself or in combination with another term refers to an alkylene group consisting of the stated number of carbon atoms in which one or more of the carbon atoms, such as 1, 2, 3 or 4 carbon atom(s), are independently replaced with the same or different heteroatoms selected from oxygen, sulfur and nitrogen. Examples of heteroalkylene include, but not limited to —$CH_2$—O—, —$CH_2$—$CH_2$—O—, —$CH_2$—$CH_2$—$CH_2$—O—, —$CH_2$—NH—, —$CH_2$—$CH_2$—NH—, —$CH_2$—$CH_2$—$CH_2$—NH—, —$CH_2$—$CH_2$—NH—$CH_2$—, —O—$CH_2$—$CH_2$—O—$CH_2$—$CH_2$—O—, —O—$CH_2$—$CH_2$—O—$CH_2$—$CH_2$—, and the like.

As used herein, "alkylidene" refers to a divalent group, such as =CR'R", which is attached to one carbon of another group, forming a double bond. Alkylidene groups include, but are not limited to, methylidene (=$CH_2$) and ethylidene (=$CHCH_3$). As used herein, "arylalkylidene" refers to an alkylidene group in which either R' or R" is an aryl group. An alkylidene group may be substituted.

As used herein, "alkoxy" refers to the group —OR wherein R is an alkyl, e.g. methoxy, ethoxy, n-propoxy, cyclopropoxy, 1-methylethoxy (isopropoxy), n-butoxy, iso-butoxy, sec-butoxy, tert-butoxy, amoxy, tert-amoxy and the like. An alkoxy may be substituted.

As used herein, "alkylthio" refers to the formula —SR wherein R is an alkyl is defined as above, e.g. methylmercapto, ethylmercapto, n-propylmercapto, 1-methylethylmercapto (isopropylmercapto), n-butylmercapto, iso-butylmercapto, sec-butylmercapto, tert-butylmercapto, and the like. An alkylthio may be substituted.

As used herein, "aryloxy" and "arylthio" refers to RO- and RS-, in which R is an aryl as defined above, e.g., phenoxy, naphthalenyloxy, azulenyloxy, anthracenyloxy, naphthalenylthio, phenylthio and the like. Both an aryloxy and arylthio may be substituted.

As used herein, "alkenyloxy" refers to the formula —OR wherein R is an alkenyl as defined above, e.g., vinyloxy, propenyloxy, n-butenyloxy, iso-butenyloxy, sec-pentenyloxy, tert-pentenyloxy, and the like. The alkenyloxy may be substituted.

As used herein, "acyl" refers to a hydrogen, alkyl, alkenyl, alkynyl, or aryl connected, as substituents, via a carbonyl group. Examples include formyl, acetyl, propanoyl, benzoyl, and acryl. An acyl may be substituted.

As used herein, "cycloalkyl" refers to a completely saturated (no double bonds) mono- or multi-cyclic hydrocarbon ring system. When composed of two or more rings, the rings may be joined together in a fused, bridged or spiro-connected fashion. Cycloalkyl groups may range from $C_3$ to $C_{10}$, such as from $C_3$ to $C_6$. A cycloalkyl group may be unsubstituted or substituted. Typical cycloalkyl groups include, but are in no way limited to, cyclopropyl, cyclobutyl, cyclopentyl, cyclohexyl, and the like. If substituted, the substituent(s) may be an alkyl or selected from those indicated above with regard to substitution of an alkyl group unless otherwise indicated. When substituted, substituents on a cycloalkyl group may form an aromatic ring fused to the cycloalkyl group, including an aryl and a heteroaryl.

As used herein, "cycloalkenyl" refers to a cycloalkyl group that contains one or more double bonds in the ring although, if there is more than one, they cannot form a fully delocalized pi-electron system in the ring (otherwise the group would be "aryl," as defined herein). When composed of two or more rings, the rings may be connected together in a fused, bridged or spiro-connected fashion. Cycloalkenyl groups may range from $C_3$ to $C_{10}$, such as from $C_3$ to $C_8$ or from $C_5$ to $C_{10}$. For example, $C_{3-8}$ cycloalkenyl includes $C_{4-8}$ cycloalkenyl, $C_{5-8}$ cycloalkenyl or $C_{6-8}$ cycloalkenyl. A cycloalkenyl group may be unsubstituted or substituted. When substituted, the substituent(s) may be an alkyl or selected from the groups disclosed above with regard to alkyl group substitution unless otherwise indicated. When substituted, substituents on a cycloalkenyl group may form an aromatic ring fused to the cycloalkenyl group, including an aryl and a heteroaryl.

As used herein, "cycloalkynyl" refers to a cycloalkyl group that contains one or more triple bonds in the ring. When composed of two or more rings, the rings may be joined together in a fused, bridged or spiro-connected fashion. Cycloalkynyl groups may range from $C_8$ to $C_{12}$. A cycloalkynyl group may be unsubstituted or substituted. When substituted, the substituent(s) may be an alkyl or selected from the groups disclosed above with regard to alkyl group substitution unless otherwise indicated. When substituted, substituents on a cycloalkynyl group may form an aromatic ring fused to the cycloalkynyl group, including an aryl and a heteroaryl.

As used herein, "heteroalicyclic" or "heteroalicyclyl" refers to a 3- to 18 membered ring which consists of carbon atoms and from one to five heteroatoms selected from the group consisting of nitrogen, oxygen and sulfur. The heteroalicyclic or heteroalicyclyl groups may range from $C_2$ to $C_{10}$, in some embodiments it may range from $C_2$ to $C_9$, and in other embodiments it may range from $C_2$ to $C_8$. In some embodiments The "heteroalicyclic" or "heteroalicyclyl" may be monocyclic, bicyclic, tricyclic, or tetracyclic ring system, which may be joined together in a fused, bridged or spiro-connected fashion; and the nitrogen, carbon and sulfur atoms in the "heteroalicyclic" or "heteroalicyclyl" may be oxidized; the nitrogen may be quaternized; and the rings may also contain one or more double bonds provided that they do not form a fully delocalized pi-electron system throughout all the rings, examples are 2H-benzo[b][1,4]oxazin-3(4H)-one, 3,4-dihydroquinolin-2(1H)-one, 1,2,3,4-tetrahydroquinoline, 3,4-dihydro-2H-benzo[b][1,4]oxazine, 2,3-dihydrobenzo[d]oxazole, 2,3-dihydro-1H-benzo[d]imidazole, indoline, and 1,3-dihydro-2H-benzo[d]imidazol-2-one, and benzo[d]oxazol-2(3H)-one. Heteroalicyclyl groups may be unsubstituted or substituted. When substituted, the substituent(s) may be one or more groups independently selected from the group consisting of alkyl, alkenyl, alkynyl, cycloalkyl, cycloalkenyl, cycloalkynyl, aryl, heteroaryl, heteroalicyclyl, aralkyl, heteroaralkyl, (heteroalicyclyl)alkyl, hydroxy, oxo, alkoxy, aryloxy, acyl, ester, O-carboxy, mercapto, alkylthio, arylthio, cyano, halogen, C-amido, N-amido, S-sulfonamido, N-sulfonamido, isocyanato, thiocyanato, isothiocyanato, nitro, silyl, haloalkyl, hydroxyalkyl, hydroxyhaloalkyl, haloalkoxy, trihalomethanesulfonyl, trihalomethanesulfonamido, and amino, including mono- and di-substituted amino groups, and the protected derivatives thereof. Examples of such "heteroalicyclic" or "heteroalicyclyl" include but are not limited to, azepinyl, dioxolanyl, imidazolinyl, morpholinyl, oxetanyl, oxiranyl, piperidinyl N-Oxide, piperidinyl, piperazinyl, pyrrolidinyl, pyranyl, 4-piperidonyl, pyrazolidinyl, 2-oxopyrrolidinyl, tetrahydrofuranyl, tetrahydropyranyl, thiamorpholinyl, thiamorpholinyl sulfoxide, and thiamorpholinyl sulfone. When substituted, substituents on a heteroalicyclyl group may form an aromatic ring fused to the heteroalicyclyl group, including an aryl and a heteroaryl.

A "(cycloalkyl)alkyl" is a cycloalkyl group connected, as a substituent, via an alkylene group. The alkylene and cycloalkyl of a (cycloalkyl)alkyl may be substituted. Examples include but are not limited cyclopropylmethyl, cyclobutylmethyl, cyclopropylethyl, cyclopropylbutyl, cyclobutylethyl, cyclopropylisopropyl, cyclopentylmethyl, cyclopentylethyl, cyclohexylmethyl, cyclohexylethyl, cycloheptylmethyl, and the like. In some cases, the alkylene group is a lower alkylene group.

A "(cycloalkenyl)alkyl" is a cycloalkenyl group connected, as a substituent, via an alkylene group. The alkylene and cycloalkenyl of a (cycloalkenyl)alkyl may be substituted. In some cases, the alkylene group is a lower alkylene group.

A "(cycloalkynyl)alkyl" is a cycloalkynyl group connected, as a substituent, via an alkylene group. The alkylene and cycloalkynyl of a (cycloalkynyl)alkyl may be substituted. In some cases, the alkylene group is a lower alkylene group.

As used herein, "halo" or "halogen" refers to F (fluoro), Cl (chloro), Br (bromo) or I (iodo).

As used herein, "haloalkyl" refers to an alkyl group in which one or more of the hydrogen atoms are replaced by halogen. Such groups include but are not limited to, chloromethyl, fluoromethyl, difluoromethyl, fluoroethyl, difluoroethyl, trifluoromethyl, 1,1,1,3,3,3-hexafluoropropan-2-yl, 1-chloro-2-fluoromethyl and 2-fluoroisobutyl. A haloalkyl may be substituted or unsubstituted, and some embodiments relate to a haloalkyl having 1 to 10 carbon atoms, such as $C_{1-6}$ haloalkyl.

As used herein, "hydroxyhaloalkyl" refers to a halohalkyl group in which one or more of the hydrogen atoms is replaced by hydroxyl. Such hydroxyhaloalkyl groups include but are not limited to 1,1,1,3,3,3-hexafluoro-2-hydroxypropan-2-yl and 1,1-difluoro-2-hydroxyethyl. A hydroxyhaloalkyl can have 1 to 10 carbon atoms, such as $C_{1-6}$ hydroxyhaloalkyl, or $C_{1-4}$ hydroxyhaloalkyl.

As used herein, "haloalkoxy" refers to a RO-group in which R is a haloalkyl group. Such groups include but are not limited to, chloromethoxy, fluoromethoxy, difluoromethoxy, trifluoromethoxy and 1-chloro-2-fluoromethoxy, 2-fluoroisobutyoxy. A haloalkoxy may be substituted.

As used herein, the term "hydroxyalkyl" refers to an alkyl group in which one or more of the hydrogen atoms are replaced by a hydroxyl group. Such groups include but are not limited to hydroxymethyl, hydroxyethyl, hydroxypropyl, hydroxybutyl, hydroxypentyl and hydroxyhexyl. A hydroxyalkyl group may be substituted or unsubstituted, and some embodiments relate to a hydroxyalkyl having 1 to 10 carbon atoms, such as $C_{1-6}$ hydroxyalkyl or $C_{1-4}$ hydroxyalkyl.

An "O-carboxy" group refers to a "RC(=O)O—" group in which R can be hydrogen, alkyl, alkenyl, alkynyl, cycloalkyl, cycloalkenyl, cycloalkynyl, aryl, heteroaryl, heteroalicyclyl, aralkyl, or (heteroalicyclyl)alkyl, as defined herein. An O-carboxy may be substituted.

A "C-carboxy" group refers to a "—C(=O)OR" group in which R can be the same as defined with respect to O-carboxy. A C-carboxy may be substituted.

A "trihalomethanesulfonyl" group refers to an "$X_3CSO_2$—" group" wherein X is a halogen.

A dashed bond, -----, represents an optional unsaturation between the atoms forming the bond. This bond may be unsaturated (e.g. C=C, C=N, C=O) or saturated (e.g. C—C, C—N, C—O). When a dashed bond is present in a ring system it may form part of an aromatic ring system.

As used herein, a straight (unwedged) bolded or hashed bond, ▬ or "ııııı", refers to relative stereochemistry inclusive of all possible stereoisomers at that position.

As used herein, and unless otherwise indicated, a wedged-bond (bolded, hashed, or otherwise), ◀, ◁, or ıııııı, refers to absolute stereochemistry referring to the particular stereoisomer as depicted at that position.

A "nitro" group refers to a "—$NO_2$" group
A "cyano" group refers to a "—CN" group.
A "cyanato" group refers to an "—OCN" group.
An "isocyanato" group refers to a "—NCO" group.
A "thiocyanato" group refers to a "—SCN" group.
A "carbonyl" group refers to a "—C(=O)—" group.
A "thiocarbonyl" group refers to a "—C(=S)—" group.
An "oxo" group refers to a "=O" group.
A "hydroxy" group or "hydroxyl" group refers to an "—OH" group.
An "isothiocyanato" group refers to an "—NCS" group.
A "sulfinyl" group refers to an "—S(=O)—R" group in which R can be the same as defined with respect to O-carboxy. A sulfinyl may be substituted.

A "sulfonyl" group refers to an "SO$_2$R" group in which R can be the same as defined with respect to O-carboxy. A sulfonyl may be substituted.

An "S-sulfonamido" group refers to a "—SO$_2$NR$_A$R$_B$" group in which R$_A$ and R$_B$ independently of each other can be the same as defined with respect to the R group as defined for O-carboxy, or combined to form a ring system selected from the group consisting of substituted or unsubstituted C$_{3-8}$ cycloalkyl, substituted or unsubstituted C$_{3-8}$ cycloalkenyl, substituted or unsubstituted C$_{3-8}$ cycloalkyl, substituted or unsubstituted C$_{3-8}$ cycloalkenyl substituted or unsubstituted heteroalicyclyl, substituted or unsubstituted aryl, and substituted or unsubstituted heteroaryl. A S-sulfonamido may be substituted.

An "N-sulfonamido" group refers to a "RSO$_2$N(R$_A$)—" group in which R and R$_A$ independently of each other can be the same as defined with respect to the R group as defined for O-carboxy. An N-sulfonamido may be substituted.

A "trihalomethanesulfonamido" group refers to an "X$_3$CSO$_2$N(R)—" group with X as halogen and R can be the same as defined with respect to O-carboxy. A trihalomethanesulfonamido may be substituted.

A "C-amido" group refers to a "—C(=O)NR$_A$R$_B$" group in which R$_A$ and R$_B$ independently of each other can be the same as defined with respect to the R group as defined for O-carboxy, or combined to form a ring system selected from the group consisting of substituted or unsubstituted C$_{3-8}$ cycloalkyl, substituted or unsubstituted C$_{3-8}$ cycloalkenyl, substituted or unsubstituted C$_{3-8}$ cycloalkyl, substituted or unsubstituted C$_{3-8}$ cycloalkenyl substituted or unsubstituted heteroalicyclyl, substituted or unsubstituted aryl, and substituted or unsubstituted heteroaryl. A C-amido may be substituted.

An "N-amido" group refers to a "RC(=O)NR$_A$—" group in which R and R$_A$ independently of each other can be the same as defined with respect to the R group as defined for O-carboxy. An N-amido may be substituted.

An "ester" refers to a "—C(=O)OR" group in which R can be the same as defined with respect to O-carboxy. An ester may be substituted.

A lower alkoxyalkyl refers to an alkoxy group connected via a lower alkylene group. A lower alkoxyalkyl may be substituted.

An "amine" or "amino" refers to "RNH$_2$" (a primary amine), "R$_2$NH" (a secondary amine), "R$_3$N" (a tertiary amine). An amino group may be substituted.

A lower aminoalkyl refers to an amino group connected via a lower alkylene group. A lower aminoalkyl may be substituted.

Any unsubstituted or monosubstituted amine group on a compound herein can be converted to an amide, any hydroxyl group can be converted to an ester and any carboxyl group can be converted to either an amide or ester using techniques well-known to those skilled in the art (see, for example, Greene and Wuts, Protective Groups in Organic Synthesis, 3$^{rd}$ Ed., John Wiley & Sons, New York, N.Y., 1999).

As used herein, the abbreviations for any protective groups, amino acids and other compounds, are, unless indicated otherwise, in accord with their common usage, recognized abbreviations, or the IUPAC-IUB Commission on Biochemical Nomenclature (See, Biochem. 11:942-944 (1972)).

LIST OF ABBREVIATIONS

DMF dimethylformamide
DMSO dimethylsulfoxide
MeOH methanol
EtOH ethanol
THF tetrahydrofurane
DCM dichloromethane, methylene chloride
DCE 1,2-dichloroethane
LRMS low resolution mass spectrometry
HPLC high pressure liquid chromatography
Prep-HPLC preparative high pressure liquid chromatography
h hour
min minutes
EA ethyl acetate
EDC.HCl 3-((ethylimino)methyleneamino)-N,N-dimethylpropan-1-aminium chloride
DIEA diisopropylethyamine
TEA triethylamine
TFA trifluoroacetic acid
HCl hydrochloric acid, hydrogen chloride
HOBt 1-hydroxybenzotriazole hydrate
HOAt 1-hydroxy-7-azabenzotriazole
HATU 1-[bis(dimethylamino)methylene]-1H-1,2,3-triazolo[4,5-b]pyridinium 3-oxid hexafluorophosphate
DMAP 4-(dimethylamino)pyridine
DAST (diethylamino)sulfur trifluoride
DMP Dess-Martin Periodinane, 1,1,1-tris(acetyloxy)-1,1-dihydro-1,2-benziodoxol-3-(1H)-one
TBAF tetrabutylammonium fluoride trihydrate
TBDMSCl tert-butyldimethylsilyl chloride
MsCl methanesulfonyl chloride
TsCl 4-toluenesulfonyl chloride
NAS nucleophilic aromatic substitution
nBuLi n-Butyllithium
iPr isopropyl
DIAD Diisopropyl azodicarboxylate
Boc tert-Butyloxycarbonyl
Flash CC Flash Column Chromatography
on overnight
rt room temperature
aq aqueous
ND Not Determined
Cbz Carboxybenzyl
Hex hexane
Hept heptane
DEA diethylamine
PE petroleum ether
DAD Diode Array Detctor
TOF Time of Flight
IPA isopropanol
Pg Protective group
lg Leaving group
atm atmosphere
" enantiomerically enriched (in certain chemical structures denotes enantiomerically enriched)

It is understood that, in any compound disclosed herein having one or more chiral centers, if an absolute stereochemistry is not expressly indicated, then each center may independently be of R-configuration or S-configuration or a mixture thereof. Thus, the compounds provided herein may be enantiomerically pure or be stereoisomeric mixtures. Further, compounds provided herein may be scalemic mixtures. In addition, it is understood that in any compound having one or more double bond(s) generating geometrical isomers that can be defined as E or Z each double bond may independently be E or Z or a mixture thereof. Likewise, all tautomeric forms are also intended to be included.

As used herein, the term "rac" refers to "racemic", "racemate", etc., as is understood by one of ordinary skill in the art. For example, a racemate comprises a mixture of enantiomers of a chiral molecule in equivalent amounts. Typically, a racemate does not exhibit optical activity.

As used herein, the term "rel" refers to the relative, but not absolute, configuration of a stereogenic center with respect to any other stereogenic center within the same compound, as is understood by one of ordinary skill in the art.

As used herein, "tautomer" and "tautomeric" refer to alternate forms of a compound disclosed herein that differ in the position of a proton. Non-limiting examples include enol-keto and imine-enamine tautomers, or the tautomeric forms of heteroaryl groups containing a ring atom attached to both a ring —NH— moiety and a ring =N— moiety such as pyrazoles, imidazoles, benzimidazoles, triazoles, and tetrazoles.

It is understood that isotopes may be present in the compounds described herein. Each chemical element as represented in a compound structure may include any isotope of said element. For example, in a compound described herein a hydrogen atom can be any isotope of hydrogen, including but not limited to hydrogen-1 (protium) and hydrogen-2 (deuterium). Thus, reference herein to a compound encompasses all potential isotopic forms unless the context clearly dictates otherwise.

As used herein, reference to an element, whether by description or chemical structure, encompasses all isotopes of that element unless otherwise described. By way of example, the term "hydrogen" or "H" in a chemical structure as used herein is understood to encompass, for example, not only $^1$H, but also deuterium ($^2$H), tritium ($^3$H), and mixtures thereof unless otherwise denoted by use of a specific isotope. Other specific non-limiting examples of elements for which isotopes are encompassed include carbon, phosphorous, iodine, and fluorine.

As used herein, "pharmaceutically acceptable salt" refers to a salt of a compound that does not abrogate the biological activity and properties of the compound. Pharmaceutical salts can be obtained by reaction of a compound disclosed herein with an acid or base. Base-formed salts include, without limitation, ammonium salt ($NH_4^+$); alkali metal, such as, without limitation, sodium or potassium, salts; alkaline earth, such as, without limitation, calcium or magnesium, salts; salts of organic bases such as, without limitation, dicyclohexylamine, piperidine, piperazine, methylpiperazine, N-methyl-D-glucamine, diethylamine, ethylenediamine, tris(hydroxymethyl)methylamine; and salts with the amino group of amino acids such as, without limitation, arginine and lysine. Useful acid-based salts include, without limitation, acetates, adipates, aspartates, ascorbates, benzoates, butyrates, caparate, caproate, caprylate, camsylates, citrates, decanoates, formates, fumarates, gluconates, glutarate, glycolates, hexanoates, laurates, lactates, maleates, nitrates, oleates, oxalates, octanoates, propanoates, palmitates, phosphates, sebacates, succinates, stearates, sulfates, sulfonates, such as methanesulfonates, ethanesulfonates, p-toluenesulfonates, salicylates, tartrates, and tosylates.

As used herein, to "modulate" the activity of a receptor means either to activate it, i.e., to increase its cellular function over the base level measured in the particular environment in which it is found, or deactivate it, i.e., decrease its cellular function to less than the measured base level in the environment in which it is found and/or render it unable to perform its cellular function at all, even in the presence of a natural binding partner. A natural binding partner is an endogenous molecule that is an agonist for the receptor.

An "agonist" is defined as a compound that increases the basal activity of a receptor (i.e. signal transduction mediated by the receptor).

As used herein, "partial agonist" refers to a compound that has an affinity for a receptor but, unlike an agonist, when bound to the receptor it elicits only a fractional degree of the pharmacological response normally associated with the receptor even if a large number of receptors are occupied by the compound.

An "inverse agonist" is defined as a compound, which reduces, or suppresses the basal activity of a receptor, such that the compound is not technically an antagonist but, rather, is an agonist with negative intrinsic activity.

As used herein, "antagonist" refers to a compound that binds to a receptor to form a complex that does not give rise to any response, as if the receptor was unoccupied. An antagonist attenuates the action of an agonist on a receptor. An antagonist may bind reversibly or irreversibly, effectively eliminating the activity of the receptor permanently or at least until the antagonist is metabolized or dissociates or is otherwise removed by a physical or biological process.

As used herein, a "subject" refers to an animal that is the object of treatment, observation or experiment. "Animal" includes cold- and warm-blooded vertebrates and invertebrates such as birds, fish, shellfish, reptiles and, in particular, mammals. "Mammal" includes, without limitation, mice; rats; rabbits; guinea pigs; dogs; cats; sheep; goats; cows; horses; primates, such as monkeys, chimpanzees, and apes, and, in particular, humans.

As used herein, a "patient" refers to a subject that is being treated by a medical professional such as an M.D. or a D.V.M. to attempt to cure, or at least ameliorate the effects of, a particular disease or disorder or to prevent the disease or disorder from occurring in the first place.

As used herein, a "carrier" refers to a compound that facilitates the incorporation of a compound into cells or tissues. For example, without limitation, dimethyl sulfoxide (DMSO) is a commonly utilized carrier that facilitates the uptake of many organic compounds into cells or tissues of a subject.

As used herein, a "diluent" refers to an ingredient in a pharmaceutical composition that lacks pharmacological activity but may be pharmaceutically necessary or desirable. For example, a diluent may be used to increase the bulk of a potent drug whose mass is too small for manufacture or administration. It may also be a liquid for the dissolution of a drug to be administered by injection, ingestion or inhalation. A common form of diluent in the art is a buffered aqueous solution such as, without limitation, phosphate buffered saline that mimics the composition of human blood.

As used herein, an "excipient" refers to an inert substance that is added to a pharmaceutical composition to provide, without limitation, bulk, consistency, stability, binding ability, lubrication, disintegrating ability etc., to the composition. A "diluent" is a type of excipient.

A "receptor" is intended to include any molecule present inside or on the surface of a cell that may affect cellular physiology when it is inhibited or stimulated by a ligand. Typically, a receptor comprises an extracellular domain with ligand-binding properties, a transmembrane domain that anchors the receptor in the cell membrane, and a cytoplasmic domain that generates a cellular signal in response to ligand binding ("signal transduction"). A receptor also includes any intracellular molecule that in response to ligation generates a signal. A receptor also includes any molecule having the characteristic structure of a receptor, but with no identifiable ligand. In addition, a receptor includes a truncated, modified, mutated receptor, or any molecule comprising partial or all of the sequences of a receptor.

"Ligand" is intended to include any substance that interacts with a receptor.

"Selective" or "selectivity" is defined as a compound's ability to generate a desired response from a particular receptor type, subtype, class or subclass while generating less or little response from other receptor types. "Selective" or "selectivity" of one or more particular subtypes of a compound means a compound's ability to increase the activity of the subtypes while causing less, little or no increase in the activity of other subtypes.

As used herein, "coadministration" of pharmacologically active compounds refers to the delivery of two or more separate chemical entities, whether in vitro or in vivo. Coadministration means the simultaneous delivery of separate agents; the simultaneous delivery of a mixture of agents; as well as the delivery of one agent followed by delivery of a second agent or additional agents. Agents that are coadministered are typically intended to work in conjunction with each other.

The term "an effective amount" as used herein means an amount of active compound or pharmaceutical agent that elicits the biological or medicinal response in a tissue, system, animal or human that is being sought by a researcher, veterinarian, medical doctor or other clinician, which includes alleviation or palliation of the symptoms of the disease being treated.

When used herein, "prevent/preventing" should not be construed to mean that a condition and/or a disease never might occur again after use of a compound or pharmaceutical composition according to embodiments disclosed herein to achieve prevention. Further, the term should neither be construed to mean that a condition not might occur, at least to some extent, after such use to prevent said condition. Rather, "prevent/preventing" is intended to mean that the condition to be prevented, if occurring despite such use, will be less severe than without such use.

Compounds

In one embodiment the present disclosure relates to compounds or pharmaceutically acceptable salts, stereoisomers, or salts of stereoisomers of Formula (I)

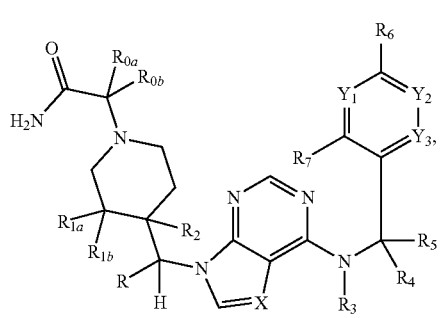

a stereoisomer thereof, or a pharmaceutically acceptable salt of the compound or stereoisomer, wherein:
$Y_1$, $Y_2$ and $Y_3$ are independently —N— or —CR$_8$—;
X is —CR$_9$—, or —N—;
$R_{0a}$ and $R_{0b}$ independently are selected from the group consisting of hydrogen, $C_{1-4}$ alkyl, $C_{1-4}$ hydroxyalkyl, and $C_{1-4}$ haloalkyl;

R is selected from the group consisting of hydrogen, $C_{1-6}$ alkyl and $C_{1-4}$ hydroxyalkyl;
$R_{1a}$ and $R_{1b}$ are independently selected from the group consisting of hydrogen, hydroxyl, halogen, amino, $C_{1-4}$ alkyl, $C_{1-4}$ hydroxyalkyl, and $C_{1-4}$ haloalkyl;
$R_2$ is selected from the group consisting of hydrogen, hydroxyl, amino, cyano, halogen, $C_{1-4}$ alkyl, $C_{1-4}$ haloalkyl, $C_{1-4}$ hydroxyalkyl, —C(=O)NH$_2$, —C(=O)OH, —C(=O)O—$C_{1-4}$ alkyl, and substituted or unsubstituted heteroaryl;
$R_3$ is selected from the group consisting of $C_{1-4}$ alkyl, $C_{1-4}$ alkenyl, $C_{1-4}$ haloalkyl, $C_{1-4}$ hydroxyalkyl, $C_{3-7}$ cycloalkyl, and $C_{3-7}$ cycloalkenyl; or
$R_3$ and $R_4$ are taken together with the atoms to which they are attached to form a 4-6 membered heteroalicyclic ring system optionally substituted with one to three substituents selected from halogen, hydroxyl, and $C_{1-4}$ alkyl;
$R_4$ is hydrogen or $C_{1-4}$ alkyl, provided $R_3$ and $R_4$ are not taken together with the atoms to which they are attached to form a 4-6 membered heteroalicyclic ring system; or $R_4$ and $R_5$ are taken together with the carbon atom to which they are attached to form a $C_{3-4}$ cycloalkyl;
$R_5$ is absent, hydrogen or $C_{1-4}$ alkyl, provided $R_4$ and $R_5$ are not taken together with the carbon atom to which they are attached to form a $C_{3-4}$ cycloalkyl;
$R_6$ is selected from the group consisting of hydrogen, —CN, halogen, $C_{1-4}$ alkyl, $C_{1-4}$ hydroxyalkyl, $C_{1-4}$ haloalkyl, $C_{1-6}$ hydroxyhaloalkyl, $C_{1-4}$ alkoxy, $C_{1-4}$ haloalkoxy, and 5-6 membered heteroaryl, wherein 5-6 membered heteroaryl is optionally substituted with $C_{1-4}$ alkyl;
$R_7$ is selected from the group consisting of hydrogen, hydroxyl, —CN, halogen, $C_{1-4}$ alkyl, $C_{1-4}$ haloalkyl, $C_{1-4}$ hydroxyalkyl, $C_{1-4}$ alkoxy, and $C_{1-4}$ haloalkoxy;
each $R_8$ is independently selected from the group consisting of hydrogen, hydroxyl, —CN, halogen, $C_{1-4}$ alkyl, $C_{1-4}$ haloalkyl, $C_{1-4}$ alkoxy, and $C_{1-4}$ haloalkoxy; and whenever $R_7$ is hydrogen and each $R_8$ present is hydrogen, then $R_6$ is selected from the group consisting of —CN, halogen, $C_{1-4}$ alkyl, $C_{1-4}$ haloalkyl, $C_{1-6}$ hydroxyhaloalkyl, $C_{1-4}$ hydroxyalkyl, $C_{1-4}$ alkoxy, $C_{1-4}$ haloalkoxy, and 5-6 membered heteroaryl, wherein 5-6 membered heteroaryl is optionally substituted with $C_{1-4}$ alkyl; and
$R_9$ is selected from the group consisting of hydrogen, halogen, cyano, and $C_{1-4}$ alkyl.

In some embodiments disclosed herein, R is hydrogen. In some embodiments disclosed herein, R is $C_{1-6}$ alkyl. In some embodiments disclosed herein, R is $C_{1-4}$ hydroxyalkyl.

In some embodiments disclosed herein, $R_{0a}$ is selected from the group consisting of hydrogen, methyl, —CH$_2$OH, —CH$_2$CH$_2$OH, —CH$_2$F, and —CHF$_2$; and $R_{0b}$ is selected from the group consisting of hydrogen, $C_{1-4}$ alkyl, $C_{1-4}$ hydroxyalkyl, and $C_{1-4}$ haloalkyl. In some embodiments disclosed herein, $R_{0a}$ is selected from the group consisting of hydrogen, methyl, —CH$_2$OH, and —CH$_2$CH$_2$OH. In some embodiments disclosed herein, $R_{0a}$ is selected from the group consisting of hydrogen, methyl, and —CH$_2$OH. In some embodiments disclosed herein, $R_{0a}$ is hydrogen. In some embodiments disclosed herein, $R_{0a}$ is methyl. In some embodiments disclosed herein, $R_{0a}$ is —CH$_2$OH. In some embodiments disclosed herein, $R_{0b}$ is hydrogen. In some embodiments disclosed herein, $R_{0a}$ is selected from the group consisting of hydrogen, methyl, —CH$_2$OH, —CH$_2$CH$_2$OH and $R_{0b}$ is hydrogen.

In some embodiments disclosed herein, at least one of $R_{1a}$, $R_{1b}$ and $R_2$ is not hydrogen.

In some embodiments disclosed herein, $R_{1a}$ is hydrogen. In some embodiments disclosed herein, $R_{1a}$ is hydroxyl, halogen, or $C_{1-4}$ haloalkyl. In some embodiments disclosed herein, $R_{1a}$ is hydroxyl or halogen. In some embodiments disclosed herein, $R_{1a}$ is hydroxyl. In some embodiments disclosed herein, $R_{1a}$ is halogen. In some embodiments disclosed herein, $R_{1a}$ is fluoro. In some embodiments disclosed herein, $R_{1a}$ is $C_{1-4}$ alkyl or $C_{1-4}$ haloalkyl. In some embodiments disclosed herein, $R_{1a}$ is $C_{1-4}$ alkyl. In some embodiments disclosed herein, $R_{1a}$ is $C_{1-4}$ haloalkyl. In some embodiments disclosed herein, $R_{1a}$ is —$CF_3$. In some embodiments disclosed herein, Rib is selected from the group consisting of hydrogen, halogen, and $C_{1-4}$ alkyl. In some embodiments disclosed herein, $R_{1b}$ is selected from the group consisting of hydrogen, fluoro, and methyl. In some embodiments disclosed herein, $R_{1b}$ is hydrogen. In some embodiments disclosed herein, $R_{1b}$ is fluoro. In some embodiments disclosed herein, $R_{1b}$ is methyl. In some embodiments disclosed herein, $R_{1a}$ is selected from the group consisting of hydroxyl, fluoro and —$CF_3$ and $R_{1b}$ is selected from the group consisting of hydrogen, fluoro, and methyl.

In some embodiments disclosed herein, $R_2$ is selected from the group consisting of hydrogen, halogen, hydroxyl, cyano, methyl, ethyl, —$CH_2OH$, —$CH_2CH_2OH$ and —$C(=O)O$—$C_{1-2}$ alkyl. In some embodiments disclosed herein, $R_2$ is selected from the group consisting of hydrogen, fluoro and hydroxyl. In some embodiments disclosed herein, $R_2$ is hydroxyl or cyano. In some embodiments disclosed herein, $R_2$ is hydrogen. In some embodiments disclosed herein, $R_2$ is hydroxyl. In some embodiments disclosed herein, $R_2$ is cyano.

In some embodiments disclosed herein, $R_3$ is selected from the group consisting of methyl, ethyl, n-propyl, iso-propyl, n-butyl, iso-butyl, tert-butyl, cyclopropyl and cyclobutyl. In some embodiments disclosed herein, $R_3$ is methyl, ethyl, isopropyl, or cyclopropyl. In some embodiments disclosed herein, $R_3$ is ethyl or cyclopropyl. In some embodiments disclosed herein, $R_3$ is methyl. In some embodiments disclosed herein, $R_3$ is ethyl. In some embodiments disclosed herein, $R_3$ is isopropyl. In some embodiments disclosed herein, $R_3$ is cyclopropyl.

In some embodiments disclosed herein, $R_4$ is hydrogen or $C_{1-4}$ alkyl. In some embodiments disclosed herein, $R_4$ is hydrogen. In some embodiments disclosed herein, $R_4$ is $C_{1-4}$ alkyl. In some embodiments disclosed herein, $R_4$ is methyl.

In some embodiments disclosed herein, $R_5$ is absent, hydrogen or $C_{1-4}$ alkyl. In some embodiments disclosed herein, $R_5$ is absent. In some embodiments disclosed herein, $R_5$ is hydrogen. In some embodiments disclosed herein, $R_5$ is $C_{1-4}$ alkyl. In some embodiments disclosed herein, $R_5$ is methyl. In In some embodiments disclosed herein, $R_4$ and $R_5$ independently are hydrogen or methyl. In some embodiments disclosed herein, $R_4$ and $R_5$ are hydrogen. In some embodiments disclosed herein, $R_4$ and $R_5$ are methyl.

In some embodiments disclosed herein, $R^3$ and $R^4$, taken together with the atoms to which they are attached, form a 4-6 membered heteroalicyclic ring. In some embodiments disclosed herein, the heteroalicyclic ring system comprising $R_3$ and $R_4$ is selected from the group consisting of 4 membered heteroalicyclyl, 5 membered heteroalicyclyl, and 6 membered heteroalicyclyl. In some embodiments disclosed herein, $R_3$ and $R_4$ taken together with the atoms to which they are attached form a 4 membered heteroalicyclyl. In some embodiments disclosed herein, $R_3$ and $R_4$ taken together with the atoms to which they are attached form a 5 membered heteroalicyclyl. In some embodiments disclosed herein, $R_3$ and $R_4$ taken together with the atoms to which they are attached form a 6 membered heteroalicyclyl. In some embodiments disclosed herein, the heteroalicyclic ring system is unsubstituted. In some embodiments disclosed herein, the heteroalicyclic ring system is optionally substituted with one or two substituents selected from halogen, hydroxyl and $C_{1-4}$ alkyl. In some embodiments disclosed herein, the heteroalicyclic ring system is substituted with one or two substituents selected from halogen, hydroxyl and $C_{1-4}$ alkyl. In some embodiments disclosed herein, $R^3$ and $R^4$, taken together with the atoms to which they are attached, form a 4-6 membered heteroalicyclic ring comprising a double bond, and $R^5$ is absent.

In some embodiments disclosed herein, the heteroalicyclic ring system comprising $R_3$ and $R_4$ is selected from the group consisting of azetidinyl, pyrrolidinyl, piperidinyl, morpholinyl, 2-azabicyclo[3.1.0]hexanyl, and 3-azabicyclo[3.1.0]hexanyl; wherein the heteroalicyclic ring system is optionally substituted with one or two substituents selected from halogen, hydroxyl and $C_{1-4}$ alkyl, and whenever the heteroalicyclic ring system is 2-azabicyclo[3.1.0]hexanyl then $R_5$ is absent. In some embodiments disclosed herein, the heteroalicyclic ring system comprising $R_3$ and $R_4$ is morpholinyl optionally substituted with one or two substituents selected from halogen and methyl; and $R_5$ is hydrogen, provided the heteroalicyclic ring system is not 2-azabicyclo[3.1.0]hexanyl. In some embodiments disclosed herein, the heteroalicyclic ring system comprising $R_3$ and $R_4$ is unsubstituted morpholinyl.

In some embodiments disclosed herein, $R_6$ is selected from the group consisting of hydrogen, halogen, $C_{1-4}$ haloalkyl, $C_{1-6}$ hydroxyhaloalkyl, $C_{1-4}$ haloalkoxy, $C_{1-4}$ hydroxyalkyl, and 5 membered heteroaryl optionally substituted with $C_{1-4}$ alkyl. In some embodiments disclosed herein, $R_6$ is selected from the group consisting of hydrogen, halogen, —$CF_3$, —$CHF_2$, —$CCH_3F_2$, —$OCF_3$, —$OCHF_2$, —$C(CF_3)_2$ OH, and 5 membered heteroaryl optionally substituted with one or two methyl groups. In some embodiments disclosed herein, $R_6$ is —$CF_3$, or pyrazole optionally substituted with one methyl group. In some embodiments disclosed herein, $R_6$ is —$CF_3$. In some embodiments disclosed herein, $R_6$ is unsubstituted pyrazole. In some embodiments disclosed herein, $R_6$ is pyrazole substituted with one methyl.

In some embodiments disclosed herein, $R_7$ is selected from the group consisting of hydrogen, halogen, hydroxyl, cyano, —$CF_3$, —$OCHF_2$, —$CHF_2$ and —$OCF_3$. In some embodiments disclosed herein, $R_7$ is selected from the group consisting of hydrogen, fluoro, $CF_3$ and hydroxyl. In some embodiments disclosed herein, $R_7$ is hydrogen or fluoro. In some embodiments disclosed herein, $R_7$ is hydrogen.

In some embodiments disclosed herein, $Y_1$, $Y_2$ and $Y_3$ are —CH—; or $Y_1$ is —N— and $Y_2$ and $Y_3$ are —CH—; or $Y_2$ is —N— and $Y_1$ and $Y_3$ are —CH—; or $Y_3$ is —N— and $Y_1$ and $Y_2$ are —CH—; or $Y_3$ is —CH— and $Y_1$ and $Y_2$ are —N—. In some embodiments disclosed herein, $Y_1$, $Y_2$ and $Y_3$ are —CH—. In some embodiments disclosed herein, $Y_1$ is —N— and $Y_2$ and $Y_3$ are —CH—. In some embodiments disclosed herein, $Y_2$ is —N— and $Y_1$ and $Y_3$ are —CH—. In some embodiments disclosed herein, $Y_3$ is —N— and $Y_1$ and $Y_2$ are —CH—. In some embodiments disclosed herein, $Y_3$ is —CH— and $Y_1$ and $Y_2$ are —N—. In some embodiments disclosed herein, $Y_1$ is —CH—, and $Y_2$ and $Y_3$ are —$CR_8$— wherein each $R_8$ independently is selected from the group consisting of hydrogen, methyl, fluoro, hydroxyl and —$CF_3$. In some embodiments disclosed herein, each $R_8$ is hydrogen. In some embodiments disclosed herein, each $R_8$ is methyl. In some embodiments disclosed herein, each $R_8$ is —CF$_3$. In some embodiments disclosed herein, Y$_2$ is —N— and Y$_1$ and Y$_3$ are —CH—, or Y$_3$ is —N— and Y$_1$ and Y$_2$ are —CH—.

In some embodiments disclosed herein, X is —CR$_9$— and R$_9$ is hydrogen, cyano or fluoro. In some embodiments disclosed herein, R$_9$ is hydrogen. In some embodiments disclosed herein, R$_9$ is fluoro. In some embodiments disclosed herein, R$_9$ is cyano. In some embodiments disclosed herein, X is —CH—. In some embodiments disclosed herein, X is —N—.

In some embodiments disclosed herein, the compound has the structure of Formula (II), (III), (IV), or (V):

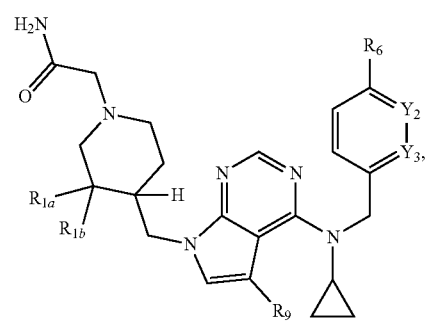

(II)

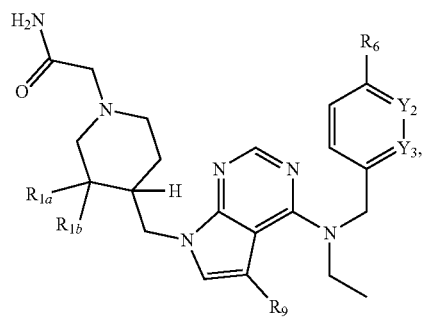

(III)

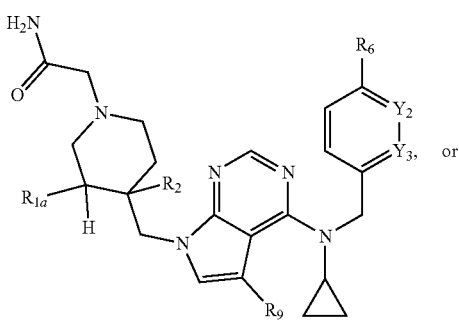

(IV)

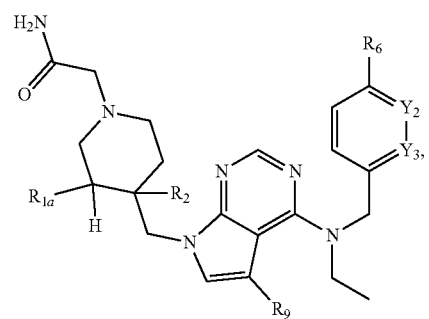

(V)

wherein R$_{1a}$ is fluoro or hydroxyl; R$_{1b}$ is hydrogen or fluoro; R$_2$ is hydrogen or hydroxyl; R$_6$ is —CF$_3$; R$_9$ is hydrogen or fluoro, and Y$_2$ and Y$_3$ are independently —N—, —CH, or —CF. In some embodiments disclosed herein, the compound has the structure of Formula (II):

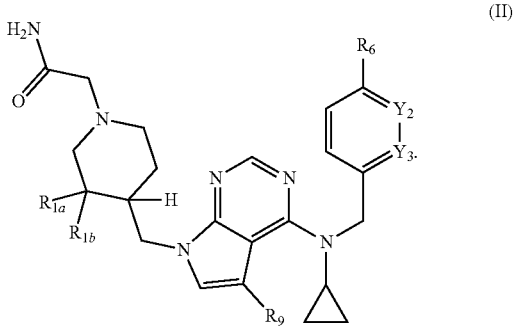

(II)

In some embodiments disclosed herein, the compound has the structure of Formula (III):

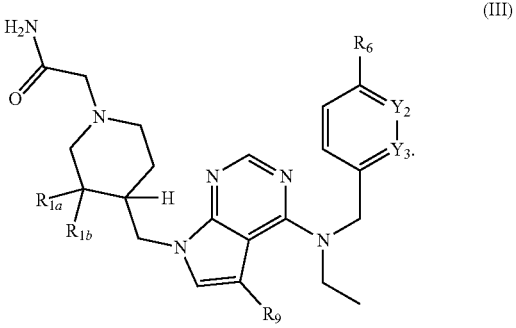

(III)

In some embodiments disclosed herein, the compound has the structure of Formula (IV):

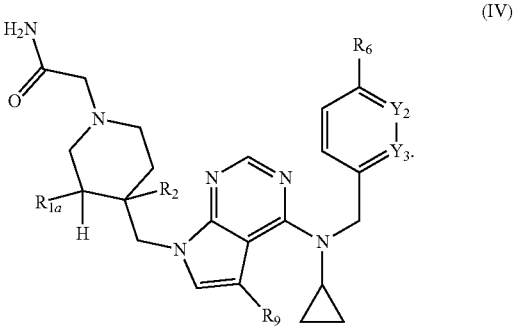

(IV)

In some embodiments disclosed herein, the compound has the structure of Formula (V):

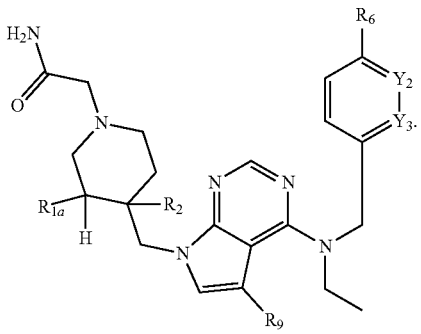

In some embodiments disclosed herein, the compound is selected from Formulae (II) or (III). In some embodiments disclosed herein, the compound is selected from Formulae (IV) or (V).

In some embodiments disclosed herein, $Y_2$ and $Y_3$ are independently —CH— or —CF. In some embodiments disclosed herein, $Y_2$ is —CH— and $Y_3$ is —N—.

In some embodiments disclosed herein, $R_{0a}$ and $R_{0b}$ are independently selected from the group consisting of hydrogen, methyl and —CH$_2$OH;

$R_{1a}$ and $R_{1b}$ are independently selected from the group consisting of hydrogen, fluoro, and hydroxyl;

$R_2$ is selected from the group consisting of hydrogen, cyano and hydroxyl;

R is hydrogen;

X is —CR$_9$— or —N—, wherein R$_9$ is selected from the group consisting of hydrogen, cyano, and fluoro;

$R_3$ is selected from the group consisting of methyl, ethyl, isopropyl and cyclopropyl, and $R_4$ and $R_5$ independently are hydrogen, or $R_3$ and $R_4$ are taken together with the atoms to which they are attached to form an unsubstituted morpholinyl, and $R_5$ is H;

$R_6$ is selected from the group consisting of hydrogen, —CF$_3$ and pyrazole, wherein the pyrazole is optionally substituted by methyl;

$R_7$ is hydrogen; and $Y_1, Y_2$ and $Y_3$ are —CH—; or
$Y_1$ is —CH—, $Y_2$ is —CF— and $Y_3$ is —CH—; or
$Y_1$ is —CH—, $Y_2$ is —CH— and $Y_3$ is —CF—; or
$Y_1$ is —CH—, $Y_2$ is —CH— and $Y_3$ is —N—; or
$Y_1$ is —CH—, $Y_2$ is —N— and $Y_3$ is —CH—; or
$Y_1$ is —N—, $Y_2$ is —N— and $Y_3$ is —CH—; or
$Y_1$ is —CH—, $Y_2$ is —C(CF$_3$)— and $Y_3$ is —CH—.

Certain embodiments relate to a compound, pharmaceutically acceptable salt, stereoisomer, or salt of the stereoisomer according Formulae (II) or (III); other embodiments relate to a compound, pharmaceutically acceptable salt, stereoisomer, or salt of the stereoisomer according Formulae (IV) or (V); and in some of those embodiments R$_9$ is hydrogen, in others R$_9$ is fluoro.

In one embodiment, the compound, salt, stereoisomer, or salt of the stereoisomer of Formula (I) is selected from the group consisting of:

2-(4-((4-(cyclopropyl(4-(trifluoromethyl)benzyl)amino)-5-fluoro-7H-pyrrolo[2,3-d]pyrimidin-7-yl)methyl)-4-hydroxypiperidin-1-yl)acetamide, 2-(4-((4-(cyclopropyl(4-(trifluoromethyl)benzyl)amino)-7H-pyrrolo[2,3-d]pyrimidin-7-yl)methyl)-4-hydroxypiperidin-1-yl)acetamide, 2-(4-((6-(cyclopropyl(4-(trifluoromethyl)benzyl)amino)-9H-purin-9-yl)methyl)-4-hydroxypiperidin-1-yl)acetamide, 2-(4-((5-cyano-4-(cyclopropyl(4-(trifluoromethyl)benzyl)amino)-7H-pyrrolo[2,3-d]pyrimidin-7-yl)methyl)-4-hydroxypiperidin-1-yl)acetamide, 2-(4-((5-fluoro-4-(methyl(4-(trifluoromethyl)benzyl)amino)-7H-pyrrolo[2,3-d]pyrimidin-7-yl)methyl)-4-hydroxypiperidin-1-yl)acetamide, rel-(R)-2-(4-((4-(cyclopropyl(4-(trifluoromethyl)benzyl)amino)-7H-pyrrolo[2,3-d]pyrimidin-7-yl)methyl)-3,3-difluoropiperidin-1-yl)acetamide, rel-2-((3R,4R)-4-((4-(cyclopropyl(4-(trifluoromethyl)benzyl)amino)-7H-pyrrolo[2,3-d]pyrimidin-7-yl)methyl)-3-fluoropiperidin-1-yl)acetamide, rel-2-((3R,4R)-4-((4-(cyclopropyl((5-(trifluoromethyl)pyridin-2-yl)methyl)amino)-7H-pyrrolo[2,3-d]pyrimidin-7-yl)methyl)-3-fluoropiperidin-1-yl)acetamide, rel-2-((3R,4R)-4-((4-(cyclopropyl(4-(trifluoromethyl)benzyl)amino)-7H-pyrrolo[2,3-d]pyrimidin-7-yl)methyl)-3,4-dihydroxypiperidin-1-yl)acetamide, rel-2-((3R,4R)-4-((4-(ethyl(4-(trifluoromethyl)benzyl)amino)-7H-pyrrolo[2,3-d]pyrimidin-7-yl)methyl)-3,4-dihydroxypiperidin-1-yl)acetamide, rac-2-((3R,4R)-4-((4-(ethyl(2-fluoro-4-(trifluoromethyl)benzyl)amino)-7H-pyrrolo[2,3-d]pyrimidin-7-yl)methyl)-3,4-dihydroxypiperidin-1-yl)acetamide, rel-2-((3R,4R)-4-((4-(ethyl(2-fluoro-4-(trifluoromethyl)benzyl)amino)-7H-pyrrolo[2,3-d]pyrimidin-7-yl)methyl)-3,4-dihydroxypiperidin-1-yl)acetamide, 2-((3R*,4R*)-3-hydroxy-4-((4-((S)-3-(4-(trifluoromethyl)phenyl)morpholino)-7H-pyrrolo[2,3-d]pyrimidin-7-yl)methyl)piperidin-1-yl)acetamide rel-(R)-2-(4-((4-(3-(4-(trifluoromethyl)phenyl)morpholino)-7H-pyrrolo[2,3-d]pyrimidin-7-yl)methyl)piperidin-1-yl)acetamide, rel-2-((3R,4R)-3-hydroxy-4-((4-((R)-3-(3-(trifluoromethyl)phenyl)morpholino)-7H-pyrrolo[2,3-d]pyrimidin-7-yl)methyl)piperidin-1-yl)acetamide, rel-2-((3R,4R)-3-hydroxy-4-((4-((S)-3-(3-(trifluoromethyl)phenyl)morpholino)-7H-pyrrolo[2,3-d]pyrimidin-7-yl)methyl)piperidin-1-yl)acetamide, 2-(4-((4-(cyclopropyl(4-(trifluoromethyl)benzyl)amino)-5-fluoro-7H-pyrrolo[2,3-d]pyrimidin-7-yl)methyl)piperidin-1-yl)acetamide, 2-(4-((6-(cyclopropyl(4-(trifluoromethyl)benzyl)amino)-9H-purin-9-yl)methyl)piperidin-1-yl)acetamide, 2-(4-((5-cyano-4-(cyclopropyl(4-(trifluoromethyl)benzyl)amino)-7H-pyrrolo[2,3-d]pyrimidin-7-yl)methyl)piperidin-1-yl)acetamide, 2-(4-((6-(cyclopropyl(4-(trifluoromethyl)benzyl)amino)-9H-purin-9-yl)methyl)piperidin-1-yl)propanamide, 2-(4-((6-(cyclopropyl(4-(trifluoromethyl)benzyl)amino)-9H-purin-9-yl)methyl)piperidin-1-yl)-2-methylpropanamide, 2-(4-((4-(cyclopropyl((6-(trifluoromethyl)pyridin-3-yl)methyl)amino)-5-fluoro-7H-pyrrolo[2,3-d]pyrimidin-7-yl)methyl)piperidin-1-yl)acetamide, 2-(4-cyano-4-((4-(cyclopropyl(4-(trifluoromethyl)benzyl)amino)-5-fluoro-7H-pyrrolo[2,3-d]pyrimidin-7-yl)methyl)piperidin-1-yl)acetamide, rac-2-((3R,4R)-4-((5-fluoro-4-(methyl(4-(trifluoromethyl)benzyl)amino)-7H-pyrrolo[2,3-d]pyrimidin-7-yl)methyl)-3-hydroxypiperidin-1-yl)acetamide, rac-2-((3R,4R)-4-((4-(cyclopropyl(4-(trifluoromethyl)benzyl)amino)-7H-pyrrolo[2,3-d]pyrimidin-7-yl)methyl)-3-hydroxypiperidin-1-yl)acetamide, rel-2-((3R,4R)-4-((4-(cyclopropyl(4-(trifluoromethyl)benzyl)amino)-7H-pyrrolo[2,3-d]pyrimidin-7-yl)methyl)-3-hydroxypiperidin-1-yl)acetamide, rac-2-((3R,4R)-4-((4-(cyclopropyl(4-(trifluoromethyl)benzyl)amino)-5-fluoro-7H-pyrrolo[2,3-d]pyrimidin-7-yl)methyl)-3-hydroxypiperidin-1-yl)acetamide, rel-2-((3R,4R)-4-((4-(cyclopropyl(4-(trifluoromethyl)benzyl)amino)-5-fluoro-7H-pyrrolo[2,3-d]pyrimidin-7-yl)methyl)-3-hydroxypiperidin-1-yl)acetamide, rac-2-((3R,4R)-4-((4-(cyclopropyl((6-(trifluoromethyl)pyridin-3-yl)methyl)amino)-5-fluoro-7H-pyrrolo[2,3-d]pyrimidin-7-yl)methyl)-3-hydroxypiperidin-1-yl)acetamide, rac-2-((3R,4R)-4-((4-(cyclopropyl((6-(trifluoromethyl)pyridin-3-yl)methyl)amino)-7H-pyrrolo[2,3-d]pyrimidin-7-yl)methyl)-3-hydroxypiperidin-1-yl)acetamide, rac-2-((3R,4R)-4-((4-(cyclopropyl((2-(trifluoromethyl)pyrimidin-5-yl)methyl)amino)-5-fluoro-7H-pyrrolo[2,3-d]pyrimidin-7-yl)methyl)-3-hydroxypiperidin-1-yl)acetamide, rac-2-((3R,4R)-4-((4-(cyclopropyl((5-(trifluoromethyl)pyridin-2-yl)methyl)amino)-5-fluoro-7H-pyrrolo[2,3-d]pyrimidin-7-yl)methyl)-3-hydroxypiperidin-1-yl)acetamide, rac-2-((3R,4R)-4-((5-fluoro-4-(isopropyl(4-(trifluoromethyl)benzyl)amino)-7H-pyrrolo[2,3-d]pyrimidin-7-yl)methyl)-3-hydroxypiperidin-1-yl)acetamide, rac-2-((3R,4R)-4-((6-(cyclopropyl(3-(trifluoromethyl)benzyl)amino)-9H-purin-9-yl)methyl)-3-hydroxypiperidin-1-yl)acetamide, rac-2-((3R,4R)-4-((4-(ethyl(4-(trifluoromethyl)benzyl)amino)-5-fluoro-7H-pyrrolo[2,3-d]pyrimidin-7-yl)methyl)-3-hydroxypiperidin-1-yl)acetamide, rac-2-((3R,4R)-3-hydroxy-4-((6-(isopropyl(4-(trifluoromethyl)benzyl)amino)-9H-purin-9-yl)methyl)piperidin-1-yl)acetamide, rac-2-((3R,4R)-4-((4-(cyclopropyl((5-(trifluoromethyl)pyridin-2-yl)methyl)amino)-7H-pyrrolo[2,3-d]pyrimidin-7-yl)methyl)-3-hydroxypiperidin-1-yl)acetamide, rel-2-((3R,4R)-4-((4-(cyclopropyl((5-(trifluoromethyl)pyridin-2-yl)methyl)amino)-7H-pyrrolo[2,3-d]pyrimidin-7-yl)methyl)-3-hydroxypiperidin-1-yl)acetamide, rac-2-((3R,4R)-4-((4-(ethyl(4-(trifluoromethyl)benzyl)amino)-7H-pyrrolo[2,3-d]pyrimidin-7-yl)methyl)-3-hydroxypiperidin-1-yl)acetamide, rel-2-((3R,4R)-4-((4-(ethyl(4-(trifluoromethyl)benzyl)amino)-7H-pyrrolo[2,3-d]pyrimidin-7-yl)methyl)-3-hydroxypiperidin-1-yl)acetamide, rac-2-((3R,4R)-3-hydroxy-4-((4-(isopropyl(4-(trifluoromethyl)benzyl)amino)-7H-pyrrolo[2,3-d]pyrimidin-7-yl)methyl)piperidin-1-yl)acetamide, rel-2-((3R,4R)-3-hydroxy-4-((4-(isopropyl(4-(trifluoromethyl)benzyl)amino)-7H-pyrrolo[2,3-d]pyrimidin-7-yl)methyl)piperidin-1-yl)acetamide rel-2-((3R,4R)-4-((6-(cyclopropyl(4-(trifluoromethyl)benzyl)amino)-9H-purin-9-yl)methyl)-3-hydroxypiperidin-1-yl)acetamide, rel-2-((3R,4R)-4-((4-(ethyl((5-(trifluoromethyl)pyridin-2-yl)methyl)amino)-7H-pyrrolo[2,3-d]pyrimidin-7-yl)methyl)-3-hydroxypiperidin-1-yl)acetamide, rel-2-((3R,4R)-4-((4-(ethyl((5-(trifluoromethyl)pyridin-2-yl)methyl)amino)-5-fluoro-7H-pyrrolo[2,3-d]pyrimidin-7-yl)methyl)-3-hydroxypiperidin-1-yl)acetamide, rel-2-((3R,4R)-4-((4-((4-cyanobenzyl)(ethyl)amino)-7H-pyrrolo[2,3-d]pyrimidin-7-yl)methyl)-3-hydroxypiperidin-1-yl)acetamide, rel-2-((3R,4R)-4-((4-((4-(1H-pyrazol-1-yl)benzyl)(ethyl)amino)-7H-pyrrolo[2,3-d]pyrimidin-7-yl)methyl)-3-hydroxypiperidin-1-yl)acetamide, rel-2-((3R,4R)-4-((4-(ethyl(3-fluoro-4-(trifluoromethyl)benzyl)amino)-7H-pyrrolo[2,3-d]pyrimidin-7-yl)methyl)-3-hydroxypiperidin-1-yl)acetamide, rel-2-((3R,4R)-4-((4-(ethyl(2-fluoro-4-(trifluoromethyl)benzyl)amino)-7H-pyrrolo[2,3-d]pyrimidin-7-yl)methyl)-3-hydroxypiperidin-1-yl)acetamide, rel-2-((3R,4R)-4-((4-((4-(1H-pyrazol-1-yl)benzyl)(cyclopropyl)amino)-7H-pyrrolo[2,3-d]pyrimidin-7-yl)methyl)-3-hydroxypiperidin-1-yl)acetamide, rel-2-((3R,4R)-4-((4-(ethyl(4-(1-methyl-1H-pyrazol-4-yl)benzyl)amino)-7H-pyrrolo[2,3-d]pyrimidin-7-yl)methyl)-3-hydroxypiperidin-1-yl)acetamide, rel-2-((3R,4R)-4-((4-(ethyl(2-fluoro-4-(1-methyl-1H-pyrazol-4-yl)benzyl)amino)-7H-pyrrolo[2,3-d]pyrimidin-7-yl)methyl)-3-hydroxypiperidin-1-yl)acetamide, rel-2-((3R,4R)-4-((4-(ethyl(2-fluoro-4-(1H-pyrazol-1-yl)benzyl)amino)-7H-pyrrolo[2,3-d]pyrimidin-7-yl)methyl)-3-hydroxypiperidin-1-yl)acetamide, rac-2-((3R,4R)-4-((4-(cyclopropyl(4-(trifluoromethyl)benzyl)amino)-7H-pyrrolo[2,3-d]pyrimidin-7-yl)methyl)-3-hydroxypiperidin-1-yl)-3-hydroxypropanamide, 2-((3R*,4R*)-3-fluoro-4-((4-((S)-3-(5-(trifluoromethyl)pyridin-2-yl)morpholino)-7H-pyrrolo[2,3-d]pyrimidin-7-yl)methyl)piperidin-1-yl)acetamide, (S)-2-(4-((4-(3-(5-(trifluoromethyl)pyridin-2-yl)morpholino)-7H-pyrrolo[2,3-d]pyrimidin-7-yl)methyl)piperidin-1-yl)acetamide, rel-2-((3R,4R)-4-((4-((4-(1H-pyrazol-1-yl)benzyl)(ethyl)amino)-7H-pyrrolo[2,3-d]pyrimidin-7-yl)methyl)-3,4-dihydroxypiperidin-1-yl)acetamide, rel-2-((3R,4R)-4-((4-((4-(1H-pyrazol-1-yl)benzyl)(cyclopropyl)amino)-7H-pyrrolo[2,3-d]pyrimidin-7-yl)methyl)-3,4-dihydroxypiperidin-1-yl)acetamide, rel-2-((3R,4R)-4-((4-(cyclopropyl(2-fluoro-4-(1-methyl-1H-pyrazol-4-yl)benzyl)amino)-7H-pyrrolo[2,3-d]pyrimidin-7-yl)methyl)-3,4-dihydroxypiperidin-1-yl)acetamide, rel-2-((3R,4R)-4-((4-(cyclopropyl(2-fluoro-4-(1H-pyrazol-1-yl)benzyl)amino)-7H-pyrrolo[2,3-d]pyrimidin-7-yl)methyl)-3,4-dihydroxypiperidin-1-yl)acetamide, and rel-2-((3R,4R)-4-((4-(ethyl(2-fluoro-4-(1H-pyrazol-1-yl)benzyl)amino)-7H-pyrrolo[2,3-d]pyrimidin-7-yl)methyl)-3,4-dihydroxypiperidin-1-yl)acetamide.

In some embodiments disclosed herein, the compound, salt, stereoisomer, or salt of the stereoisomer of Formula (I) is selected from the group consisting of:

25
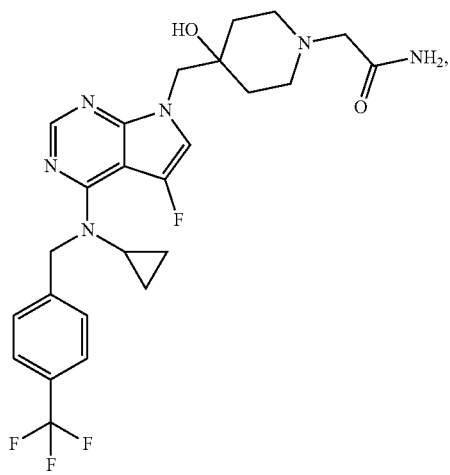
26
-continued
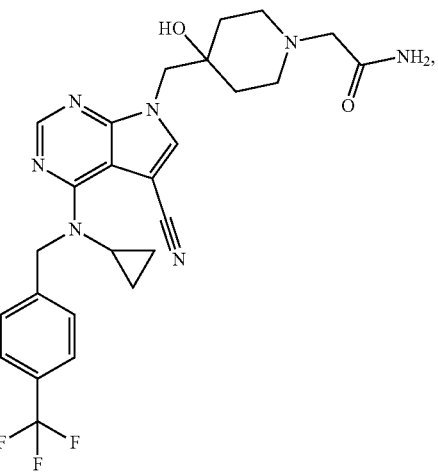
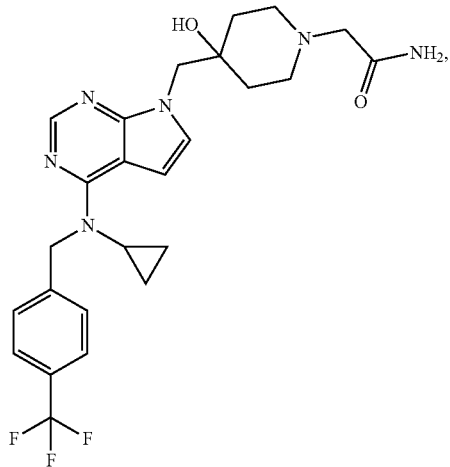
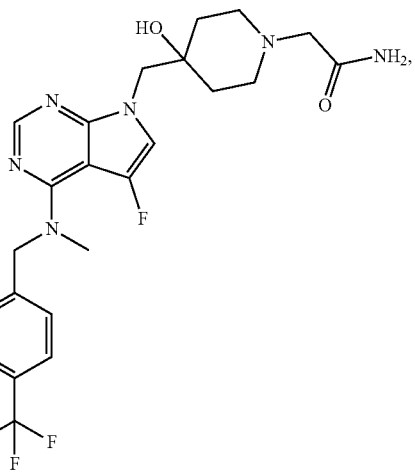
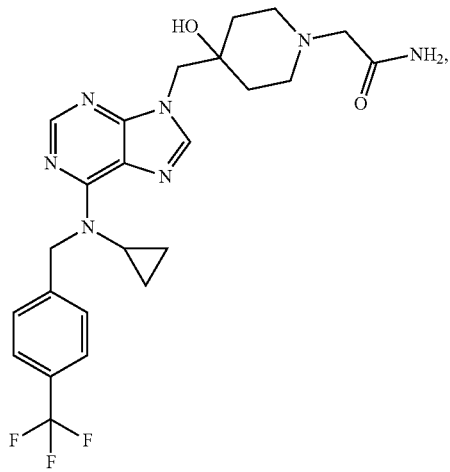
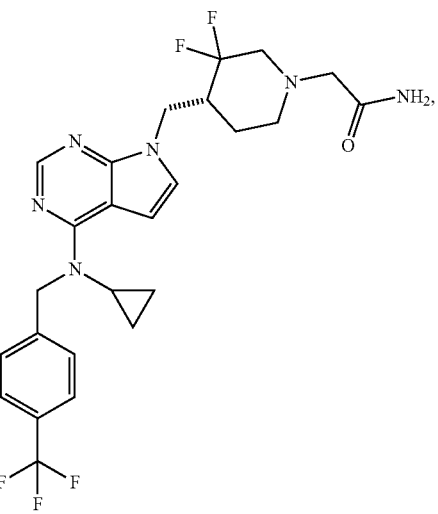

27
-continued
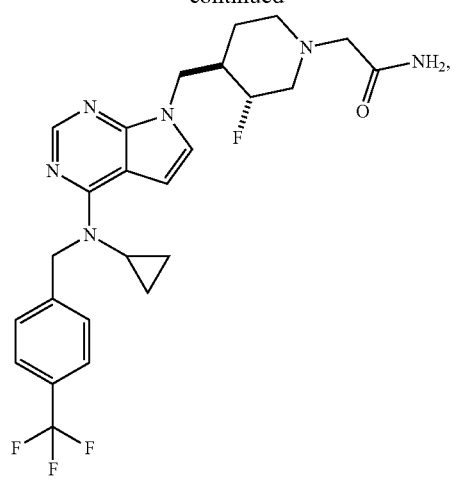
28
-continued
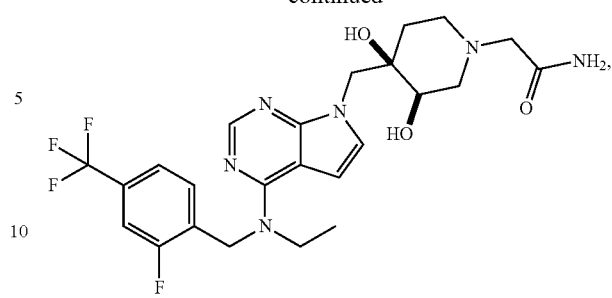
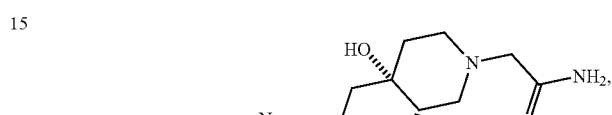
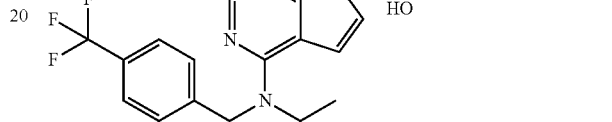
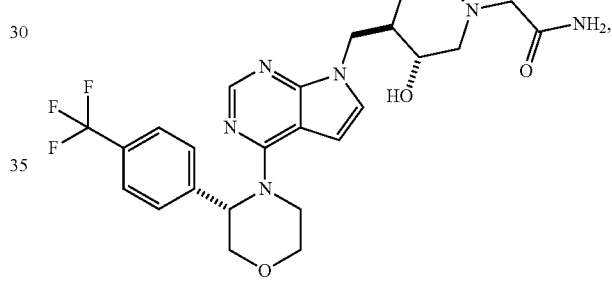
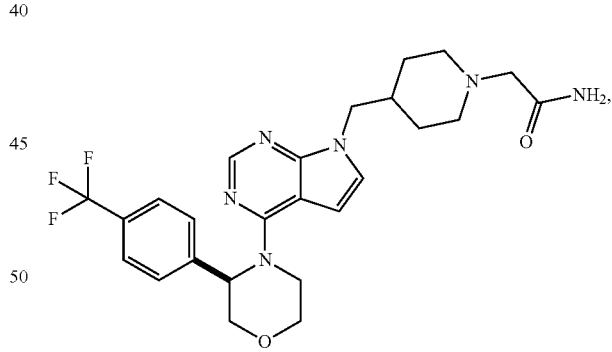
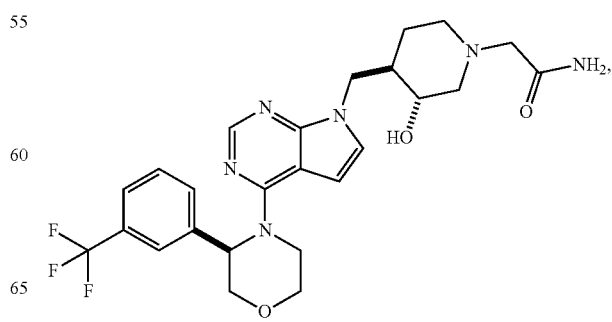

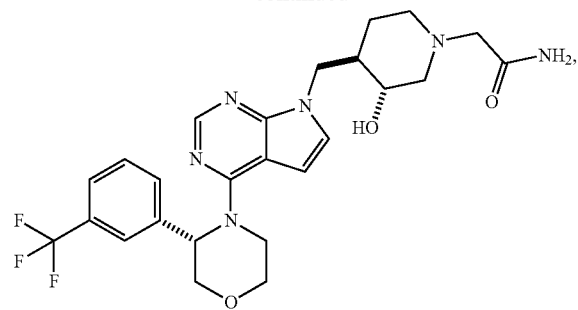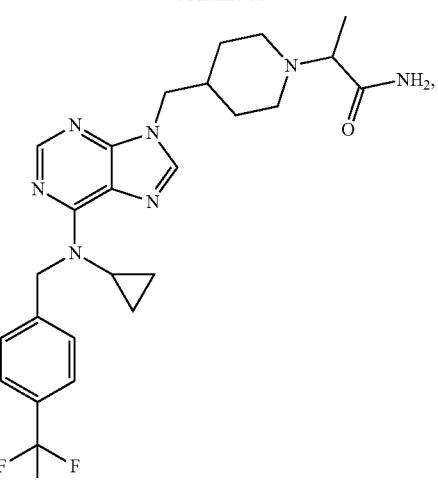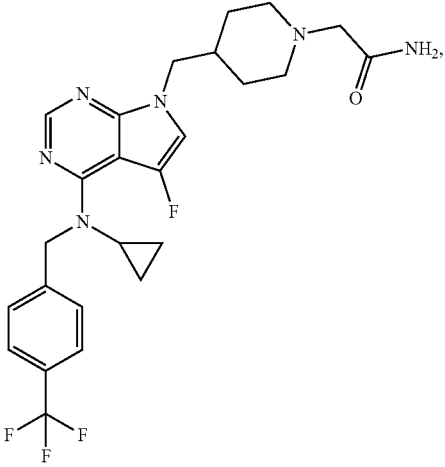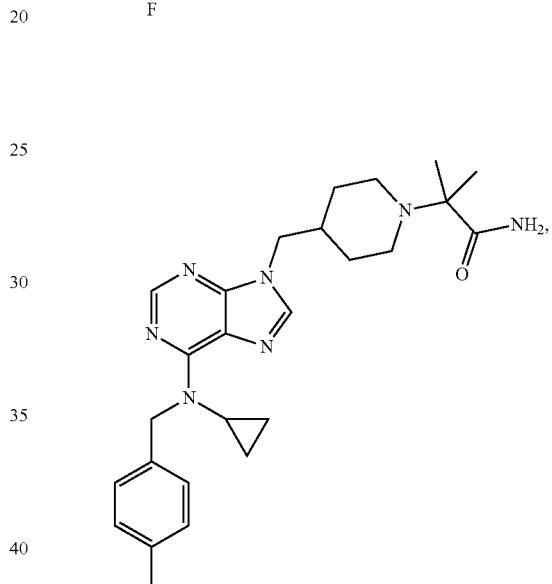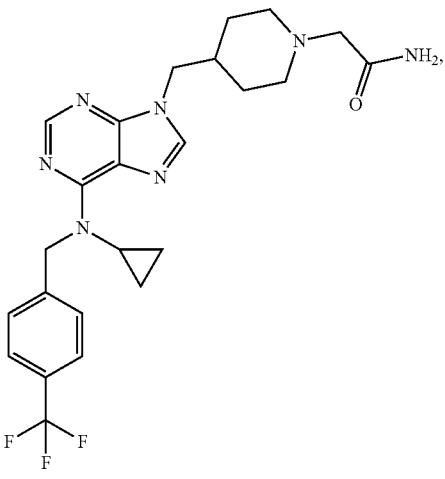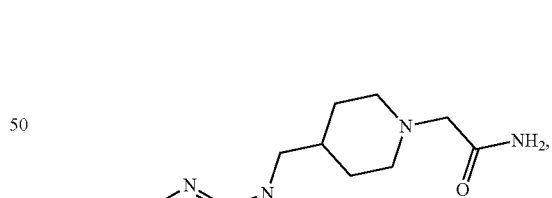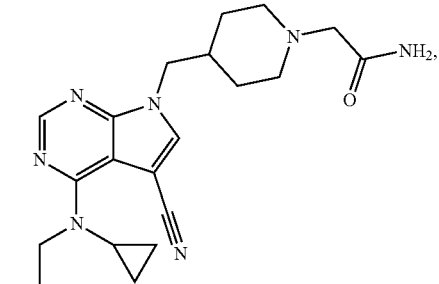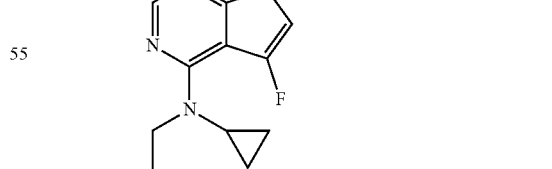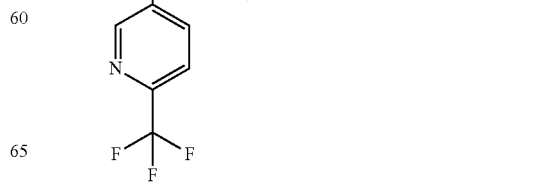

31
-continued
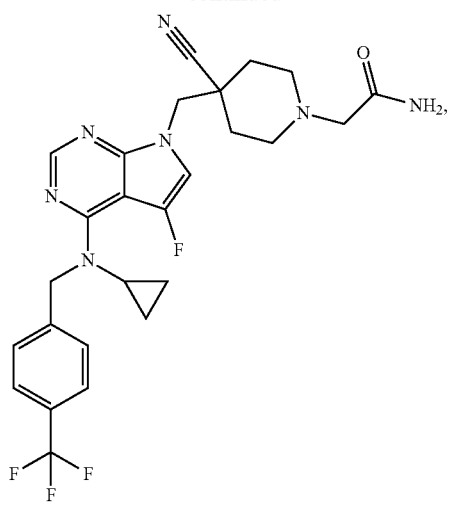
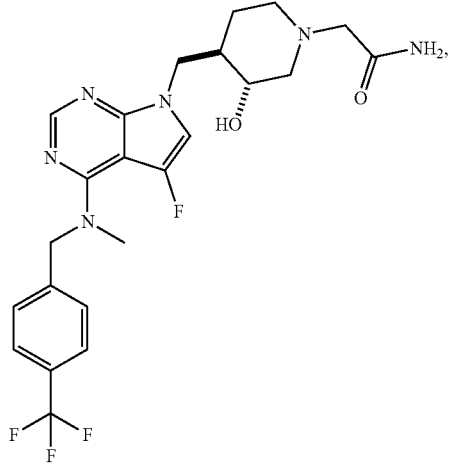
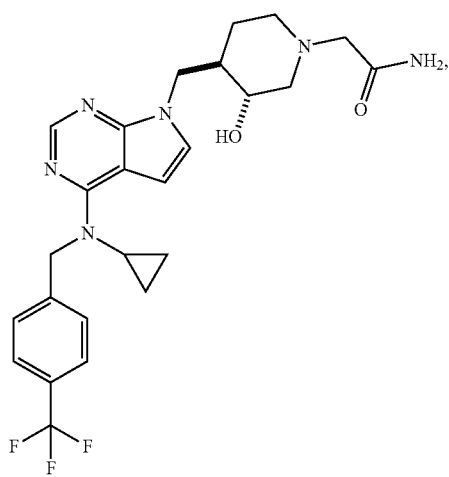
32
-continued
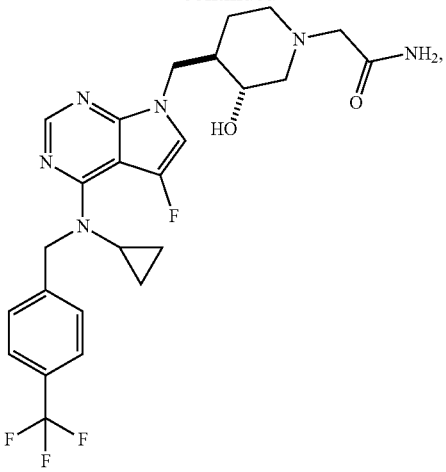
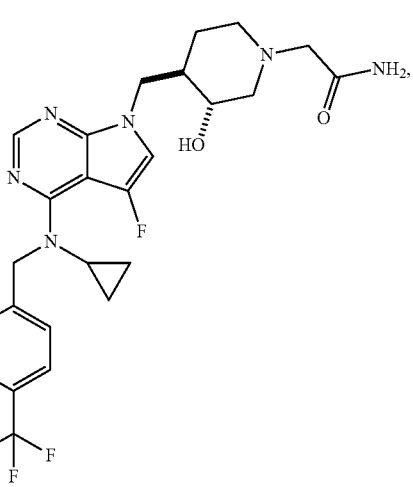
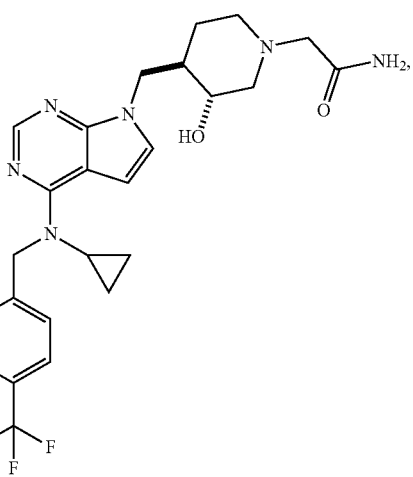

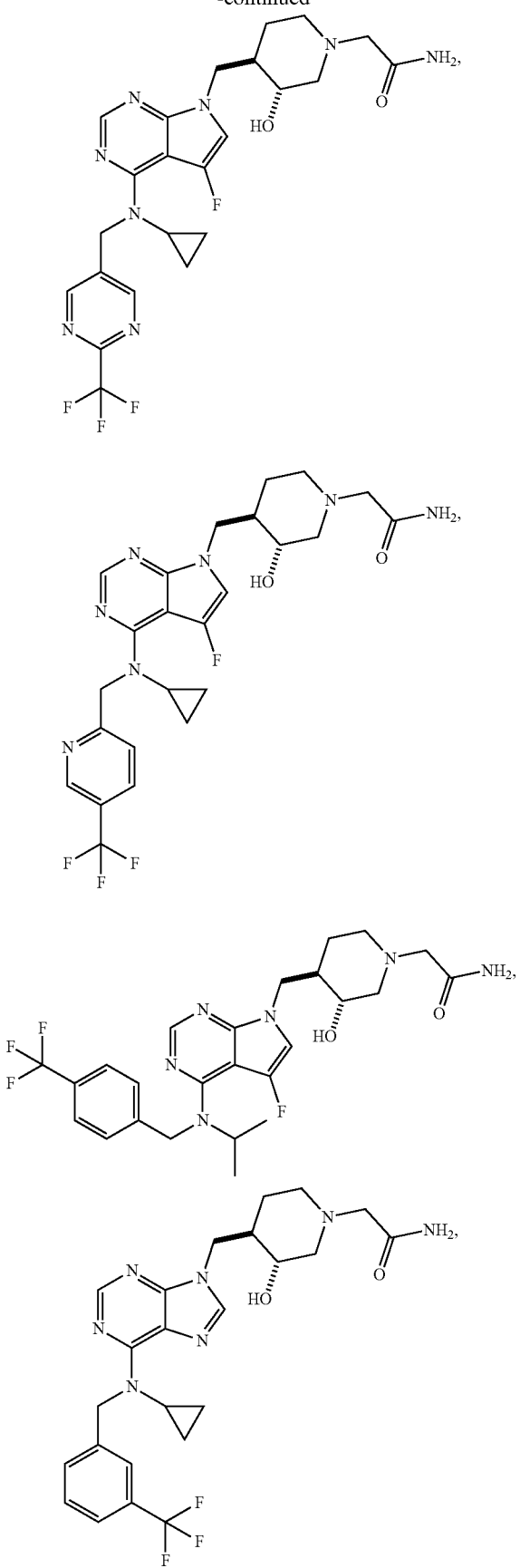
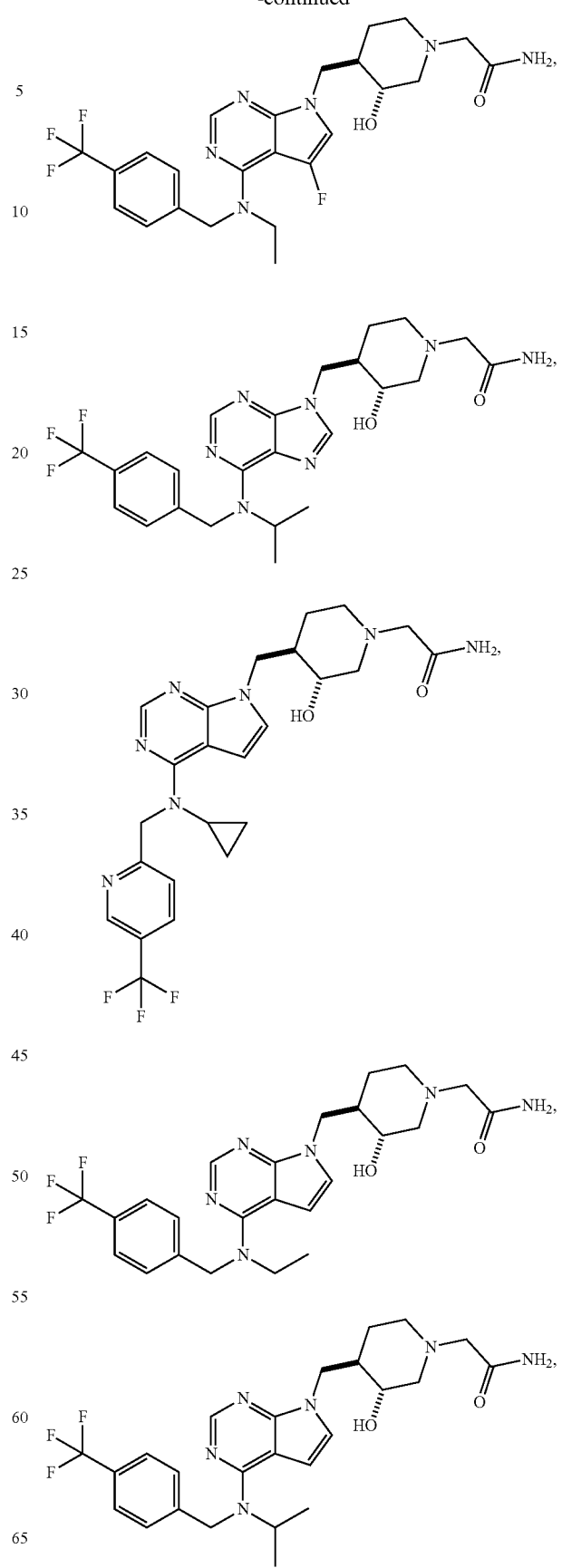

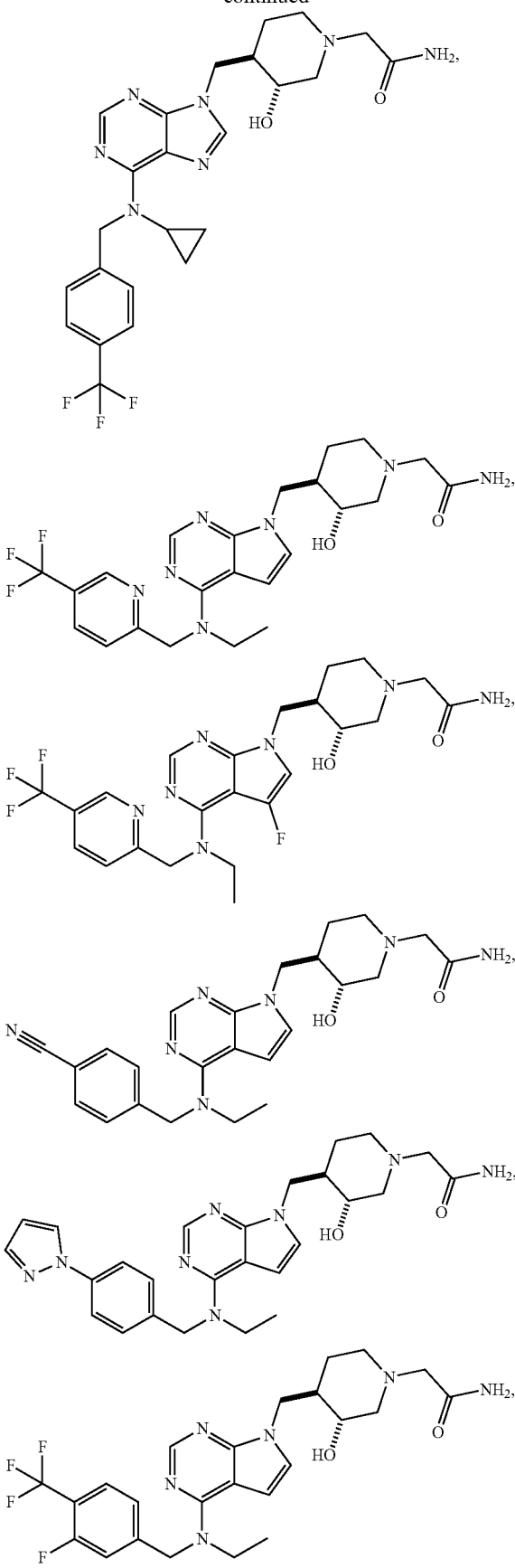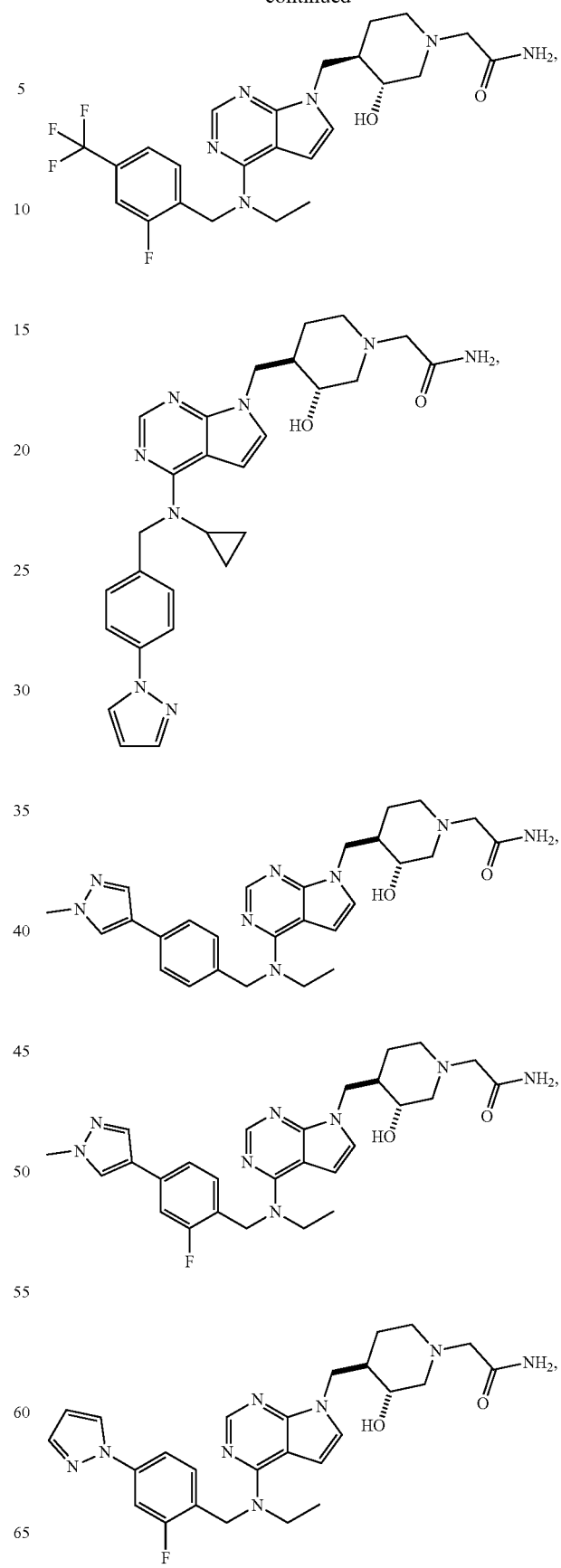

37
-continued
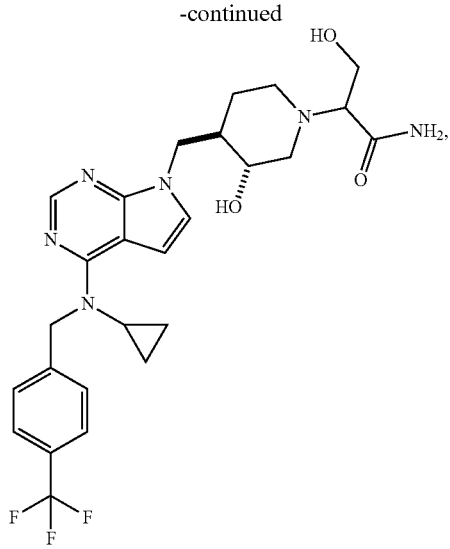
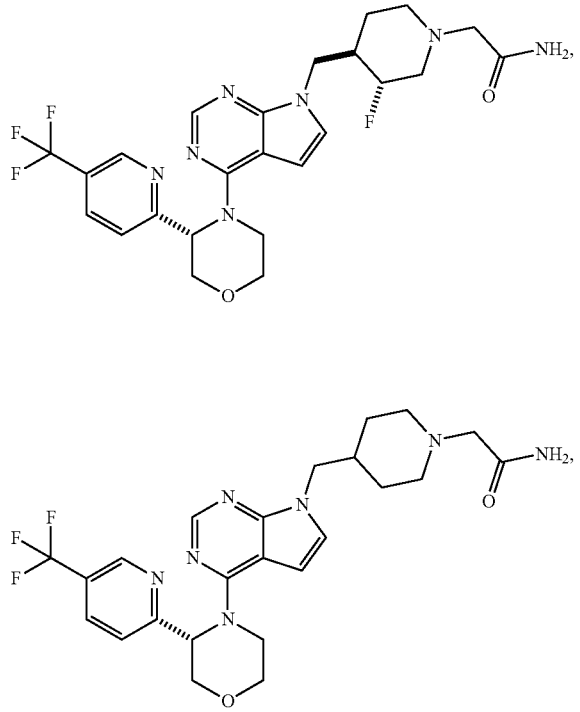
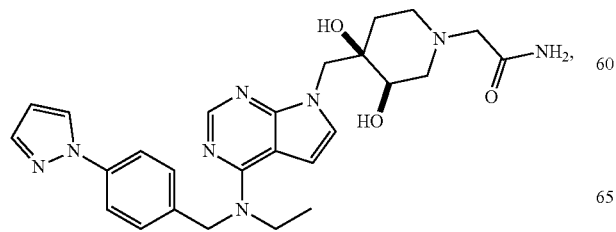
38
-continued
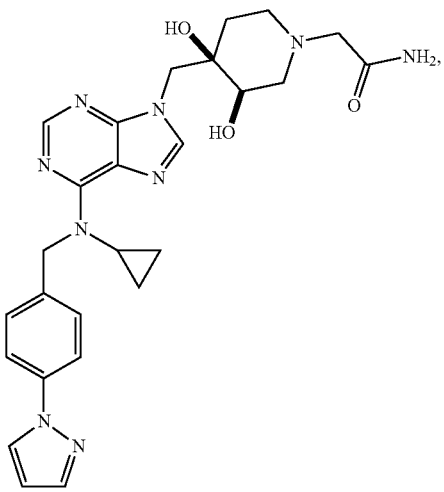
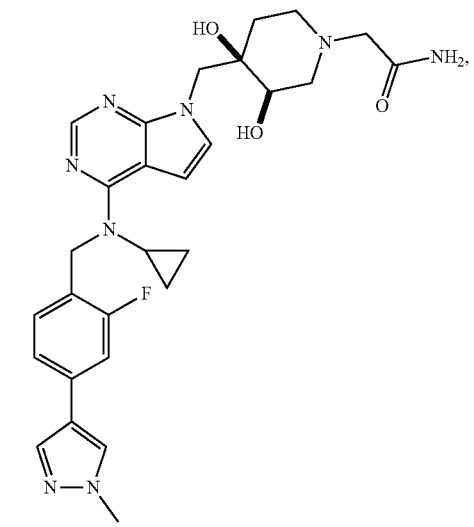
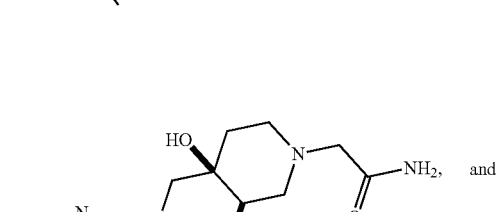
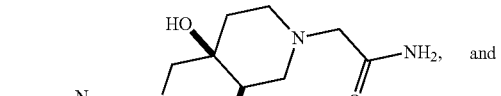
and
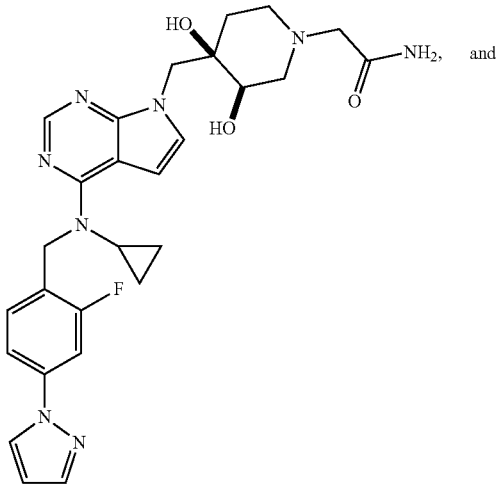

-continued

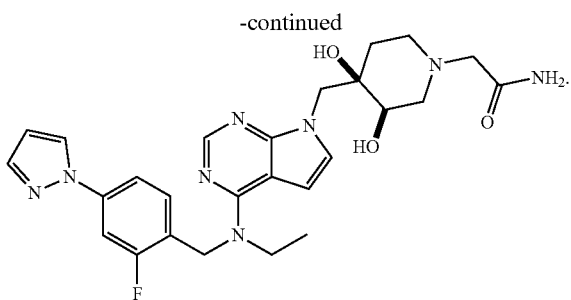

In some embodiments disclosed herein, the compound, salt, stereoisomer, or salt of the stereoisomer of Formula (I) is selected from the group consisting of:

2-(4-((4-(cyclopropyl(4-(trifluoromethyl)benzyl)amino)-5-fluoro-7H-pyrrolo[2,3-d]pyrimidin-7-yl)methyl)-4-hydroxypiperidin-1-yl)acetamide, 2-(4-((4-(cyclopropyl(4-(trifluoromethyl)benzyl)amino)-7H-pyrrolo[2,3-d]pyrimidin-7-yl)methyl)-4-hydroxypiperidin-1-yl)acetamide, 2-(4-((6-(cyclopropyl(4-(trifluoromethyl)benzyl)amino)-9H-purin-9-yl)methyl)-4-hydroxypiperidin-1-yl)acetamide, 2-(4-((5-cyano-4-(cyclopropyl(4-(trifluoromethyl)benzyl)amino)-7H-pyrrolo[2,3-d]pyrimidin-7-yl)methyl)-4-hydroxypiperidin-1-yl)acetamide, 2-(4-((5-fluoro-4-(methyl(4-(trifluoromethyl)benzyl)amino)-7H-pyrrolo[2,3-d]pyrimidin-7-yl)methyl)-4-hydroxypiperidin-1-yl)acetamide, 2-(4-((4-(cyclopropyl(4-(trifluoromethyl)benzyl)amino)-7H-pyrrolo[2,3-d]pyrimidin-7-yl)methyl)-3,3-difluoropiperidin-1-yl)acetamide, 2-(4-((4-(cyclopropyl(4-(trifluoromethyl)benzyl)amino)-7H-pyrrolo[2,3-d]pyrimidin-7-yl)methyl)-3-fluoropiperidin-1-yl)acetamide, 2-(4-((4-(cyclopropyl((5-(trifluoromethyl)pyridin-2-yl)methyl)amino)-7H-pyrrolo[2,3-d]pyrimidin-7-yl)methyl)-3-fluoropiperidin-1-yl)acetamide, 2-(4-((4-(cyclopropyl(4-(trifluoromethyl)benzyl)amino)-7H-pyrrolo[2,3-d]pyrimidin-7-yl)methyl)-3,4-dihydroxypiperidin-1-yl)acetamide, 2-(4-((4-(ethyl(4-(trifluoromethyl)benzyl)amino)-7H-pyrrolo[2,3-d]pyrimidin-7-yl)methyl)-3,4-dihydroxypiperidin-1-yl)acetamide, 2-(4-((4-(ethyl(2-fluoro-4-(trifluoromethyl)benzyl)amino)-7H-pyrrolo[2,3-d]pyrimidin-7-yl)methyl)-3,4-dihydroxypiperidin-1-yl)acetamide, 2-(3-hydroxy-4-((4-(3-(4-(trifluoromethyl)phenyl)morpholino)-7H-pyrrolo[2,3-d]pyrimidin-7-yl)methyl)piperidin-1-yl)acetamide 2-(4-((4-(3-(4-(trifluoromethyl)phenyl)morpholino)-7H-pyrrolo[2,3-d]pyrimidin-7-yl)methyl)piperidin-1-yl)acetamide, 2-(3-hydroxy-4-((4-(3-(3-(trifluoromethyl)phenyl)morpholino)-7H-pyrrolo[2,3-d]pyrimidin-7-yl)methyl)piperidin-1-yl)acetamide, 2-(4-((4-(cyclopropyl(4-(trifluoromethyl)benzyl)amino)-5-fluoro-7H-pyrrolo[2,3-d]pyrimidin-7-yl)methyl)piperidin-1-yl)acetamide, 2-(4-((6-(cyclopropyl(4-(trifluoromethyl)benzyl)amino)-9H-purin-9-yl)methyl)piperidin-1-yl)acetamide, 2-(4-((5-cyano-4-(cyclopropyl(4-(trifluoromethyl)benzyl)amino)-7H-pyrrolo[2,3-d]pyrimidin-7-yl)methyl)piperidin-1-yl)acetamide, 2-(4-((6-(cyclopropyl(4-(trifluoromethyl)benzyl)amino)-9H-purin-9-yl)methyl)piperidin-1-yl)propanamide, 2-(4-((6-(cyclopropyl(4-(trifluoromethyl)benzyl)amino)-9H-purin-9-yl)methyl)piperidin-1-yl)-2-methylpropanamide, 2-(4-((4-(cyclopropyl((6-(trifluoromethyl)pyridin-3-yl)methyl)amino)-5-fluoro-7H-pyrrolo[2,3-d]pyrimidin-7-yl)methyl)piperidin-1-yl)acetamide, 2-(4-cyano-4-((4-(cyclopropyl(4-(trifluoromethyl)benzyl)amino)-5-fluoro-7H-pyrrolo[2,3-d]pyrimidin-7-yl)methyl)piperidin-1-yl)acetamide, 2-(4-((5-fluoro-4-(methyl(4-(trifluoromethyl)benzyl)amino)-7H-pyrrolo[2,3-d]pyrimidin-7-yl)methyl)-3-hydroxypiperidin-1-yl)acetamide, 2-(4-((4-(cyclopropyl(4-(trifluoromethyl)benzyl)amino)-7H-pyrrolo[2,3-d]pyrimidin-7-yl)methyl)-3-hydroxypiperidin-1-yl)acetamide, 2-(4-((4-(cyclopropyl(4-(trifluoromethyl)benzyl)amino)-5-fluoro-7H-pyrrolo[2,3-d]pyrimidin-7-yl)methyl)-3-hydroxypiperidin-1-yl)acetamide, 2-(4-((4-(cyclopropyl((6-(trifluoromethyl)pyridin-3-yl)methyl)amino)-5-fluoro-7H-pyrrolo[2,3-d]pyrimidin-7-yl)methyl)-3-hydroxypiperidin-1-yl)acetamide, 2-(4-((4-(cyclopropyl((6-(trifluoromethyl)pyridin-3-yl)methyl)amino)-7H-pyrrolo[2,3-d]pyrimidin-7-yl)methyl)-3-hydroxypiperidin-1-yl)acetamide, 2-(4-((4-(cyclopropyl((2-(trifluoromethyl)pyrimidin-5-yl)methyl)amino)-5-fluoro-7H-pyrrolo[2,3-d]pyrimidin-7-yl)methyl)-3-hydroxypiperidin-1-yl)acetamide, 2-(4-((4-(cyclopropyl((5-(trifluoromethyl)pyridin-2-yl)methyl)amino)-5-fluoro-7H-pyrrolo[2,3-d]pyrimidin-7-yl)methyl)-3-hydroxypiperidin-1-yl)acetamide, 2-(4-((5-fluoro-4-(isopropyl(4-(trifluoromethyl)benzyl)amino)-7H-pyrrolo[2,3-d]pyrimidin-7-yl)methyl)-3-hydroxypiperidin-1-yl)acetamide, 2-(4-((6-(cyclopropyl(3-(trifluoromethyl)benzyl)amino)-9H-purin-9-yl)methyl)-3-hydroxypiperidin-1-yl)acetamide, 2-(4-((4-(ethyl(4-(trifluoromethyl)benzyl)amino)-5-fluoro-7H-pyrrolo[2,3-d]pyrimidin-7-yl)methyl)-3-hydroxypiperidin-1-yl)acetamide, 2-(3-hydroxy-4-((6-(isopropyl(4-(trifluoromethyl)benzyl)amino)-9H-purin-9-yl)methyl)piperidin-1-yl)acetamide, 2-(4-((4-(cyclopropyl((5-(trifluoromethyl)pyridin-2-yl)methyl)amino)-7H-pyrrolo[2,3-d]pyrimidin-7-yl)methyl)-3-hydroxypiperidin-1-yl)acetamide, 2-(4-((4-(ethyl(4-(trifluoromethyl)benzyl)amino)-7H-pyrrolo[2,3-d]pyrimidin-7-yl)methyl)-3-hydroxypiperidin-1-yl)acetamide, 2-(3-hydroxy-4-((4-(isopropyl(4-(trifluoromethyl)benzyl)amino)-7H-pyrrolo[2,3-d]pyrimidin-7-yl)methyl)piperidin-1-yl)acetamide 2-(4-((6-(cyclopropyl(4-(trifluoromethyl)benzyl)amino)-9H-purin-9-yl)methyl)-3-hydroxypiperidin-1-yl)acetamide, 2-(4-((4-(ethyl((5-(trifluoromethyl)pyridin-2-yl)methyl)amino)-7H-pyrrolo[2,3-d]pyrimidin-7-yl)methyl)-3-hydroxypiperidin-1-yl)acetamide, 2-(4-((4-(ethyl((5-(trifluoromethyl)pyridin-2-yl)methyl)amino)-5-fluoro-7H-pyrrolo[2,3-d]pyrimidin-7-yl)methyl)-3-hydroxypiperidin-1-yl)acetamide, 2-(4-((4-((4-cyanobenzyl)(ethyl)amino)-7H-pyrrolo[2,3-d]pyrimidin-7-yl)methyl)-3-hydroxypiperidin-1-yl)acetamide, 2-(4-((4-((4-(1H-pyrazol-1-yl)benzyl)(ethyl)amino)-7H-pyrrolo[2,3-d]pyrimidin-7-yl)methyl)-3-hydroxypiperidin-1-yl)acetamide, 2-(4-((4-(ethyl(3-fluoro-4-(trifluoromethyl)benzyl)amino)-7H-pyrrolo[2,3-d]pyrimidin-7-yl)methyl)-3-hydroxypiperidin-1-yl)acetamide,
2-(4-((4-(ethyl(2-fluoro-4-(trifluoromethyl)benzyl)amino)-7H-pyrrolo[2,3-d]pyrimidin-7-yl)methyl)-3-hydroxypiperidin-1-yl)acetamide,
2-(4-((4-((4-(1H-pyrazol-1-yl)benzyl)(cyclopropyl)amino)-7H-pyrrolo[2,3-d]pyrimidin-7-yl)methyl)-3-hydroxypiperidin-1-yl)acetamide,
2-(4-((4-(ethyl(4-(1-methyl-1H-pyrazol-4-yl)benzyl)amino)-7H-pyrrolo[2,3-d]pyrimidin-7-yl)methyl)-3-hydroxypiperidin-1-yl)acetamide,
2-(4-((4-(ethyl(2-fluoro-4-(1-methyl-1H-pyrazol-4-yl)benzyl)amino)-7H-pyrrolo[2,3-d]pyrimidin-7-yl)methyl)-3-hydroxypiperidin-1-yl)acetamide,
2-(4-((4-(ethyl(2-fluoro-4-(1H-pyrazol-1-yl)benzyl)amino)-7H-pyrrolo[2,3-d]pyrimidin-7-yl)methyl)-3-hydroxypiperidin-1-yl)acetamide,
2-(4-((4-(cyclopropyl(4-(trifluoromethyl)benzyl)amino)-7H-pyrrolo[2,3-d]pyrimidin-7-yl)methyl)-3-hydroxypiperidin-1-yl)-3-hydroxypropanamide,
2-(3-fluoro-4-((4-(3-(5-(trifluoromethyl)pyridin-2-yl)morpholino)-7H-pyrrolo[2,3-d]pyrimidin-7-yl)methyl)piperidin-1-yl)acetamide,
2-(4-((4-(3-(5-(trifluoromethyl)pyridin-2-yl)morpholino)-7H-pyrrolo[2,3-d]pyrimidin-7-yl)methyl)piperidin-1-yl)acetamide,
2-(4-((4-((4-(1H-pyrazol-1-yl)benzyl)(ethyl)amino)-7H-pyrrolo[2,3-d]pyrimidin-7-yl)methyl)-3,4-dihydroxypiperidin-1-yl)acetamide,
2-(4-((4-((4-(1H-pyrazol-1-yl)benzyl)(cyclopropyl)amino)-7H-pyrrolo[2,3-d]pyrimidin-7-yl)methyl)-3,4-dihydroxypiperidin-1-yl)acetamide,
2-(4-((4-(cyclopropyl(2-fluoro-4-(1-methyl-1H-pyrazol-4-yl)benzyl)amino)-7H-pyrrolo[2,3-d]pyrimidin-7-yl)methyl)-3,4-dihydroxypiperidin-1-yl)acetamide,
2-(4-((4-(cyclopropyl(2-fluoro-4-(1H-pyrazol-1-yl)benzyl)amino)-7H-pyrrolo[2,3-d]pyrimidin-7-yl)methyl)-3,4-dihydroxypiperidin-1-yl)acetamide, and
2-(4-((4-(ethyl(2-fluoro-4-(1H-pyrazol-1-yl)benzyl)amino)-7H-pyrrolo[2,3-d]pyrimidin-7-yl)methyl)-3,4-dihydroxypiperidin-1-yl)acetamide.

In some embodiments disclosed herein, the compound, salt, stereoisomer, or salt of the stereoisomer of Formula (I) is selected from the group consisting of:

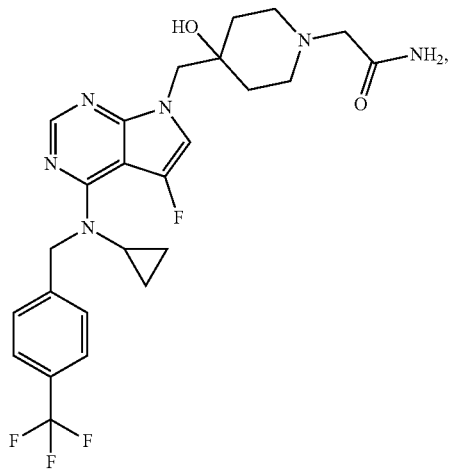

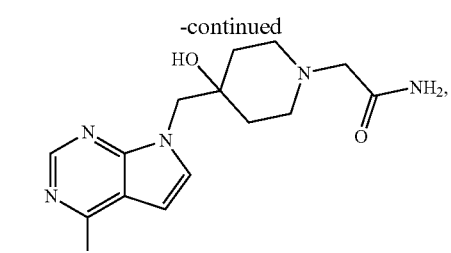

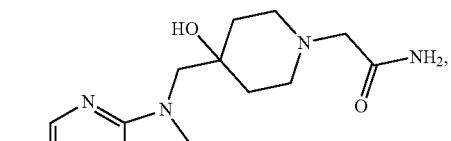

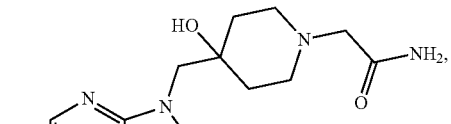

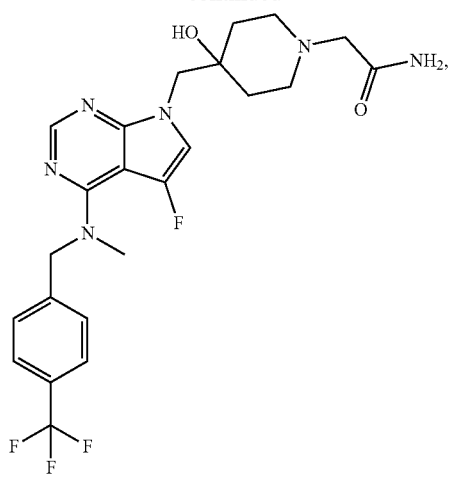
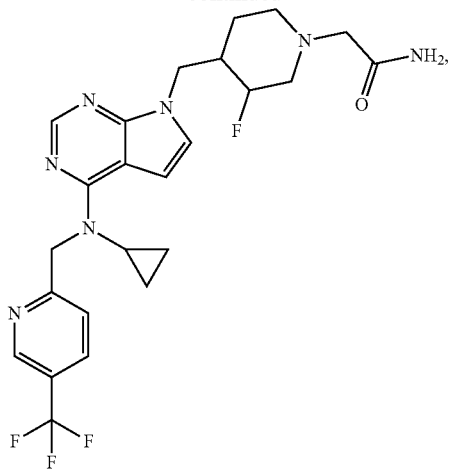
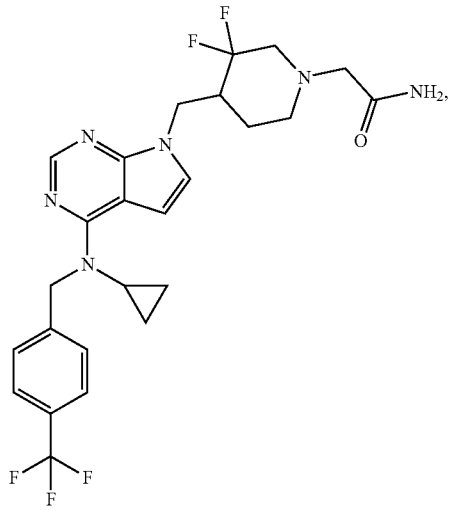
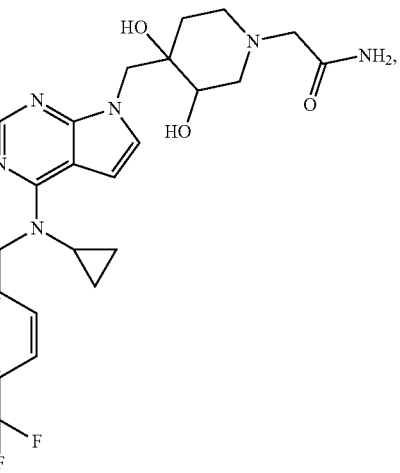
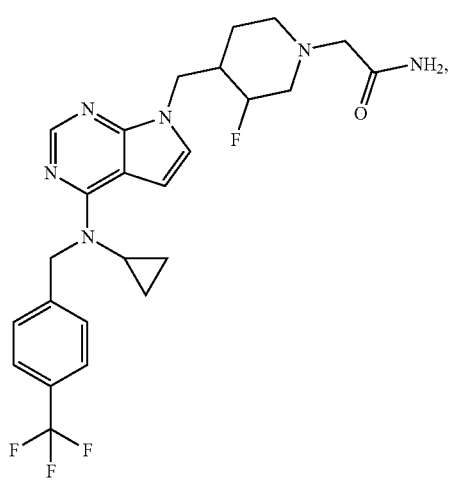
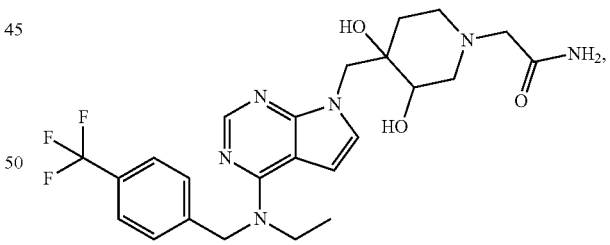
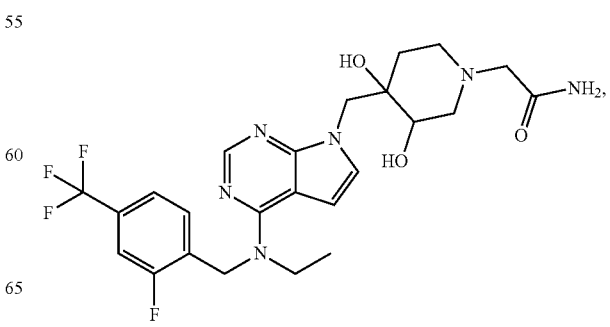

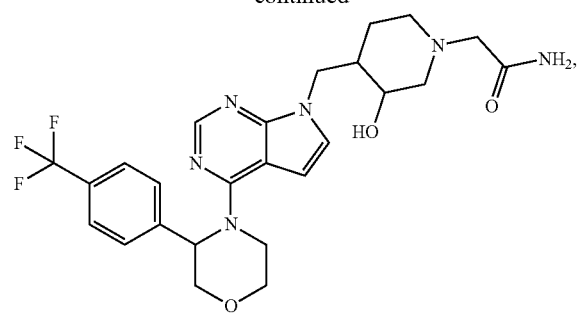
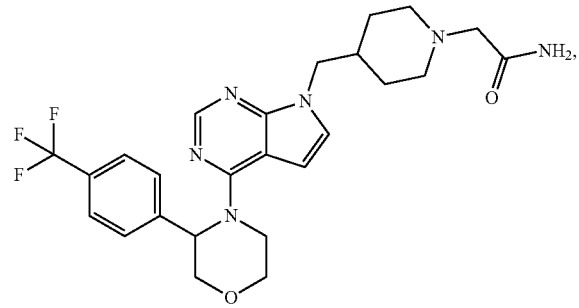
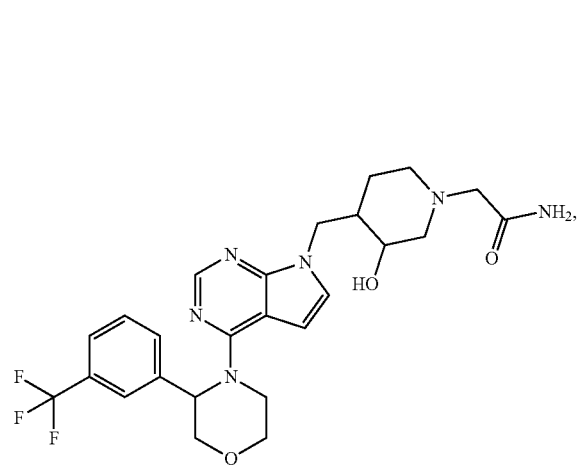
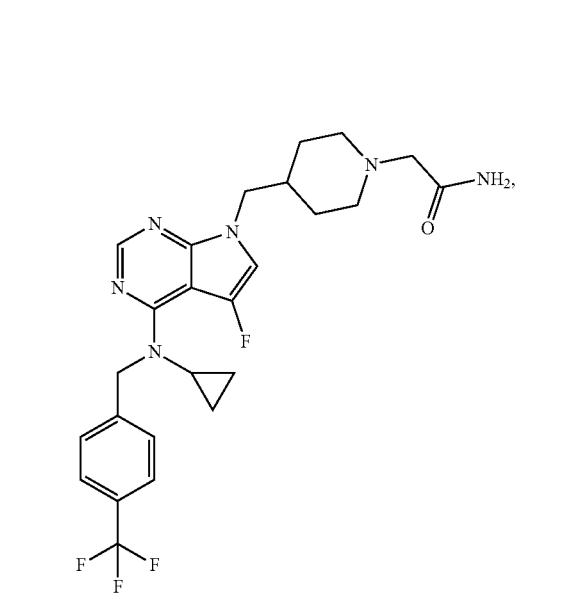
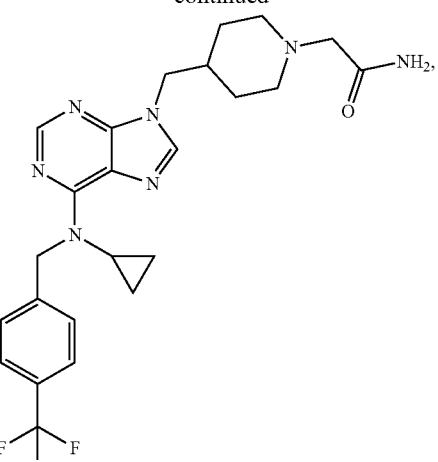
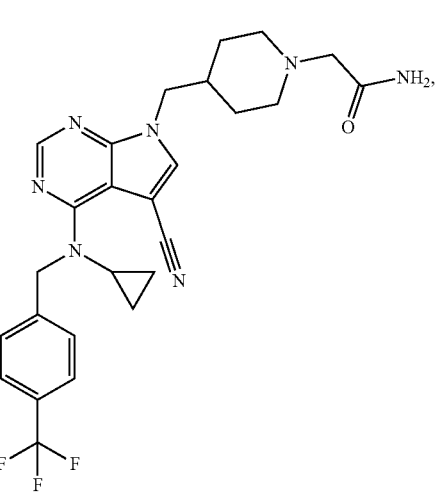
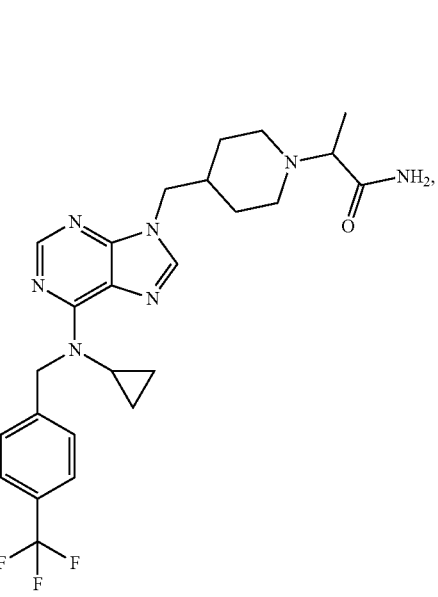

47
-continued
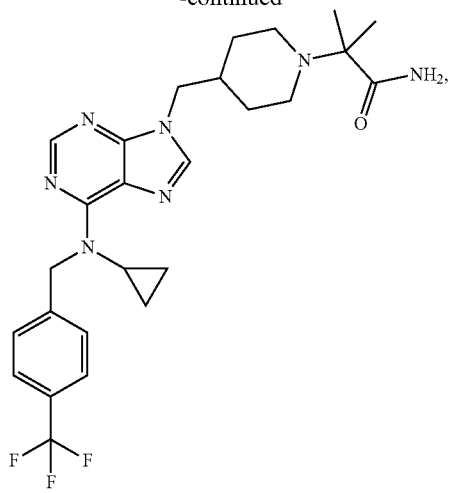
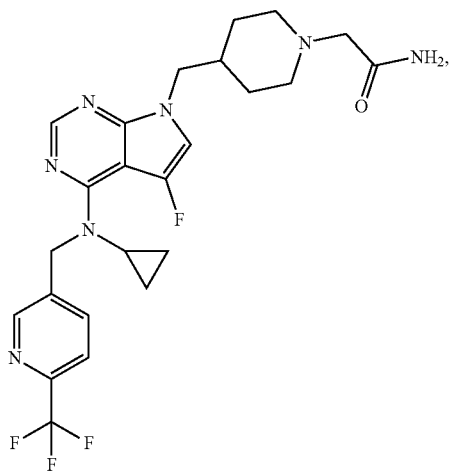
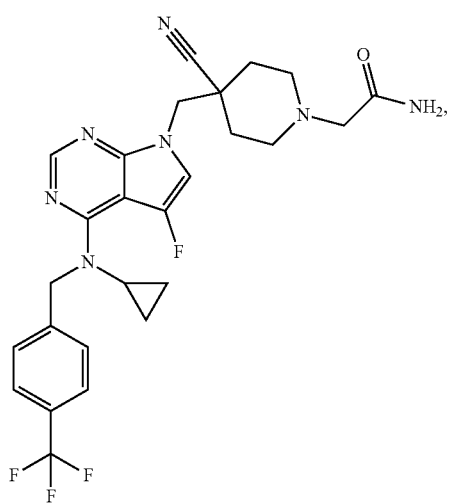
48
-continued
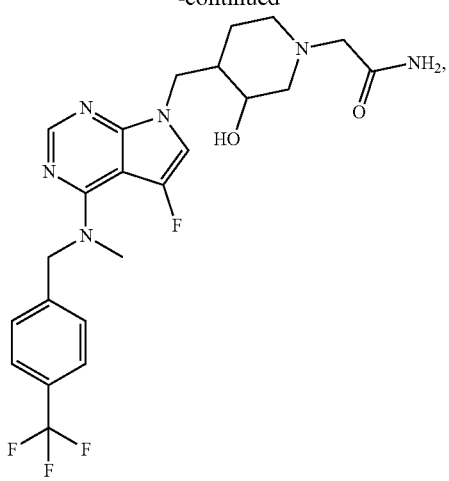
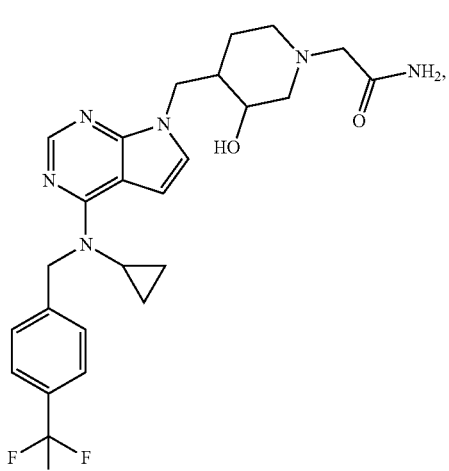

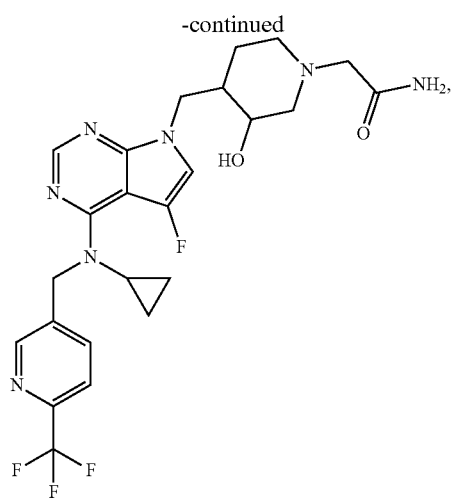

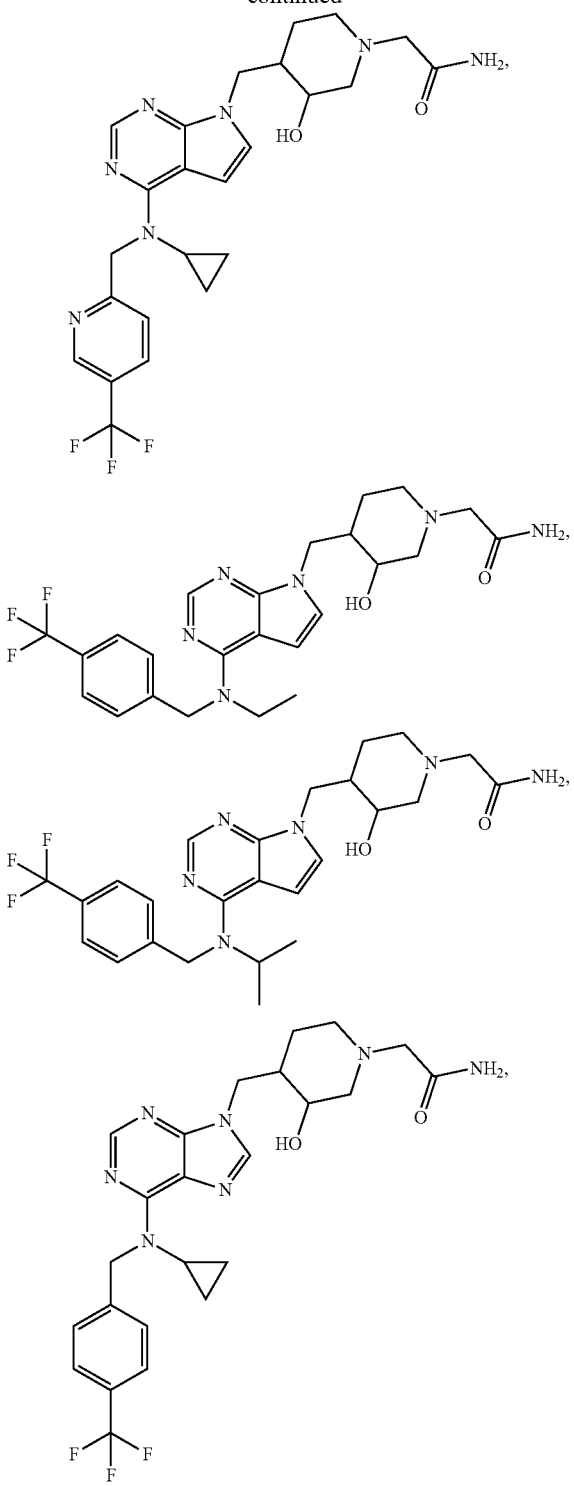
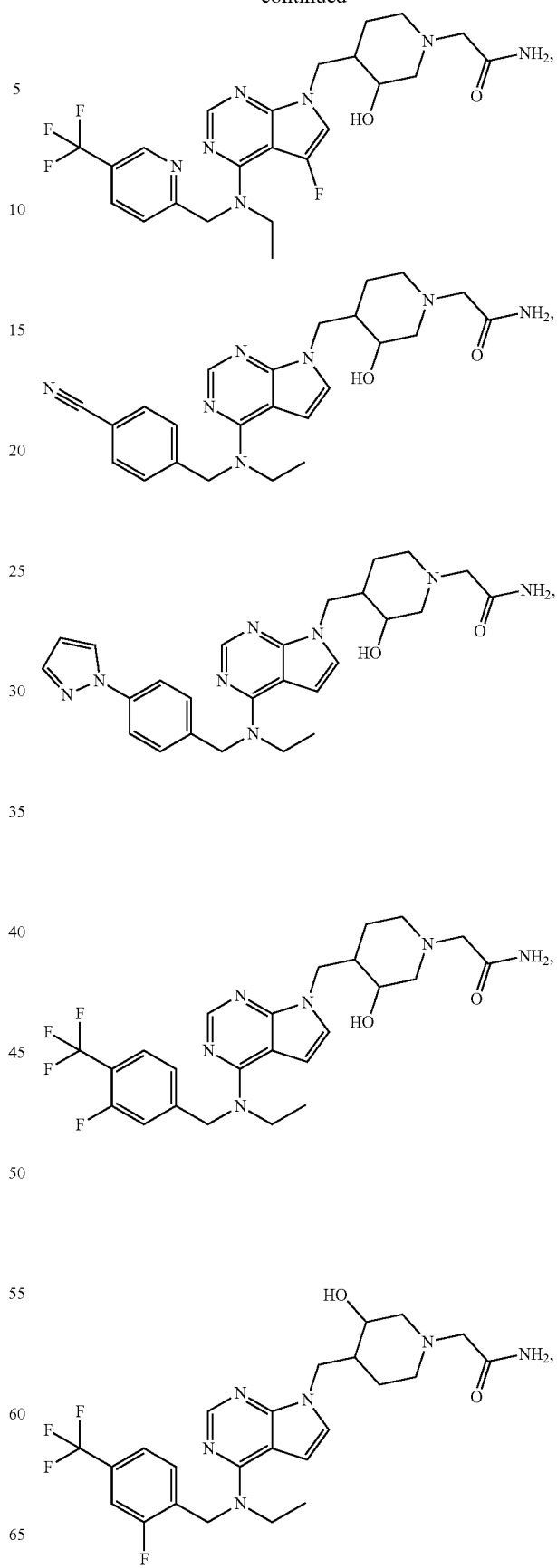

53 54
-continued -continued
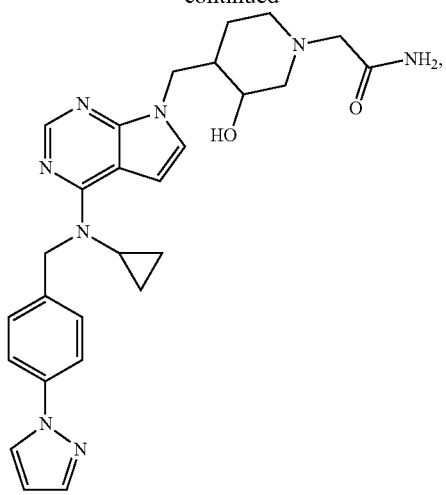
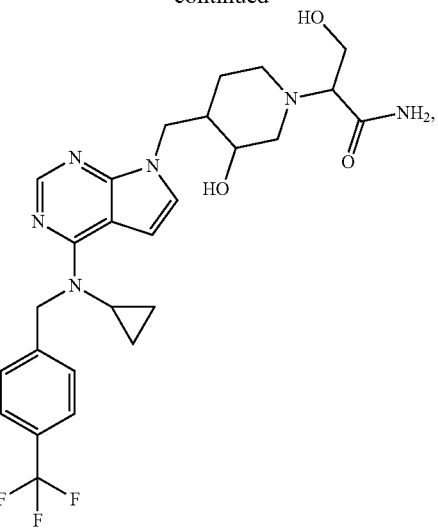
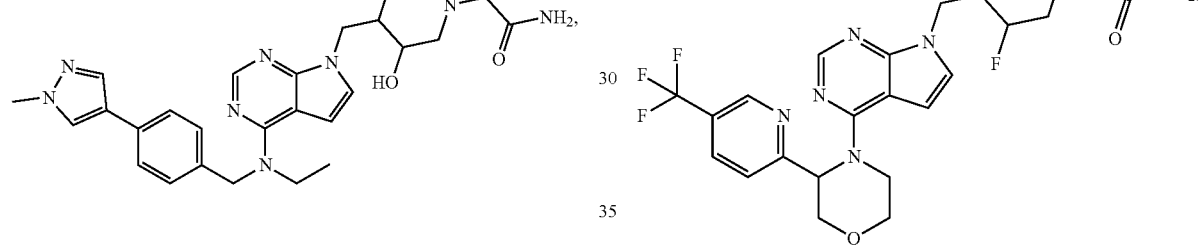
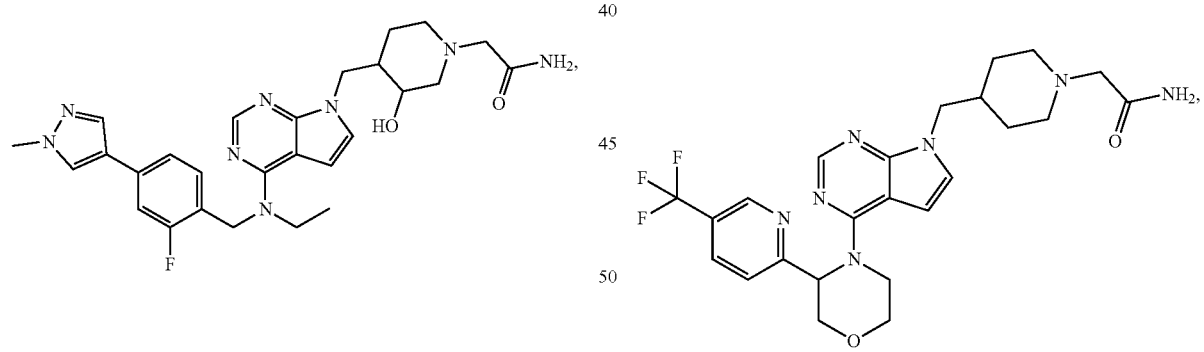
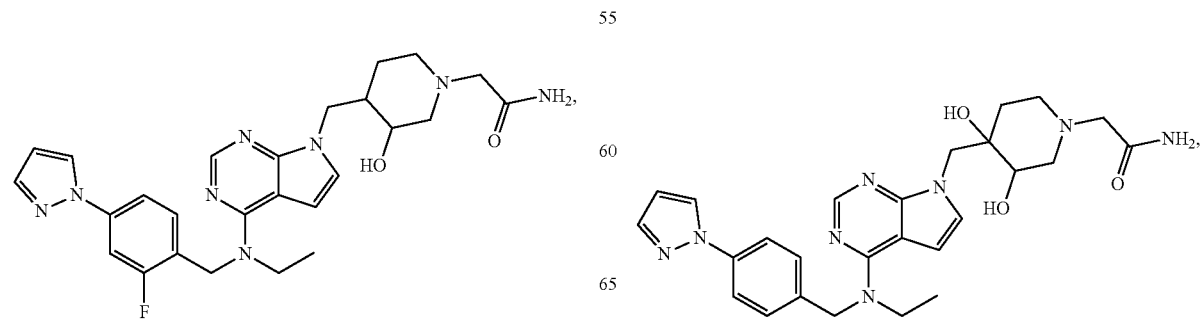

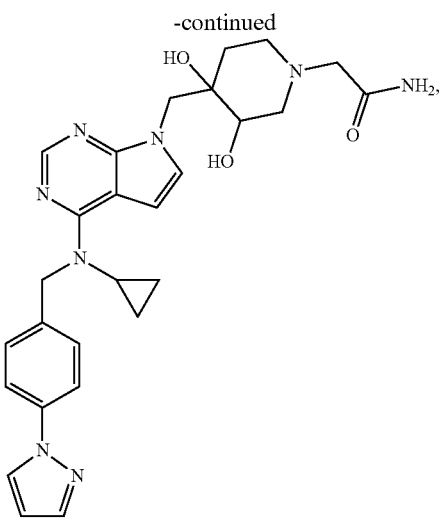
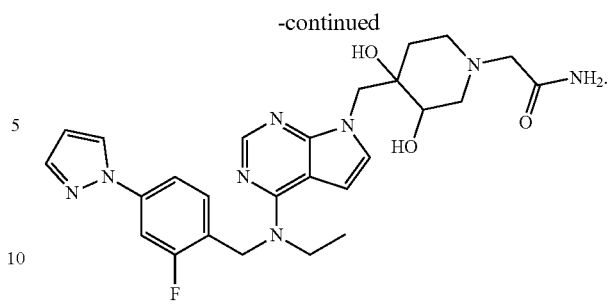

In some embodiments disclosed herein, the compound, salt, stereoisomer, or salt of the stereoisomer of Formula (I) is selected from the group consisting of:
2-(4-((4-(cyclopropyl(4-(trifluoromethyl)benzyl)amino)-5-fluoro-7H-pyrrolo[2,3-d]pyrimidin-7-yl)methyl)-4-hydroxypiperidin-1-yl)acetamide,
2-(4-((4-(cyclopropyl(4-(trifluoromethyl)benzyl)amino)-7H-pyrrolo[2,3-d]pyrimidin-7-yl)methyl)-4-hydroxypiperidin-1-yl)acetamide,
rel-(R)-2-(4-((4-(cyclopropyl(4-(trifluoromethyl)benzyl)amino)-7H-pyrrolo[2,3-d]pyrimidin-7-yl)methyl)-3,3-difluoropiperidin-1-yl)acetamide,
rel-2-((3R,4R)-4-((4-(cyclopropyl(4-(trifluoromethyl)benzyl)amino)-7H-pyrrolo[2,3-d]pyrimidin-7-yl)methyl)-3-fluoropiperidin-1-yl)acetamide,
rel-2-((3R,4R)-4-((4-(cyclopropyl(4-(trifluoromethyl)benzyl)amino)-7H-pyrrolo[2,3-d]pyrimidin-7-yl)methyl)-3,4-dihydroxypiperidin-1-yl)acetamide,
rel-2-((3R,4R)-4-((4-(ethyl(4-(trifluoromethyl)benzyl)amino)-7H-pyrrolo[2,3-d]pyrimidin-7-yl)methyl)-3,4-dihydroxypiperidin-1-yl)acetamide,
rel-2-((3R,4R)-4-((4-(ethyl(2-fluoro-4-(trifluoromethyl)benzyl)amino)-7H-pyrrolo[2,3-d]pyrimidin-7-yl)methyl)-3,4-dihydroxypiperidin-1-yl)acetamide,
rel-2-((3R,4R)-4-((4-(cyclopropyl(4-(trifluoromethyl)benzyl)amino)-7H-pyrrolo[2,3-d]pyrimidin-7-yl)methyl)-3-hydroxypiperidin-1-yl)acetamide,
rel-2-((3R,4R)-4-((4-(cyclopropyl(4-(trifluoromethyl)benzyl)amino)-5-fluoro-7H-pyrrolo[2,3-d]pyrimidin-7-yl)methyl)-3-hydroxypiperidin-1-yl)acetamide,
rel-2-((3R,4R)-4-((4-(ethyl(4-(trifluoromethyl)benzyl)amino)-7H-pyrrolo[2,3-d]pyrimidin-7-yl)methyl)-3-hydroxypiperidin-1-yl)acetamide,
rel-2-((3R,4R)-4-((4-(ethyl(3-fluoro-4-(trifluoromethyl)benzyl)amino)-7H-pyrrolo[2,3-d]pyrimidin-7-yl)methyl)-3-hydroxypiperidin-1-yl)acetamide,
rel-2-((3R,4R)-4-((4-(ethyl(2-fluoro-4-(trifluoromethyl)benzyl)amino)-7H-pyrrolo[2,3-d]pyrimidin-7-yl)methyl)-3-hydroxypiperidin-1-yl)acetamide,
rel-2-((3R,4R)-4-((4-((4-(1H-pyrazol-1-yl)benzyl)(cyclopropyl)amino)-7H-pyrrolo[2,3-d]pyrimidin-7-yl)methyl)-3-hydroxypiperidin-1-yl)acetamide,
rac-2-((3R,4R)-4-((4-(cyclopropyl(4-(trifluoromethyl)benzyl)amino)-7H-pyrrolo[2,3-d]pyrimidin-7-yl)methyl)-3-hydroxypiperidin-1-yl)-3-hydroxypropanamide
rel-2-((3R,4R)-4-((4-((4-(1H-pyrazol-1-yl)benzyl)(cyclopropyl)amino)-7H-pyrrolo[2,3-d]pyrimidin-7-yl)methyl)-3,4-dihydroxypiperidin-1-yl)acetamide,
rel-2-((3R,4R)-4-((4-(cyclopropyl(2-fluoro-4-(1-methyl-1H-pyrazol-4-yl)benzyl)-amino)-7H-pyrrolo[2,3-d]pyrimidin-7-yl)methyl)-3,4-dihydroxypiperidin-1-yl)acetamide, and rel-2-((3R,4R)-4-((4-(cyclopropyl(2-fluoro-4-(1H-pyrazol-1-yl)benzyl)amino)-7H-pyrrolo[2,3-d]pyrimidin-7-yl)methyl)-3,4-dihydroxypiperidin-1-yl)acetamide.

In some embodiments disclosed herein, the compound, salt, stereoisomer, or salt of the stereoisomer of Formula (I) is selected from the group consisting of:

2-(4-((4-(cyclopropyl(4-(trifluoromethyl)benzyl)amino)-5-fluoro-7H-pyrrolo[2,3-d]pyrimidin-7-yl)methyl)-4-hydroxypiperidin-1-yl)acetamide, 2-(4-((4-(cyclopropyl(4-(trifluoromethyl)benzyl)amino)-7H-pyrrolo[2,3-d]pyrimidin-7-yl)methyl)-4-hydroxypiperidin-1-yl)acetamide, 2-(4-((4-(cyclopropyl(4-(trifluoromethyl)benzyl)amino)-7H-pyrrolo[2,3-d]pyrimidin-7-yl)methyl)-3,3-difluoropiperidin-1-yl)acetamide, 2-(4-((4-(cyclopropyl(4-(trifluoromethyl)benzyl)amino)-7H-pyrrolo[2,3-d]pyrimidin-7-yl)methyl)-3-fluoropiperidin-1-yl)acetamide, 2-(4-((4-(cyclopropyl(4-(trifluoromethyl)benzyl)amino)-7H-pyrrolo[2,3-d]pyrimidin-7-yl)methyl)-3,4-dihydroxypiperidin-1-yl)acetamide, 2-(4-((4-(ethyl(4-(trifluoromethyl)benzyl)amino)-7H-pyrrolo[2,3-d]pyrimidin-7-yl)methyl)-3,4-dihydroxypiperidin-1-yl)acetamide, 2-(4-((4-(ethyl(2-fluoro-4-(trifluoromethyl)benzyl)amino)-7H-pyrrolo[2,3-d]pyrimidin-7-yl)methyl)-3,4-dihydroxypiperidin-1-yl)acetamide, 2-(4-((4-(cyclopropyl(4-(trifluoromethyl)benzyl)amino)-7H-pyrrolo[2,3-d]pyrimidin-7-yl)methyl)-3-hydroxypiperidin-1-yl)acetamide, 2-(4-((4-(cyclopropyl(4-(trifluoromethyl)benzyl)amino)-5-fluoro-7H-pyrrolo[2,3-d]pyrimidin-7-yl)methyl)-3-hydroxypiperidin-1-yl)acetamide, 2-(4-((4-(ethyl(4-(trifluoromethyl)benzyl)amino)-7H-pyrrolo[2,3-d]pyrimidin-7-yl)methyl)-3-hydroxypiperidin-1-yl)acetamide, 2-(4-((4-(ethyl(3-fluoro-4-(trifluoromethyl)benzyl)amino)-7H-pyrrolo[2,3-d]pyrimidin-7-yl)methyl)-3-hydroxypiperidin-1-yl)acetamide, 2-(4-((4-(ethyl(2-fluoro-4-(trifluoromethyl)benzyl)amino)-7H-pyrrolo[2,3-d]pyrimidin-7-yl)methyl)-3-hydroxypiperidin-1-yl)acetamide, 2-(4-((4-((4-(1H-pyrazol-1-yl)benzyl)(cyclopropyl)amino)-7H-pyrrolo[2,3-d]pyrimidin-7-yl)methyl)-3-hydroxypiperidin-1-yl)acetamide, 2-(4-((4-(cyclopropyl(4-(trifluoromethyl)benzyl)amino)-7H-pyrrolo[2,3-d]pyrimidin-7-yl)methyl)-3-hydroxypiperidin-1-yl)-3-hydroxypropanamide 2-(4-((4-((4-(1H-pyrazol-1-yl)benzyl)(cyclopropyl)amino)-7H-pyrrolo[2,3-d]pyrimidin-7-yl)methyl)-3,4-dihydroxypiperidin-1-yl)acetamide, 2-(4-((4-(cyclopropyl(2-fluoro-4-(1-methyl-1H-pyrazol-4-yl)benzyl)amino)-7H-pyrrolo[2,3-d]pyrimidin-7-yl)methyl)-3,4-dihydroxypiperidin-1-yl)acetamide, and 2-(4-((4-(cyclopropyl(2-fluoro-4-(1H-pyrazol-1-yl)benzyl)amino)-7H-pyrrolo[2,3-d]pyrimidin-7-yl)methyl)-3,4-dihydroxypiperidin-1-yl)acetamide.

In some embodiments disclosed herein, the compound, salt, stereoisomer, or salt of the stereoisomer of Formula (I) is selected from the group consisting of:

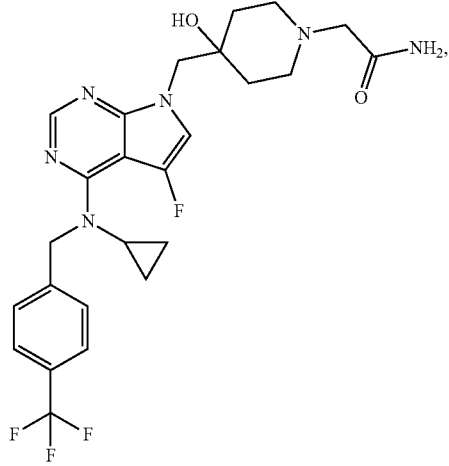

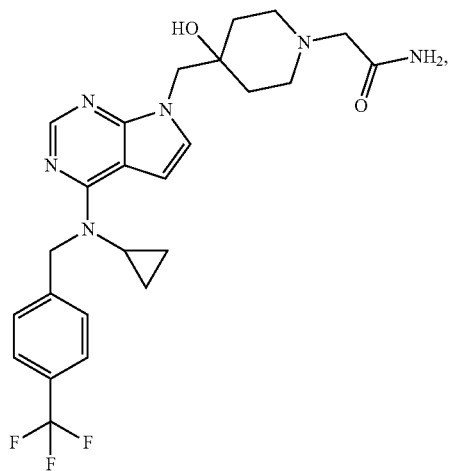

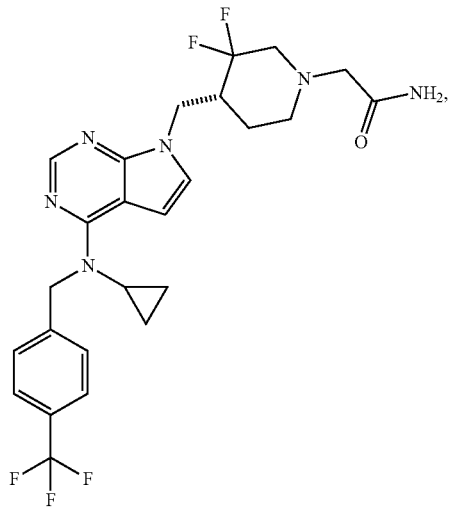

59
-continued

60
-continued

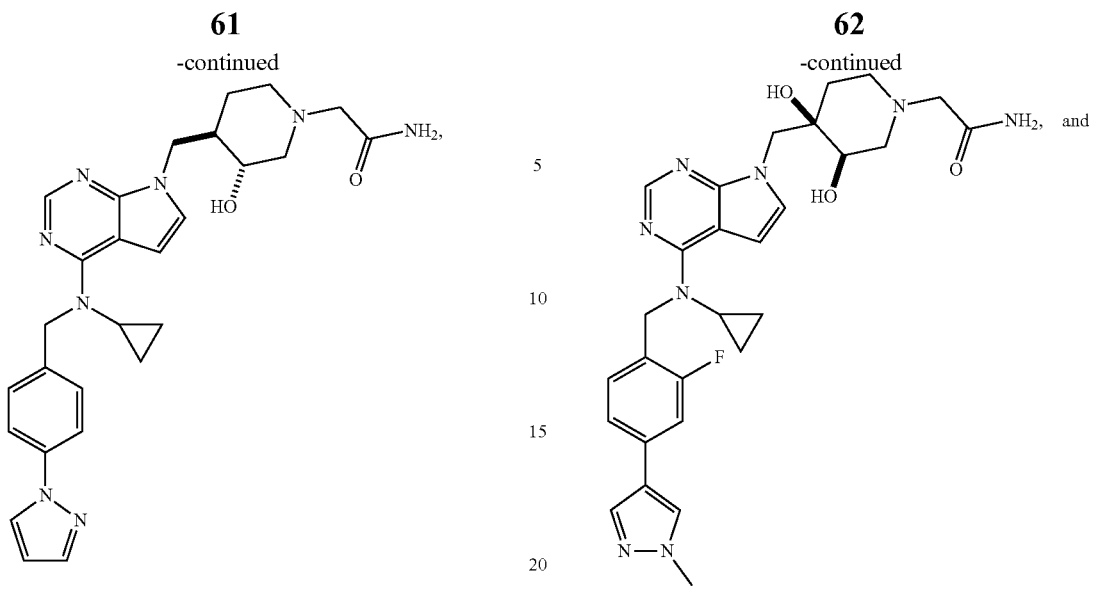
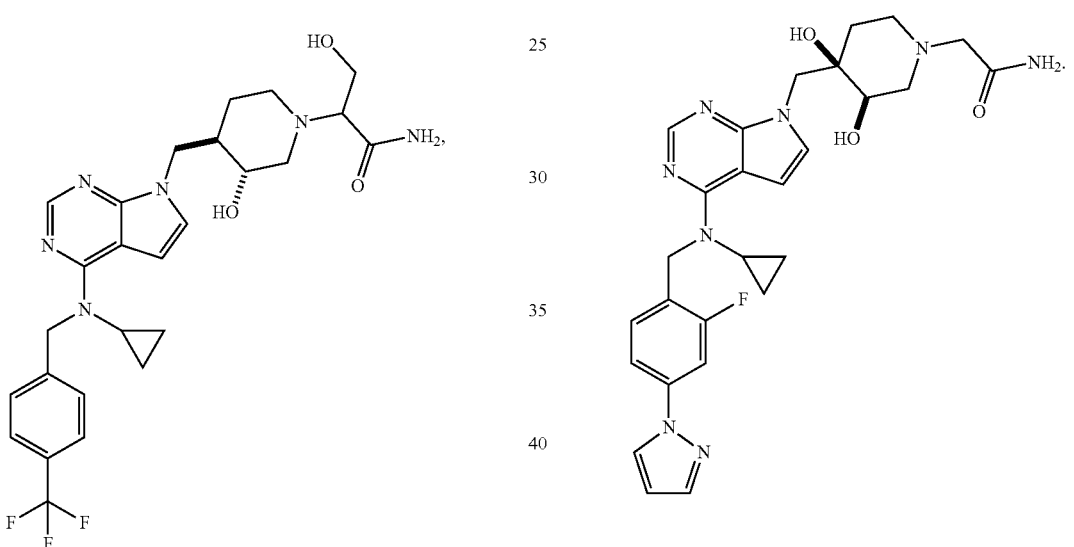
In some embodiments disclosed herein, the compound, salt, stereoisomer, or salt of the stereoisomer of Formula (I) is selected from the group consisting of:
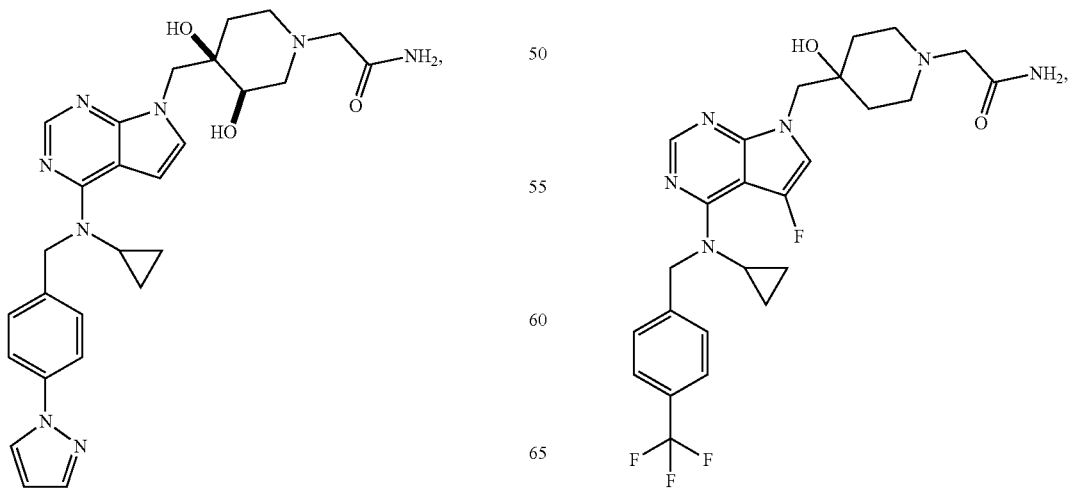

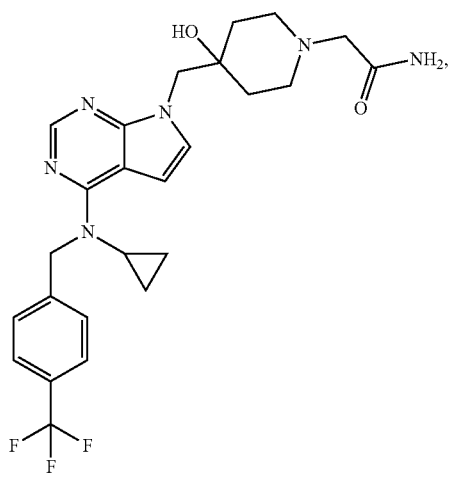
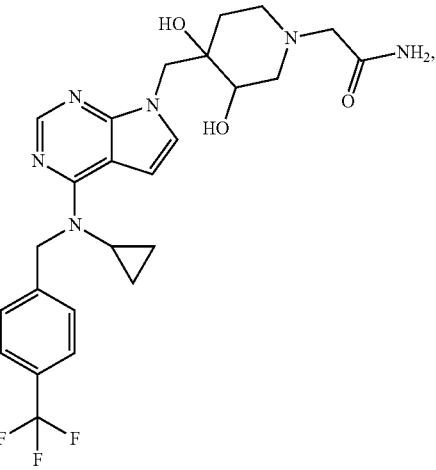
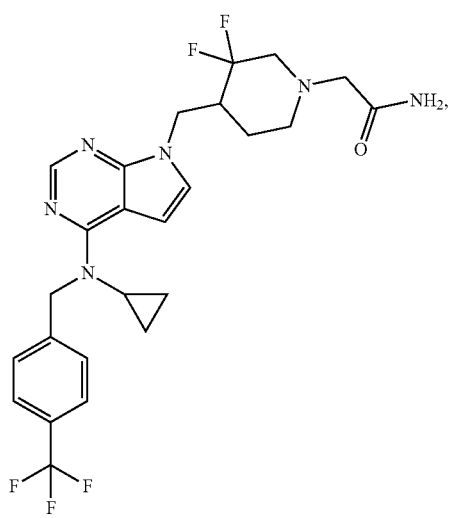
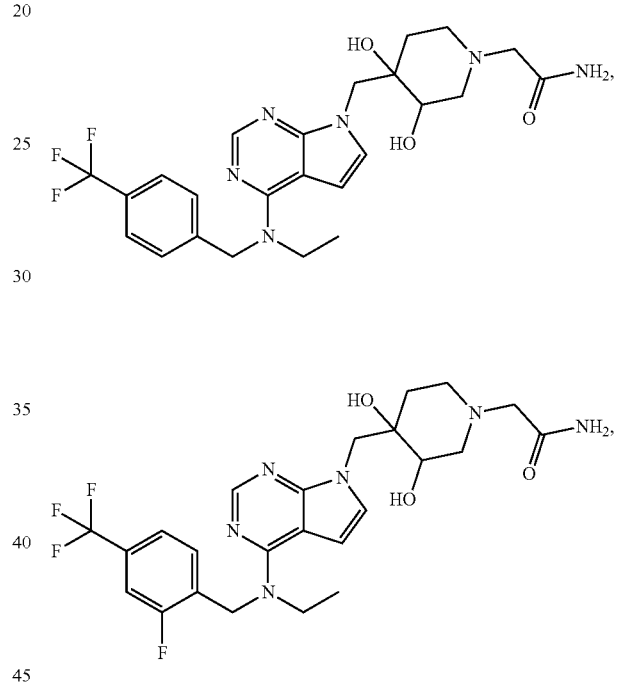
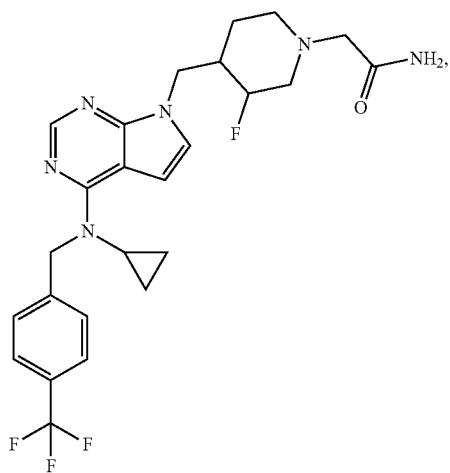

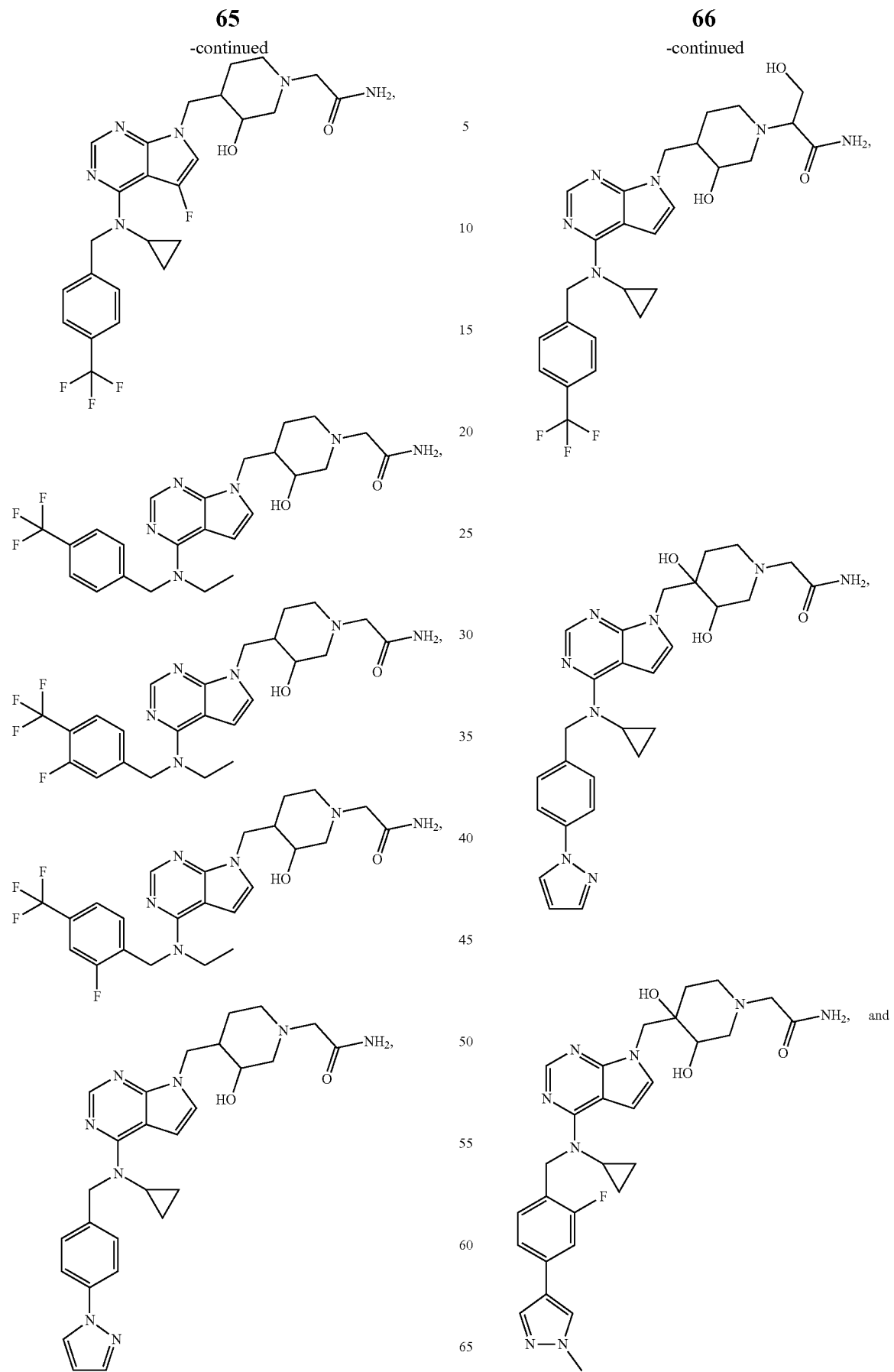

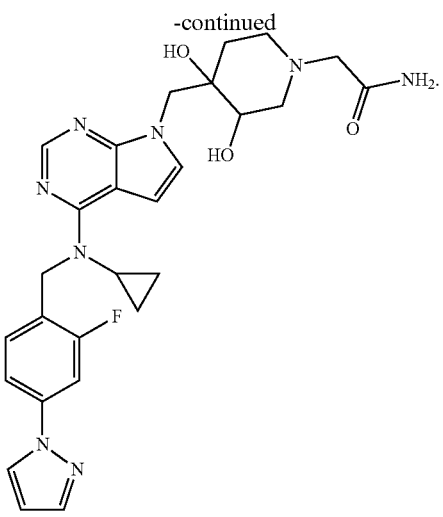

In some embodiments whenever a halogen is specified as a substituent the halogen is selected from fluoro or chloro.

Embodiments and particular disclosures used herein are to illustrate different alternatives of the disclosure and embodiments may be combined with other applicable embodiments.

Specific examples of compounds are disclosed in Table 1 below.

TABLE 1

Example compounds by Structure and Name.

| Example No: | Structure | Name |
|---|---|---|
| 3P6-1 | 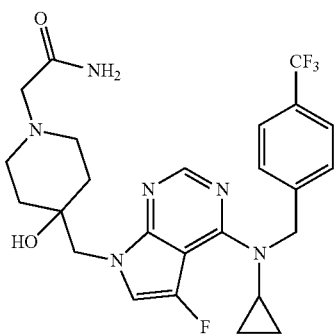 [SMILES: NC(=O)CN1CCC(O)(Cn2cc(F)c3c(N(Cc4ccc(C(F)(F)F)cc4)C4CC4)ncnc32)CC1] | 2-(4-((4-(cyclopropyl(4-(trifluoromethyl)benzyl)amino)-5-fluoro-7H-pyrrolo[2,3-d]pyrimidin-7-yl)methyl)-4-hydroxypiperidin-1-yl)acetamide |
| 3P6-2 | 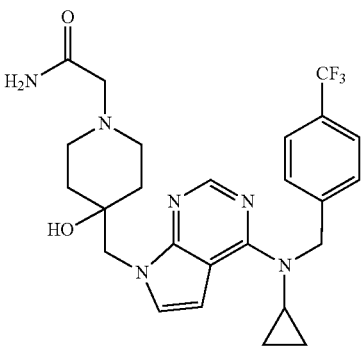 [SMILES: NC(=O)CN1CCC(O)(Cn2ccc3c(N(Cc4ccc(C(F)(F)F)cc4)C4CC4)ncnc32)CC1] | 2-(4-((4-(cyclopropyl(4-(trifluoromethyl)benzyl)amino)-7H-pyrrolo[2,3-d]pyrimidin-7-yl)methyl)-4-hydroxypiperidin-1-yl)acetamide |

TABLE 1-continued

Example compounds by Structure and Name.

| Example No: | Structure | Name |
|---|---|---|
| 3P6-3 | 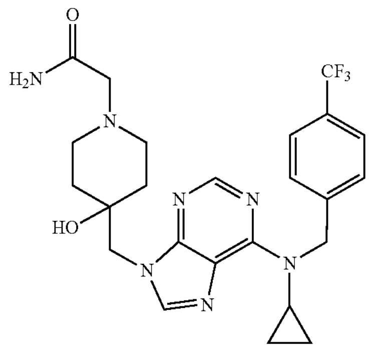 [SMILES: NC(=O)CN1CCC(O)(Cn2cnc3c(N(Cc4ccc(C(F)(F)F)cc4)C4CC4)ncnc32)CC1] | 2-(4-((6-(cyclopropyl(4-(trifluoromethyl)benzyl)amino)-9H-purin-9-yl)methyl)-4-hydroxypiperidin-1-yl)acetamide |
| 3P6-4 | 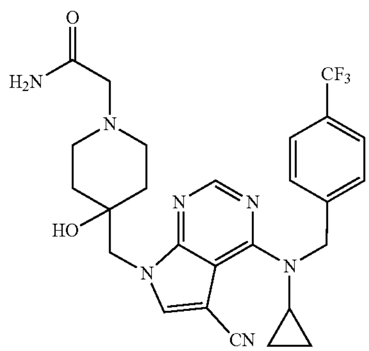 [SMILES: N#Cc1cn(CC2(O)CCN(CC(N)=O)CC2)c2ncnc(N(Cc3ccc(C(F)(F)F)cc3)C3CC3)c12] | 2-(4-((5-cyano-4-(cyclopropyl(4-(trifluoromethyl)benzyl)amino)-7H-pyrrolo[2,3-d]pyrimidin-7-yl)methyl)-4-hydroxypiperidin-1-yl)acetamide |
| 3P6-5 | 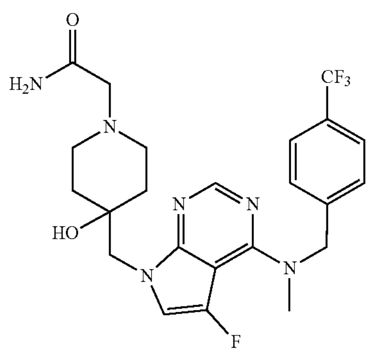 [SMILES: CN(Cc1ccc(C(F)(F)F)cc1)c1ncnc2c1c(F)cn2CC1(O)CCN(CC(N)=O)CC1] | 2-(4-((5-fluoro-4-(methyl(4-(trifluoromethyl)benzyl)amino)-7H-pyrrolo[2,3-d]pyrimidin-7-yl)methyl)-4-hydroxypiperidin-1-yl)acetamide |
| K8-1-1 | 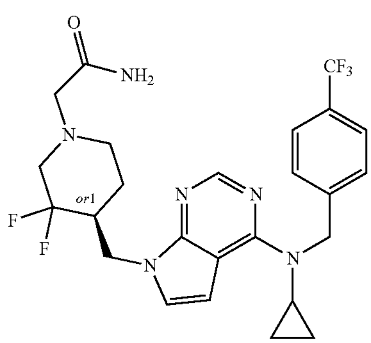 [SMILES: NC(=O)CN1CC[C@@H](Cn2ccc3c(N(Cc4ccc(C(F)(F)F)cc4)C4CC4)ncnc32)C(F)(F)C1] | rel-(R)-2-(4-((4-(cyclopropyl(4-(trifluoromethyl)benzyl)amino)-7H-pyrrolo[2,3-d]pyrimidin-7-yl)methyl)-3,3-difluoropiperidin-1-yl)acetamide, 1$^{st}$ eluting isomer |
| K8-1-2 | | rel-(R)-2-(4-((4-(cyclopropyl(4-(trifluoromethyl)benzyl)amino)-7H-pyrrolo[2,3-d]pyrimidin-7-yl)methyl)-3,3-difluoropiperidin-1-yl)acetamide, 2$^{nd}$ eluting isomer |

TABLE 1-continued

Example compounds by Structure and Name.

| Example No: | Structure | Name |
|---|---|---|
| K8-2-1 | 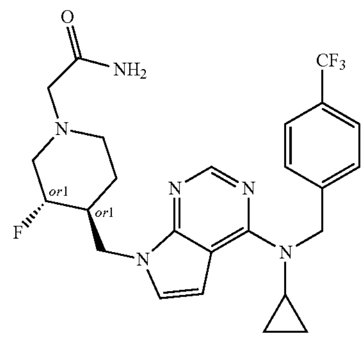 [SMILES: NC(=O)CN1CC[C@@H](Cn2ccc3c(N(Cc4ccc(C(F)(F)F)cc4)C4CC4)ncnc32)[C@H](F)C1] | rel-2-((3R,4R)-4-((4-(cyclopropyl(4-(trifluoromethyl)benzyl)amino)-7H-pyrrolo[2,3-d]pyrimidin-7-yl)methyl)-3-fluoropiperidin-1-yl)acetamide, 1$^{st}$ eluting isomer |
| K8-2-2 | | rel-2-((3R,4R)-4-((4-(cyclopropyl(4-(trifluoromethyl)benzyl)amino)-7H-pyrrolo[2,3-d]pyrimidin-7-yl)methyl)-3-fluoropiperidin-1-yl)acetamide, 2$^{nd}$ eluting isomer |
| K8-3-1 | 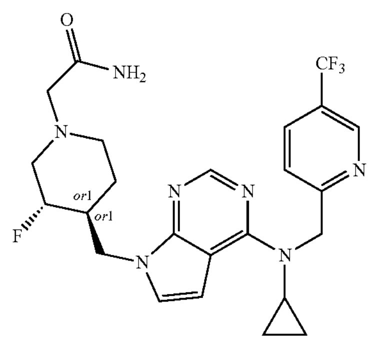 [SMILES: NC(=O)CN1CC[C@@H](Cn2ccc3c(N(Cc4ccc(C(F)(F)F)cn4)C4CC4)ncnc32)[C@H](F)C1] | rel-2-((3R,4R)-4-((4-(cyclopropyl((5-(trifluoromethyl)pyridin-2-yl)methyl)amino)-7H-pyrrolo[2,3-d]pyrimidin-7-yl)methyl)-3-fluoropiperidin-1-yl)acetamide, 1$^{st}$ eluting isomer |
| K8-3-2 | | rel-2-((3R,4R)-4-((4-(cyclopropyl((5-(trifluoromethyl)pyridin-2-yl)methyl)amino)-7H-pyrrolo[2,3-d]pyrimidin-7-yl)methyl)-3-fluoropiperidin-1-yl)acetamide, 2$^{nd}$ eluting isomer |
| L5-1-1-1 | 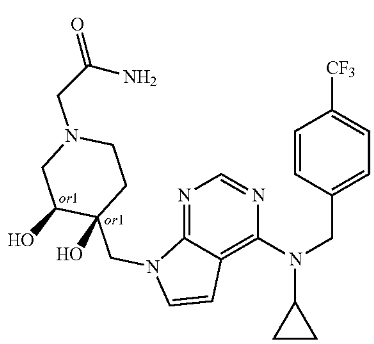 [SMILES: NC(=O)CN1CC[C@](O)(Cn2ccc3c(N(Cc4ccc(C(F)(F)F)cc4)C4CC4)ncnc32)[C@@H](O)C1] | rel-2-((3R,4R)-4-((4-(cyclopropyl(4-(trifluoromethyl)benzyl)amino)-7H-pyrrolo[2,3-d]pyrimidin-7-yl)methyl)-3,4-dihydroxypiperidin-1-yl)acetamide, 1st eluting isomer |
| L5-1-1-2 | | rel-2-((3R,4R)-4-((4-(cyclopropyl(4-(trifluoromethyl)benzyl)amino)-7H-pyrrolo[2,3-d]pyrimidin-7-yl)methyl)-3,4-dihydroxypiperidin-1-yl)acetamide, 2$^{nd}$ eluting isomer |

TABLE 1-continued

Example compounds by Structure and Name.

| Example No: | Structure | Name |
|---|---|---|
| L5-2-1-1 | 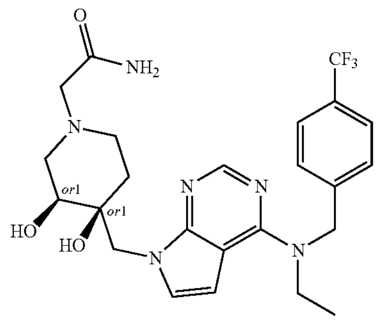 [SMILES: CCN(Cc1ccc(C(F)(F)F)cc1)c1ncnc2c1ccn2C[C@@]1(O)CCN(CC(N)=O)C[C@@H]1O] | rel-2-((3R,4R)-4-((4-(ethyl(4-(trifluoromethyl)benzyl)amino)-7H-pyrrolo[2,3-d]pyrimidin-7-yl)methyl)-3,4-dihydroxypiperidin-1-yl)acetamide, 1st eluting isomer |
| L5-2-1-2 | | rel-2-((3R,4R)-4-((4-(ethyl(4-(trifluoromethyl)benzyl)amino)-7H-pyrrolo[2,3-d]pyrimidin-7-yl)methyl)-3,4-dihydroxypiperidin-1-yl)acetamide, 2nd eluting isomer |
| L5-3-1 | 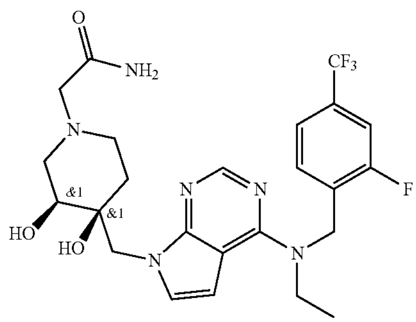 [SMILES: CCN(Cc1ccc(C(F)(F)F)cc1F)c1ncnc2c1ccn2C[C@@]1(O)CCN(CC(N)=O)C[C@@H]1O] | rac-2-((3R,4R)-4-((4-(ethyl(2-fluoro-4-(trifluoromethyl)benzyl)amino)-7H-pyrrolo[2,3-d]pyrimidin-7-yl)methyl)-3,4-dihydroxypiperidin-1-yl)acetamide |
| L5-3-1-1 | 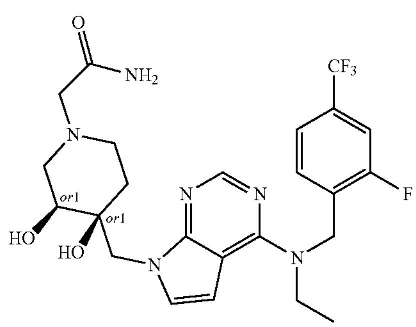 [SMILES: CCN(Cc1ccc(C(F)(F)F)cc1F)c1ncnc2c1ccn2C[C@@]1(O)CCN(CC(N)=O)C[C@@H]1O] | rel-2-((3R,4R)-4-((4-(ethyl(2-fluoro-4-(trifluoromethyl)benzyl)amino)-7H-pyrrolo[2,3-d]pyrimidin-7-yl)methyl)-3,4-dihydroxypiperidin-1-yl)acetamide, 1st eluting isomer |
| L5-3-1-2 | | rel-2-((3R,4R)-4-((4-(ethyl(2-fluoro-4-(trifluoromethyl)benzyl)amino)-7H-pyrrolo[2,3-d]pyrimidin-7-yl)methyl)-3,4-dihydroxypiperidin-1-yl)acetamide, 2nd eluting isomer |
| P6-1-1 | 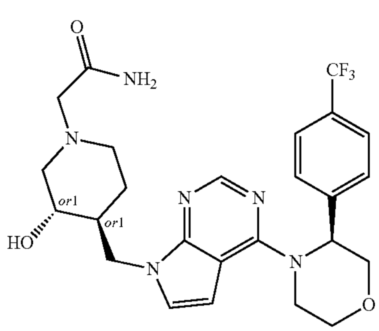 [SMILES: NC(=O)CN1CC[C@@H](Cn2ccc3c(N4CCOC[C@@H]4c4ccc(C(F)(F)F)cc4)ncnc32)[C@H](O)C1] | 2-((3R*,4R*)-3-hydroxy-4-((4-((S)-3-(4-(trifluoromethyl)phenyl)morpholino)-7H-pyrrolo[2,3-d]pyrimidin-7-yl)methyl)piperidin-1-yl)acetamide, 1st eluting isomer, |

TABLE 1-continued

Example compounds by Structure and Name.

| Example No: | Structure | Name |
|---|---|---|
| P6-1-2 | | 2-((3R*,4R*)-3-hydroxy-4-((4-((S)-3-(4-(trifluoromethyl)phenyl)morpholino)-7H-pyrrolo[2,3-d]pyrimidin-7-yl)methyl)piperidin-1-yl)acetamide, 2nd eluting isomer |
| P6-2-1 | 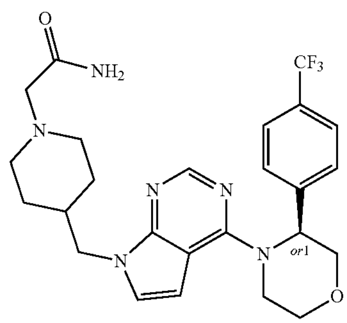 [SMILES: NC(=O)CN1CCC(Cn2ccc3c(N4CCOC[C@@H]4c4ccc(C(F)(F)F)cc4)ncnc32)CC1] | rel-(R)-2-(4-((4-(3-(4-(trifluoromethyl)phenyl)morpholino)-7H-pyrrolo[2,3-d]pyrimidin-7-yl)methyl)piperidin-1-yl)acetamide, 1st eluting isomer |
| P6-2-2 | | rel-(R)-2-(4-((4-(3-(4-(trifluoromethyl)phenyl)morpholino)-7H-pyrrolo[2,3-d]pyrimidin-7-yl)methyl)piperidin-1-yl)acetamide, 2nd eluting isomer |
| P6-3-1 | 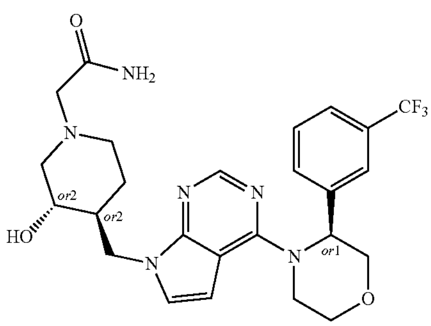 [SMILES: NC(=O)CN1CC[C@@H](Cn2ccc3c(N4CCOC[C@@H]4c4cccc(C(F)(F)F)c4)ncnc32)[C@H](O)C1] | rel-2-((3R,4R)-3-hydroxy-4-((4-((R)-3-(3-(trifluoromethyl)phenyl)morpholino)-7H-pyrrolo[2,3-d]pyrimidin-7-yl)methyl)piperidin-1-yl)acetamide OR rel-2-((3R,4R)-3-hydroxy-4-((4-((S)-3-(3-(trifluoromethyl)phenyl)morpholino)-7H-pyrrolo[2,3-d]pyrimidin-7-yl)methyl)piperidin-1-yl)acetamide, 1st eluting isomer |
| P6-3-2 | | rel-2-((3R,4R)-3-hydroxy-4-((4-((R)-3-(3-(trifluoromethyl)phenyl)morpholino)-7H-pyrrolo[2,3-d]pyrimidin-7-yl)methyl)piperidin-1-yl)acetamide OR rel-2-((3R,4R)-3-hydroxy-4-((4-((S)-3-(3-(trifluoromethyl)phenyl)morpholino)-7H-pyrrolo[2,3-d]pyrimidin-7-yl)methyl)piperidin-1-yl)acetamide, 2nd eluting isomer |
| P6-4-1 | 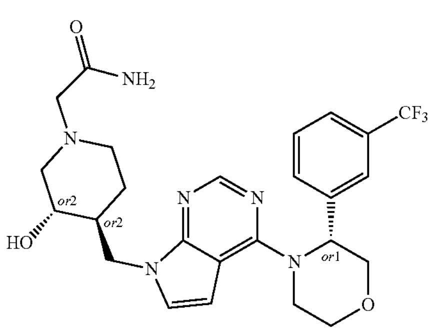 [SMILES: NC(=O)CN1CC[C@@H](Cn2ccc3c(N4CCOC[C@H]4c4cccc(C(F)(F)F)c4)ncnc32)[C@H](O)C1] | rel-2-((3R,4R)-3-hydroxy-4-((4-((R)-3-(3-(trifluoromethyl)phenyl)morpholino)-7H-pyrrolo[2,3-d]pyrimidin-7-yl)methyl)piperidin-1-yl)acetamide OR rel-2-((3R,4R)-3-hydroxy-4-((4-((S)-3-(3-(trifluoromethyl)phenyl)morpholino)-7H-pyrrolo[2,3-d]pyrimidin-7-yl)methyl)piperidin-1-yl)acetamide, 1st eluting isomer |

TABLE 1-continued

Example compounds by Structure and Name.

| Example No: | Structure | Name |
|---|---|---|
| P6-4-2 | | rel-2-((3R,4R)-3-hydroxy-4-((4-((R)-3-(3-(trifluoromethyl)phenyl)morpholino)-7H-pyrrolo[2,3-d]pyrimidin-7-yl)methyl)piperidin-1-yl)acetamide OR rel-2-((3R,4R)-3-hydroxy-4-((4-((S)-3-(3-(trifluoromethyl)phenyl)morpholino)-7H-pyrrolo[2,3-d]pyrimidin-7-yl)methyl)piperidin-1-yl)acetamide, 2$^{nd}$ eluting isomer |
| P6-5 | 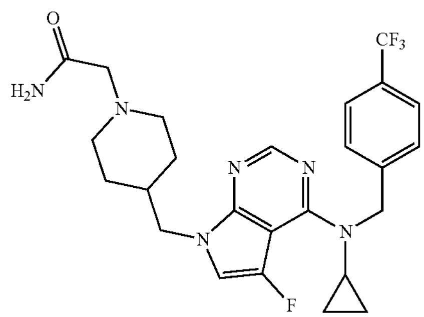 [SMILES: NC(=O)CN1CCC(Cn2cc(F)c3c(N(Cc4ccc(C(F)(F)F)cc4)C4CC4)ncnc32)CC1] | 2-(4-((4-(cyclopropyl(4-(trifluoromethyl)benzyl)amino)-5-fluoro-7H-pyrrolo[2,3-d]pyrimidin-7-yl)methyl)piperidin-1-yl)acetamide |
| P6-6 | 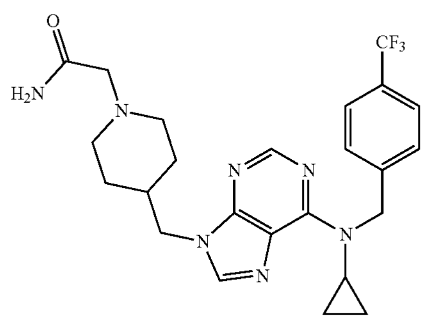 [SMILES: NC(=O)CN1CCC(Cn2cnc3c(N(Cc4ccc(C(F)(F)F)cc4)C4CC4)ncnc32)CC1] | 2-(4-((6-(cyclopropyl(4-(trifluoromethyl)benzyl)amino)-9H-purin-9-yl)methyl)piperidin-1-yl)acetamide |
| P6-7 | 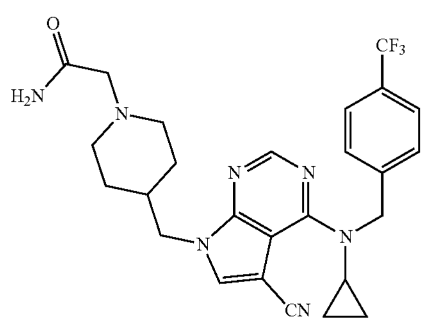 [SMILES: N#Cc1cn(CC2CCN(CC(N)=O)CC2)c2ncnc(N(Cc3ccc(C(F)(F)F)cc3)C3CC3)c12] | 2-(4-((5-cyano-4-(cyclopropyl(4-(trifluoromethyl)benzyl)amino)-7H-pyrrolo[2,3-d]pyrimidin-7-yl)methyl)piperidin-1-yl)acetamide |
| P6-8 | 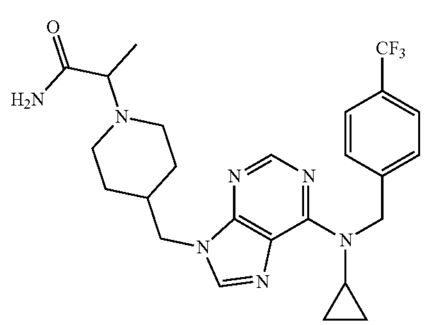 [SMILES: CC(C(N)=O)N1CCC(Cn2cnc3c(N(Cc4ccc(C(F)(F)F)cc4)C4CC4)ncnc32)CC1] | 2-(4-((6-(cyclopropyl(4-(trifluoromethyl)benzyl)amino)-9H-purin-9-yl)methyl)piperidin-1-yl)propanamide |

TABLE 1-continued

Example compounds by Structure and Name.

| Example No: | Structure | Name |
|---|---|---|
| P6-9 | 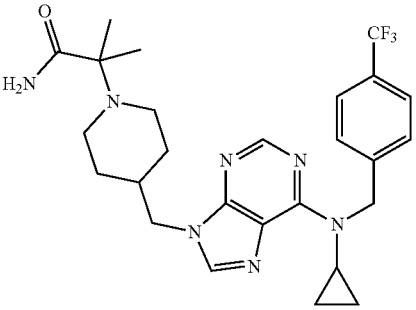 [SMILES: CC(C)(C(N)=O)N1CCC(Cn2cnc3c(N(Cc4ccc(C(F)(F)F)cc4)C4CC4)ncnc32)CC1] | 2-(4-((6-(cyclopropyl(4-(trifluoromethyl)benzyl)amino)-9H-purin-9-yl)methyl)piperidin-1-yl)-2-methylpropanamide |
| P6-10 | 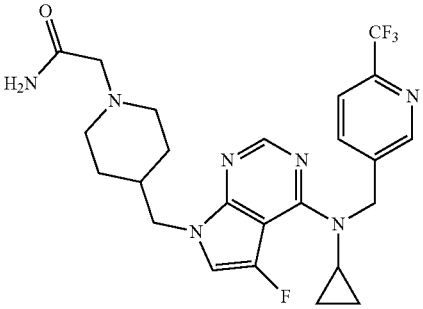 [SMILES: NC(=O)CN1CCC(Cn2cc(F)c3c(N(Cc4ccc(C(F)(F)F)nc4)C4CC4)ncnc32)CC1] | 2-(4-((4-(cyclopropyl((6-(trifluoromethyl)pyridin-3-yl)methyl)amino)-5-fluoro-7H-pyrrolo[2,3-d]pyrimidin-7-yl)methyl)piperidin-1-yl)acetamide |
| P6-11 | 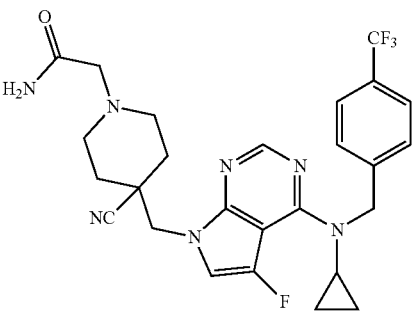 [SMILES: N#CC1(Cn2cc(F)c3c(N(Cc4ccc(C(F)(F)F)cc4)C4CC4)ncnc32)CCN(CC(N)=O)CC1] | 2-(4-cyano-4-((4-(cyclopropyl(4-(trifluoromethyl)benzyl)amino)-5-fluoro-7H-pyrrolo[2,3-d]pyrimidin-7-yl)methyl)piperidin-1-yl)acetamide |
| P6-12 | 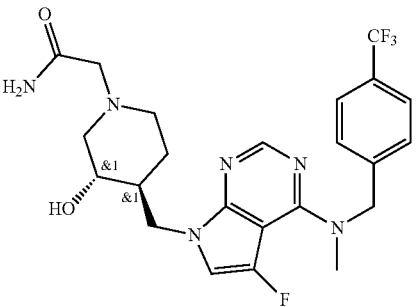 [SMILES: CN(Cc1ccc(C(F)(F)F)cc1)c1ncnc2c1c(F)cn2C[C@@H]1CCN(CC(N)=O)C[C@H]1O] | rac-2-((3R,4R)-4-((5-fluoro-4-(methyl(4-(trifluoromethyl)benzyl)amino)-7H-pyrrolo[2,3-d]pyrimidin-7-yl)methyl)-3-hydroxypiperidin-1-yl)acetamide |

TABLE 1-continued

Example compounds by Structure and Name.

| Example No: | Structure | Name |
|---|---|---|
| P6-13 | 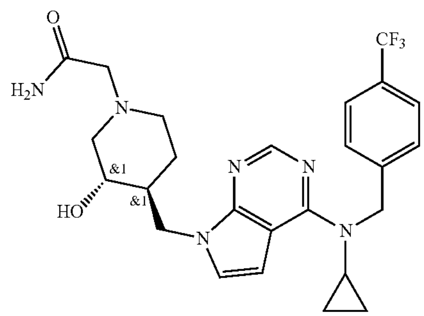 [SMILES: NC(=O)CN1CC[C@@H](Cn2ccc3c(N(Cc4ccc(C(F)(F)F)cc4)C4CC4)ncnc32)[C@H](O)C1] | rac-2-((3R,4R)-4-((4-(cyclopropyl(4-(trifluoromethyl)benzyl)amino)-7H-pyrrolo[2,3-d]pyrimidin-7-yl)methyl)-3-hydroxypiperidin-1-yl)acetamide |
| P6-13-1 | 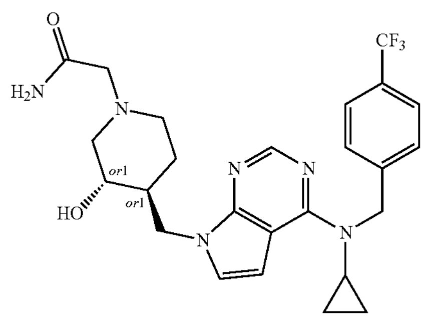 [SMILES: NC(=O)CN1CC[C@@H](Cn2ccc3c(N(Cc4ccc(C(F)(F)F)cc4)C4CC4)ncnc32)[C@H](O)C1] | rel-2-((3R,4R)-4-((4-(cyclopropyl(4-(trifluoromethyl)benzyl)amino)-7H-pyrrolo[2,3-d]pyrimidin-7-yl)methyl)-3-hydroxypiperidin-1-yl)acetamide, 1$^{st}$ eluting isomer |
| P6-13-2 | 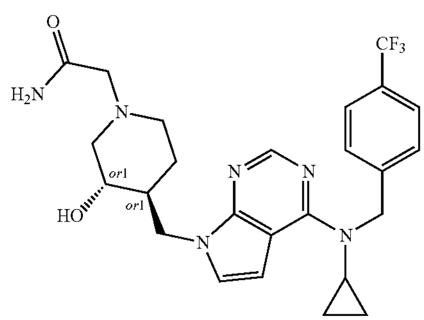 [SMILES: NC(=O)CN1CC[C@@H](Cn2ccc3c(N(Cc4ccc(C(F)(F)F)cc4)C4CC4)ncnc32)[C@H](O)C1] | rel-2-((3R,4R)-4-((4-(cyclopropyl(4-(trifluoromethyl)benzyl)amino)-7H-pyrrolo[2,3-d]pyrimidin-7-yl)methyl)-3-hydroxypiperidin-1-yl)acetamide, 2$^{nd}$ eluting isomer |
| P6-14 | 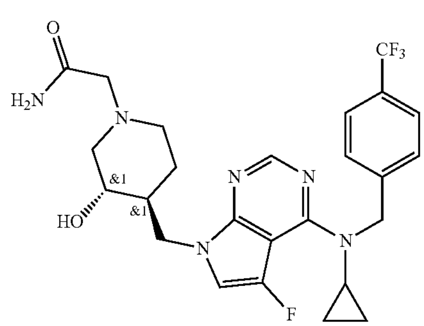 [SMILES: NC(=O)CN1CC[C@@H](Cn2cc(F)c3c(N(Cc4ccc(C(F)(F)F)cc4)C4CC4)ncnc32)[C@H](O)C1] | rac-2-((3R,4R)-4-((4-(cyclopropyl(4-(trifluoromethyl)benzyl)amino)-5-fluoro-7H-pyrrolo[2,3-d]pyrimidin-7-yl)methyl)-3-hydroxypiperidin-1-yl)acetamide |

TABLE 1-continued

Example compounds by Structure and Name.

| Example No: | Structure | Name |
|---|---|---|
| P6-14-1 | 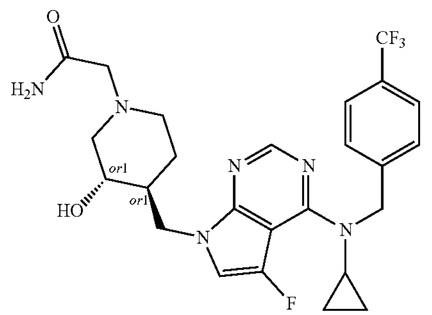 [SMILES: NC(=O)CN1CC[C@@H](Cn2cc(F)c3c(N(Cc4ccc(C(F)(F)F)cc4)C4CC4)ncnc32)[C@H](O)C1] | rel-2-((3R,4R)-4-((4-(cyclopropyl(4-(trifluoromethyl)benzyl)amino)-5-fluoro-7H-pyrrolo[2,3-d]pyrimidin-7-yl)methyl)-3-hydroxypiperidin-1-yl)acetamide, 1st eluting isomer |
| P6-14-2 | 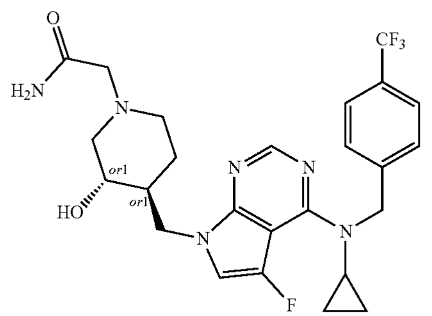 [SMILES: NC(=O)CN1CC[C@@H](Cn2cc(F)c3c(N(Cc4ccc(C(F)(F)F)cc4)C4CC4)ncnc32)[C@H](O)C1] | rel-2-((3R,4R)-4-((4-(cyclopropyl(4-(trifluoromethyl)benzyl)amino)-5-fluoro-7H-pyrrolo[2,3-d]pyrimidin-7-yl)methyl)-3-hydroxypiperidin-1-yl)acetamide, 2nd eluting isomer |
| P6-15 | 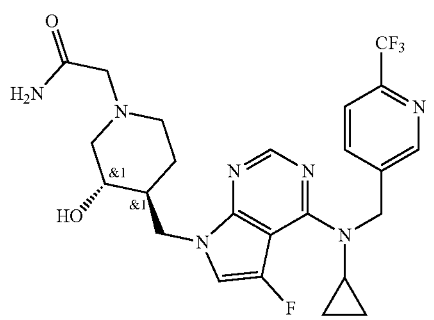 [SMILES: NC(=O)CN1CC[C@@H](Cn2cc(F)c3c(N(Cc4ccc(C(F)(F)F)nc4)C4CC4)ncnc32)[C@H](O)C1] | rac-2-((3R,4R)-4-((4-(cyclopropyl((6-(trifluoromethyl)pyridin-3-yl)methyl)amino)-5-fluoro-7H-pyrrolo[2,3-d]pyrimidin-7-yl)methyl)-3-hydroxypiperidin-1-yl)acetamide |
| P6-16 | 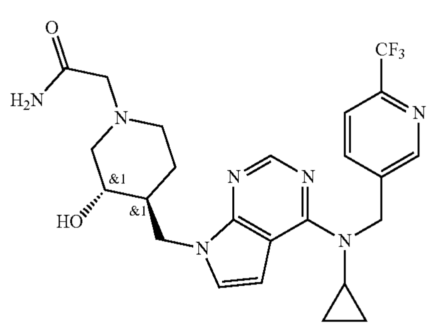 [SMILES: NC(=O)CN1CC[C@@H](Cn2ccc3c(N(Cc4ccc(C(F)(F)F)nc4)C4CC4)ncnc32)[C@H](O)C1] | rac-2-((3R,4R)-4-((4-(cyclopropyl((6-(trifluoromethyl)pyridin-3-yl)methyl)amino)-7H-pyrrolo[2,3-d]pyrimidin-7-yl)methyl)-3-hydroxypiperidin-1-yl)acetamide |

TABLE 1-continued

Example compounds by Structure and Name.

| Example No: | Structure | Name |
|---|---|---|
| P6-17 | 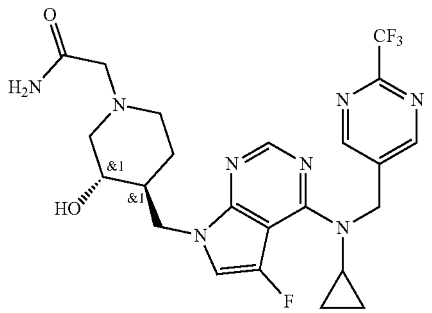 [SMILES: NC(=O)CN1CC[C@@H](Cn2cc(F)c3c(N(Cc4cnc(C(F)(F)F)nc4)C4CC4)ncnc32)[C@H](O)C1] | rac-2-((3R,4R)-4-((4-(cyclopropyl((2-(trifluoromethyl)pyrimidin-5-yl)methyl)amino)-5-fluoro-7H-pyrrolo[2,3-d]pyrimidin-7-yl)methyl)-3-hydroxypiperidin-1-yl)acetamide |
| P6-18 | 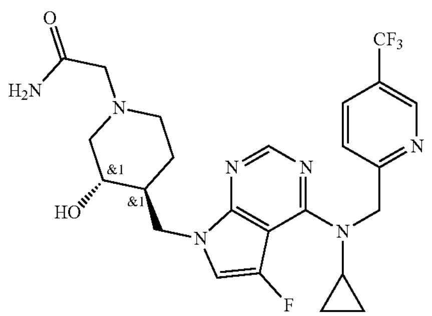 [SMILES: NC(=O)CN1CC[C@@H](Cn2cc(F)c3c(N(Cc4ccc(C(F)(F)F)cn4)C4CC4)ncnc32)[C@H](O)C1] | rac-2-((3R,4R)-4-((4-(cyclopropyl((5-(trifluoromethyl)pyridin-2-yl)methyl)amino)-5-fluoro-7H-pyrrolo[2,3-d]pyrimidin-7-yl)methyl)-3-hydroxypiperidin-1-yl)acetamide |
| P6-19 | 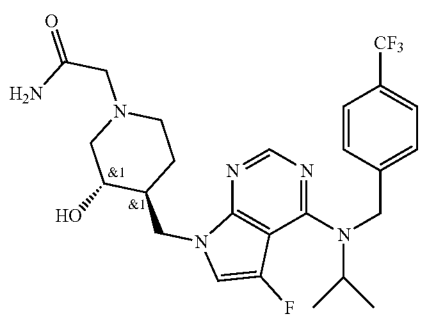 [SMILES: CC(C)N(Cc1ccc(C(F)(F)F)cc1)c1ncnc2c1c(F)cn2C[C@@H]1CCN(CC(N)=O)C[C@H]1O] | rac-2-((3R,4R)-4-((5-fluoro-4-(isopropyl(4-(trifluoromethyl)benzyl)amino)-7H-pyrrolo[2,3-d]pyrimidin-7-yl)methyl)-3-hydroxypiperidin-1-yl)acetamide |
| P6-20 | 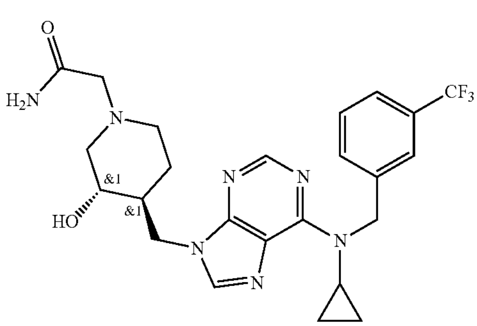 [SMILES: NC(=O)CN1CC[C@@H](Cn2cnc3c(N(Cc4cccc(C(F)(F)F)c4)C4CC4)ncnc32)[C@H](O)C1] | rac-2-((3R,4R)-4-((6-(cyclopropyl(3-(trifluoromethyl)benzyl)amino)-9H-purin-9-yl)methyl)-3-hydroxypiperidin-1-yl)acetamide |

TABLE 1-continued

Example compounds by Structure and Name.

| Example No: | Structure | Name |
|---|---|---|
| P6-21 | 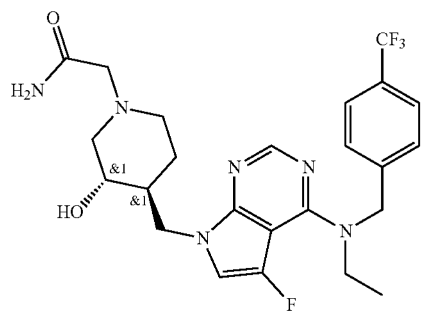 [SMILES: CCN(Cc1ccc(C(F)(F)F)cc1)c1ncnc2c1c(F)cn2C[C@@H]1CCN(CC(N)=O)C[C@H]1O] | rac-2-((3R,4R)-4-((4-(ethyl(4-(trifluoromethyl)benzyl)amino)-5-fluoro-7H-pyrrolo[2,3-d]pyrimidin-7-yl)methyl)-3-hydroxypiperidin-1-yl)acetamide |
| P6-22 | 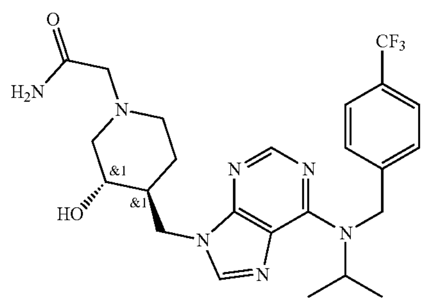 [SMILES: CC(C)N(Cc1ccc(C(F)(F)F)cc1)c1ncnc2c1ncn2C[C@@H]1CCN(CC(N)=O)C[C@H]1O] | rac-2-((3R,4R)-3-hydroxy-4-((6-(isopropyl(4-(trifluoromethyl)benzyl)amino)-9H-purin-9-yl)methyl)piperidin-1-yl)acetamide |
| P6-23 | 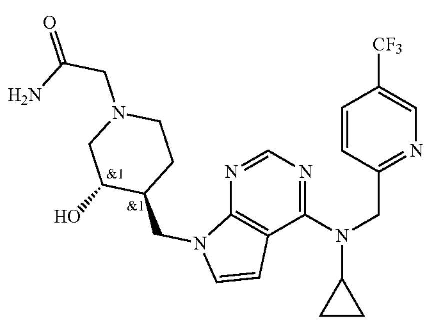 [SMILES: NC(=O)CN1CC[C@@H](Cn2ccc3c(N(Cc4ccc(C(F)(F)F)cn4)C4CC4)ncnc32)[C@H](O)C1] | rac-2-((3R,4R)-4-((4-(cyclopropyl((5-(trifluoromethyl)pyridin-2-yl)methyl)amino)-7H-pyrrolo[2,3-d]pyrimidin-7-yl)methyl)-3-hydroxypiperidin-1-yl)acetamide |
| P6-23-1 | 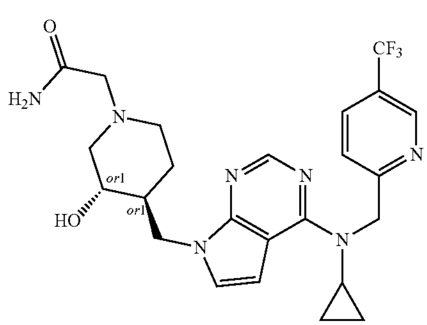 [SMILES: NC(=O)CN1CC[C@@H](Cn2ccc3c(N(Cc4ccc(C(F)(F)F)cn4)C4CC4)ncnc32)[C@H](O)C1] | rel-2-((3R,4R)-4-((4-(cyclopropyl((5-(trifluoromethyl)pyridin-2-yl)methyl)amino)-7H-pyrrolo[2,3-d]pyrimidin-7-yl)methyl)-3-hydroxypiperidin-1-yl)acetamide, 1$^{st}$ eluting isomer |

TABLE 1-continued

Example compounds by Structure and Name.

| Example No: | Structure | Name |
|---|---|---|
| P6-23-2 | 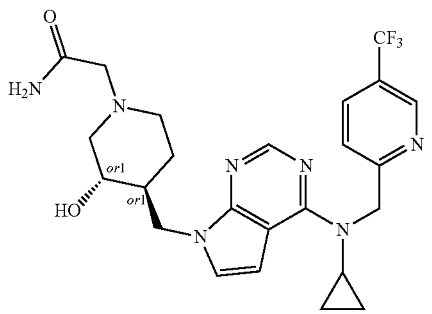 [SMILES: NC(=O)CN1CC[C@@H](Cn2ccc3c(N(Cc4ccc(C(F)(F)F)cn4)C4CC4)ncnc32)[C@H](O)C1] | rel-2-((3R,4R)-4-((4-(cyclopropyl((5-(trifluoromethyl)pyridin-2-yl)methyl)amino)-7H-pyrrolo[2,3-d]pyrimidin-7-yl)methyl)-3-hydroxypiperidin-1-yl)acetamide, 2$^{nd}$ eluting isomer |
| P6-24 | 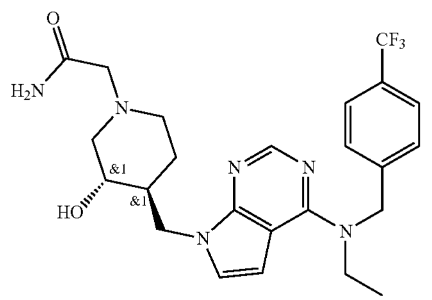 [SMILES: CCN(Cc1ccc(C(F)(F)F)cc1)c1ncnc2c1ccn2C[C@@H]1CCN(CC(N)=O)C[C@H]1O] | rac-2-((3R,4R)-4-((4-(ethyl(4-(trifluoromethyl)benzyl)amino)-7H-pyrrolo[2,3-d]pyrimidin-7-yl)methyl)-3-hydroxypiperidin-1-yl)acetamide |
| P6-24-1 | 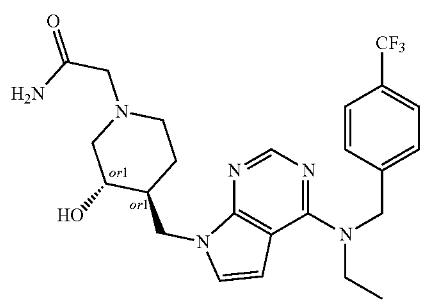 [SMILES: CCN(Cc1ccc(C(F)(F)F)cc1)c1ncnc2c1ccn2C[C@@H]1CCN(CC(N)=O)C[C@H]1O] | rel-2-((3R,4R)-4-((4-(ethyl(4-(trifluoromethyl)benzyl)amino)-7H-pyrrolo[2,3-d]pyrimidin-7-yl)methyl)-3-hydroxypiperidin-1-yl)acetamide, 1$^{st}$ eluting isomer |
| P6-24-2 | 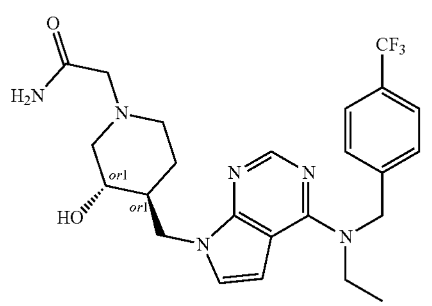 [SMILES: CCN(Cc1ccc(C(F)(F)F)cc1)c1ncnc2c1ccn2C[C@@H]1CCN(CC(N)=O)C[C@H]1O] | rel-2-((3R,4R)-4-((4-(ethyl(4-(trifluoromethyl)benzyl)amino)-7H-pyrrolo[2,3-d]pyrimidin-7-yl)methyl)-3-hydroxypiperidin-1-yl)acetamide, 2$^{nd}$ eluting isomer |
| P6-25 | 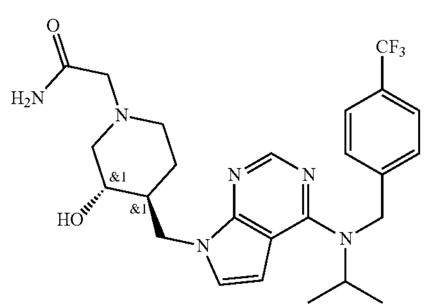 | rac-2-((3R,4R)-3-hydroxy-4-((4-(isopropyl(4-(trifluoromethyl)benzyl)amino)-7H-pyrrolo[2,3-d]pyrimidin-7-yl)methyl)piperidin-1-yl)acetamide |

TABLE 1-continued

Example compounds by Structure and Name.

| Example No: | Structure | Name |
|---|---|---|
| P6-25-1 | 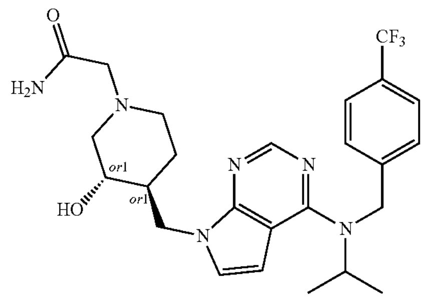 | rel-2-((3R,4R)-3-hydroxy-4-((4-(isopropyl(4-(trifluoromethyl)benzyl)amino)-7H-pyrrolo[2,3-d]pyrimidin-7-yl)methyl)piperidin-1-yl)acetamide, 1st eluting isomer |
| P6-25-2 | 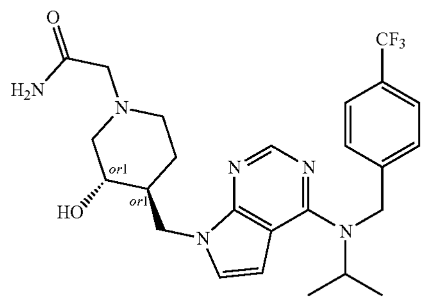 [SMILES: CC(C)N(Cc1ccc(C(F)(F)F)cc1)c1ncnc2c1ccn2C[C@@H]1CCN(CC(N)=O)C[C@H]1O] | rel-2-((3R,4R)-3-hydroxy-4-((4-(isopropyl(4-(trifluoromethyl)benzyl)amino)-7H-pyrrolo[2,3-d]pyrimidin-7-yl)methyl)piperidin-1-yl)acetamide, 2$^{nd}$ eluting isomer |
| P6-26″ | | rel-2-((3R,4R)-4-((6-(cyclopropyl(4-(trifluoromethyl)benzyl)amino)-9H-purin-9-yl)methyl)-3-hydroxypiperidin-1-yl)acetamide, enantiomerically enriched |
| P6-26-1 | 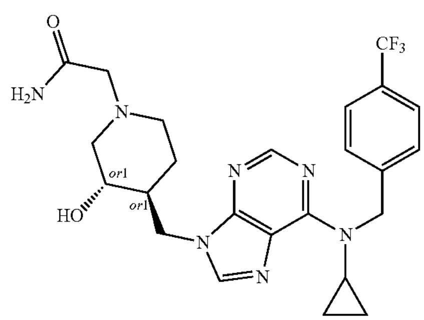 [SMILES: NC(=O)CN1CC[C@@H](Cn2cnc3c(N(Cc4ccc(C(F)(F)F)cc4)C4CC4)ncnc32)[C@H](O)C1] | rel-2-((3R,4R)-4-((6-(cyclopropyl(4-(trifluoromethyl)benzyl)amino)-9H-purin-9-yl)methyl)-3-hydroxypiperidin-1-yl)acetamide, 1$^{st}$ eluting (minor) isomer |
| P6-26-2 | 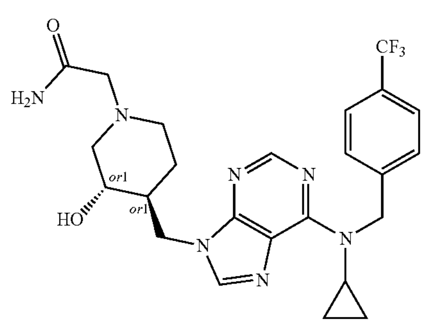 [SMILES: NC(=O)CN1CC[C@@H](Cn2cnc3c(N(Cc4ccc(C(F)(F)F)cc4)C4CC4)ncnc32)[C@H](O)C1] | rel-2-((3R,4R)-4-((6-(cyclopropyl(4-(trifluoromethyl)benzyl)amino)-9H-purin-9-yl)methyl)-3-hydroxypiperidin-1-yl)acetamide, 2$^{nd}$ eluting (major) isomer |

TABLE 1-continued

Example compounds by Structure and Name.

| Example No: | Structure | Name |
|---|---|---|
| P6-27" | 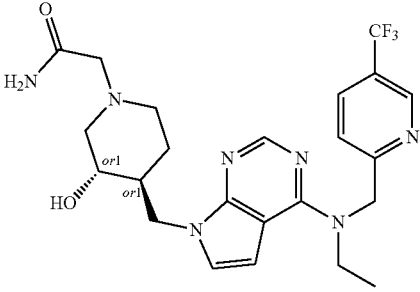 [SMILES: CCN(Cc1ccc(C(F)(F)F)cn1)c1ncnc2c1ccn2C[C@@H]1CCN(CC(N)=O)C[C@H]1O] | rel-2-((3R,4R)-4-((4-(ethyl((5-(trifluoromethyl)pyridin-2-yl)methyl)amino)-7H-pyrrolo[2,3-d]pyrimidin-7-yl)methyl)-3-hydroxypiperidin-1-yl)acetamide, enantiomerically enriched |
| P6-28" | 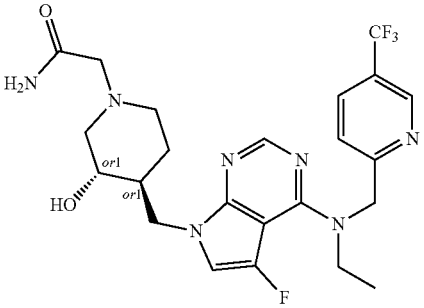 [SMILES: CCN(Cc1ccc(C(F)(F)F)cn1)c1ncnc2c1c(F)cn2C[C@@H]1CCN(CC(N)=O)C[C@H]1O] | rel-2-((3R,4R)-4-((4-(ethyl((5-(trifluoromethyl)pyridin-2-yl)methyl)amino)-5-fluoro-7H-pyrrolo[2,3-d]pyrimidin-7-yl)methyl)-3-hydroxypiperidin-1-yl)acetamide, enantiomerically enriched |
| P6-29" | 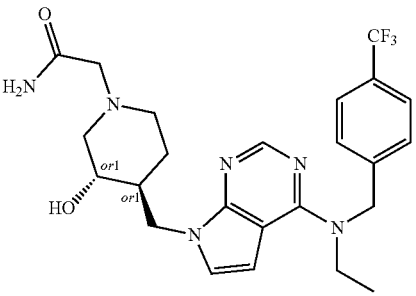 | rel-2-((3R,4R)-4-((4-((4-cyanobenzyl)(ethyl)amino)-7H-pyrrolo[2,3-d]pyrimidin-7-yl)methyl)-3-hydroxypiperidin-1-yl)acetamide, enantiomerically enriched |
| P6-30" | 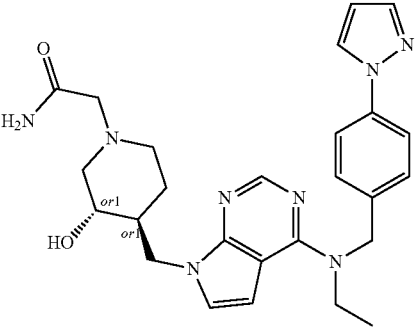 [SMILES: CCN(Cc1ccc(-n2cccn2)cc1)c1ncnc2c1ccn2C[C@@H]1CCN(CC(N)=O)C[C@H]1O] | rel-2-((3R,4R)-4-((4-((4-(1H-pyrazol-1-yl)benzyl)(ethyl)amino)-7H-pyrrolo[2,3-d]pyrimidin-7-yl)methyl)-3-hydroxypiperidin-1-yl)acetamide, enantiomerically enriched |

TABLE 1-continued

Example compounds by Structure and Name.

| Example No: | Structure | Name |
|---|---|---|
| P6-31" | 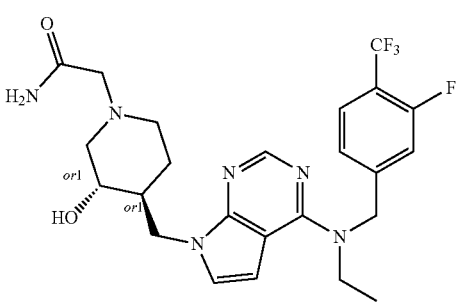 [SMILES: CCN(Cc1ccc(C(F)(F)F)c(F)c1)c1ncnc2c1ccn2C[C@@H]1CCN(CC(N)=O)C[C@H]1O] | rel-2-((3R,4R)-4-((4-(ethyl(3-fluoro-4-(trifluoromethyl)benzyl)amino)-7H-pyrrolo[2,3-d]pyrimidin-7-yl)methyl)-3-hydroxypiperidin-1-yl)acetamide, enantiomerically enriched |
| P6-32" | 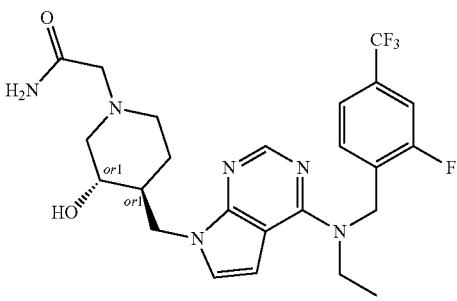 [SMILES: CCN(Cc1ccc(C(F)(F)F)cc1F)c1ncnc2c1ccn2C[C@@H]1CCN(CC(N)=O)C[C@H]1O] | rel-2-((3R,4R)-4-((4-(ethyl(2-fluoro-4-(trifluoromethyl)benzyl)amino)-7H-pyrrolo[2,3-d]pyrimidin-7-yl)methyl)-3-hydroxypiperidin-1-yl)acetamide, enantiomerically enriched |
| P6-33" | 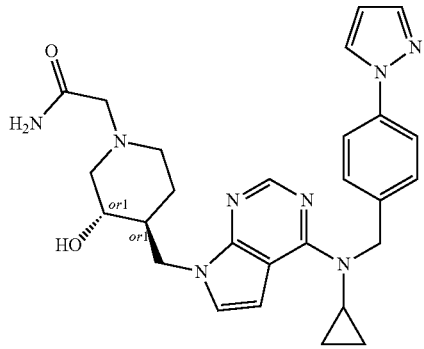 [SMILES: NC(=O)CN1CC[C@@H](Cn2ccc3c(N(Cc4ccc(-n5cccn5)cc4)C4CC4)ncnc32)[C@H](O)C1] | rel-2-((3R,4R)-4-((4-((4-(1H-pyrazol-1-yl)benzyl)(cyclopropyl)amino)-7H-pyrrolo[2,3-d]pyrimidin-7-yl)methyl)-3-hydroxypiperidin-1-yl)acetamide, enantiomerically enriched |
| P6-34" | 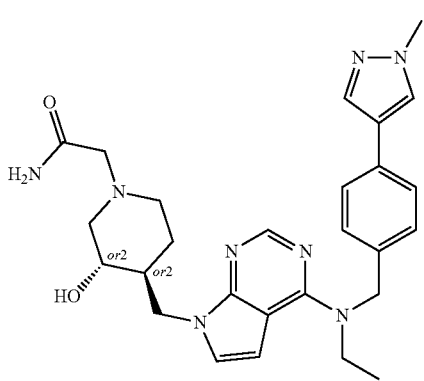 [SMILES: CCN(Cc1ccc(-c2cnn(C)c2)cc1)c1ncnc2c1ccn2C[C@@H]1CCN(CC(N)=O)C[C@H]1O] | rel-2-((3R,4R)-4-((4-(ethyl(4-(1-methyl-1H-pyrazol-4-yl)benzyl)amino)-7H-pyrrolo[2,3-d]pyrimidin-7-yl)methyl)-3-hydroxypiperidin-1-yl)acetamide, enantiomerically enriched |

TABLE 1-continued

Example compounds by Structure and Name.

| Example No: | Structure | Name |
|---|---|---|
| P6-35" | 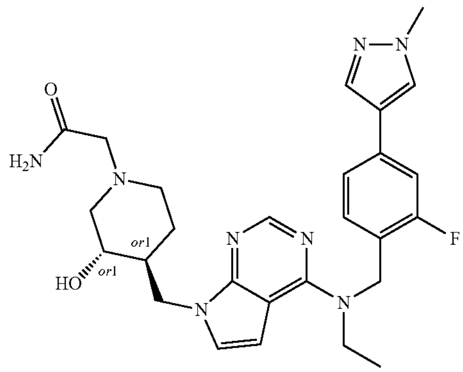 [SMILES: CCN(Cc1ccc(-c2cnn(C)c2)cc1F)c1ncnc2c1ccn2C[C@@H]1CCN(CC(N)=O)C[C@H]1O] | rel-2-((3R,4R)-4-((4-(ethyl(2-fluoro-4-(1-methyl-1H-pyrazol-4-yl)benzyl)amino)-7H-pyrrolo[2,3-d]pyrimidin-7-yl)methyl)-3-hydroxypiperidin-1-yl)acetamide, enantiomerically enriched |
| P6-36" | 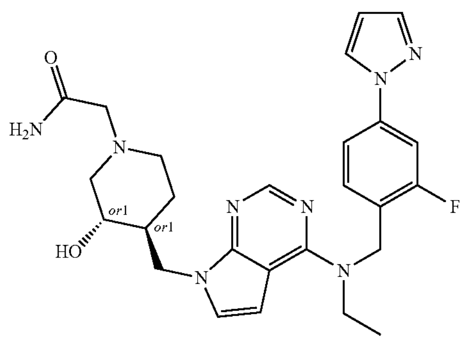 [SMILES: CCN(Cc1ccc(-n2cccn2)cc1F)c1ncnc2c1ccn2C[C@@H]1CCN(CC(N)=O)C[C@H]1O] | rel-2-((3R,4R)-4-((4-(ethyl(2-fluoro-4-(1H-pyrazol-1-yl)benzyl)amino)-7H-pyrrolo[2,3-d]pyrimidin-7-yl)methyl)-3-hydroxypiperidin-1-yl)acetamide, enantiomerically enriched |
| P6-37 | 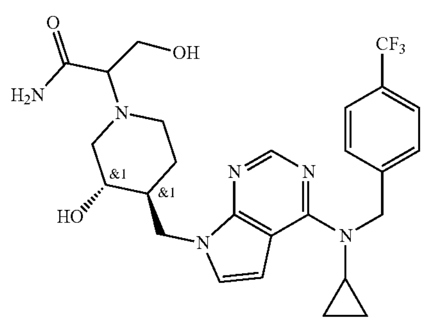 [SMILES: NC(=O)C(CO)N1CC[C@@H](Cn2ccc3c(N(Cc4ccc(C(F)(F)F)cc4)C4CC4)ncnc32)[C@H](O)C1] | rac-2-((3R,4R)-4-((4-(cyclopropyl(4-(trifluoromethyl)benzyl)amino)-7H-pyrrolo[2,3-d]pyrimidin-7-yl)methyl)-3-hydroxypiperidin-1-yl)-3-hydroxypropanamide |
| Q4-1-1 | 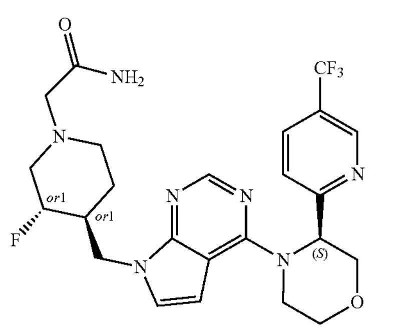 | 2-((3R*,4R*)-3-fluoro-4-((4-((S)-3-(5-(trifluoromethyl)pyridin-2-yl)morpholino)-7H-pyrrolo[2,3-d]pyrimidin-7-yl)methyl)piperidin-1-yl)acetamide, 1st stereoisomer |
| Q4-1-2 | | 2-((3R*,4R*)-3-fluoro-4-((4-((S)-3-(5-(trifluoromethyl)pyridin-2-yl)morpholino)-7H-pyrrolo[2,3-d]pyrimidin-7-yl)methyl)piperidin-1-yl)acetamide, 2nd stereoisomer |

TABLE 1-continued

Example compounds by Structure and Name.

| Example No: | Structure | Name |
|---|---|---|
| Q4-2 | 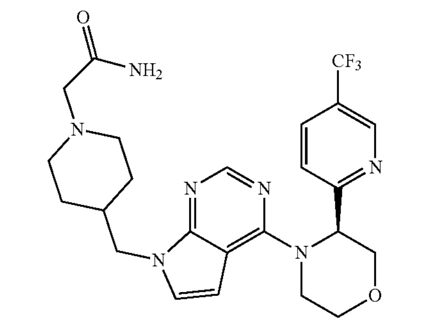 [SMILES: NC(=O)CN1CCC(Cn2ccc3c(N4CCOC[C@@H]4c4ccc(C(F)(F)F)cn4)ncnc32)CC1] | (S)-2-(4-((4-(3-(5-(trifluoromethyl)pyridin-2-yl)morpholino)-7H-pyrrolo[2,3-d]pyrimidin-7-yl)methyl)piperidin-1-yl)acetamide |
| R5-1" | 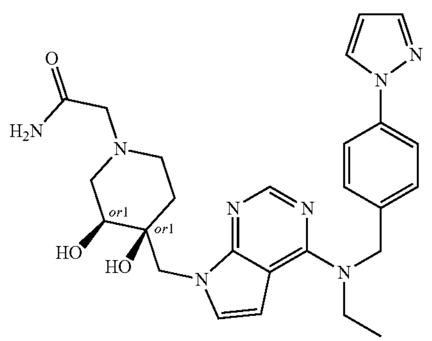 [SMILES: CCN(Cc1ccc(-n2cccn2)cc1)c1ncnc2c1ccn2C[C@@]1(O)CCN(CC(N)=O)C[C@@H]1O] | rel-2-((3R,4R)-4-((4-((4-(1H-pyrazol-1-yl)benzyl)(ethyl)amino)-7H-pyrrolo[2,3-d]pyrimidin-7-yl)methyl)-3,4-dihydroxypiperidin-1-yl)acetamide, enantiomerically enriched |
| R5-2" | 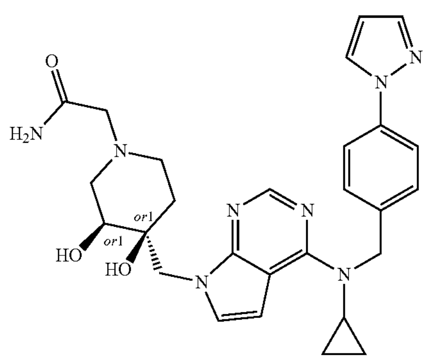 [SMILES: NC(=O)CN1CC[C@](O)(Cn2ccc3c(N(Cc4ccc(-n5cccn5)cc4)C4CC4)ncnc32)[C@@H](O)C1] | rel-2-((3R,4R)-4-((4-((4-(1H-pyrazol-1-yl)benzyl)(cyclopropyl)amino)-7H-pyrrolo[2,3-d]pyrimidin-7-yl)methyl)-3,4-dihydroxypiperidin-1-yl)acetamide, enantiomerically enriched |
| R5-2-1 | 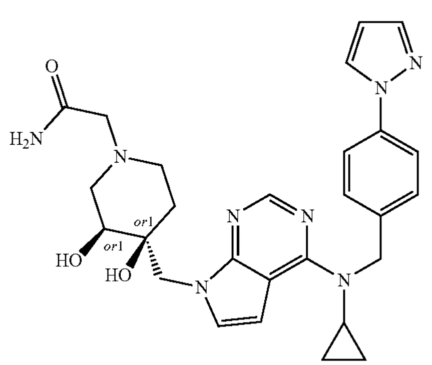 [SMILES: NC(=O)CN1CC[C@](O)(Cn2ccc3c(N(Cc4ccc(-n5cccn5)cc4)C4CC4)ncnc32)[C@@H](O)C1] | rel-2-((3R,4R)-4-((4-((4-(1H-pyrazol-1-yl)benzyl)(cyclopropyl)amino)-7H-pyrrolo[2,3-d]pyrimidin-7-yl)methyl)-3,4-dihydroxypiperidin-1-yl)acetamide, 1$^{st}$ eluting isomer (minor isomer) |

TABLE 1-continued

Example compounds by Structure and Name.

| Example No: | Structure | Name |
|---|---|---|
| R5-2-2 | 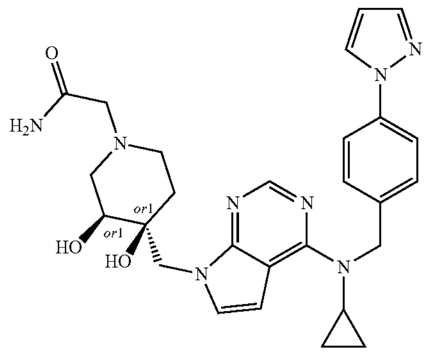 [SMILES: NC(=O)CN1CC[C@](O)(Cn2ccc3c(N(Cc4ccc(-n5cccn5)cc4)C4CC4)ncnc32)[C@@H](O)C1] | rel-2-((3R,4R)-4-((4-((4-(1H-pyrazol-1-yl)benzyl)(cyclopropyl)amino)-7H-pyrrolo[2,3-d]pyrimidin-7-yl)methyl)-3,4-dihydroxypiperidin-1-yl)acetamide, 2<sup>nd</sup> eluting isomer (major isomer) |
| R5-3" | 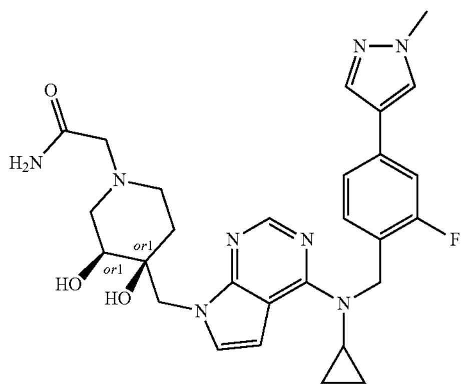 [SMILES: Cn1cc(-c2ccc(CN(c3ncnc4c3ccn4C[C@@]3(O)CCN(CC(N)=O)C[C@@H]3O)C3CC3)c(F)c2)cn1] | rel-2-((3R,4R)-4-((4-(cyclopropyl(2-fluoro-4-(1-methyl-1H-pyrazol-4-yl)benzyl)amino)-7H-pyrrolo[2,3-d]pyrimidin-7-yl)methyl)-3,4-dihydroxypiperidin-1-yl)acetamide, enantiomerically enriched |
| R5-4" | 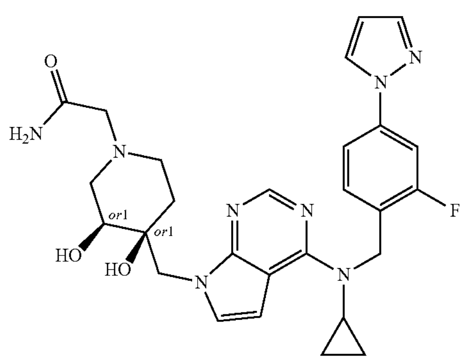 [SMILES: NC(=O)CN1CC[C@](O)(Cn2ccc3c(N(Cc4ccc(-n5cccn5)cc4F)C4CC4)ncnc32)[C@@H](O)C1] | rel-2-((3R,4R)-4-((4-(cyclopropyl(2-fluoro-4-(1H-pyrazol-1-yl)benzyl)amino)-7H-pyrrolo[2,3-d]pyrimidin-7-yl)methyl)-3,4-dihydroxypiperidin-1-yl)acetamide |
| R5-5" | 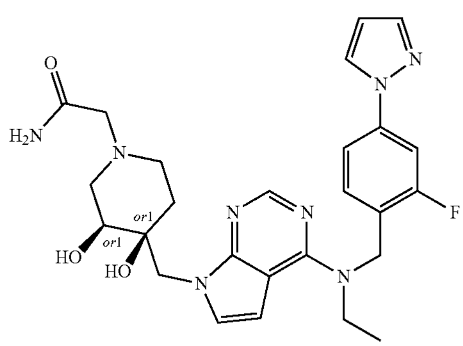 [SMILES: CCN(Cc1ccc(-n2cccn2)cc1F)c1ncnc2c1ccn2C[C@@]1(O)CCN(CC(N)=O)C[C@@H]1O] | rel-2-((3R,4R)-4-((4-(ethyl(2-fluoro-4-(1H-pyrazol-1-yl)benzyl)amino)-7H-pyrrolo[2,3-d]pyrimidin-7-yl)methyl)-3,4-dihydroxypiperidin-1-yl)acetamide, enantiomerically enriched |

"Enantiomerically enriched.

In a related aspect there is provided a prodrug of a compound of Formula (I) as described herein.

The compounds of the present disclosure are active, e.g. having a RORγ Ga14<1000 nM, such as <500 nM, such as <100 nM, and have a log P substantially lower (e.g. a decreased log P of 1.5, such as 2.0, such as 2.5 log units) than compounds disclosed in WO2016020288 and WO2016020295. In certain embodiments Log D and Log P are substantially lower than compounds in WO2016020288 and WO2016020295. The compounds disclosed herein thus have an improved lipophilicity at similar potency. The compounds disclosed herein may thus be improved modulators of RORγ, e.g. having an attractive interaction (e.g. higher binding ability) to the hydrophobic binding sites of the ligand binding domain (LBD) of the RORγ and a low log P and/or low log D.

Pharmaceutical Compositions

In another aspect, the present disclosure relates to a pharmaceutical composition comprising physiologically acceptable surface active agents, carriers, diluents, excipients, smoothing agents, suspension agents, film forming substances, and coating assistants, or a combination thereof; and a compound as disclosed herein, e.g., a compound of Formulae (I), (II), (III), and (IV) as disclosed herein, or a salt, stereoisomer, or salt of a stereoisomer thereof. The compound of Formulae (I), (II), (III) and (IV) included in the pharmaceutical composition may also be any compound of the preferred embodiments described above. In another aspect, the present disclosure relates to a pharmaceutical composition comprising physiologically acceptable surface active agents, carriers, diluents, excipients, smoothing agents, suspension agents, film forming substances, and coating assistants, or a combination thereof; and a compound of any one of Formulae I, II, III, or IV as disclosed herein. Acceptable carriers or diluents, as well as other additives to be combined with one or more compound(s) of Formula I, II, III or IV as disclosed herein to provide a pharmaceutical composition, for therapeutic use are well known in the pharmaceutical art, and are described, for example, in Remington's Pharmaceutical Sciences, 18th Ed., Mack Publishing Co., Easton, Pa. (1990), which is incorporated herein by reference in its entirety. Preservatives, stabilizers, dyes, sweeteners, fragrances, flavoring agents, taste masking agents, and the like may be provided in the pharmaceutical composition. For example, sodium benzoate, ascorbic acid and esters of p-hydroxybenzoic acid may be added as preservatives. In addition, antioxidants and suspending agents may be used. In various embodiments, alcohols, esters, sulfated aliphatic alcohols, and the like may be used as surface active agents; sucrose, glucose, lactose, starch, crystallized cellulose, mannitol, light anhydrous silicate, magnesium aluminate, magnesium methasilicate aluminate, synthetic aluminum silicate, calcium carbonate, sodium acid carbonate, calcium hydrogen phosphate, calcium carboxymethyl cellulose, and the like may be used as excipients; magnesium stearate, talc, hardened oil and the like may be used as smoothing agents; coconut oil, olive oil, sesame oil, peanut oil, soya may be used as suspension agents or lubricants; cellulose acetate phthalate as a derivative of a carbohydrate such as cellulose or sugar, or methylacetate-methacrylate copolymer as a derivative of polyvinyl may be used as suspension agents; and plasticizers such as ester phthalates and the like may be used as suspension agents.

The term "pharmaceutical composition" refers to a mixture of a compound disclosed herein with other chemical components, such as diluents or carriers. The pharmaceutical composition facilitates administration of the compound to an organism. Multiple techniques of administering a compound exist in the art including, but not limited to, oral, injection, aerosol, parenteral, and topical administration. Pharmaceutical compositions can also be obtained by reacting compounds with inorganic or organic acids such as hydrochloric acid, hydrobromic acid, sulfuric acid, nitric acid, phosphoric acid, methanesulfonic acid, ethanesulfonic acid, p-toluenesulfonic acid, salicylic acid and the like. Similar, pharmaceutical compositions can also be obtained by reacting compounds with inorganic or organic bases, such as ammonia, sodium carbonate, sodium hydrogen carbonate, sodium hydroxide, and the like.

The term "carrier" defines a chemical compound that facilitates the incorporation of a compound into cells or tissues. For example, and without limitation dimethyl sulfoxide (DMSO) is a commonly utilized carrier as it facilitates the uptake of many organic compounds into the cells or tissues of an organism.

The term "diluent" defines chemical compounds diluted in water that will dissolve the compound of interest as well as stabilize the biologically active form of the compound. Salts dissolved in buffered solutions are utilized as diluents in the art. One commonly used buffered solution is phosphate buffered saline because it mimics the salt conditions of human blood. Since buffer salts can control the pH of a solution at low concentrations, a buffered diluent rarely modifies the biological activity of a compound.

The term "physiologically acceptable" defines a carrier or diluent that does not abrogate the biological activity and properties of the compound.

The pharmaceutical compositions described herein can be administered to a human patient per se, or in pharmaceutical compositions where they are mixed with other active ingredients, as in combination therapy, or suitable carriers or excipient(s). Techniques for formulation and administration of the compounds of the instant application may be found in "Remington's Pharmaceutical Sciences," Mack Publishing Co., Easton, Pa., 18th edition, 1990.

Suitable routes of administration may, for example, include oral, rectal, transmucosal, topical, or intestinal administration; parenteral delivery, including intramuscular, subcutaneous, intravenous, intramedullary injections, as well as intrathecal, direct intraventricular, intraperitoneal, intranasal, or intraocular injections. The compounds can also be administered in sustained or controlled release dosage forms, including depot injections, osmotic pumps, pills, transdermal (including electrotransport) patches, and the like, for prolonged and/or timed, pulsed administration at a predetermined rate.

The pharmaceutical compositions may be manufactured in a manner that is itself known, e.g., by means of conventional mixing, dissolving, granulating, dragee-making, levigating, emulsifying, encapsulating, entrapping or tableting processes.

Pharmaceutical compositions for use as described herein may be formulated in conventional manner using one or more physiologically acceptable carriers comprising excipients and auxiliaries which facilitate processing of the active compounds into preparations which can be used pharmaceutically. Proper formulation is dependent upon the route of administration chosen. Any of the well-known techniques, carriers, and excipients may be used as suitable and as understood in the art; e.g., in Remington's Pharmaceutical Sciences, above.

Injectables can be prepared in conventional forms, either as liquid solutions or suspensions, solid forms suitable for solution or suspension in liquid prior to injection, or as emulsions. Suitable excipients are, for example, water, saline, dextrose, mannitol, lactose, lecithin, albumin, sodium glutamate, cysteine hydrochloride, and the like. In addition, if desired, the injectable pharmaceutical compositions may contain minor amounts of nontoxic auxiliary substances, such as wetting agents, pH buffering agents, and the like. Physiologically compatible buffers include, but are not limited to, Hanks's solution, Ringer's solution, or physiological saline buffer. If desired, absorption enhancing preparations (for example, liposomes), may be utilized.

For transmucosal administration, penetrants appropriate to the barrier to be permeated may be used in the formulation.

Pharmaceutical formulations for parenteral administration, e.g., by bolus injection or continuous infusion, include aqueous solutions of the active compounds in water-soluble form. Additionally, suspensions of the active compounds may be prepared as appropriate oily injection suspensions. Suitable lipophilic solvents or vehicles include fatty oils such as sesame oil, or other organic oils such as soybean, grapefruit or almond oils, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents that increase the solubility of the compounds to allow for the preparation of highly concentrated solutions. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

For oral administration, the compounds can be formulated readily by combining the active compounds with pharmaceutically acceptable carriers well known in the art. Such carriers enable the compounds disclosed herein to be formulated as tablets, pills, dragees, capsules, liquids, gels, syrups, slurries, suspensions and the like, for oral ingestion by a patient to be treated. Pharmaceutical preparations for oral use can be obtained by combining the active compounds with solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate. Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

For buccal administration, the compositions may take the form of tablets or lozenges formulated in conventional manner.

For administration by inhalation, the compounds for use as described herein are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of, e.g., gelatin for use in an inhaler or insufflator may be formulated containing a powder mix of the compound and a suitable powder base such as lactose or starch.

Further disclosed herein are various pharmaceutical compositions well known in the pharmaceutical art for uses that include intraocular, intranasal, and intraauricular delivery. Suitable penetrants for these uses are generally known in the art. Topical ophthalmic compositions may be formulated as a solution in water buffered at a pH of 5.0 to 8.0. Other ingredients that may be desirable to use in the ophthalmic preparations include preservatives (such as benzalkonium chloride, stabilized oxychloro complex, which is sold as Purite™, or stabilized chlorine dioxide), cosolvents (such as polysorbate 20, 60 and 80, Pluronic® F-68, F-84 and P-103, cyclodextrin, or Solutol) and viscosity-building agents (such as polyvinyl alcohol, polyvinyl pyrrolidone, methyl cellulose, hydroxypropyl methyl cellulose, hydroxyethyl cellulose, carboxymethyl cellulose, or hydroxypropyl cellulose). The compounds disclosed herein may also be used in an intraocular implant as described in U.S. Pat. No. 7,931,909 which is hereby incorporated by reference. Pharmaceutical compositions for intraocular delivery include aqueous ophthalmic solutions of the active compounds in water-soluble form, such as eyedrops, or in gellan gum (Shedden et al., *Clin. Ther.*, 23(3):440-50 (2001)) or hydrogels (Mayer et al., *Ophthalmologica*, 210(2):101-3 (1996)); ophthalmic ointments; ophthalmic suspensions, such as microparticulates, drug-containing small polymeric particles that are suspended in a liquid carrier medium (Joshi, A., *J. Ocul. Pharmacol.*, 10(1):29-45 (1994)), lipid-soluble formulations (Alm et al., *Prog. Clin. Biol. Res.*, 312:447-58 (1989)), and microspheres (Mordenti, *Toxicol. Sci.*, 52(1):101-6 (1999)); and ocular inserts. All of the above-mentioned references, are incorporated herein by reference in their entireties. Such suitable pharmaceutical formulations for intraocular delivery are most often and preferably formulated to be sterile, isotonic and buffered for stability and comfort. Pharmaceutical compositions for intranasal delivery may also include drops and sprays often prepared to simulate in many respects nasal secretions to ensure maintenance of normal ciliary action. As disclosed in Remington's Pharmaceutical Sciences, 18th Ed., Mack Publishing Co., Easton, Pa. (1990), which is incorporated herein by reference in its entirety, and well-known to those skilled in the art, suitable formulations are most often and preferably isotonic, slightly buffered to maintain a pH of 5.5 to 6.5, and most often and preferably include antimicrobial preservatives and appropriate drug stabilizers. Pharmaceutical formulations for intrarticular delivery include suspensions and ointments for topical application in the ear. Common solvents for such aural formulations include glycerin and water.

The compounds disclosed herein may also be formulated in rectal compositions such as suppositories or retention enemas, e.g., containing conventional suppository bases such as cocoa butter or other glycerides.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

For hydrophobic compounds, a suitable pharmaceutical carrier may be a cosolvent system comprising benzyl alcohol, a nonpolar surfactant, a water-miscible organic polymer, and an aqueous phase. A common cosolvent system used is the VPD co-solvent system, which is a solution of 3% w/v benzyl alcohol, 8% w/v of the nonpolar surfactant Polysorbate 80™, and 65% w/v polyethylene glycol 300, made up to volume in absolute ethanol. Naturally, the proportions of a co-solvent system may be varied considerably without destroying its solubility and toxicity characteristics. Furthermore, the identity of the co-solvent components may be varied: for example, other low-toxicity nonpolar surfactants may be used instead of POLYSORBATE 80™; the fraction size of polyethylene glycol may be varied; other biocompatible polymers may replace polyethylene glycol, e.g., polyvinyl pyrrolidone; and other sugars or polysaccharides may substitute for dextrose.

Alternatively, other delivery systems for hydrophobic pharmaceutical compounds may be employed. Liposomes and emulsions are well known examples of delivery vehicles or carriers for hydrophobic drugs. Certain organic solvents such as dimethylsulfoxide also may be employed. Additionally, the compounds may be delivered using a sustained-release system, such as semipermeable matrices of solid hydrophobic polymers containing the therapeutic agent. Various sustained-release materials have been established and are well known by those skilled in the art. Sustained-release capsules may, depending on their chemical nature, release the compounds for a few weeks up to over 100 days. Depending on the chemical nature and the biological stability of the therapeutic reagent, additional strategies for protein stabilization may be employed.

Agents intended to be administered intracellularly may be administered using techniques well known to those of ordinary skill in the art. For example, such agents may be encapsulated into liposomes. All molecules present in an aqueous solution at the time of liposome formation are incorporated into the aqueous interior. The liposomal contents are both protected from the external micro-environment and, because liposomes fuse with cell membranes, are efficiently delivered into the cell cytoplasm. The liposome may be coated with a tissue-specific antibody. The liposomes will be targeted to and taken up selectively by the desired organ. Alternatively, small hydrophobic organic molecules may be directly administered intracellularly.

Additional therapeutic or diagnostic agents may be incorporated into the pharmaceutical compositions. Alternatively or additionally, pharmaceutical compositions may be combined with other compositions that contain other therapeutic or diagnostic agents.

Combinations

The compounds disclosed herein may also be combined with other active compounds in the treatment and/or prevention of inflammatory, metabolic, oncologic and autoimmune diseases or disorders or a symptom thereof.

The combinations provided herein comprise the compounds disclosed herein and one or more additional active substances, such as:

a) Corticosteroids, such as prednisone, methylprednisolone or beta-methasone;
b) Immunosuppressants, such as cyclosporine, tacrolimus methotrexate, hydroxyurea, mycophenolate mofetil, mycophenolic acid, sulfasalazine, 6-thioguanine or azathioprine;
c) Fumaric acid esters, such as dimethyl fumarate;
d) Dihydroorotate dehydrogenase (DHODH) inhibitors such as leflunomide;
e) Retinoids, such as acitretin or isotretinoin;
f) Anti-inflammatories such as apremilast, crisaborole, celecoxib, diclofenac, aceclofenac, aspirin or naproxen;
g) JAK inhibitors such as tofacitinib, baricitinib, upadacitinib, ruxolitinib or delgocitinib;
h) Antibiotics such as gentamicin;
i) Anti-cancer agents such as lenalidomide, pomalidomide, pembrolizumab, nivolumab, daratumumab, bortezomib, carfilzomib, ixazomib, bendamustine or ventoclast;
j) T-cell blockers such as alefacept or efalizumab;
k) Tumor necrosis factor-alpha (TNF-alpha) blockers such as etanercept, adalimumab, infliximab, golimumab, certolizumab pegol;
l) interleukin 12/23 blockers such as ustekinumab;
m) IL-23 blockers such as risankizumab, guselkumab or tildrakizumab;
n) anti-IL4/IL13 antagonist such as dupilumab, lebrikizumab or tralokinumab;
o) IL-1β blockers such as canakinumab;
p) IL-alpha blockers such as bermekimab;
q) CD6 blockers such as itolizumab;
r) IL-36R blockers such as BI-655130 or bimekizumab;
s) IL-6 antagonist such as tocilizumab;
t) Calcineurin inhibitors such as pimecrolimus, tacrolimus or cyclosporine;
u) Phototherapy agents commonly employed in phototherapy such as psoralen, methoxypsoralen or 5-methoxypsoralen+UVA (PUVA) or treatment with UVB (with or without tar);
v) Fixed combinations of corticosteroids and vitamin D derivatives;
w) Fixed combinations of corticosteroids and retinoids;
x) Corticosteroid tapes; and
y) one or more agents selected from the group consisting of BMS986165, PF-06700841, PF-06826647, piclidenoson, tepilamide fumarate, LYC-30937, LEO-32731, BI-730357, PRCL-02, LNP-1955, GSK-2982772, CBP-307, KD-025, MP-1032, petesicatib, JTE-451, Hemay-005, SM-04755, EDP-1815, BI-730460, SFA-002 ER, JNJ-3534, SAR-441169, BOS-172767, SCD-044, ABBV-157, BAY-1834845, AUR-101, R-835, PBF-1650, RTA-1701, AZD-0284, mirikizumab, CD20 antagonist, salicylic acid, coal tar, Mical-1, DUR-928, AM-001, BMX-010, TA-102, SNA-125, brepocitinib tosylate, pegcantratinib, ESR-114, NP-000888, SM-04755, BOS-475, SB-414, LEO-134310, CBS-3595, PF-06763809, XCUR-17 or BTX-1308.

The active compounds in the combination, i.e the compounds disclosed herein, and the other optional active compounds may be administered together in the same pharmaceutical composition or in different compositions intended for separate, simultaneous, concomitant or sequential administration by the same or a different route.

Uses

The compounds or pharmaceutical compositions disclosed herein as described above may be used to modulate the activity of a retinoic acid receptor-related orphan receptor (ROR), such as a RORα, RORβ and/or RORγ receptor. Modulators of RORγ have been reviewed by B. Fauber and S. Magnuson in J. Med. Chem., Feb. 6, 2014, and Pandya et al in J. Med. Chem. 2018, 61, 24, 10976-10995 which hereby are incorporated by reference in its entirety. Examples of RORγ receptors are RORγ1 and RORγt receptors. The compounds or pharmaceutical compositions as described above may also display selective modulation of a particular ROR receptor relative to a different ROR receptor. For example, according to some embodiments disclosed herein some compounds or pharmaceutical compositions modulate the activity of an RORγ receptor to a larger extent than they modulate the activity of RORα and/or RORβ receptors.

The compounds or pharmaceutical compositions disclosed herein may also be used to modulate the activity of cells producing IL-17A in a RORγt dependent manner, for example, γδT cells, Th17 cells, Tc17 cells and ILC3 cells. The compounds or pharmaceutical compositions disclosed herein may also be used to inhibit RORγt function upon IL-23 stimulation, which in turn negatively impacts on the differentiation and expansion of pathogenic Tc17 and Th17.

Publications providing useful background information are Arthritis & Rheumatism, 2014, 66, 579-588; Curr Top Microbial Immun, 2014, 378, 171-182; Drug Disc. Today, 2014, May; Nature Rev. Drug Disc. 2012, 11, 763-776, and Nature Rev. Drug Disc., 2014, 13, 197-216, all of which are hereby incorporated by reference in their entirety.

The compounds or pharmaceutical compositions as described herein and above may also be used in therapy or may be used to treat inflammatory, metabolic, oncologic and autoimmune diseases or disorders or a symptom thereof. Examples of such diseases or disorders are inflammatory, metabolic, oncologic and autoimmune diseases or disorders mediated or affected by IL-17A and/or RORγ. The role of RORγ in the pathogenesis of autoimmune or inflammatory diseases has been disclosed in Immunity 2007, 26(5), 643-654; Nat. Rev. Immunol. 2006, 6, 205-217; J. Immunol. 2009, 183, 7169-7177; Brain Pathol. 2004, 14, 164-174; Brain 2007, 130, 1089-1104; and Nat Rev. Immunol. 2008, 8, 183-192 all of which are hereby incorporated by reference in their entirety.

More specific examples of diseases or disorders, or a symptom thereof include asthma, acne, chronic obstructive pulmonary disease (COPD), bronchitis, atherosclerosis, *Helicobacter pylori* infection, allergic diseases including allergic rhinitis, allergic conjunctivitis and uveitis, sprue and food allergy, atopic dermatitis, lichen planus, cystic fibrosis, lung allograph rejection, multiple sclerosis, rheumatoid arthritis, juvenile idiopathic arthritis, osteoarthritis, ankylosing spondylitis, psoriasis, psoriatic arthritis, ichtyoses, bullous diseases, hidradenitis suppurativa, steatosis, steatohepatitis, non-alcoholic fatty liver disease (NAFLD), non-alcoholic steatohepatitis (NASH), lupus erythematosus, Hashimoto's disease, pancreatitis, autoimmune diabetes, autoimmune ocular disease, ulcerative colitis, colitis, Crohn's disease, inflammatory bowel disease (IBD), inflammatory bowel syndrome (IBS), Sjogren's syndrome, optic neuritis, type I diabetes, neuromyelitis optica, Myasthenia Gravis, Guillain-Barre syndrome, Graves' disease, scleritis, obesity, obesity-induced insulin resistance, type II diabetes and cancer.

More preferably, the diseases or disorders, or a symptom thereof include acne, atopic dermatitis, lichen planus, multiple sclerosis, rheumatoid arthritis, juvenile idiopathic arthritis, osteoarthritis, ankylosing spondylitis, psoriasis, psoriatic arthritis, ichtyoses, bullous diseases, hidradenitis suppurativa, ulcerative colitis, colitis, Crohn's disease, inflammatory bowel disease (IBD) and lupus erythematosus.

An example of a symptom is a physical or mental feature which is regarded as indicating a condition of disease, particularly such a feature that is apparent to the patient, e.g. treating o preventing a symptom is not considered disease-modifying but preventing or alleviating one or more symptoms commonly experience in connection with such a disease.

More specifically, compounds or pharmaceutical compositions having an antagonistic or inverse agonistic effect on RORγ may be used to reduce levels of IL-17A and/or other gene products, such as interleukins, and cytokines, regulated RORγ. This may for example be in subjects suffering from for example, asthma, acne, chronic obstructive pulmonary disease (COPD), bronchitis, atherosclerosis, *Helicobacter pylori* infection, allergic diseases including allergic rhinitis, allergic conjunctivitis and uveitis, sprue and food allergy, atopic dermatitis, lichen planus, cystic fibrosis, lung allograph rejection, multiple sclerosis, rheumatoid arthritis, juvenile idiopathic arthritis, osteoarthritis, ichtyoses, bullous diseases, hidradenitis suppurativa, ankylosing spondylitis, psoriasis, psoriatic arthritis, steatosis, steatohepatitis, non-alcoholic fatty liver disease (NAFLD), non-alcoholic steatohepatitis (NASH), lupus erythematosus, Hashimoto's disease, pancreatitis, autoimmune diabetes, autoimmune ocular disease, ulcerative colitis, colitis, Crohn's disease, inflammatory bowel disease (IBD), inflammatory bowel syndrome (IBS), Sjogren's syndrome, optic neuritis, type I diabetes, neuromyelitis optica, Myasthenia Gravis, Guillain-Barre syndrome, Graves' disease, scleritis, obesity, obesity-induced insulin resistance and type II diabetes.

Conversely, compounds or pharmaceutical compositions having an agonistic effect on RORγ may be used to increase IL-17A levels. Increasing IL-17A levels may be particularly useful in immune compromised conditions or boosting the immune system response for example during infections and in cancer.

The compounds described herein may be used in the manufacture of a medicament for the treatment and/or prevention of inflammatory, metabolic, oncologic and autoimmune diseases or disorders or a symptom thereof.

Methods of Administration

The compounds or pharmaceutical compositions may be administered to the patient by any suitable means. Non-limiting examples of methods of administration include, among others, (a) administration though oral pathways, which administration includes administration in capsule, tablet, granule, spray, syrup, or other such forms; (b) administration through non-oral pathways such as rectal, vaginal, intraurethral, intraocular, intranasal, or intraauricular, which administration includes administration as an aqueous suspension, an oily preparation or the like or as a drip, spray, suppository, salve, ointment or the like; (c) administration via injection, subcutaneously, intraperitoneally, intravenously, intramuscularly, intradermally, intraorbitally, intracapsularly, intraspinally, intrasternally, or the like, including infusion pump delivery; (d) administration locally such as by injection directly in the renal or cardiac area, e.g., by depot implantation, by intratumoral injection, or by intralymph node injection; (e) administration topically; as well as (f) administration to cells ex vivo followed by insertion of said cells into the patient; as deemed appropriate by those of skill in the art for bringing the compound disclosed herein into contact with living tissue.

Pharmaceutical compositions suitable for administration include compositions where the active ingredients are contained in an amount effective to achieve its intended purpose. The therapeutically effective amount of the compounds disclosed herein required as a dose will depend on the route of administration, the type of animal, including mammal, e.g. human, being treated, and the physical characteristics of the specific animal under consideration. The dose can be tailored to achieve a desired effect, but will depend on such factors as weight, diet, concurrent medication and other factors which those skilled in the medical arts will recognize. More specifically, a therapeutically effective amount means an amount of compound effective to prevent, alleviate or ameliorate symptoms of disease or prolong the survival of the subject being treated. Determination of a therapeutically effective amount is well within the capability of those skilled in the art, especially in light of the detailed disclosure provided herein.

As will be readily apparent to one skilled in the art, the useful in vivo dosage to be administered and the particular mode of administration will vary depending upon the age, weight and mammalian species treated, the particular compounds employed, and the specific use for which these compounds are employed. The determination of effective dosage levels, that is the dosage levels necessary to achieve the desired result, can be accomplished by one skilled in the art using routine pharmacological methods. Typically, human clinical applications of products are commenced at lower dosage levels, with dosage level being increased until the desired effect is achieved. Alternatively, acceptable in vitro studies can be used to establish useful doses and routes of administration of the compositions identified by the present methods using established pharmacological methods.

In non-human animal studies, applications of potential products are commenced at higher dosage levels, with dosage being decreased until the desired effect is no longer achieved or adverse side effects disappear. The dosage may range broadly, depending upon the desired effects and the therapeutic indication.

Typically, dosages may be between about 10 microgram/kg and 100 mg/kg body weight, preferably between about 100 microgram/kg and 10 mg/kg body weight. Alternatively dosages may be based and calculated upon the surface area of the patient, as understood by those of skill in the art.

The exact formulation, route of administration and dosage for the pharmaceutical compositions disclosed herein can be chosen by the individual physician in view of the patient's condition. (See e.g., Fingl et al. 1975, in "The Pharmacological Basis of Therapeutics", which is hereby incorporated herein by reference in its entirety, with particular reference to Ch. 1, p. 1). Typically, the dose range of the composition administered to the patient can be from about 0.5 to 1000 mg/kg of the patient's body weight. The dosage may be a single one or a series of two or more given in the course of one or more days, as is needed by the patient. In instances where human dosages for compounds have been established for at least some condition, those same dosages may be used, or dosages that are between about 0.1% and 500%, more preferably between about 25% and 250% of the established human dosage. Where no human dosage is established, as will be the case for newly-discovered pharmaceutical compounds, a suitable human dosage can be inferred from $ED_{50}$ or $ID_{50}$ values, or other appropriate values derived from in vitro or in vivo studies, as qualified by toxicity studies and efficacy studies in animals.

It should be noted that the attending physician would know how to and when to terminate, interrupt, or adjust administration due to toxicity or organ dysfunctions. Conversely, the attending physician would also know to adjust treatment to higher levels if the clinical response were not adequate (precluding toxicity). The magnitude of an administrated dose in the management of the disorder of interest will vary with the severity of the condition to be treated and to the route of administration. The severity of the condition may, for example, be evaluated, in part, by standard prognostic evaluation methods. Further, the dose and perhaps the dose frequency will also vary according to the age, body weight, and response of the individual patient. A program comparable to that discussed above may be used in veterinary medicine.

Although the exact dosage will be determined on a drug-by-drug basis, in most cases, some generalizations regarding the dosage can be made. The daily dosage regimen for an adult human patient may be, for example, an oral dose of between 0.1 mg and 2000 mg of each active ingredient, preferably between 1 mg and 500 mg, e.g. 5 to 200 mg. An ocular eye drop may range in concentration between 0.005 and 5 percent. In one embodiment, an eye drop may range between 0.01 and 1 percent, or between 0.01 and 0.3 percent in another embodiment. In other embodiments, an intravenous, subcutaneous, or intramuscular dose of each active ingredient of between 0.01 mg and 100 mg, preferably between 0.1 mg and 60 mg, e.g. 1 to 40 mg is used. In cases of administration of a pharmaceutically acceptable salt, dosages may be calculated as the free base. In some embodiments, the composition is administered 1 to 4 times per day. Alternatively the compositions disclosed herein may be administered by continuous intravenous infusion, preferably at a dose of each active ingredient up to 1000 mg per day. As will be understood by those of skill in the art, in certain situations it may be necessary to administer the compounds disclosed herein in amounts that exceed, or even far exceed, the above-stated, preferred dosage range or frequency in order to effectively and aggressively treat particularly aggressive diseases or infections. In some embodiments, the compounds will be administered for a period of continuous therapy, for example for a week or more, or for months or years.

Dosage amount and interval may be adjusted individually to provide plasma or tissue levels of the active moiety which are sufficient to maintain the modulating effects, or minimal effective concentration (MEC). The MEC will vary for each compound but can be estimated from in vitro data. Dosages necessary to achieve the MEC will depend on individual characteristics and route of administration. However, HPLC assays or bioassays can be used to determine plasma concentrations.

Dosage intervals can also be determined using MEC value. Compositions should be administered using a regimen which maintains plasma levels above the MEC for 10-90% of the time, preferably between 30-90% and most preferably between 50-90%.

In cases of local or ex vivo administration or selective uptake, the effective local concentration of the drug may not be related to plasma concentration.

The amount of composition administered may be dependent on the subject being treated, on the subject's weight, the severity of the affliction, the manner of administration and the judgment of the prescribing physician.

Compounds disclosed herein can be evaluated for efficacy and toxicity using known methods. For example, the toxicology of a particular compound, or of a subset of the compounds, sharing certain chemical moieties, may be established by determining in vitro toxicity towards a cell line, such as a mammalian, and preferably human, cell line. The results of such studies are often predictive of toxicity in animals, such as mammals, or more specifically, humans. Alternatively, the toxicity of particular compounds in an animal model, such as mice, rats, rabbits, or monkeys, may be determined using known methods. The efficacy of a particular compound may be established using several recognized methods, such as in vitro methods, animal models, or human clinical trials. Recognized in vitro models exist for nearly every class of condition, including but not limited to cancer, cardiovascular disease, and various immune dysfunction. Similarly, acceptable animal models may be used to establish efficacy of chemicals to treat such conditions. When selecting a model to determine efficacy, the skilled artisan can be guided by the state of the art to choose an appropriate model, dose, and route of administration, and regime. Of course, human clinical trials can also be used to determine the efficacy of a compound in humans.

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration. The pack or dispenser may also be accompanied with a notice associated with the container in form prescribed by a governmental agency regulating the manufacture, use, or sale of pharmaceuticals, which notice is reflective of approval by the agency of the form of the drug for human or veterinary administration. Such notice, for example, may be the labeling approved by the U.S. Food and Drug Administration for prescription drugs, or the approved product insert. Compositions comprising a compound disclosed herein formulated in a compatible pharmaceutical carrier may also be prepared, placed in an appropriate container, and labeled for treatment of an indicated condition.

General Remarks

As described above with reference to specific illustrative embodiments, it is not intended to be limited to the specific form set forth herein. Any combination of the above mentioned embodiments should be appreciated as being within the scope of the disclosure. Rather, the disclosure is limited only by the accompanying claims and other embodiments than the specific above are equally possible within the scope of these appended claims.

In the claims, the term "comprises/comprising" does not exclude the presence of other species or steps. Additionally, although individual features may be included in different claims, these may possibly advantageously be combined, and the inclusion in different claims does not imply that a combination of features is not feasible and/or advantageous. In addition, singular references do not exclude a plurality. The terms "a", "an", "first", "second" etc. do not preclude a plurality. The phrases "at least one" or "one or more" refer to 1 or a number greater than 1, such as to 1, 2, 3, 4, 5, 6, 7, 8, 9, or 10.

Whenever a chemical name or structure has been given it has been generated by conventional means or by means of a suitable software. Names for the compounds were generated with Chem Draw Professional, version 17.1.0.105 (19).

In the present disclosure, in the drawings of the structures, the labels "or n", "or 2", "&1", or "&2" at each stereogenic center specify the "stereochemical group" to which the center belongs.

In the case of the "or" groups, the meaning is a structure that represents one stereoisomer that has either the "stereochemical group" as drawn ((R, S), for instance) or the stereoisomer in which the stereogenic centers of the group have the opposite configuration (S, R).

In the case of the "&" groups, & in combination with the number given (e.g. &1) indicate a mixture of the marked asymmetrically substituted atoms. When the numbering pools several asymmetrically substituted atoms together this displays their configuration relative to each other. If they are displayed as (R,S) the opposite configuration (S,R) is also present for the specified pooled group.

In the present disclosure, the symbol " specifies enantiomerically enriched. Any compound or intermediate synthesized in a enantiomerically enriched manner and where no chiral separation has been performed is identified with ".

Experimental

The following examples are mere examples and should by no mean be interpreted to limit the scope of the disclosure. Rather, the disclosure is limited only by the accompanying claims.

General Chemical Procedures

General

Unless otherwise stated, starting materials were obtained from commercial suppliers, such as (but not limited to); AbBchem, ABCR, Alfa Aesar, Anaspec, Anichem, Apollo Scientific, ASDI-Inter, Asiba Pharmatech, Astatech, ArkPharm, Bachem, Chem-Impex, ChemCollect, Chembridge, Combi-Blocks, Enamine, FCH, Fluka, Fluorochem, Frontier Scientific, HDH Pharma, InFarmatik, InterBioScreen, Life Chemicals, Manchester organics, Matrix, MercaChem, NetChem, Oakwood Chemical, PepTech, Pharmcore, PrincetonBio, Sigma-Aldrich, TRC, Tyger Scientific and Ukrorgsyn, and were used without further purification. Solvents such as DMF, DMSO and DCM, etc were used directly or dried over molecular sieves.

Equipment

NMR $^1$H NMR spectra were recorded on the following; Bruker Avance 300 spectrometer (at 300 MHz), Bruker Avance III 400 spectrometer (at 400 MHz), Bruker Avance Neo (400 MHz), Bruker Avance III 600 (at 600 MHz), Varian VNMR spectrometer (at 400 MHz) using $CD_3OD$, $CDCl_3$ or $DMSO-d_6$ solvents. Chemical shifts are reported in ppm (δ) using residual solvent as an internal standard; $CDCl_3$: 7.26 ppm; $CD_3OD$: 3.31; $DMSO-d_6$: 2.50 ppm. Coupling constants (J) are given in Hz.

Analytical U/HPLC

The following equipment was used for analytical U/HPLC:

Waters Acquity system equipped with an Acquity BEH C18 (1.7 µm, 2.1×50 mm) with a linear gradient of a binary solvent system using a flow rate of 0.5 mL/min and DAD at ambient temperature, combined with MS detection SQD I. Agilent Infinity I/II-TOF6230B/CLND Antek 8060 equipped with Acquity BEH C18 (1.7 µm, 2.1×50 mm) with a linear gradient of a binary solvent system using a flow rate of 0.75 mL/min combined with DAD.

Agilent 1200 series-1260 Infinity equipped with a Waters XBridge C18 (5 µm, 4.6×50 mm) with a linear gradient of a binary solvent system using a flow rate of 1.5 mL/min and UV detection at 214 nm or 254 nm, combined with MS detection (Agilent).

Shimadzu Nexera equipped with a Waters XBridge C18 (5 µm, 4.6×50 mm) with a linear gradient of a binary solvent system using a flow rate of 1.5 mL/min and UV detection at 214 nm or 254 nm, combined with MS detection (Shimadzu).

Waters Acquity system equipped with an Acquity BEH C18 (1.7 µm, 2.1×50 mm) with a linear gradient of a binary solvent system using a flow rate of 0.65 mL/min and DAD at ambient temperature, combined with MS detection Waters spectrometer.

Preparative HPLC

The following equipment was used for Prep-HPLC:

Waters Acquity system equipped with a Supelco DISCOVERY C18 (5 µm, 25 cm×21.2 mm), with a linear gradient of a binary solvent system using a flow rate of 45 mL/min and UV detection at 254 nm, combined with MS detection on a Waters Micromass ZQ Quadrupole MS.

Shimadzu Nexera X2 equipped with a Merck Chromolith SpeedROD RP-18E (5 µm, 10×100 mm) with a linear gradient of a binary solvent system using a flow rate between 4 and 7 mL/min and UV detection at 254 nm, combined with MS detecting on a Shimadzu LCMS-2020.

Waters Masslynx system equipped with a Waters XBridge C18 column (5 µm, 19×150 mm) with a linear gradient of a binary solvent system using a flow rate of 15 mL/min and UV detection at 214 nm or 254 nm, combined with MS detection (Waters).

Gilson GX-281 TRILUTION equipped with a Phenomenex Gemini NX—C18 column (5 µm, 21.2×150 mm) with a linear gradient of a binary solvent system using a flow rate of 15 mL/min and UV detection at 214 nm or 254 nm, combined with MS detection (Waters).

The following linear gradients have been used:

$HCO_2H$—($H_2O/CH_3CN/HCO_2H$ (100/0/0.1% to 0/100/0.1%))

$NH_4OAc$—($H_2O/CH_3CN/NH_4OAc$ (100/0/0.02% to 0/100/0.02%))

TFA—($H_2O/CH_3CN$/TFA (100/0/0.1% to 0/100/0.1%))

$NH_4HCO_3$—($H_2O/CH_3CN/NH_4HCO_3$ (100/0/0.1% to 0/100/0.1%))

$NH_4OH$—($H_2O/CH_3CN/NH_4OH$ (100/0/0.1% to 0/100/0.1%))

$HCO_2NH_4$—($H_2O$/50% MeOH+50% $CH_3CN/HCO_2H/NH_3$ (95/5/0.05%/0.01% to 5/95/0.05%/0.01%))

Flash CC was most often performed on an Isolera® automated systems. Flash CC and Prep TLC were performed employing $SiO_2$, if not otherwise mentioned. However, C18 columns have also been employed (using a gradient of water-acetonitrile/MeOH (1:1), with or without 0.1% v/v ammonium formate in both phases, from 0% to 100% acetonitrile/MeOH (1:1)).

Analytical Chiral Chromatography

Was performed on a Waters UPC2 system coupled to a DAD detector and a Waters QDa MS detector, equipped with a chiral column with gradient elution using a flow rate of 1 mL/min. The available chiral columns were CHIRALPAK (3 µm, 4.6×100 mm) IA, IB, IC and ID and Trefoil AMY1 (2.5 µm, 2.1×150 mm). The following linear gradients have been used for analytical UPC2:

$CO_2$/MeOH/DEA (99/1/0.2% to 60/40/0.2%))

$CO_2$/EtOH/DEA (99/1/0.2% to 60/40/0.2%)

$CO_2$/IPA/DEA (99/1/0.2% to 60/40/0.2%)

Preparative Chiral Chromatography

Before chiral separation, compounds were purified by the standards methods previously described using the appropriate solvents.

Preparative chiral separations were performed either on a Gilson (306, GX-281 trilution, 156-UV/Vis, Waters 3100 MSD), or a Waters SFC-80, equipped with a chiral column with the solvents specified using flow rates between 10-50 mL/min (only 50 g/min for SCF) and detection at either 214 or 230 nm; The available chiral columns were Reprosil AMS (5 µm, 20 mm×250 mm), Lux $C_2$ (5 µm, 21.2 mm×250 mm), Lux C4 (5 µm, 21.2 mm×250 mm), Chiralpak© column IA, IB, IC, ID, IF or IG (5 µm, 20 mm×250 mm) or Chiralcel® OJ-H or OD-H. Exact column and elution conditions used for each compound are described in the experimental part.

Synthetic Methods

The compounds disclosed herein may be synthesized by one of the following three general methods: General Method K, General Method L, General Method P, General Method 2P-4P, General Method R, General Method 2R, and General Method Q.

General Method K—Mitsunobu Alkylation

General Scheme K

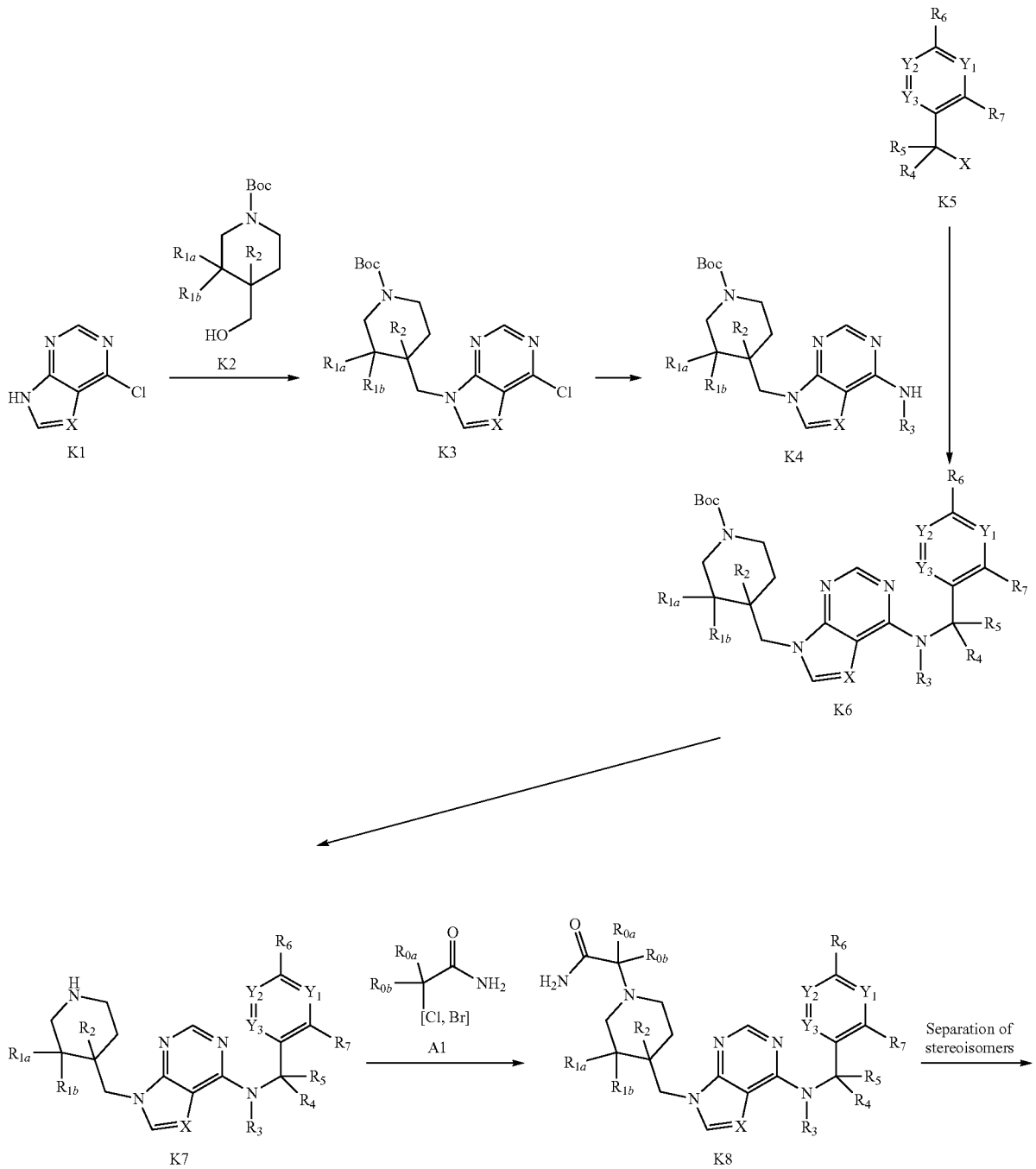

In a Mitsunobu type reaction the pyrrolopyrimidine K1 was alkylated with the primary alcohol K2 using PPh$_3$ and DIAD to form K3. K3 was then subjected to a NAS reaction with a primary alkylamine (often without an extra base) such as DIEA or TEA to produce K4. K4 was then alkylated with a benzyl halide, K5, using NaH in DMF to produce K6. The following Boc deprotection (HCl in dioxane or TFA) gave K7. K7 was then most often used directly, as the corresponding pyridinium salt (HCl of TFA), in the subsequent alkylation with the corresponding 2-haloacetamide A1 and a suitable base, such as K$_2$CO$_3$ or DIEA, to yield K8. In the cases when K8 were racemic or diastereomeric mixtures they were often (but not always) subjected to chiral chromatography to obtain the single stereoisomers.

Example K8-1

Synthesis 2-(4-((4-(cyclopropyl(4-(trifluoromethyl)benzyl)amino)-7H-pyrrolo[2,3-d]pyrimidin-7-yl)methyl)-3,3-difluoropiperidin-1-yl)acetamide and chiral Separation to its stereoisomers K8-1-1 and K8-1-2.

Scheme K8-1

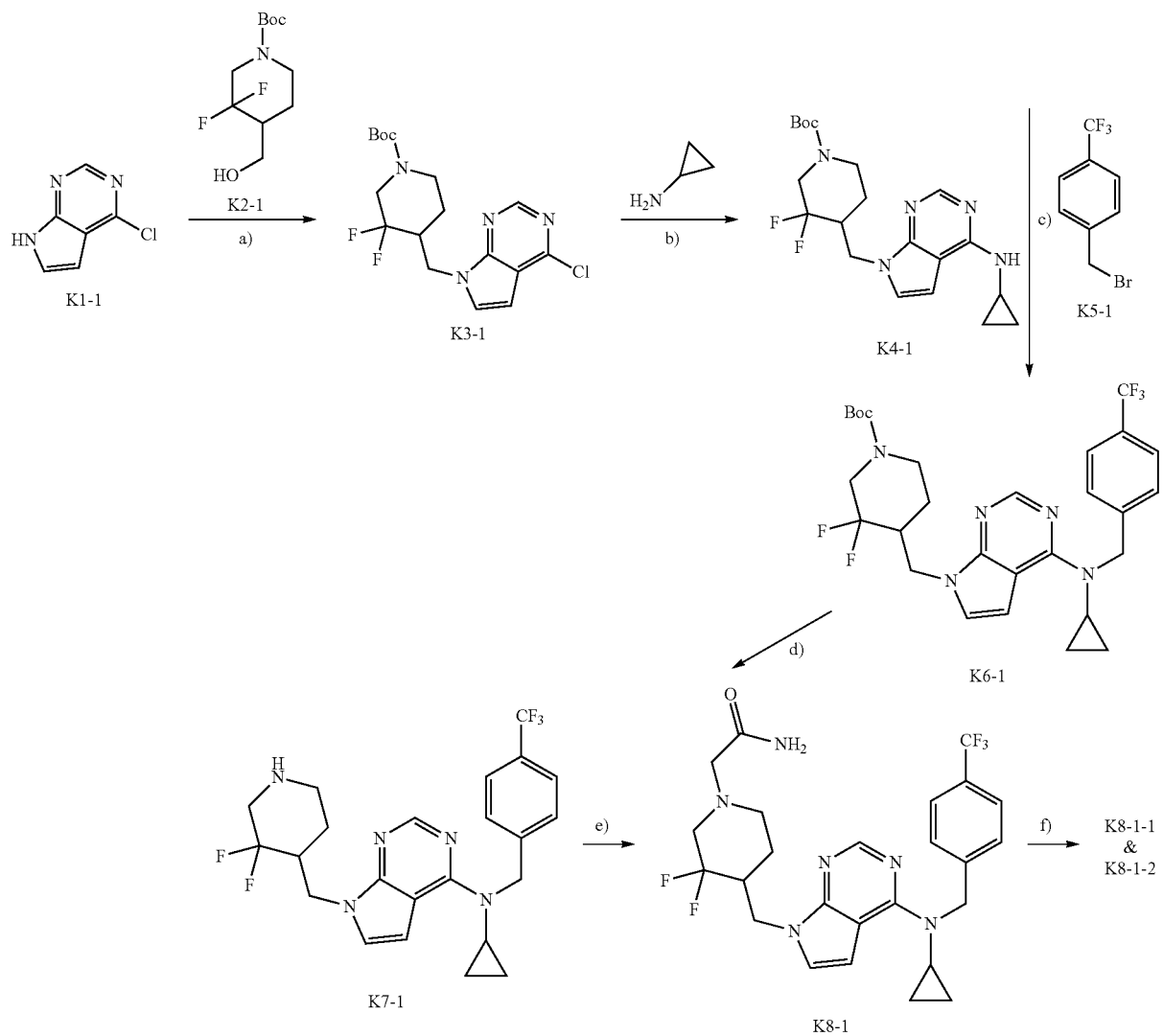

a) PPh₃, DIAD, DCM. b) Cyclopropylamine, EtOH. c) NaH, DMF. d) HCl, EA. e) K₂CO₃, 2-bromoacetamide, DMF. f) Chiral separation.

tert-Butyl 4-((4-chloro-7H-pyrrolo[2,3-d]pyrimidin-7-yl)methyl)-3,3-difluoropiperidine-1-carboxylate, K3-1.

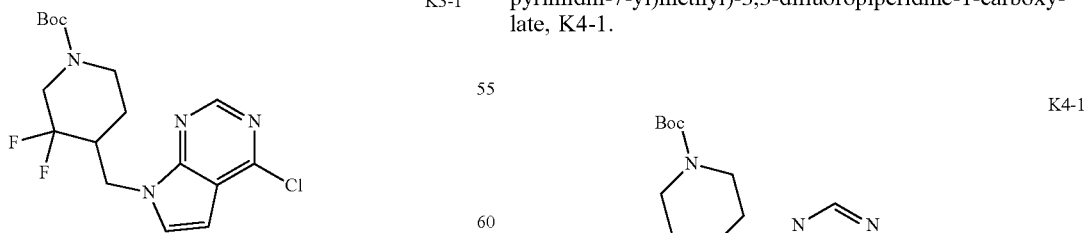

Under a N₂ atm DIAD (362 mg, 1.8 mmol), PPh₃ (626 mg, 2.39 mmol) and K2-1, tert-butyl 3,3-difluoro-4-(hydroxymethyl)piperidine-1-carboxylate, (300 mg, 2.0 mmol) was added to a cold (0° C.) solution of K1-1 (274 mg, 1.8 mmol) and in dry DCM (30 mL). The reaction was then allowed to reach rt and stirred on. Concentration under reduced pressure gave the crude product that was purified by Flash CC (PE:EA=10:1 to 8:1) to give K3-1.

LCMS: MS Calcd.: 386; MS Found: 387 ([M+H]⁺).

tert-Butyl 4-((4-(cyclopropylamino)-7H-pyrrolo[2,3-d]pyrimidin-7-yl)methyl)-3,3-difluoropiperidine-1-carboxylate, K4-1.

Cyclopropyl amine (127 mg, 2.23 mmol) was added to a solution of K3-1 (430 mg, 1.11 mmol) in EtOH (15 mL). The vial was sealed and then heated to 83° C. on. The mixture was concentrated in vacuo, and the residue was purified by Flash CC (PE:EA=5:1 to 4:1) to yield K4-1.

LCMS: MS Calcd.: 407; MS Found: 408 ([M+H]$^+$).

tert-Butyl 4-((4-(cyclopropyl(4-(trifluoromethyl)benzyl)amino)-7H-pyrrolo[2,3-d]pyrimidin-7-yl)methyl)-3,3-difluoropiperidine-1-carboxylate, K6-1.

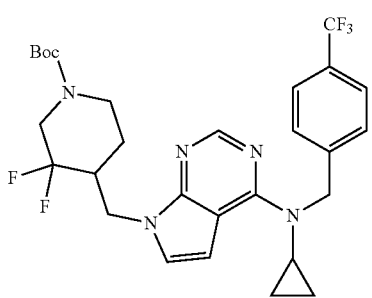

K6-1

NaH (33 mg, 1.37 mmol) was added to a solution of K4-1 (279 mg, 0.69 mmol) and 1-(bromomethyl)-4-(trifluoromethyl)benzene, K5-1, (180 mg, 0.75 mmol) in dry DMF (10 mL). The reaction was then stirred at rt for 3 h. The reaction was then quenched with H$_2$O (30 mL) and the mixture was extracted with EA (3×20 mL). The combined organic phase was dried (Na$_2$SO$_4$) filtered and concentrated in vacuo. Purification of the residue by Flash CC (PE:EA=10:1 to 4:1) gave K6-1.

LCMS: MS Calcd.: 565; MS Found: 566 ([M+H]$^+$).

N-Cyclopropyl-7-((3,3-difluoropiperidin-4-yl)methyl)-N-(4-(trifluoromethyl)benzyl)-7H-pyrrolo[2,3-d]pyrimidin-4-amine.HCl, K7-1.

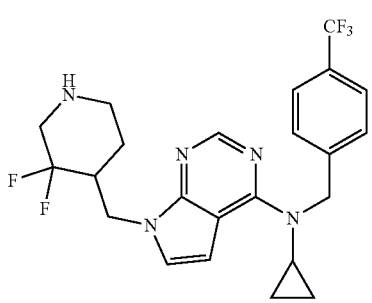

K7-1

K6-1 (240 mg, 0.43 mmol) was dissolved in EA/HCl (15 mL) and then stirred at rt for 30 min. Concentration in vacuo gave crude K7-1 that was used without further purification.

LCMS: MS Calcd.: 465; MS Found: 466 ([M+H]$^+$).

2-(4-((4-(Cyclopropyl(4-(trifluoromethyl)benzyl)amino)-7H-pyrrolo[2,3-d]pyrimidin-7-yl)methyl)-3,3-difluoropiperidin-1-yl)acetamide, K8-1.

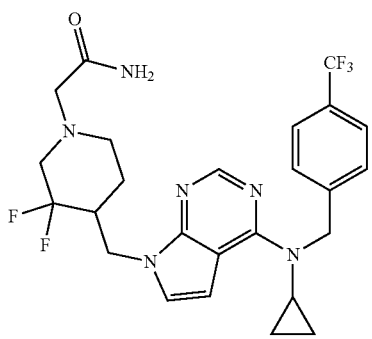

K8-1

K$_2$CO$_3$ (590 mg, 4.24 mmol) and then 2-bromoacetamide (59 mg, 0.424 mmol) were in turn added to a solution of K7-1 (213 mg, 0.424 mmol) in dry DMF (20 mL). The reaction was stirred at 50° C. on and then quenched with H$_2$O (30 mL). The mixture was extracted with EA (3×20 mL) and the combined organic phase was concentrated in vacuo. The residue thereof was purified by Flash CC (PE:EA=1:3) to give K8-1.

Isolation of the two stereoisomers rel-(R)-2-(4-((4-(cyclopropyl(4-(trifluoromethyl)benzyl)amino)-7H-pyrrolo[2,3-d]pyrimidin-7-yl)methyl)-3,3-difluoropiperidin-1-yl)acetamide, K8-1-1 and K8-1-2.

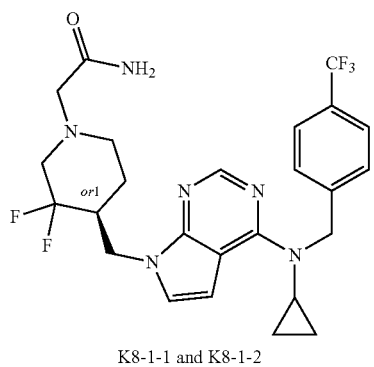 [SMILES: NC(=O)CN1CC[C@@H](Cn2ccc3c(N(Cc4ccc(C(F)(F)F)cc4)C4CC4)ncnc32)C(F)(F)C1]

K8-1-1 and K8-1-2

K8-1 (140 mg) was then subjected to chiral chromatography, to yield the optically pure compounds: K8-1-1 (1$^{st}$ eluting isomer) and K8-1-2 (2$^{nd}$ eluting isomer).

The following compounds were synthesized according to General Method K:

| K2 | K5 | K8 |
|---|---|---|
| K2-2 rac-tert-butyl (3R,4R)-3-fluoro-4-(hydroxymethyl)piperidine-1-carboxylate | K5-1 | K8-2-1 rel-2-((3R,4R)-4-((4-(cyclopropyl(4-(trifluoromethyl)benzyl)amino)-7H-pyrrolo[2,3-d]pyrimidin-7-yl)methyl)-3-fluoropiperidin-1-yl)acetamide 1$^{st}$ eluting isomer |
| K2-2 | K5-1 | K8-2-2 rel-2-((3R,4R)-4-((4-(cyclopropyl(4-(trifluoromethyl)benzyl)amino)-7H-pyrrolo[2,3-d]pyrimidin-7-yl)methyl)-3-fluoropiperidin-1-yl)acetamide 2$^{nd}$ eluting isomer |
| K2-1 | K5-2 2-(bromomethyl)-5-(trifluoromethyl)pyridine | K8-3-1 rel-2-((3R,4R)-4-((4-(cyclopropyl((5-(trifluoromethyl)pyridin-2-yl)methyl)amino)-7H-pyrrolo[2,3-d]pyrimidin-7-yl)methyl)-3-fluoropiperidin-1-yl)acetamide 1$^{st}$ eluting isomer |
| K2-1 | K5-2 | K8-3-2 rel-2-((3R,4R)-4-((4-(cyclopropyl((5-(trifluoromethyl)pyridin-2-yl)methyl)amino)-7H-pyrrolo[2,3-d]pyrimidin-7-yl)methyl)-3-fluoropiperidin-1-yl)acetamide 2$^{nd}$ eluting isomer |

General Method P:

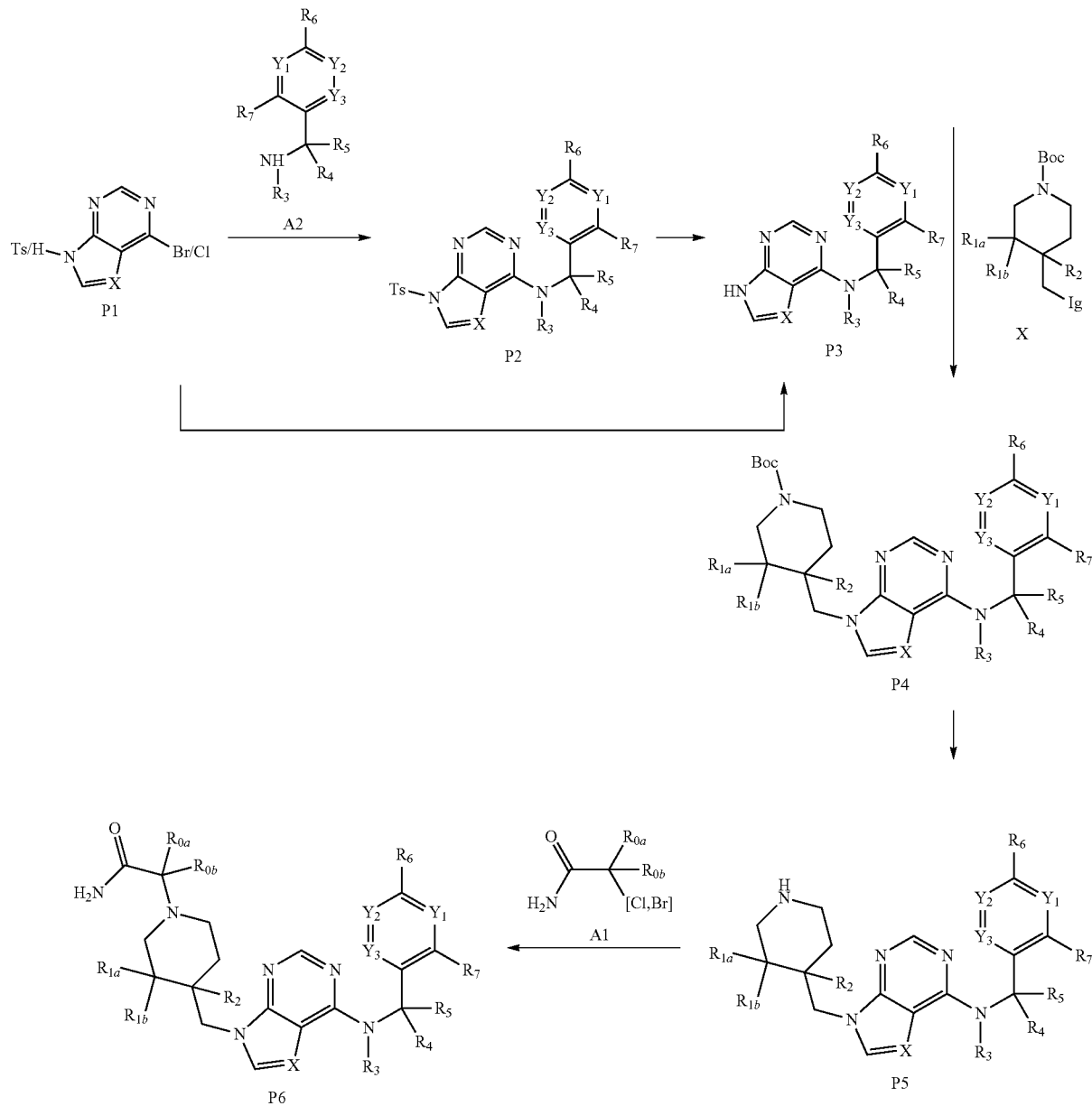

General Scheme P

The nuclear aromatic substitution (NAS) reaction between P1 and A2 gave P2, or P3 (if N-Ts was N—H) were performed in a suitable solvent (such as; DMF, DMSO, EtOH, BuOH, water) and an appropriate base (such as; DIEA, TEA or $K_2CO_3$) at an elevated temperature (80-130° C.) in a sealed vessel, often (but not always) using an additive (such as KI). The Ts-group was thereafter removed by using $K_2CO_3$ or NaOH at a slightly elevated temperature (typically 50° C.) to yield P3.

P3 was then reacted together with the Boc protected piperidine X and the subsequent Boc deprotection of P4 (employing as HCl in dioxane or TFA) gave P5 as a salt. P5 was most often used directly, as the corresponding pyridinium salt (HCl or TFA), in the following alkylation with A1 and a suitable base (such as DIEA, TEA, $Cs_2CO_3$ or $K_2CO_3$) to yield P6.

In the cases when P6 were mixtures of stereoisomers they were often (but not always) subjected to chiral chromatography to obtain the single stereoisomers as the end products.

The A2 building blocks were synthesized in accordance with the general methods described in WO2016020288 (page 167-176) or as outlined below.

Example P6-1

Synthesis of rac-2-((3R,4R)-3-hydroxy-4-((4-((S)-3-(4-(trifluoromethyl)phenyl)morpholino)-7H-pyrrolo[2,3-d]pyrimidin-7-yl)methyl)piperidin-1-yl)acetamide, P8-1, and separation of stereoisomers, P6-1-1 and P6-1-2.

Scheme P6-1

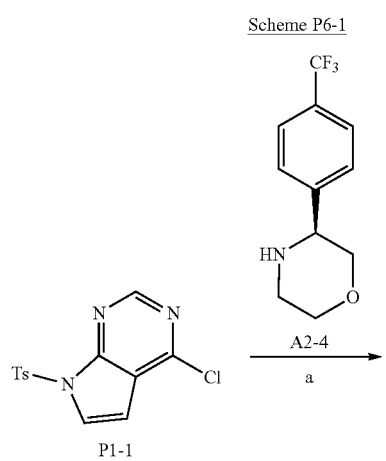

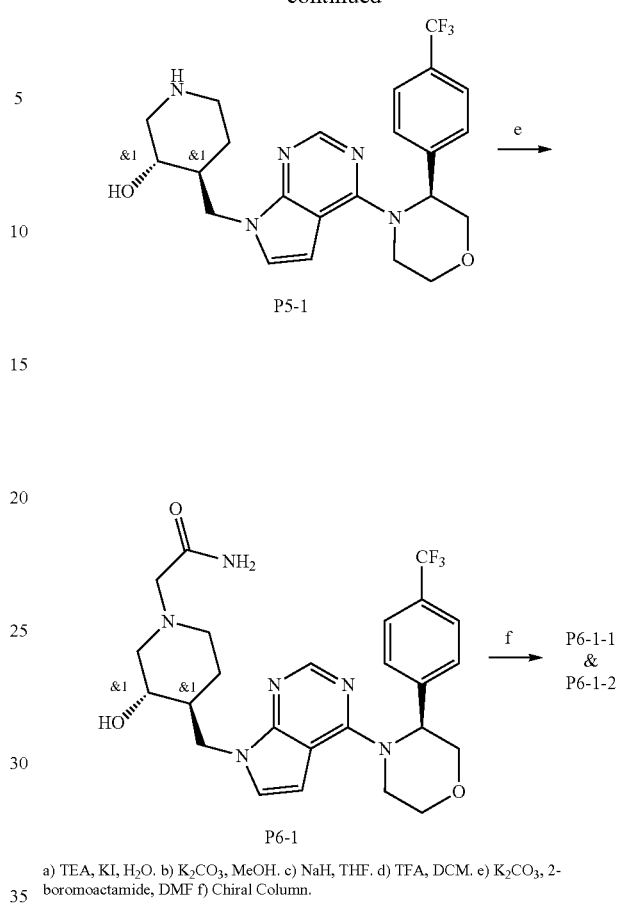

a) TEA, KI, H₂O. b) K₂CO₃, MeOH. c) NaH, THF. d) TFA, DCM. e) K₂CO₃, 2-boromoactamide, DMF f) Chiral Column.

(S)-4-(7-Tosyl-7H-pyrrolo[2,3-d]pyrimidin-4-yl)-3-(4-(trifluoromethyl)-phenyl)morpholine, P2-1

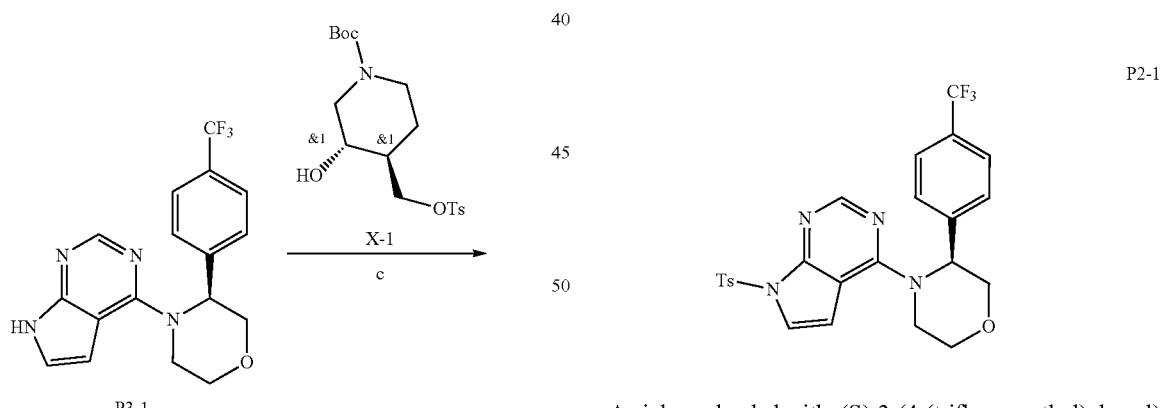

A vial was loaded with; (S)-3-(4-(trifluoromethyl)phenyl) morpholine, A2-4 (680 mg, 2.5 mmol), 1 4-chloro-7-tosyl-7H-pyrrolo[2,3-d]pyrimidine (0.84 mg, 2.75 mmol), KI (210 mg, 1.8 mmol), TEA (760 mg, 7.5 mmol) and H₂O (10 mL). The vial was sealed, and then stirred at 130° C. on. After cooling to rt, the vial was opened and extracted with EA (3×15 mL). The combined organic phase was then concentrated in vacuo to yield crude P2-1 that was used without further purification.

LCMS: MS Calcd.: 502; MS Found: 503 ([M+H]⁺).

(S)-4-(7H-pyrrolo[2,3-d]pyrimidin-4-yl)-3-(4-(trifluoromethyl)phenyl)-morpholine, P3-1.

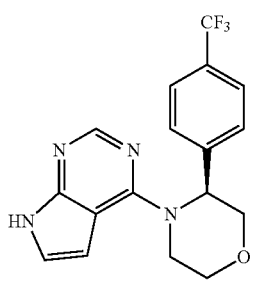

P3-1

K₂CO₃ (1.45 g, 10.5 mmol) was added to a solution of P2-1 (1.05 g, 2.1 mmol) in MeOH (15 mL). The reaction was heated to 50° C. for 6 h. After cooling to rt, the reaction was extracted with EA (3×20 mL). The combined organic phase was concentrated in vacuo. The residue was purified by Flash CC (PE:EA=5:1 to 1:1) to give P3-1.

LCMS: MS Calcd.: 348; MS Found: 349 ([M+H]⁺).

tert-Butyl (3RS,4RS)-3-hydroxy-4-((4-((S)-3-(4-(trifluoromethyl)phenyl)morpholino)-7H-pyrrolo[2,3-d]pyrimidin-7-yl)methyl)piperidine-1-carboxylate P4-1.

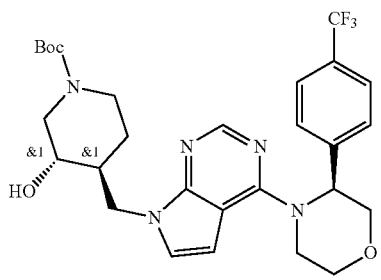

P4-1

Under N₂ atm NaH was added to an ice cooled solution of P3-1 in dry THF (5 mL). After 20 min a solution of X-1 in dry THF (2 mL) was added drop-wise and the reaction. After the addition was complete the reaction was heated to 65° C. on. The reaction was quenched with NH₄Cl (sat aq 20 mL) and H₂O (20 mL) and the resulting mixture was extracted with DCM (2×50 mL). The combined organic layer was washed with H₂O (20 mL), brine (20 mL), dried (Na₂SO₄), filtered and concentrated in vacuo. The residue was then purified by Flash CC (MeOH:DCM=1:10) to yield P4-1.

LCMS: MS Calcd.: 561; MS Found: 506 ([M−56+H]⁺).

(3RS,4RS)-4-((4-((S)-3-(4-(trifluoromethyl)phenyl)morpholino)-7H-pyrrolo[2,3-d]pyrimidin-7-yl)methyl)piperidin-3-ol, P5-1.

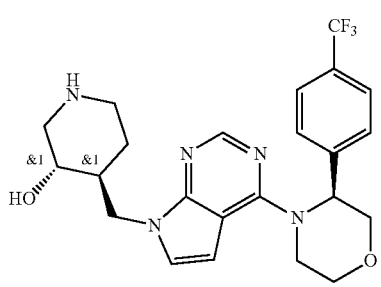

P5-1

Under N₂ atm TFA (4 mL) was added to a solution of P4-1 (90 mg, 0.16 mmol) in DCM (4 mL) and the reaction was stirred a rt for 3 h. Concentration in vacuo gave crude P5-1 that was used without further purification.

LCMS: MS Calcd.: 461; MS Found: 462 ([M+H]⁺).

2-((3RS,4RS)-3-hydroxy-4-((4-((S)-3-(4-(trifluoromethyl)phenyl)morpholino)-7H-pyrrolo[2,3-d]pyrimidin-7-yl)methyl)piperidin-1-yl)acetamide, P6-1.

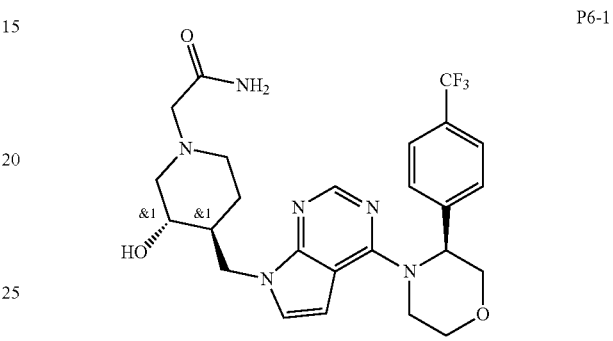

P6-1

Under N₂ atm K₂CO₃ (88 mg, 0.64 mmol) and thereafter 1-bromoacetoamide (27 mg, 0.19 mmol) was added to a suspension of crude P5-1 (110 mg) in dry DMF (4 mL). The reaction was then allowed to stir on and thereafter quenched with H₂O (40 mL). The resulting mixture was extracted with DCM (2×50 mL). The combine organic layer was washed with H₂O (40 mL), brine (40 mL), dried (Na₂SO₄) filtered and concentrated in vacuo. The crude was thereafter purified by Flash CC (MeOH:DCM=1:10) to yield P6-1.

Isolation of the two stereoisomers 2-((3R*,4R*)-3-hydroxy-4-((4-((S)-3-(4-(trifluoromethyl)phenyl)morpholino)-7H-pyrrolo[2,3-d]pyrimidin-7-yl)methyl)piperidin-1-yl)acetamide, P6-1-1 and P6-1-2.

P6-1-1 and P6-1-2

P6-((70 mg) was then subjected to chiral chromatography, to yield the stereoisomers: P6-1-1 (1ˢᵗ eluting isomer) and P6-1-2 (2ⁿᵈ eluting isomer).

The following compounds were synthesized according to General Method P:

| P1 | A2 | X | P6 |
|---|---|---|---|
| P1-1<br>4-chloro-7-tosyl-7H-pyrrolo[2,3-d]pyrimidine | A2-2<br>3-(4-(trifluoromethyl)phenyl)morpholine | X-2<br>tert-butyl 4-(bromomethyl)piperidine-1-carboxylate | P6-2-1<br>rel-(R)-2-(4-((4-(3-(4-(trifluoromethyl)phenyl)morpholino)-7H-pyrrolo[2,3-d]pyrimidin-7-yl)methyl)piperidin-1-yl)acetamide<br>1st eluting isomer |
| P1-1 | A2-2 | X-2 | P6-2-2<br>rel-(R)-2-(4-((4-(3-(4-(trifluoromethyl)phenyl)morpholino)-7H-pyrrolo[2,3-d]pyrimidin-7-yl)methyl)piperidin-1-yl)acetamide<br>2nd eluting isomer |
| P1-1 | A2-5<br>rel-(R)-3-(3-(trifluoromethyl)phenyl)morpholine | X-1<br>rac-tert-butyl (3R,4R)-3-hydroxy-4-((tosyloxy)methyl)piperidine-1-carboxylate | P6-3-1<br>rel-2-((3R,4R)-3-hydroxy-4-((4-((R)-3-(3-(trifluoromethyl)phenyl)morpholino)-7H-pyrrolo[2,3-d]pyrimidin-7-yl)methyl)piperidin-1-yl)acetamide<br>OR<br>rel-2-((3R,4R)-3-hydroxy-4-((4-((S)-3-(3-(trifluoromethyl)phenyl)morpholino)-7H-pyrrolo[2,3-d]pyrimidin-7-yl)methyl)piperidin-1-yl)acetamide<br>1st eluting isomer |
| P1-1 | A2-5 | X-1 | P6-3-2<br>rel-2-((3R,4R)-3-hydroxy-4-((4-((R)-3-(3-(trifluoromethyl)phenyl)morpholino)-7H-pyrrolo[2,3-d]pyrimidin-7-yl)methyl)piperidin-1-yl)acetamide<br>OR |

-continued

| P1 | A2 | X | P6 |
|---|---|---|---|
| | | | rel-2-((3R,4R)-3-hydroxy-4-((4-((S)-3-(3-(trifluoromethyl)phenyl)morpholino)-7H-pyrrolo[2,3-d]pyrimidin-7-yl)methyl)piperidin-1-yl)acetamide 2nd eluting isomer |
| P1-1 | A2-6 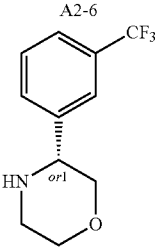 rel-(R)-3-(3-(trifluoromethyl)phenyl) morpholine | X-1 | P6-4-1 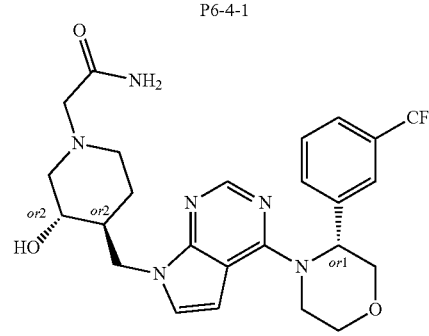 rel-2-((3R,4R)-3-hydroxy-4-(4-((R)-3-(3-(trifluoromethyl)phenyl)morpholino)-7H-pyrrolo[2,3-d]pyrimidin-7-yl)methyl)piperidin-1-yl)acetamide OR rel-2-((3R,4R)-3-hydroxy-4-((4-((S)-3-(3-(trifluoromethyl)phenyl)morpholino)-7H-pyrrolo[2,3-d]pyrimidin-7-yl)methyl)piperidin-1-yl)acetamide 1st eluting isomer |
| P1-1 | A2-6 | X-1 | P6-4-2 rel-2-((3R,4R)-3-hydroxy-4-(4-((R)-3-(3-(trifluoromethyl)phenyl)morpholino)-7H-pyrrolo[2,3-d]pyrimidin-7-yl)methyl)piperidin-1-yl)acetamide OR rel-2-((3R,4R)-3-hydroxy-4-(4-((S)-3-(3-(trifluoromethyl)phenyl)morpholino)-7H-pyrrolo[2,3-d]pyrimidin-7-yl)methyl)piperidin-1-yl)acetamide 2nd eluting isomer |
| P1-2 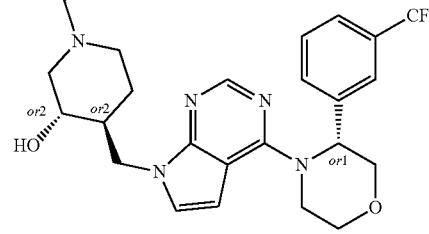 4-chloro-5-fluoro-7H- | A2-1 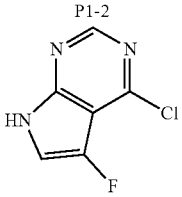 N-(4-(trifluoromethyl) | X-2 | P6-5 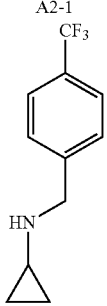 2-(4-((4-(cyclopropyl(4-(trifluoromethyl)benzyl)amino)- |

-continued

| P1 | A2 | X | P6 |
|---|---|---|---|
| pyrrolo[2,3-d]pyrimidine | benzyl)cyclopropanamine | | 5-fluoro-7H-pyrrolo[2,3-d]pyrimidin-7-yl)methyl)piperidin-1-yl)acetamide |
| P1-3 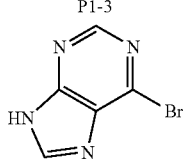 6-bromo-9H-purine | A2-1 | X-2 | P6-6  2-(4-((6-(cyclopropyl(4-(trifluoromethyl)benzyl)amino)-9H-purin-9-yl)methyl)piperidin-1-yl)acetamide |
| P1-4  4-chloro-7H-pyrrolo[2,3-d]pyrimidine-5-carbonitrile | A2-1 | X-2 | P6-7 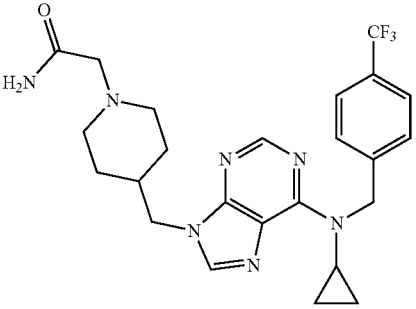 2-(4-((5-cyano-4-(cyclopropyl(4-(trifluoromethyl)benzyl)amino)-7H-pyrrolo[2,3-d]pyrimidin-7-yl)methyl)piperidin-1-yl)acetamide |
| P1-3 | A2-1 | X-2 | P6-8 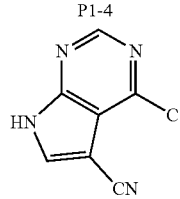 2-(4-((6-(cyclopropyl(4-(trifluoromethyl)benzyl)amino)-9H-purin-9-yl)methyl)piperidin-1-yl)propanamide |

-continued

| P1 | A2 | X | P6 |
|---|---|---|---|
| P1-3 | A2-1 | X-2 | P6-9 |
| | | | 2-(4-((6-(cyclopropyl(4-(trifluoromethyl)benzyl)amino)-9H-purin-9-yl)methyl)piperidin-1-yl)-2-methylpropanamide |
| P1-5 | A2-7 | X-2 | P6-10 |
| 4-chloro-5-fluoro-7-tosyl-7H-pyrrolo[2,3-d]pyrimidine | N-((6-(trifluoromethyl)pyridin-3-yl)methyl)cyclopropanamine | | 2-(4-((4-(cyclopropyl((6-(trifluoromethyl)pyridin-3-yl)methyl)amino)-5-fluoro-7H-pyrrolo[2,3-d]pyrimidin-7-yl)methyl)piperidin-1-yl)acetamide |
| P1-5 | A2-1 | X-3 | P6-11 |
| | | tert-butyl 4-cyano-4-(((methylsulfonyl)oxy)methyl)piperidine-1-carboxylate | 2-(4-cyano-4-((4-(cyclopropyl(4-(trifluoromethyl)benzyl)amino)-5-fluoro-7H-pyrrolo[2,3-d]pyrimidin-7-yl)methyl)piperidin-1-yl)acetamide |

-continued

| P1 | A2 | X | P6 |
|---|---|---|---|
| P1-5 | A2-8<br>N-methyl-1-(4-(trifluoromethyl)phenyl)methan-amine | X-1 | P6-12<br>rac-2-((3R,4R)-4-((5-fluoro-4-(methyl(4-(trifluoromethyl)benzyl)amino)-7H-pyrrolo[2,3-d]pyrimidin-7-yl)methyl)-3-hydroxypiperidin-1-yl)acetamide |
| P1-1 | A2-1 | X-4<br>rac-tert-butyl (3R,4R)-3-hydroxy-4-((tosyloxy)methyl)piperidine-1-carboxylate | P6-13<br>rac-2-((3R,4R)-4-((4-(cyclopropyl(4-(trifluoromethyl)benzyl)amino)-7H-pyrrolo[2,3-d]pyrimidin-7-yl)methyl)-3-hydroxypiperidin-1-yl)acetamide |
| P1-1 | A2-1 | X-4 | P6-13-1<br>rel-2-((3R,4R)-4-((4-(cyclopropyl(4-(trifluoromethyl)benzyl)amino)-7H-pyrrolo[2,3-d]pyrimidin-7-yl)methyl)-3-hydroxypiperidin-1-yl)acetamide<br>1st eluting isomer |

-continued

| P1 | A2 | X | P6 |
|---|---|---|---|
| P1-1 | A2-1 | X-4 | P6-13-2 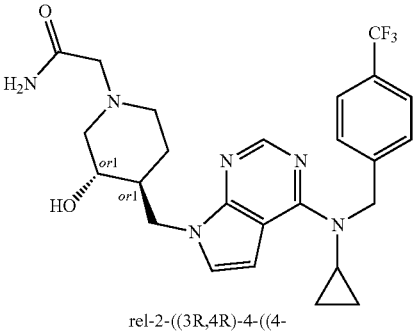<br>rel-2-((3R,4R)-4-((4-(cyclopropyl(4-(trifluoromethyl)benzyl)amino)-7H-pyrrolo[2,3-d]pyrimidin-7-yl)methyl)-3-hydroxypiperidin-1-yl)acetamide<br>2nd eluting isomer |
| P1-5 | A2-1 | X-1 | P6-14 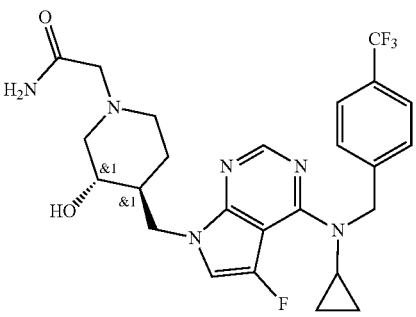<br>rac-2-((3R,4R)-4-((4-(cyclopropyl(4-(trifluoromethyl)benzyl)amino)-5-fluoro-7H-pyrrolo[2,3-d]pyrimidin-7-yl)methyl)-3-hydroxypiperidin-1-yl)acetamide |
| P1-5 | A2-1 | X-1 | P6-14-1 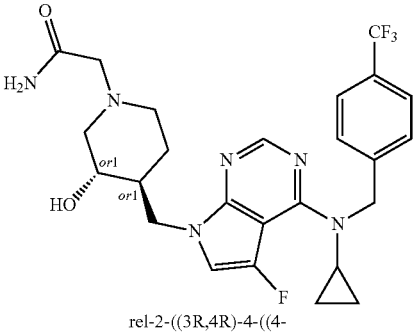<br>rel-2-((3R,4R)-4-((4-(cyclopropyl(4-(trifluoromethyl)benzyl)amino)-5-fluoro-7H-pyrrolo[2,3-d]pyrimidin-7-yl)methyl)-3-hydroxypiperidin-1-yl)acetamide<br>1st eluting isomer |

-continued

| P1 | A2 | X | P6 |
|---|---|---|---|
| P1-5 | A2-1 | X-1 | P6-14-2 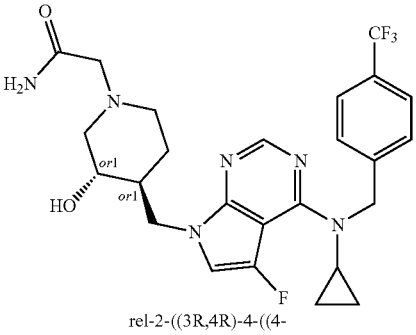 rel-2-((3R,4R)-4-((4-(cyclopropyl(4-(trifluoromethyl)benzyl)amino)-5-fluoro-7H-pyrrolo[2,3-d]pyrimidin-7-yl)methyl)-3-hydroxypiperidin-1-yl)acetamide 2<sup>nd</sup> eluting isomer |
| P1-1 | A2-7 | X-1 | P6-15 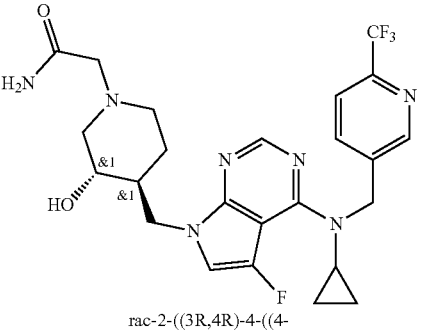 rac-2-((3R,4R)-4-((4-(cyclopropyl((6-(trifluoromethyl)pyridin-3-yl)methyl)amino)-5-fluoro-7H-pyrrolo[2,3-d]pyrimidin-7-yl)methyl)-3-hydroxypiperidin-1-yl)acetamide |
| P1-5 | A2-7 | X-1 | P6-16 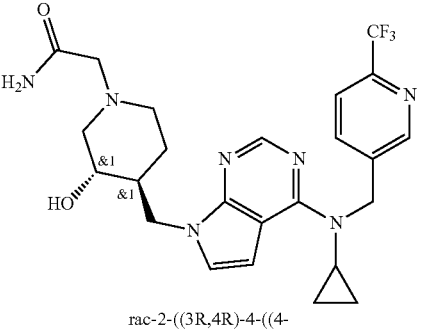 rac-2-((3R,4R)-4-((4-(cyclopropyl((6-(trifluoromethyl)pyridin-3-yl)methyl)amino)-7H-pyrrolo[2,3-d]pyrimidin-7-yl)methyl)-3-hydroxypiperidin-1-yl)acetamide |

-continued

| P1 | A2 | X | P6 |
|---|---|---|---|
| P1-2 | A2-9 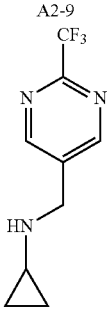<br>N-((2-(trifluoromethyl)pyrimidin-5-yl)methyl)cyclopropanamine | X-1 | P6-17 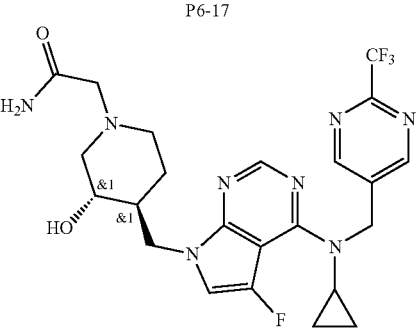<br>rac-2-((3R,4R)-4-((4-(cyclopropyl((2-(trifluoromethyl)pyrimidin-5-yl)methyl)amino)-5-fluoro-7H-pyrrolo[2,3-d]pyrimidin-7-yl)methyl)-3-hydroxypiperidin-1-yl)acetamide |
| P1-2 | A2-10 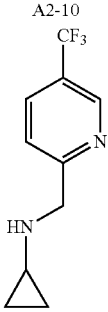<br>N-((5-(trifluoromethyl)pyridin-2-yl)methyl)cyclopropanamine | X-1 | P6-18 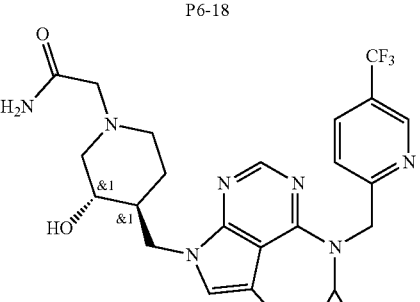<br>rac-2-((3R,4R)-4-((4-(cyclopropyl((5-(trifluoromethyl)pyridin-2-yl)methyl)amino)-5-fluoro-7H-pyrrolo[2,3-d]pyrimidin-7-yl)methyl)-3-hydroxypiperidin-1-yl)acetamide |
| P1-2 | A2-11 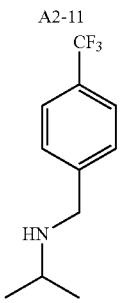<br>N-(4-(trifluoromethyl)benzyl)propan-2-amine | X-1 | P6-19 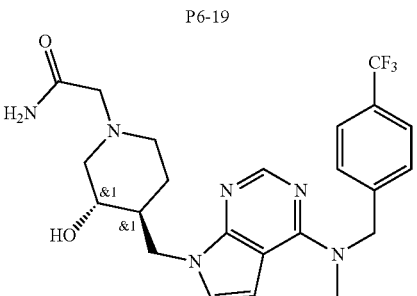<br>rac-2-((3R,4R)-4-((5-fluoro-4-(isopropyl(4-(trifluoromethyl)benzyl)amino)-7H-pyrrolo[2,3-d]pyrimidin-7-yl)methyl)-3-hydroxypiperidin-1-yl)acetamide |

-continued

| P1 | A2 | X | P6 |
|---|---|---|---|
| P1-6 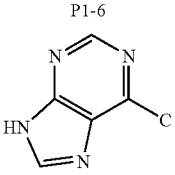 6-chloro-9H-purine | A2-12 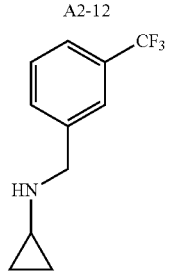 N-(3-(trifluoromethyl)benzyl)cyclopropanamine | X-1 | P6-20 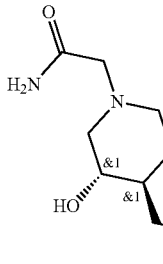 rac-2-((3R,4R)-4-((6-(cyclopropyl(3-(trifluoromethyl)benzyl)amino)-9H-purin-9-yl)methyl)-3-hydroxypiperidin-1-yl)acetamide |
| P1-2 | A2-13 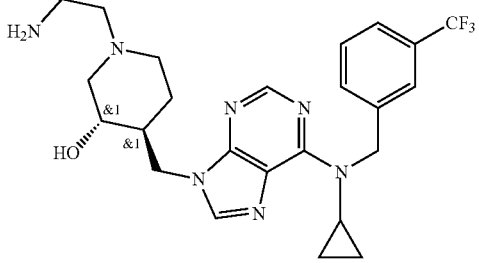 N-(4-(trifluoromethyl)benzyl)ethanamine | X-1 | P6-21 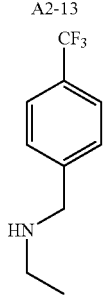 rac-2-((3R,4R)-4-((4-(ethyl(4-(trifluoromethyl)benzyl)amino)-5-fluoro-7H-pyrrolo[2,3-d]pyrimidin-7-yl)methyl)-3-hydroxypiperidin-1-yl)acetamide |
| P1-3 | A2-11 | X-1 | P6-22 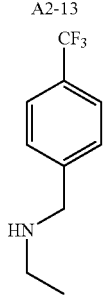 rac-2-((3R,4R)-3-hydroxy-4-((6-(isopropyl(4-(trifluoromethyl)benzyl)amino)-9H-purin-9-yl)methyl)piperidin-1-yl)acetamide |

-continued

| P1 | A2 | X | P6 |
|---|---|---|---|
| P1-1 | A2-10 | X-1 | P6-23 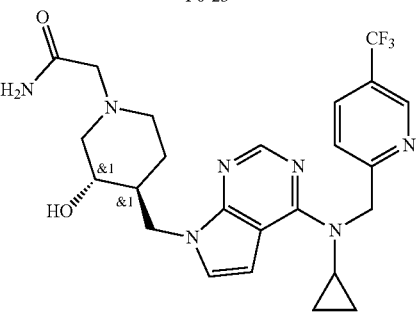 rac-2-((3R,4R)-4-((4-(cyclopropyl((5-(trifluoromethyl)pyridin-2-yl)methyl)amino)-7H-pyrrolo[2,3-d]pyrimidin-7-yl)methyl)-3-hydroxypiperidin-1-yl)acetamide |
| P1-1 | A2-10 | X-1 | P6-23-1 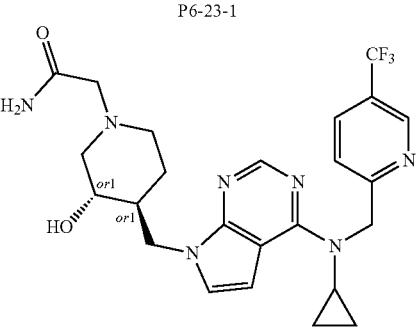 rel-2-((3R,4R)-4-((4-(cyclopropyl((5-(trifluoromethyl)pyridin-2-yl)methyl)amino)-7H-pyrrolo[2,3-d]pyrimidin-7-yl)methyl)-3-hydroxypiperidin-1-yl)acetamide 1$^{st}$ eluting isomer |
| P1-1 | A2-10 | X-1 | P6-23-2 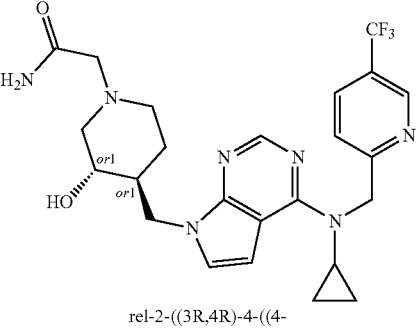 rel-2-((3R,4R)-4-((4-(cyclopropyl((5-(trifluoromethyl)pyridin-2-yl)methyl)amino)-7H-pyrrolo[2,3-d]pyrimidin-7-yl)methyl)-3-hydroxypiperidin-1-yl)acetamide 2$^{nd}$ eluting isomer |

-continued

| P1 | A2 | X | P6 |
|---|---|---|---|
| P1-1 | A2-13 | X-1 | P6-24 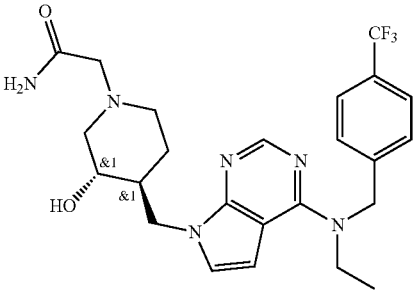 rac-2-((3R,4R)-4-((4-(ethyl(4-(trifluoromethyl)benzyl)amino)-7H-pyrrolo[2,3-d]pyrimidin-7-yl)methyl)-3-hydroxypiperidin-1-yl)acetamide |
| P1-1 | A2-13 | X-1 | P6-24-1 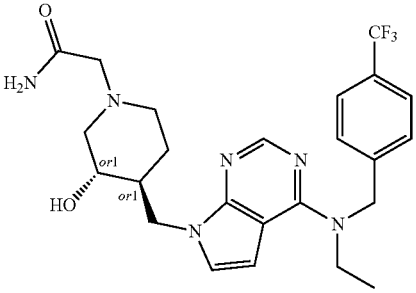 rel-2-((3R,4R)-4-((4-(ethyl(4-(trifluoromethyl)benzyl)amino)-7H-pyrrolo[2,3-d]pyrimidin-7-yl)methyl)-3-hydroxypiperidin-1-yl)acetamide 1$^{st}$ eluting isomer |
| P1-1 | A2-13 | X-1 | P6-24-2 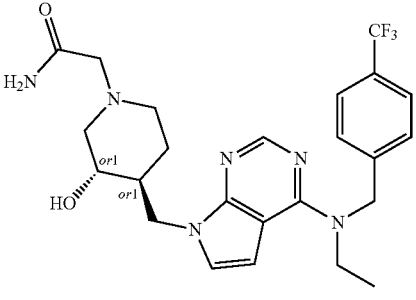 rel-2-((3R,4R)-4-((4-(ethyl(4-(trifluoromethyl)benzyl)amino)-7H-pyrrolo[2,3-d]pyrimidin-7-yl)methyl)-3-hydroxypiperidin-1-yl)acetamide 2$^{nd}$ eluting isomer |

-continued

| P1 | A2 | X | P6 |
|---|---|---|---|
| P1-1 | A2-11 | X-1 | P6-25 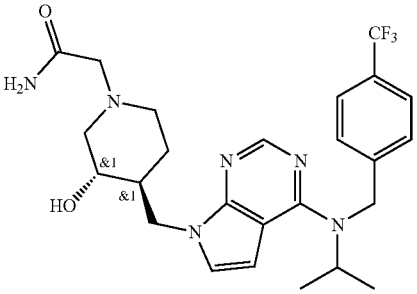 rac-2-((3R,4R)-3-hydroxy-4-((4-(isopropyl(4-(trifluoromethyl)benzyl)amino)-7H-pyrrolo[2,3-d]pyrimidin-7-yl)methyl)piperidin-1-yl)acetamide |
| P1-1 | A2-11 | X-1 | P6-25-1 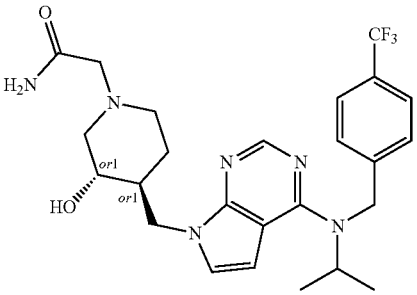 rel-2-((3R,4R)-3-hydroxy-4-((4-(isopropyl(4-(trifluoromethyl)benzyl)amino)-7H-pyrrolo[2,3-d]pyrimidin-7-yl)methyl)piperidin-1-yl)acetamide 1st eluting isomer |
| P1-1 | A2-11 | X-1 | P6-25-2 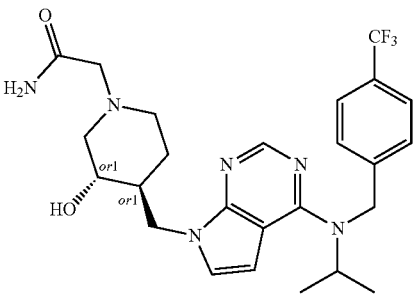 rel-2-((3R,4R)-3-hydroxy-4-((4-(isopropyl(4-(trifluoromethyl)benzyl)amino)-7H-pyrrolo[2,3-d]pyrimidin-7-yl)methyl)piperidin-1-yl)acetamide 2nd eluting isomer |

| P1 | A2 | X | P6 |
|---|---|---|---|
| P1-3 | A2-1 | X-1″<br><br>rel-tert-butyl (3R,4R)-3-hydroxy-4-((tosyloxy)methyl)piperidine-1-carboxylate<br>Enantiomerically enriched | P6-26″<br><br>rel-2-((3R,4R)-4-((6-(cyclopropyl(4-(trifluoromethyl)benzyl)amino)-9H-purin-9-yl)methyl)-3-hydroxypiperidin-1-yl)acetamide<br>Enantiomerically enriched |
| P1-3 | A2-1 | X-1″ | P6-26-1<br><br>rel-2-((3R,4R)-4-((6-(cyclopropyl(4-(trifluoromethyl)benzyl)amino)-9H-purin-9-yl)methyl)-3-hydroxypiperidin-1-yl)acetamide<br>1$^{st}$ eluting (minor) isomer |
| P1-3 | A2-1 | X-1″ | P6-26-2<br><br>rel-2-((3R,4R)-4-((6-(cyclopropyl(4-(trifluoromethyl)benzyl)amino)-9H-purin-9-yl)methyl)-3-hydroxypiperidin-1-yl)acetamide<br>2$^{nd}$ eluting (major) isomer |

-continued

| P1 | A2 | X | P6 |
|---|---|---|---|
| P1-1 | A2-14 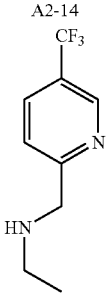 N-((5-(trifluoromethyl)pyridin-2-yl)methyl)ethan-amine | X-1" | P6-27" 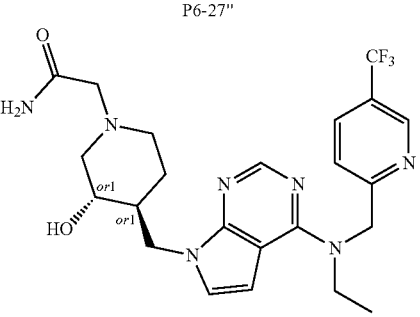 rel-2-((3R,4R)-4-((4-(ethyl((5-(trifluoromethyl)pyridin-2-yl)methyl)amino)-7H-pyrrolo[2,3-d]pyrimidin-7-yl)methyl)-3-hydroxypiperidin-1-yl)acetamide Enantiomerically enriched |
| P1-2 | A2-14 | X-1" | P6-28" 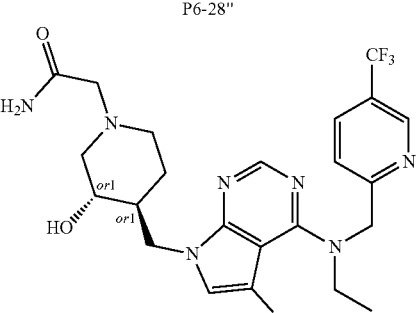 rel-2-((3R,4R)-4-((4-(ethyl((5-(trifluoromethyl)pyridin-2-yl)methyl)amino)-5-fluoro-7H-pyrrolo[2,3-d]pyrimidin-7-yl)methyl)-3-hydroxypiperidin-1-yl)acetamide Enantiomerically enriched |
| P1-1 | A2-15 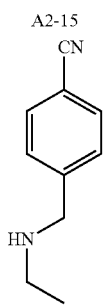 4-((ethylamino)methyl)benzo-nitrile | X-1" | P6-29" 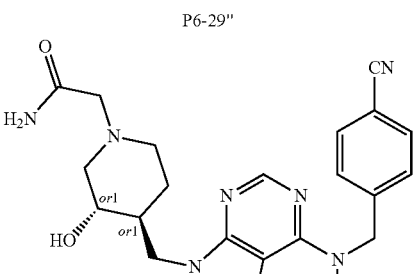 rel-2-((3R,4R)-4-((4-((4-cyanobenzyl)(ethyl)amino)-7H-pyrrolo[2,3-d]pyrimidin-7-yl)methyl)-3-hydroxypiperidin-1-yl)acetamide Enantiomerically enriched |

-continued

| P1 | A2 | X | P6 |
|---|---|---|---|
| P1-1 | A2-16<br><br>N-(4-(1H-pyrazol-1-yl)benzyl)ethanamine | X-1'' | P6-30<br><br>rel-2-((3R,4R)-4-((4-((4-(1H-pyrazol-1-yl)benzyl)(ethyl)amino)-7H-pyrrolo[2,3-d]pyrimidin-7-yl)methyl)-3-hydroxypiperidin-1-yl)acetamide<br>Enantiomerically enriched |
| P1-1 | A2-17<br><br>N-(3-fluoro-4-(trifluoromethyl)benzyl)ethanamine | X-1'' | P6-31''<br><br>rel-2-((3R,4R)-4-((4-(ethyl(3-fluoro-4-(trifluoromethyl)benzyl)amino)-7H-pyrrolo[2,3-d]pyrimidin-7-yl)methyl)-3-hydroxypiperidin-1-yl)acetamide<br>Enantiomerically enriched |
| P1-7<br><br>4-chloro-7H-pyrrolo[2,3-d]pyrimidine | A2-3<br><br>N-(2-fluoro-4-(trifluoromethyl)benzyl)ethanamine | X-1'' | P6-32''<br><br>rel-2-((3R,4R)-4-((4-(ethyl(2-fluoro-4-(trifluoromethyl)benzyl)amino)-7H-pyrrolo[2,3-d]pyrimidin-7-yl)methyl)-3-hydroxypiperidin-1-yl)acetamide<br>Enantiomerically enriched |

-continued

| P1 | A2 | X | P6 |
|---|---|---|---|
| P1-1 | A2-18 | X-1″ | P6-33″ |
| | N-(4-(1H-pyrazol-1-yl)benzyl)cyclopropanamine | | rel-2-((3R,4R)-4-((4-((4-(1H-pyrazol-1-yl)benzyl)(cyclopropyl)amino)-7H-pyrrolo[2,3-d]pyrimidin-7-yl)methyl)-3-hydroxypiperidin-1-yl)acetamide<br>Enantiomerically enriched |

Synthesis of 4-chloro-5-fluoro-7-tosyl-7H-pyrrolo[2,3-d]pyrimidine, P1-5

Scheme P1-5

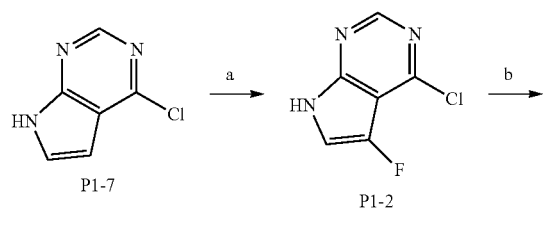

a) Select-Fluor®, CH₃CN, AcOH b) TsCl, TEA, DCM.

4-Chloro-5-fluoro-7H-pyrrolo[2,3-d]pyrimidine, P1-2

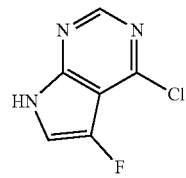 [SMILES: Fc1c[nH]c2ncnc(Cl)c12]

P1-2

To a solution of 4-chloro-7H-pyrrolo[2,3-d]pyrimidine P1-7 (1.5 g, 9.77 mmol) in a mixture of CH₃CN (75 mL) and acetic acid (15 mL) was added 1-(chloromethyl)-4-fluoro-1,4-diazabicyclo[2.2.2]octane-1,4-diium tetrafluoroborate (Select-Fluor, 5.0 g, 14.1 mmol). The resulting mixture was stirred under N₂ atm at 80° C. on. Then the solvents were removed and the residue was purified by Flash CC (Hex: EA=10:0 to 65:35) to yield 4-chloro-5-fluoro-7H-pyrrolo[2,3-d]pyrimidine P1-2.

LCMS: MS Calcd.: 171; MS Found: 172 ([M−56+H]⁺).

4-Chloro-5-fluoro-7-tosyl-7H-pyrrolo[2,3-d]pyrimidine, P1-5

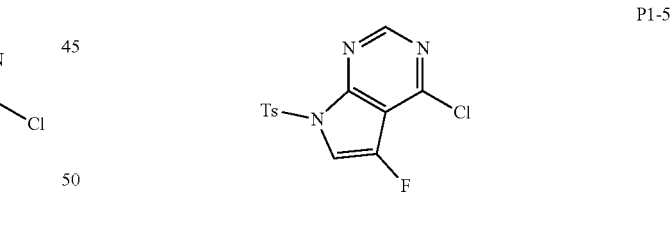

To a suspension of 4-chloro-5-fluoro-7H-pyrrolo[2,3-d]pyrimidine P1-2 (504 mg, 2.94 mmol) and TEA (615 µL, 4.41 mmol) in DCM (50 mL) was added a solution of 4-methylbenzene-1-sulfonyl chloride (840 mg, 4.41 mmol) in DCM (20 mL). The resulting mixture was stirred at rt for 2 h and then at 40° C. for 2 h more. Then the solvent was removed in vacuo and the residue was partitioned between H₂O and EA. The organic layer was separated and washed with water (×2) and brine, dried (MgSO₄), filtered and concentrated in vacuo. The residue was then purified by Flash CC (Hex:EA=10:0 to 6:4) to yield 4-chloro-5-fluoro-7-tosyl-7H-pyrrolo[2,3-d]pyrimidine P1-5.

LCMS: MS Calcd.: 325; MS Found: 326 ([M−56+H]⁺).

Synthesis of rac-tert-butyl (3R,4R)-3-hydroxy-4-((tosyloxy)methyl)-piperidine-1-carboxylate, X-1

Scheme X-1

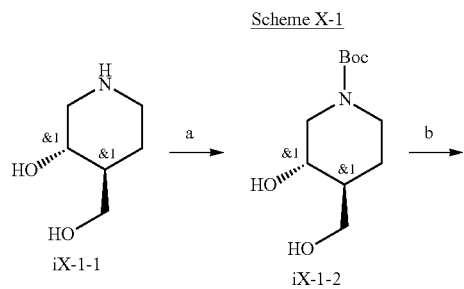

a) Boc₂O, TEA, DCM. b) TsCl, pyridine.

rac-tert-Butyl (3R,4R)-3-hydroxy-4-(hydroxymethyl)piperidine-1-carboxylate, iX-1-2

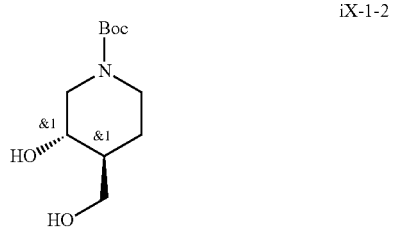 [SMILES: CC(C)(C)OC(=O)N1CC[C@@H](CO)[C@H](O)C1]

To a suspension of rac-(3R,4R)-4-(hydroxymethyl)piperidin-3-ol hydrochloride iX1-1 (1.0 g, 5.97 mmol) in MeOH (30 mL) were added trimethylamine (1.83 mL, 13.1 mmol) and Boc₂O (1.43 g, 6.55 mmol). The mixture was stirred at rt on and the volatiles were removed in vacuo. The residue was partitioned between H₂O and DCM. The organic layer was separated and washed with water (×2) and brine, dried (MgSO₄), filtered and concentrated in vacuo to obtain iX-1-2, which was used directly in the next step.

LCMS: MS Calcd.: 231; MS Found: 232 ([M+H]⁺), 176 ([M−56+H]⁺).

rac-tert-Butyl (3R,4R)-3-hydroxy-4-((tosyloxy)methyl)piperidine-1-carboxylate, X-1

To a cooled (0° C.) solution of iX1-2 (1.38 g, 5.97 mmol) in pyridine (10 mL), TsCl (1.31 g, 6.87 mmol) was added. The reaction was stirred at rt for 3 h. Excess TsCl (500 mg, 2.6 mmol) was added and the reaction was stirred for additional 2 h at rt. Then reaction mixture was diluted with DCM and washed with 1M HCl (×2), 4% NaHCO₃ aq solution (×2) and brine, dried (MgSO₄), filtered and concentrated in vacuo. The residue was purified by Flash CC (Hex:EA from 0% to 50%) to obtain X-1.

LCMS: MS Calcd.: 385; MS Found: 386 ([M+H]⁺), 286 ([M−101+H]⁺).

Alternatively, X-1 was synthesized as described below:

Scheme X-1b

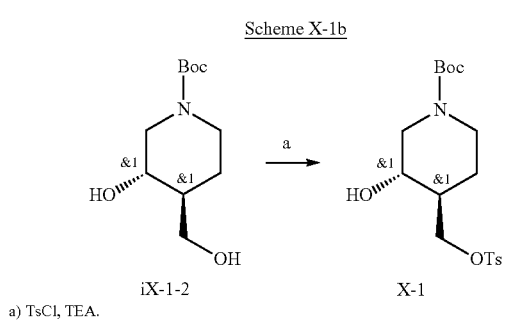

a) TsCl, TEA.

TEA (520 mg, 5.1 mmol) was added to a solution of iX-1-2 (590 mg, 2.55 mmol) in DCM (10 mL). This solution was cooled to 0° C. and then a solution of TsCl (530 mg, 2.8 mmol) in DCM (1 mL) was added. The reaction was then stirred at rt for 18 h quenched with H₂O (50 mL) and the resulting mixture was extracted with DCM (2×70 mL). The combined organic layer was washed with H₂O (50 mL), brine (50 mL), dried (Na₂SO₄) filtered and concentrated in vacuo. The residue was then purified by Flash CC (EA:PE=1:1 to MeOH:DCM=1:10) to yield X-1.

LCMS: MS Calcd.: 385; MS Found: 330 ([M−56+H]⁺).

Synthesis of enantiomerically enriched rel-tert-butyl (3R,4R)-3-hydroxy-4-((tosyloxy)methyl)piperidine-1-carboxylate, X-1″

Scheme X-1″

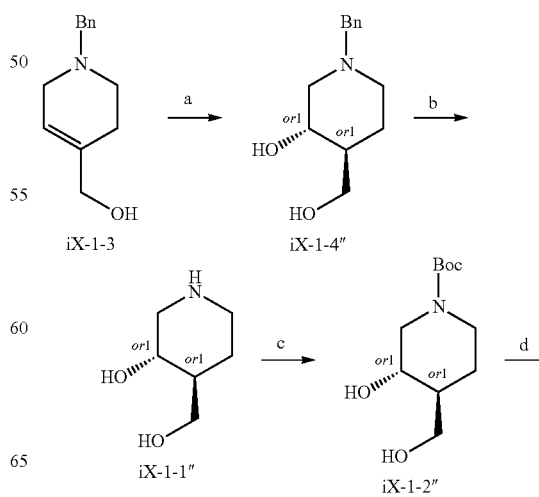

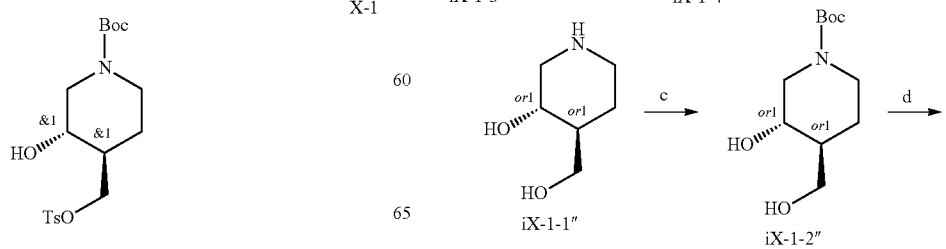

-continued

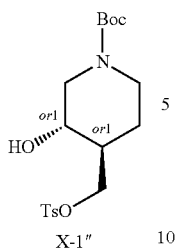

X-1″ a) (+)-alpine boramine TMEDA complex, BF₃·Et₂O, Et₂O/THF then H₂O₂, NaOH. b) Pd/C, NH₄HCO₂, MeOH. c) Boc₂O, DCM/MeOH d) TsCl, pyridine.

rel-(3R,4R)-1-Benzyl-4-(hydroxymethyl)piperidin-3-ol, iX-1-4″:

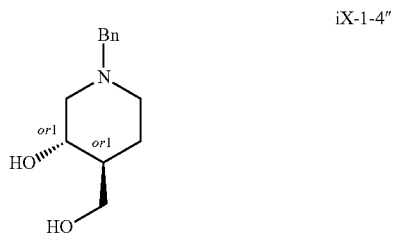 [SMILES: OC[C@@H]1CCN(Cc2ccccc2)C[C@H]1O]

iX-1-4″

BF₃·Et₂O (12 mL, 97.2 mmol) was dropwise added to a stirred solution of (+)-alpine boramine TMEDA complex (20.28 g, 48.7 mmol) in a mixture of dry Et₂O (150 mL) and dry THF (32 mL) under an Ar atm at rt resulting in a white suspension. After 2 h 15 min, a solution of (1-benzyl-1,2,3,6-tetrahydropyridin-4-yl) (7.6 g, 37.0 mmol) in THF (32 mL) was added dropwise over ca. 15 mins and the mixture was stirred at rt for 2.5 h, then heated to 55° C. and stirred on. The mixture was cooled in an ice bath and then H₂O (7.6 mL) was added dropwise followed by 5M aq. NaOH (12 mL) and 35% aqueous H₂O₂ solution (19.2 mL) and finally 50% aqueous NaOH (48 mL). The mixture was then stirred and heated to reflux (oil bath 60° C.) for 4 h, then cooled to rt. A saturated aq solution of K₂CO₃ (80 mL) was added and the mixture was extracted with EA (3×400 mL). The combined organic phase was dried and concentrated in vacuo to give an oil (26 g). This crude material was dissolved in EA (220 mL) and extracted with 5M HCl (2×110 mL). The combined acidic aqueous layer was extracted with further EA (200 mL) and then was cooled in an ice bath and solid K₂CO₃ (ca. 101 g) was added in portions until the pH of the aqueous phase remained strongly basic. The mixture was thereafter extracted with EA (4×200 mL) and the combined organic phase was dried and concentrated in vacuo to give iX-1-4″.

MS Calcd.: 221; MS Found: 222 ([M+H]⁺).

¹H NMR (400 MHz, CDCl₃) δ 1.16-1.31 (m, 1H), 1.42-1.61 (m, 2H), 1.79-1.88 (m, 1H), 1.90-1.99 (m, 1H), 2.79 (dd, J=9.4, 1.8 Hz, 1H), 2.91-3.00 (m, 1H), 3.46 (d, J=13.0 Hz, 1H), 3.52 (d, J=13.0 Hz, 1H), 3.59-3.74 (m, 3H), 7.17-7.34 (m, 5H).

HPLC analysis (Chiralpak ID, gradient: 1-45% isopropanol (+0.2% DEA) in CO₂ over 17 min) indicated 76% ee.

Enantiomerically enriched rel-(3R,4R)-4-(hydroxymethyl)piperidin-3-ol, iX1-1″

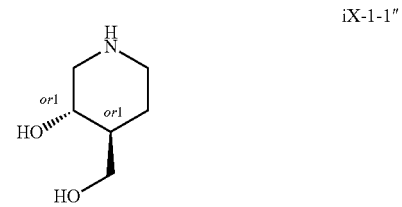

iX-1-1″

Ammonium formate (6.91 g, 109.6 mmol) and 10% Pd/C (0.711 g, 0.67 mmol) were added to a solution of iX-1-4″ (8.08 g, 36.5 mmol) in MeOH (110 mL) and the mixture was stirred and heated to reflux (oil bath temp 80° C.). Further portions of 10% Pd/C (0.711 g, 0.67 mmol) were added after 30 mins and again after 60 mins. After 3.5 h, the reaction mixture was cooled and filtered through Celite®. The filter cake was washed with MeOH and the filtrate and washings were combined and concentrated in vacuo at 60° C. to give iX1-1″.

MS Calcd.: 131; MS Found: 132 ([M+H]⁺).

¹H NMR (400 MHz, DMSO-d6) δ 0.98-1.13 (m, 1H), 1.20-1.33 (m, 1H), 1.59-1.69 (m, 1H), 2.07-2.18 (m, 1H), 2.24-2.36 (m, 1H), 2.80 (d, J=12.0 Hz, 1H), 2.90 (dd, J=11.5, 4.5 Hz, 1H), 3.11 (d, J=4.1 Hz, 1H), 3.25-3.36 (m, 1H), 3.59 (dd, J=10.2, 4.1 Hz, 1H), 4.32 (br s, 1H), 4.49 (br s, 1H).

Enantiomerically enriched rel-tert-butyl (3R,4R)-3-hydroxy-4-(hydroxymethyl)piperidine-1-carboxylate, iX-1-2″

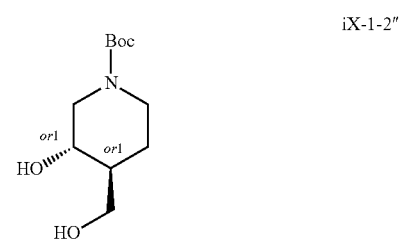 [SMILES: CC(C)(C)OC(=O)N1CC[C@@H](CO)[C@H](O)C1]

iX-1-2″

A solution of Boc₂O (7.82 g, 35.8 mmol) in DCM (20 mL) was added dropwise to a stirred, cooled (ice bath) solution of iX-1-1″ (4.70 g, 35.8 mmol) in a mixture of DCM (30 mL) and MeOH (12 mL). After stirring on, the mixture was evaporated and the residue was purified by Flash CC (MeOH:DCM=0-5%) to yield iX-1-2″.

MS Calcd.: 231; MS Found: 232 ([M+H]+).

¹H NMR (400 MHz, CDCl₃) δ 1.07-1.21 (m, 1H), 1.45 (s, 9H), 1.53-1.62 (m, 2H), 1.64-1.75 (m, 1H), 2.47-2.58 (m, 1H), 2.59-2.73 (m, 1H), 3.49-3.60 (m, 1H), 3.65-3.74 (m, 1H), 3.74-3.83 (m, 1H), 3.98-4.31 (m, 2H).

Enantiomerically enriched rel-tert-butyl (3R,4R)-3-hydroxy-4-((tosyloxy)methyl)piperidine-1-carboxylate, X-1″

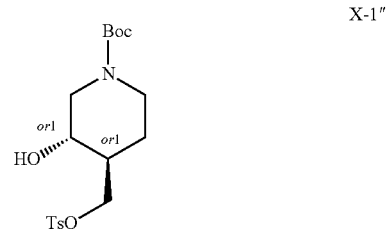 [SMILES: Cc1ccc(S(=O)(=O)OC[C@@H]2CCN(C(=O)OC(C)(C)C)C[C@H]2O)cc1]

X-1″

A solution of iX-1-2" (7.96 g, 34.4 mmol) in dry pyridine (17 mL) was stirred and cooled in an ice bath and TsCl (7.22 g, 37.9 mmol) was added in portions over 10 min. The mixture was allowed to warm to rt over 3 h. Subsequently, the mixture was diluted with DCM, washed with 1M aqueous HCl (1M), NaHCO$_3$(4% aq) brine, dried and evaporated to give a thick yellow oil. The residue was purified by Flash CC (EA:Hex=0-60%) to yield X-1".

MS Calcd.: 385; MS Found: 386 ([M+H]$^+$).

$^1$H NMR (400 MHz, CDCl$_3$) δ 1.36-1.42 (m, 1H), 1.45 (s, 9H), 1.62-1.73 (m, 2H), 2.42-2.54 (m, 4H), 2.55-2.71 (m, 1H), 3.40-3.52 (m, 1H), 3.93-4.14 (m, 2H), 4.15-4.32 (m, 2H), 7.35 (d, J=8.0 Hz, 2H), 7.76-7.81 (d, J=8.0 Hz, 2H).

Synthesis of tert-butyl 4-cyano-4-(((methylsulfonyl)oxy) methyl)piperidine-1-carboxylate, X-3

Scheme X-3

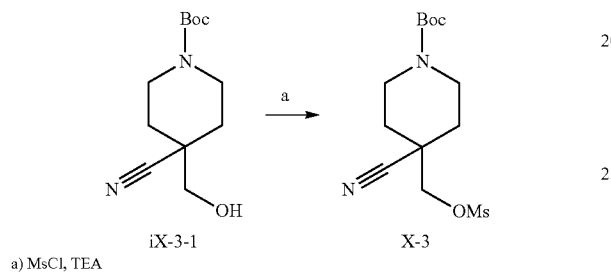

a) MsCl, TEA

TEA (726 μL, 5 mmol) and MsCl (193 μL, 2.5 mmol) were in turn added to a solution of tert-butyl 4-cyano-4-(hydroxymethyl)piperidine-1-carboxylate iX-3-1 (500 mg, 2 mmol) in dry DCM (20 mL) and the reaction was stirred at rt for 2 h. Afterwards, more DCM (20 mL) was added and the organic phase was washed with H$_2$O (30 mL) and brine (30 mL), dried (MgSO$_4$) and concentrated in vacuo to afford X-3.

LCMS: MS Calcd.: 318; MS Found: 363 ([M+H]$^+$), 263 ([M−101+H]$^+$).

Synthesis of rac-tert-butyl (3R,4R)-3-hydroxy-4-(((methylsulfonyl)oxy)-methyl)piperidine-1-carboxylate, X-4

Scheme X-4

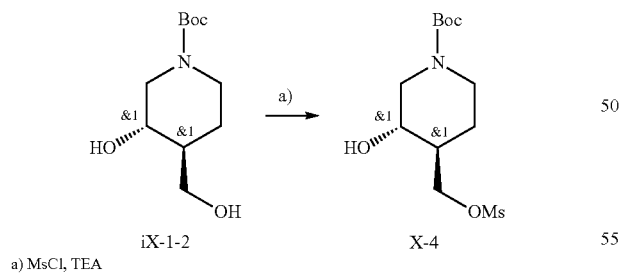

a) MsCl, TEA

To a solution of iX-1-2 (300 mg, 1.30 mmol) and TEA (0.272 mL, 1.94 mmol) in DCM (15 ml), MsCl (0.110 mL, 1.42 mmol) was added. The reaction was then stirred overnight. The reaction was diluted with chloroform and washed with water (×3), brine, dried (MgSO$_4$), filtered and concentrated in vacuo. The residue was purified by Flash CC (Hex:EA=0% to 100%) to obtain X-4.

LCMS: MS Calcd.: 309; MS Found: 310 ([M+H]$^+$), 210 ([M−101+H]$^+$).

General Method 2P

When R$_6$ was a heterocyclic ring the General Method 2P was also employed.

General Scheme 2P

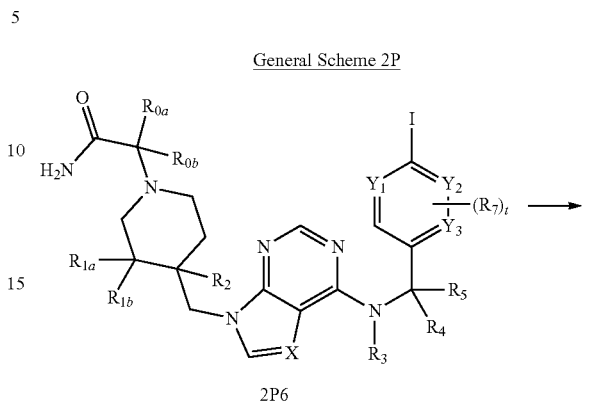

2P6

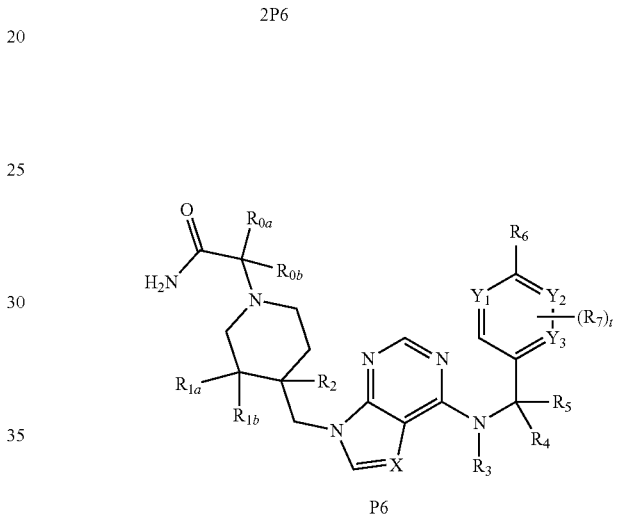

P6

When R$_6$ was a heterocyclic ring the iodo-intermediate 2P6, synthesized as outlined in General Method P from the corresponding iodo-benzylamine, underwent either Suzuki coupling (together with Pd and boronic acid, or esters) or a standard Buchwald coupling (together with Cu and a nitrogen containing heterocyclic ring) to give P6.

Example P6-34"

Synthesis of enantiomerically enriched rel-2-((3R,4R)-4-((4-(ethyl(4-(1-methyl-1H-pyrazol-4-yl)benzyl)amino)-7H-pyrrolo[2,3-d]pyrimidin-7-yl)methyl)-3-hydroxypiperidin-1-yl)acetamide

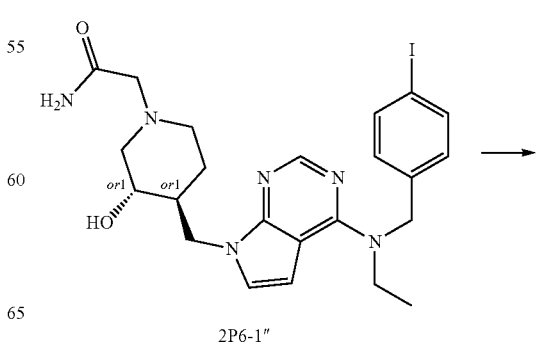

2P6-1"

-continued

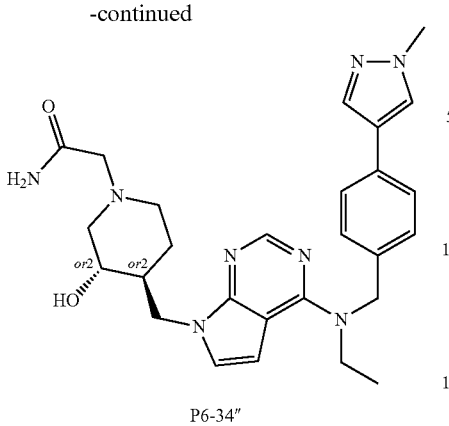

P6-34″

Under a N₂ atm 1-methyl-4-(4,4,5,5-tetramethyl-1,3,2-dioxaborolan-2-yl)-1H-pyrazole (43 mg, 0.21 mmol), 2M Cs₂CO₃ (205 µL, 0.41 mmol) and [1,1'-bis(diphenylphosphino) ferrocene]dichloropalladium(II), complex with DCM (11 mg, 13.5 µmol) were added to a solution of 2P6-1″ (75 mg, 0.14 mmol) in dioxane (2 mL). The reaction mixture was stirred at 100° C. for 4 h. Water was added, and the product was extracted with EA (×3). The combined organic layer was washed with H₂O, brine, dried (MgSO₄), filtered and concentrated in vacuo. The residue was then purified by Flash CC (MeOH:DCM=15:85) to yield P6-34″.

LCMS: MS Calcd.: 502.6; MS Found: 503 ([M+H]⁺).

The following compounds were synthesized according to General Method 2P:

Example P6-36″
Synthesis of enantiomerically enriched rel-2-((3R,4R)-4-((4-(ethyl(2-fluoro-4-(1H-pyrazol-1-yl)benzyl)amino)-7H-pyrrolo[2,3-d]pyrimidin-7-yl)methyl)-3-hydroxypiperidin-1-yl)acetamide

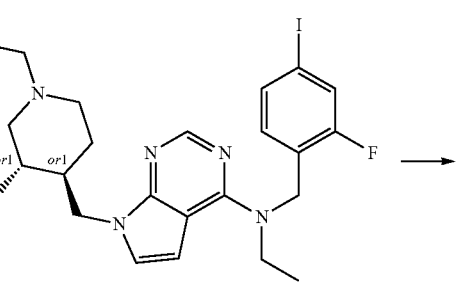

2P6-2″

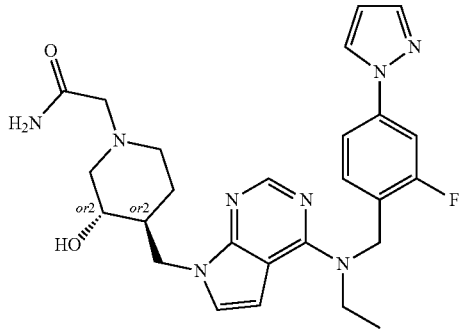

P6-36″

Under N₂ atm 1H-pyrazole (18 mg, 0.26 mmol), K₂CO₃ (36.5 mg, 0.26 mmol), trans-1,2-cyclohexane-1,2-diamine (6.5 µL, 54 µmol) and CuI (2.5 mg, 13 µmol) were added to a solution of 2P6-2″ in NMP (2 mL). The reaction was stirred on at 120° C. H₂O was added and the resulting mixture was extracted with EA (×3). The combined organic layer was washed with H₂O, brine, dried (MgSO₄), filtered and concentrated in vacuo. The residue was first purified by Flash CC (MeOH:DCM=15:85) and thereafter by C18-column (H₂O:MeOH: 100:0 to 0:100) to yield P6-36″.

LCMS: MS Calcd.: 506.6; MS Found: 507 ([M+H]⁺).

| 2P6 | P6 |
|---|---|
| 2P6-2″ | P6-35″ |
| 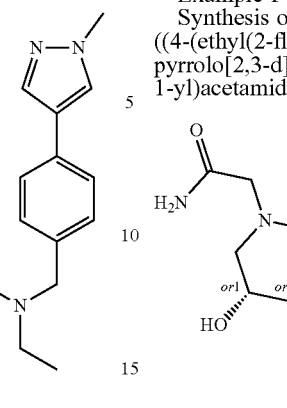 | |
| rel-2-((3R,4R)-4-((4-(ethyl(2-fluoro-4-iodobenzyl)amino)-7H-pyrrolo[2,3-d]pyrimidin-7-yl)methyl)-3-hydroxypiperidin-1-yl)acetamide Enantiomerically enriched | rel-2-((3R,4R)-4-((4-(ethyl(2-fluoro-4-(1-methyl-1H-pyrazol-4-yl)benzyl)amino)-7H-pyrrolo[2,3-d]pyrimidin-7-yl)methyl)-3-hydroxypiperidin-1-yl)acetamide Enantiomerically enriched |

General Method 3P—Synthesis of Alcohols from Epoxide

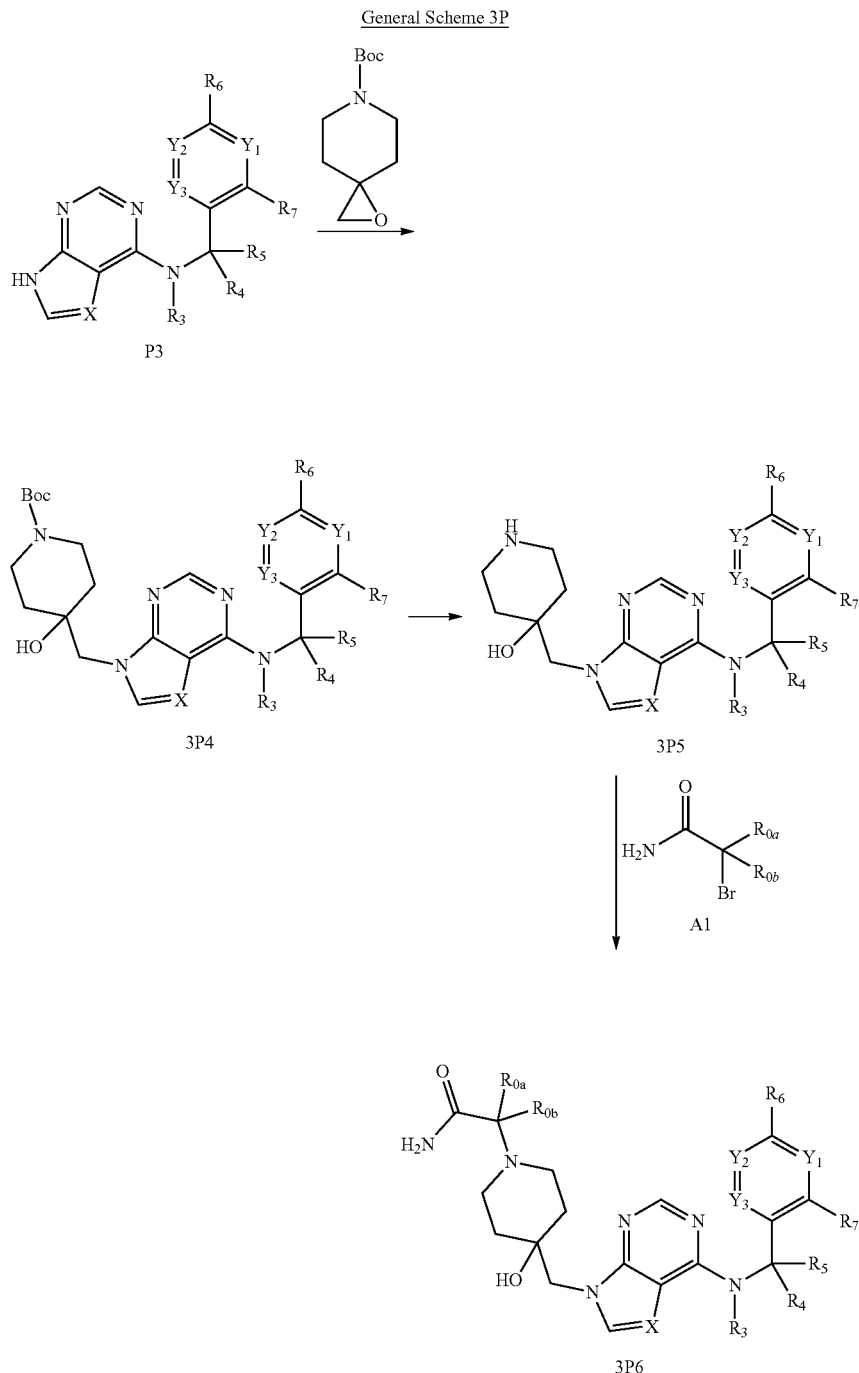

General Scheme 3P

In these cases P3 was alkylated using tert-butyl 1-oxa-6-azaspiro[2.5]octane-6-carboxylate and a suitable base (such as $K_2CO_3$, TEA, DIEA or NaH) producing the intermediate 3P4. Subsequent deprotected with an acid (such as HCl or TFA) in a suitable solvent at rt gave 3P5, that was most often used directly as the corresponding pyridinium salts (HCl or TFA), or as the free amine, in the alkylation with the corresponding 2-bromoacetamide (A1) and a suitable base (such as TEA, DIEA or $K_2CO_3$) to produce 3P6.

Synthesis of 2-(4-((4-(cyclopropyl(4-(trifluoromethyl)benzyl)amino)-5-fluoro-7H-pyrrolo[2,3-d]pyrimidin-7-yl)methyl)-4-hydroxypiperidin-1-yl)acetamide, 3P6-1

Scheme 3P6-1

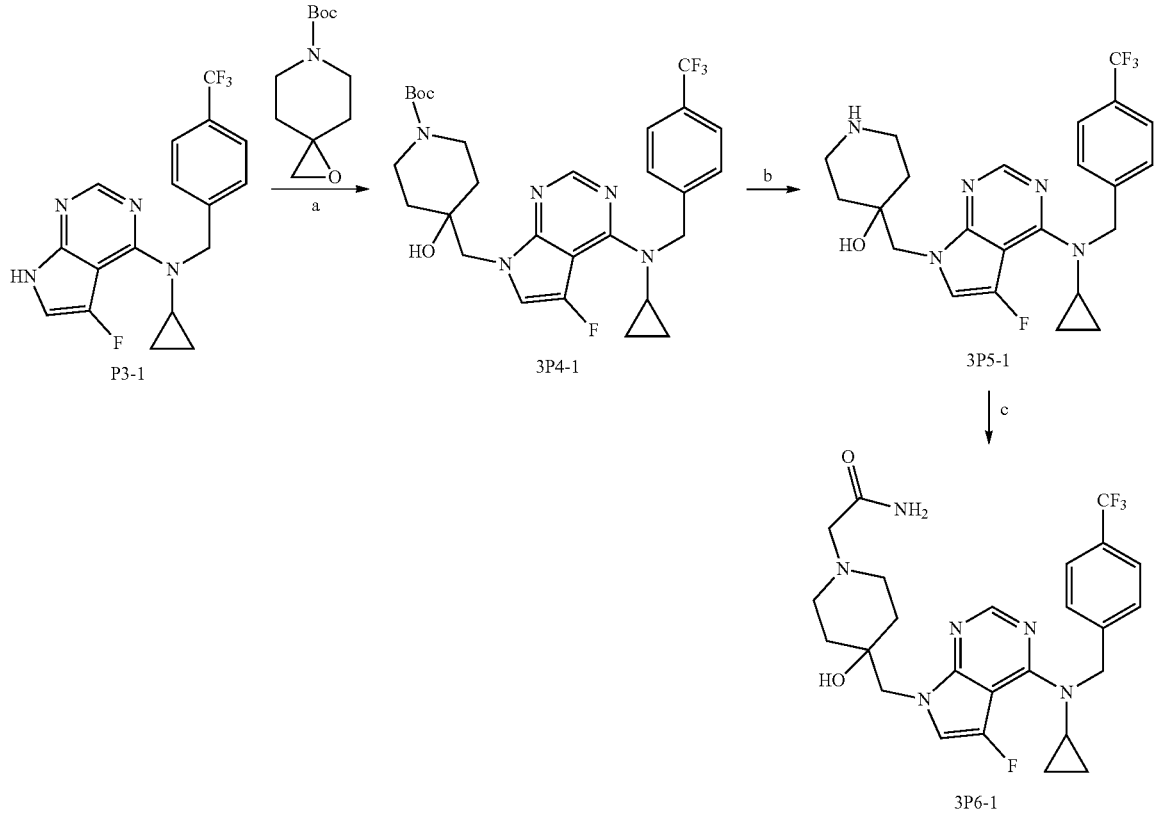

a) K₂CO₃, DMF b) HCl/dioxane. g) 2-bromoacetamide, TEA, DCM.

Synthesis of tert-butyl 4-((4-(cyclopropyl(4-(trifluoromethyl)benzyl)amino)-5-fluoro-7H-pyrrolo[2,3-d]pyrimidin-7-yl)methyl)-4-hydroxypiperidine-1-carboxylate, 3P4-1

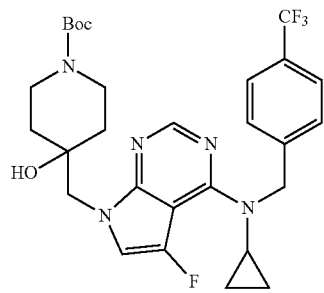

To a solution of P3-1 (55 mg, 0.157 mmol) in dry DMF (2 mL), tert-butyl 1-oxa-6-azaspiro[2.5]octane-6-carboxylate (38 mg, 0.178 mmol) was added. The resulting mixture was stirred at 70° C. on and then the reaction was quenched by the addition of water. The mixture was extracted with EA and the combined organic phase was washed with water (×3), brine, dried (MgSO₄), filtered and concentrated in vacuo. The residue was purified by Flash CC (Hex:EA=1:0 to 1:1) to give 3P4-1.

LCMS: MS Calcd.: 563; MS Found: 564 ([M+H]⁺).

4-((4-(Cyclopropyl(4-(trifluoromethyl)benzyl)amino)-5-fluoro-7H-pyrrolo[2,3-d]pyrimidin-7-yl)methyl)piperidin-4-ol, 3P5-1

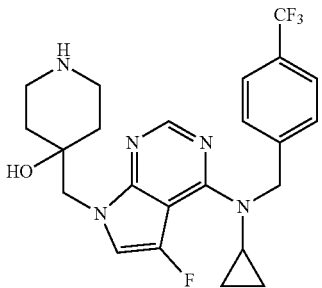

To a solution of 3P4-1 (55 mg, 0.087 mmol) in dioxane (2 mL) HCl in dioxane a (2 mL, 4 M) was added and the resulting mixture was stirred at rt for 2 h and then the volatiles were removed. The residue was redissolved in water and aq K₂CO₃ was added until the pH of the solution was >8. The product was then extracted with DCM (×3) and the combined organic phase was washed with water (×3), brine, dried (MgSO₄), filtered and concentrated in vacuo to give 3P5-1.

LCMS: MS Calcd.: 463; MS Found: 464 ([M+H]⁺).

2-(4-((4-(Cyclopropyl(4-(trifluoromethyl)benzyl)amino)-5-fluoro-7H-pyrrolo[2,3-d]pyrimidin-7-yl)methyl)-4-hydroxypiperidin-1-yl)acetamide, 3P6-1.

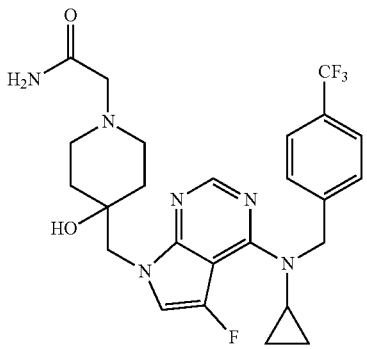

3P6-1

To a solution of 3P5-1 (45 mg, 0.097 mmol) in DCM (2 mL), trimethylamine (0.032 mL) and 2-bromoacetamide (16 mg) were added. The resulting mixture was stirred at rt on and then it was diluted with DCM. This diluted solution was washed with water (×3), brine, dried (MgSO$_4$), filtered and concentrated in vacuo. The remaining residue was purified by Flash CC (DCM:MeOH=1:0 to 9:1) to give 3P6-1.

LCMS: MS Calcd.: 520; MS Found: 521 ([M+H]$^+$).

The following compounds were synthesized according to General Method 3P:

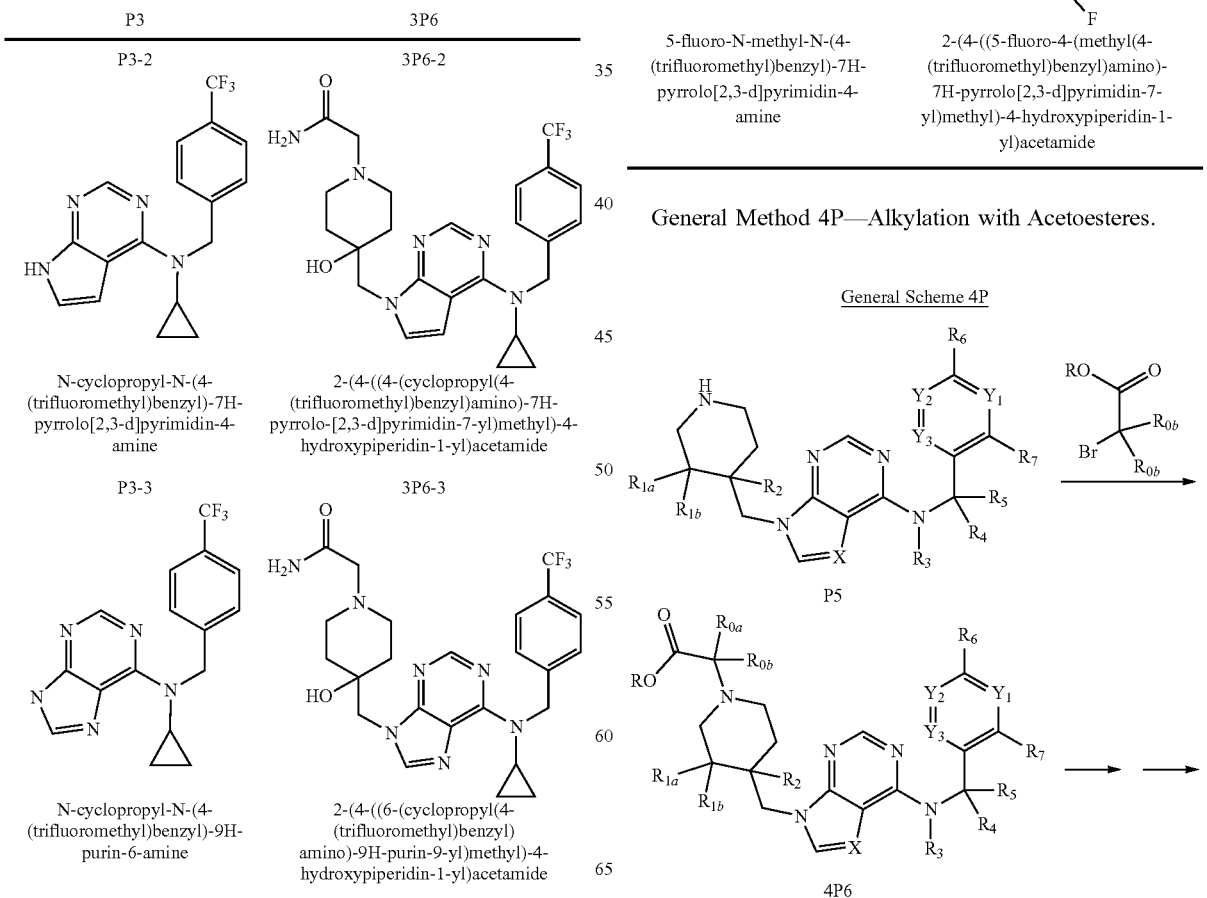

General Method 4P—Alkylation with Acetoesters.

-continued

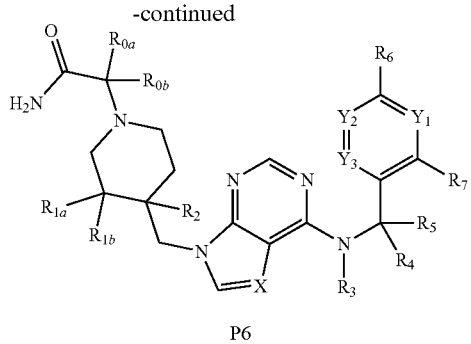

P6

When the R₀ group was not H, the alkylation of P5 was performed with the corresponding substituted 2-bromoacetoester and a suitable base (as described above) to give 4P6. Thereafter, subsequent aminolysis (NH₃ in MeOH) gave P6.

Synthesis of rac-2-((3R,4R)-4-((4-(cyclopropyl(4-(trifluoromethyl)benzyl)amino)-7H-pyrrolo[2,3-d]pyrimidin-7-yl)methyl)-3-hydroxypiperidin-1-yl)-3-hydroxypropanamide, P6-37

Example P6-37

Scheme P6-37

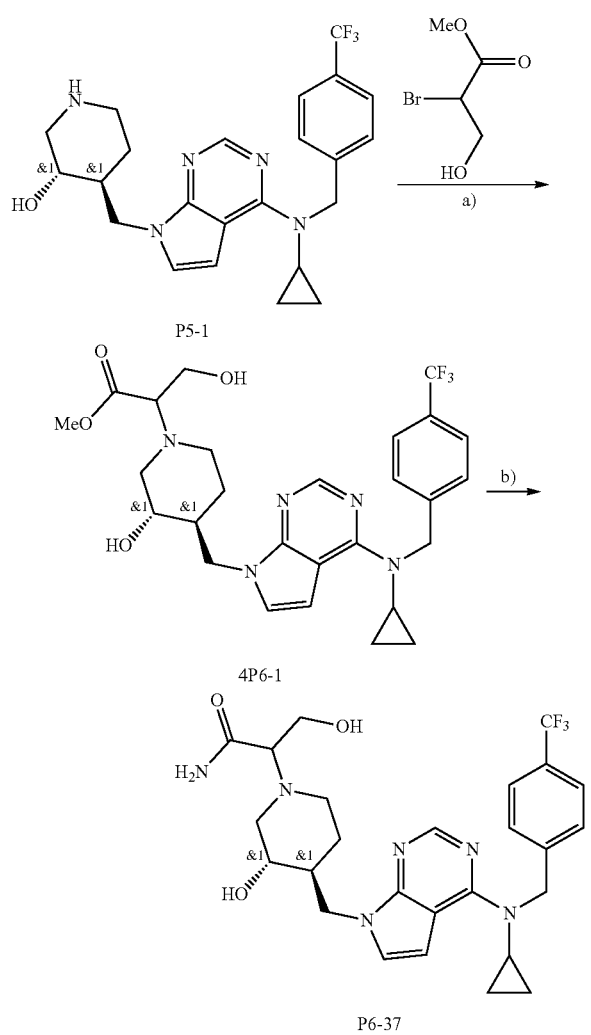

a) DIEA, DMF b) 7M NH₃/MeOH.

rac-Methyl 2-((3R,4R)-4-((4-(cyclopropyl(4-(trifluoromethyl)benzyl)amino)-7H-pyrrolo[2,3-d]pyrimidin-7-yl)methyl)-3-hydroxypiperidin-1-yl)-3-hydroxypropanoate, 4P6-1.

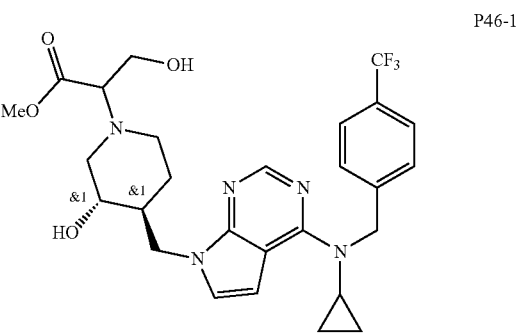

To a solution of P5-1 (102 mg, 0.229 mmol) in dry DMF (3 mL), DIEA (120 μL, 0.689 mmol) and methyl 2-bromo-3-hydroxypropanoate (84 mg, 0.459 mmol) were added. The resulting mixture was stirred at rt on. Excess DIEA (1.5 eq) and methyl 2-bromo-3-hydroxypropanoate (1 eq.) were added and the mixture was stirred for additional 4 h. Then the reaction mixture was diluted with water and the product was extracted with EA (×3). The combined organic solution was washed with water (×3), brine, dried (MgSO₄), filtered and concentrated in vacuo to give 4P6-1.

LCMS: MS Calcd.: 547; MS Found: 548 ([M+H]⁺).

rac-2-((3R,4R)-4-((4-(Cyclopropyl(4-(trifluoromethyl)benzyl)amino)-7H-pyrrolo[2,3-d]pyrimidin-7-yl)methyl)-3-hydroxypiperidin-1-yl)-3-hydroxypropanamide, P6-37

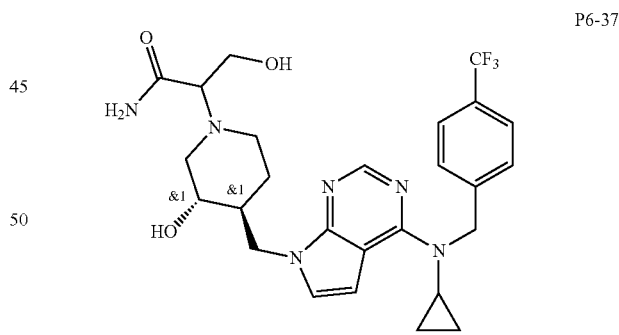

Intermediate 4P6-1 was treated with a 7M solution of ammonia in MeOH (10 mL) and the resulting solution was heated using microwave irradiation to 80° C. for 20 h. Then the solution was concentrated and the same treatment with ammonia was repeated two more times. After three cycles the reaction was concentrated in vacuo and the residue was purified by Flash CC (DCM:MeOH=1:0 to 9:1) to give P6-37.

LCMS: MS Calcd.: 532; MS Found: 533 ([M+H]⁺).

General Method L—Synthesis of Diols from Epoxide

General Scheme L

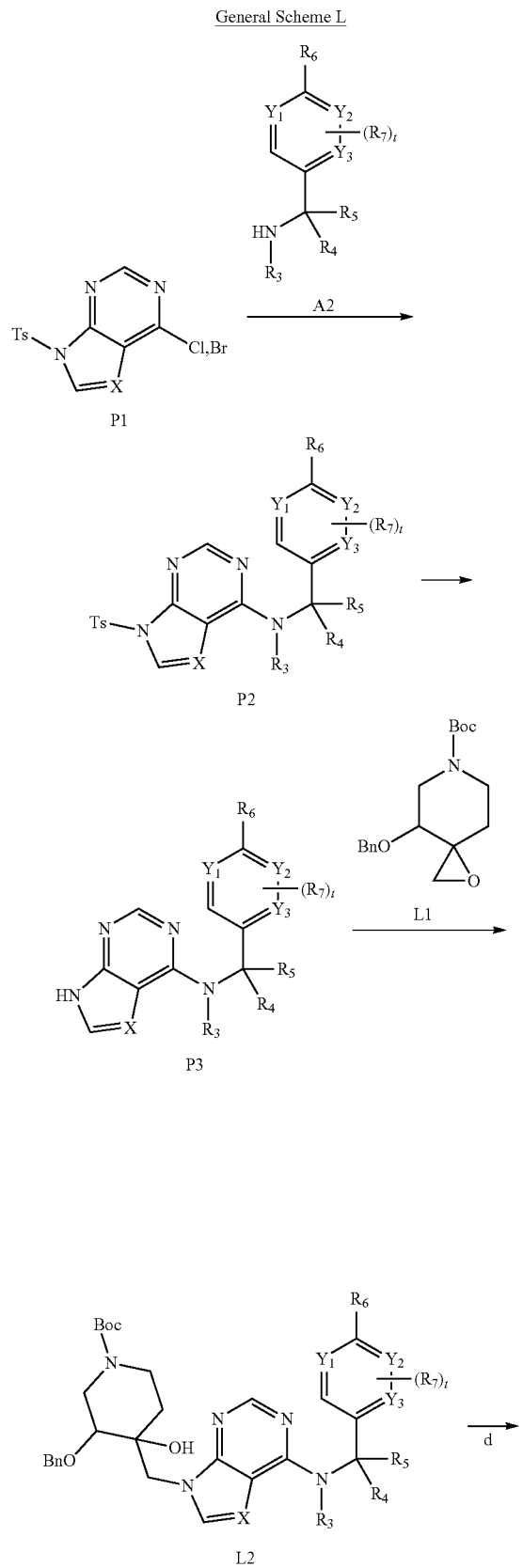

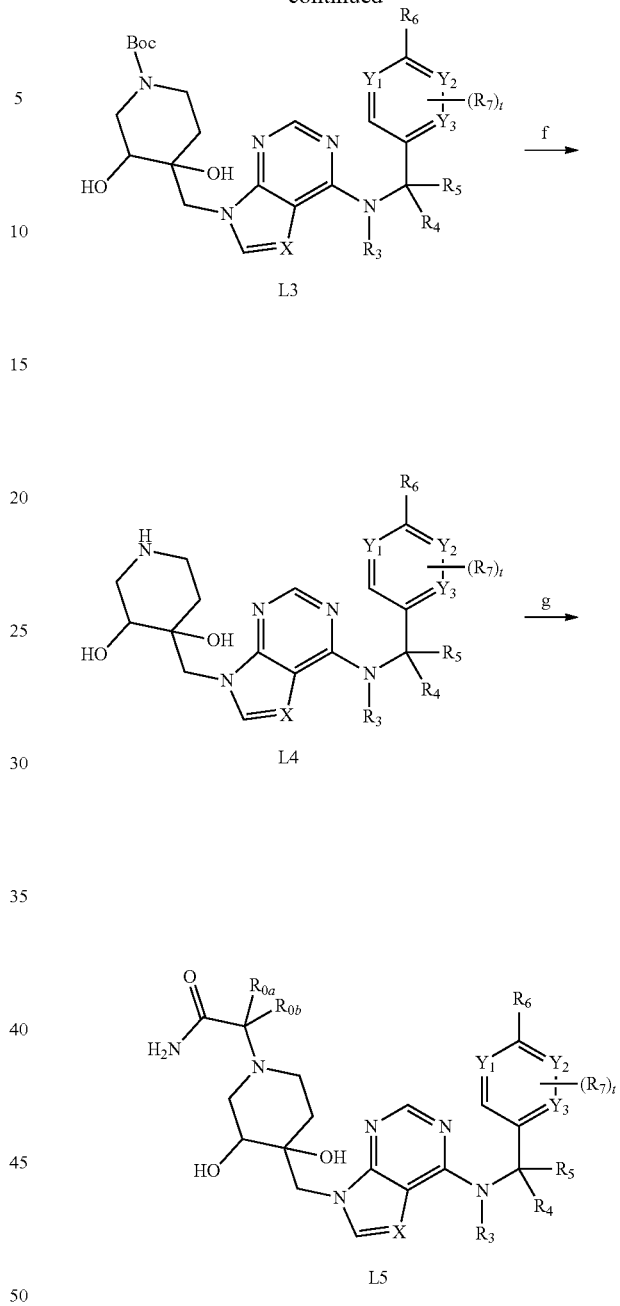

P1 was substituted with the secondary amine A2 employing a suitable bas (ie TEA) in water to yield P2. Then the Tosyl group was removed by heating P2 in MeOH with $K_2CO_3$ at a slightly elevated temperature. Thereafter, P3 was deprotonated with NaH and alkylated with the epoxide L1 in DMF to produce L2. Benzyl deprotection of L2 to L3 was accomplished with Pd/C and $NH_4HCO_2$ in MeOH. The following Boc deprotection (HCl in dioxane or TFA) gave L4. L4 was thereafter most often used directly, as the corresponding pyridinium salt (HCl of TFA), in the subsequent alkylation with the corresponding 2-bromoacetamide A1 and a suitable base, such as $K_2CO_3$ or DIEA, to yield L5. In the cases when L5 were mixtures of stereoisomers they were often (but not always) subjected to chiral chromatography to obtain the single stereoisomers.

Example L5-1

Synthesis of 2-(4-((4-(cyclopropyl(4-(trifluoromethyl)benzyl)amino)-7H-pyrrolo[2,3-d]pyrimidin-7-yl)methyl)-3,4-dihydroxypiperidin-1-yl)acetamide, L5-1, and including separation and isolation of two stereoisomers L5-1-1-1 and L5-1-1-2.

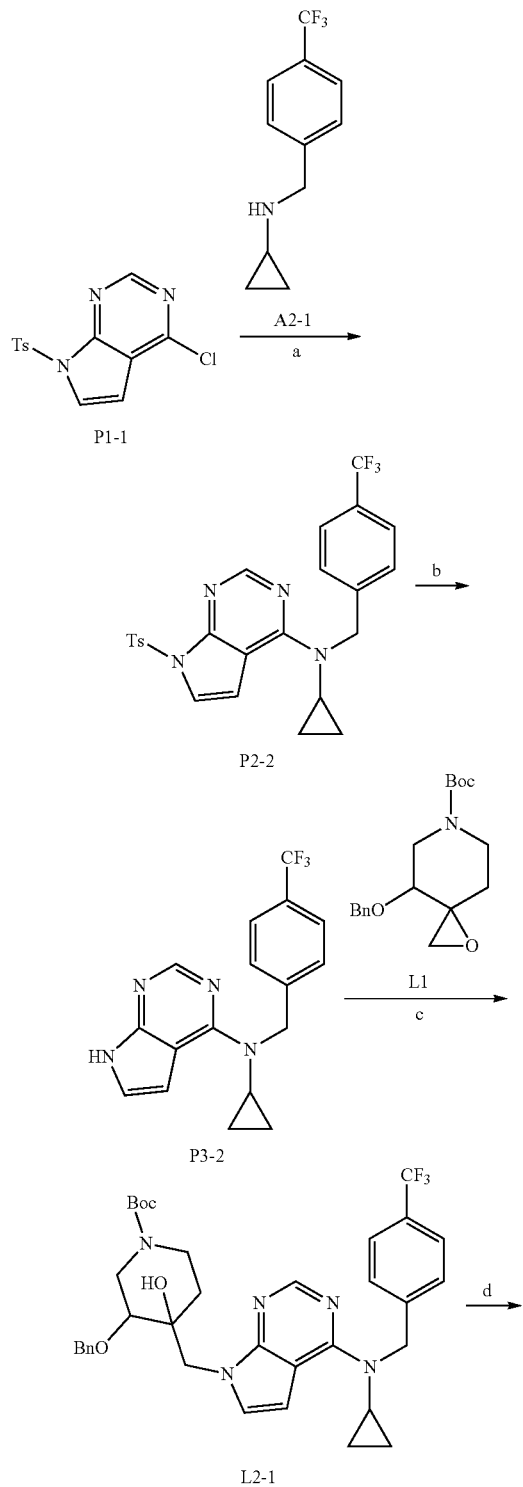

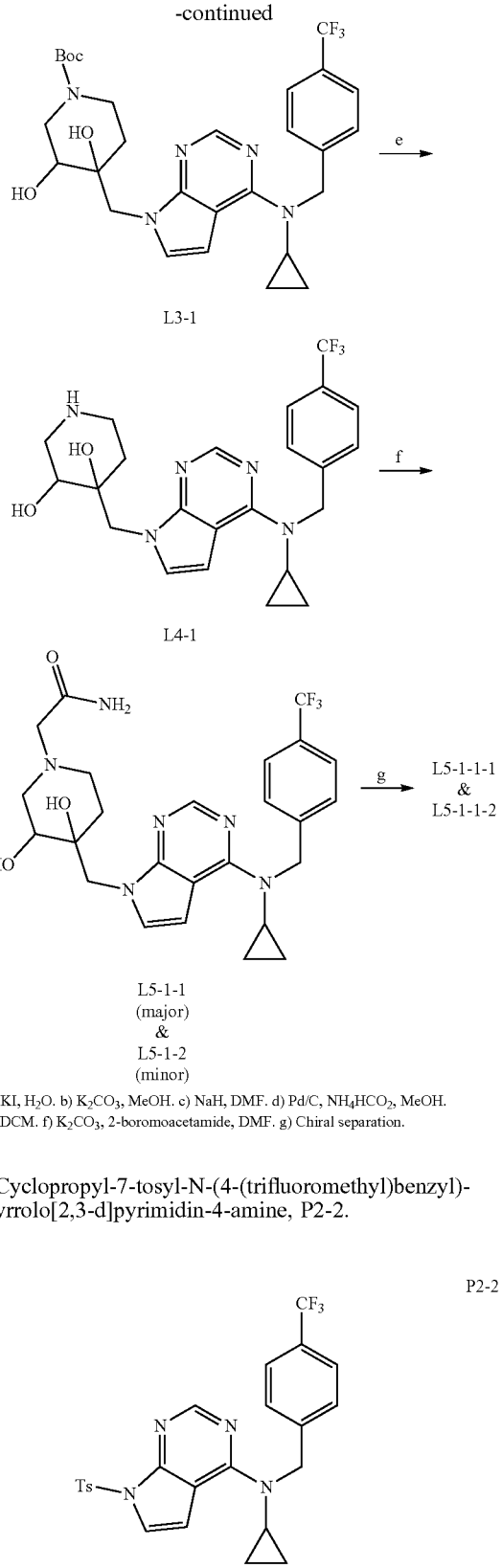

a) TEA, KI, H$_2$O. b) K$_2$CO$_3$, MeOH. c) NaH, DMF. d) Pd/C, NH$_4$HCO$_2$, MeOH. e) TFA, DCM. f) K$_2$CO$_3$, 2-boromoacetamide, DMF. g) Chiral separation.

N-Cyclopropyl-7-tosyl-N-(4-(trifluoromethyl)benzyl)-7H-pyrrolo[2,3-d]pyrimidin-4-amine, P2-2.

A vial was loaded with P1-1 (4.0 g, 13.3 mmol), A2-1 (N-(4-(trifluoromethyl)benzyl)cyclopropanamine) (3.1 g, 14.3 mmol), TEA (4.0 g, 39 mmol), KI (1.1 g, 6.5 mmol) and H$_2$O (30 mL). The vial was sealed and heated to 130° C. on.

The reaction was extracted with EA (3×50 mL) and the pooled organic phase was concentrated in vacuo. The remains were purified by Flash CC (PE:EA=8:1 to 5:1) to give P2-2.

LCMS: MS Calcd.: 486; MS Found: 487 ([M+H]⁺).

N-Cyclopropyl-N-(4-(trifluoromethyl)benzyl)-7H-pyrrolo[2,3-d]pyrimidin-4-amine, P3-2.

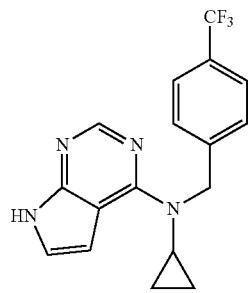 [SMILES: FC(F)(F)c1ccc(CN(c2ncnc3[nH]ccc23)C2CC2)cc1]

P3-2

K₂CO₃ was added to a solution of P2-2 (5.5 g, 11.3 mmol) in MeOH (45 mL) and the reaction was heated to 50° C. for 5 h. The reaction was thereafter quenched with water and then concentrated in vacuo to remove MeOH. The mixture was then extracted with EA (3×50 mL) and the combined organic phase was concentrated in vacuo. The remains were then washed with PE:EA=10:1 to yield P3-2.

LCMS: MS Calcd.: 332; MS Found: 333 ([M+H]⁺).

tert-Butyl 3-(benzyloxy)-4-((4-(cyclopropyl(4-(trifluoromethyl)benzyl)amino)-7H-pyrrolo[2,3-d]pyrimidin-7-yl)methyl)-4-hydroxypiperidine-1-carboxylate, L2-1.

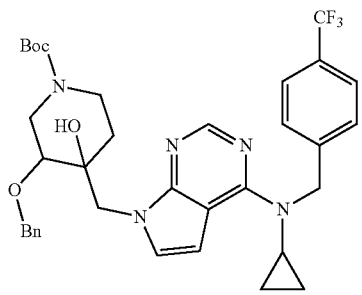

L2-1

Under a N₂ atm NaH (96 mg, 2.4 mmol, 60%) was added to a solution of P3-2 (400 mg, 1.2 mmol) in dry DMF (16 mL). The reaction was stirred at rt for 30 min and then a solution of L1 (845 mg, 2.65 mmol, in 5 mL of dry DMF) was added dropwise. The reaction was then stirred at 60° C. on before it was quenched by the addition of H₂O (40 mL). The mixture was extracted with EA (3×20 mL) and the combined organic phase was washed with brine (3×15 mL), dried (Na₂SO₄), filtered and concentrated in vacuo. The residue was purified by Flash CC (PE:EA=1:4 to 1:2) to give L2-1.

LCMS: MS Calcd.: 651; MS Found: 652 ([M+H]⁺).

tert-Butyl 4-((4-(cyclopropyl(4-(trifluoromethyl)benzyl)amino)-7H-pyrrolo[2,3-d]pyrimidin-7-yl)methyl)-3,4-dihydroxypiperidine-1-carboxylate, L3-1.

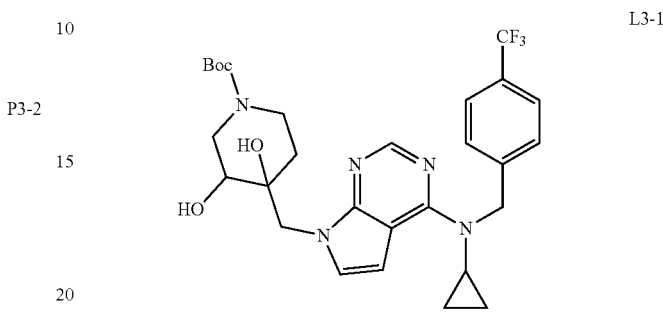

L3-1

Pd/C (500 mg, 10%) was added to a solution of L2-1 (680 mg, 1.0 mmol) and NH₄HCO₂ (1.6 g, 25.1 mmol) in MeOH. The reaction was refluxed on. After cooling to ambient temperature, the mixture was filtered and concentrated in vacuo. The residue was purified by Prep-TLC (EA:PE=1:1) to yield L3-1.

LCMS: MS Calcd.: 561; MS Found: 562 ([M+H]⁺).

4-((4-(Cyclopropyl(4-(trifluoromethyl)benzyl)amino)-7H-pyrrolo[2,3-d]pyrimidin-7-yl)methyl)piperidine-3,4-diol, L4-1.

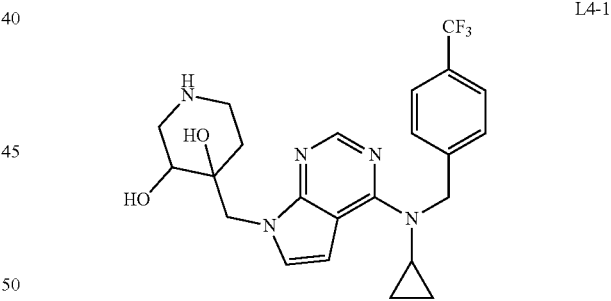

L4-1

A solution of L3-1 (320 mg, 0.57 mmol) in a mixture of TFA (0.5 mL) and DCM (8 mL) was stirred at rt for 1 h. The mixture was concentrated in vacuo to yield crude L4-1, that was used without further purification.

LCMS: MS Calcd.: 461; MS Found: 462 ([M+H]⁺).

Synthesis of 2-(4-((4-(cyclopropyl(4-(trifluoromethyl)benzyl)amino)-7H-pyrrolo[2,3-d]pyrimidin-7-yl)methyl)-3,4-dihydroxypiperidin-1-yl)acetamide, L5-1 and separation of the diastereomers rac-2-((3R,4R)-4-((4-(cyclopropyl(4-(trifluoromethyl)benzyl)amino)-7H-pyrrolo[2,3-d]pyrimidin-7-yl)methyl)-3,4-dihydroxypiperidin-1-yl)acetamide, L5-1-1 and rac-2-((3R,4S)-4-((4-(cyclopropyl(4-(trifluoromethyl)benzyl)amino)-7H-pyrrolo[2,3-d]pyrimidin-7-yl)methyl)-3,4-dihydroxypiperidin-1-yl)acetamide, L5-1-2.

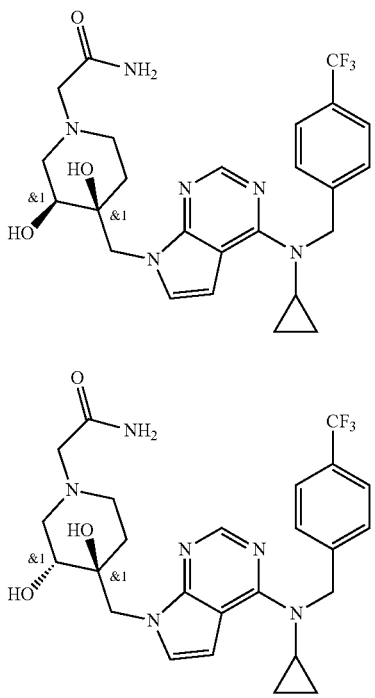

K₂CO₃ (787 mg, 5.7 mmol) and 2-bromoacetamide (157 mg, 1.1 mmol) were in turn added to a solution of L4-1 (746 mg, crude) in DMF (12 mL). The reaction was stirred at rt on. Thereafter, H₂O (50 mL) was added and the mixture was extracted with EA (3×20 mL). The combined organic phase was washed with brine (2×15 mL), dried (Na₂SO₄), filtered and concentrated in vacuo. The residue was then purified by Prep-TLC (MeOH:DCM=1:10) to give two diastereomeric products L5-1-1 and L5-1-2.

Separation of the enantiomers of L5-1-1 to rel-2-((3R, 4R)-4-((4-(cyclopropyl(4-(trifluoromethyl)benzyl)amino)-7H-pyrrolo[2,3-d]pyrimidin-7-yl)methyl)-3,4-dihydroxypiperidin-1-yl)acetamide, L5-1-1-1 and L5-1-1-2

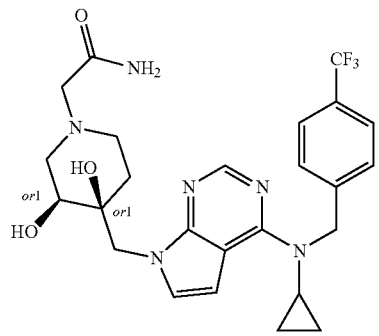

L5-1-1 was then separated into the enantiomers;

L5-1-1-1, 1ˢᵗ eluting enantiomer, and L5-1-1-2, 2ⁿᵈ eluting enantiomer.

The following compounds were synthesized according to General Method L:

| A2 | L8 |
|---|---|
| A2-13 | L5-2-1-1 |
| N-(4-(trifluoromethyl)benzyl)ethanamine | rel-2-((3R,4R)-4-((4-(ethyl(4-(trifluoromethyl)benzyl)amino)-7H-pyrrolo[2,3-d]pyrimidin-7-yl)methyl)-3,4-dihydroxypiperidin-1-yl)acetamide 1ˢᵗ eluting isomer |
| A2-13 | L5-2-1-2 rel-2-((3R,4R)-4-((4-(ethyl(4-(trifluoromethyl)benzyl)amino)-7H-pyrrolo[2,3-d]pyrimidin-7-yl)methyl)-3,4-dihydroxypiperidin-1-yl)acetamide 2ⁿᵈ eluting isomer |
| A2-3 | L5-3-1 |
| N-(2-fluoro-4-(trifluoromethyl)benzyl)ethanamine | rac-2-((3R,4R)-4-((4-(ethyl(2-fluoro-4-(trifluoromethyl)benzyl)amino)-7H-pyrrolo[2,3-d]pyrimidin-7-yl)methyl)-3,4-dihydroxypiperidin-1-yl)acetamide |
| A2-3 | L5-3-1-1 |
| N-(2-fluoro-4-(trifluoromethyl)benzyl)ethanamine | rel-2-((3R,4R)-4-((4-(ethyl(2-fluoro-4-(trifluoromethyl)benzyl)amino)-7H-pyrrolo[2,3-d]pyrimidin-7-yl)methyl)-3,4-dihydroxypiperidin-1-yl)acetamide 1ˢᵗ eluting isomer |
| A2-3 | L5-3-1-2 rel-2-((3R,4R)-4-((4-(ethyl(2-fluoro-4-(trifluoromethyl)benzyl)amino)-7H-pyrrolo[2,3-d]pyrimidin-7-yl)methyl)-3,4-dihydroxypiperidin-1-yl)acetamide 2ⁿᵈ eluting isomer |

Synthesis of tert-butyl 4-(benzyloxy)-1-oxa-6-azaspiro[2.5]octane-6-carboxylate, L4

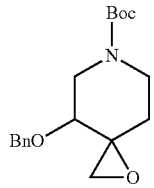

L4

Under a $N_2$ atm NaH (283 mg, 7.1 mmol, 60%) was added to a 0° C. solution of trimethylsulfonium iodide (1.44 g, 7.1 mmol) in dry DMF (20 mL) and the reaction was allowed to stir for 30 min. Thereafter, a solution of iL4 (tert-butyl 3-(benzyloxy)-4-oxopiperidine-1-carboxylate) (1.8 g, 5.9 mmol) in dry DMF (5 mL) was added slowly and then stirred at rt on. The reaction was quenched with $NH_4Cl$ (sat aq 50 mL) and the mixture was extracted with EA (3×15 mL). The combined organic layer was washed with brine (2×10 mL), dried ($Na_2SO_4$) filtered, concentrated in vacuo to yield crude L4 that was used without further purification.

LCMS: MS Calcd.: 319; MS Found: 342 ([M+Na]+).

General Method R. Synthesis diols via Sharpless Dihydroxylation

The enantiomerically enriched R5 diols were also synthesized by employing the Sharpless Dihydroxylation.

General Scheme R

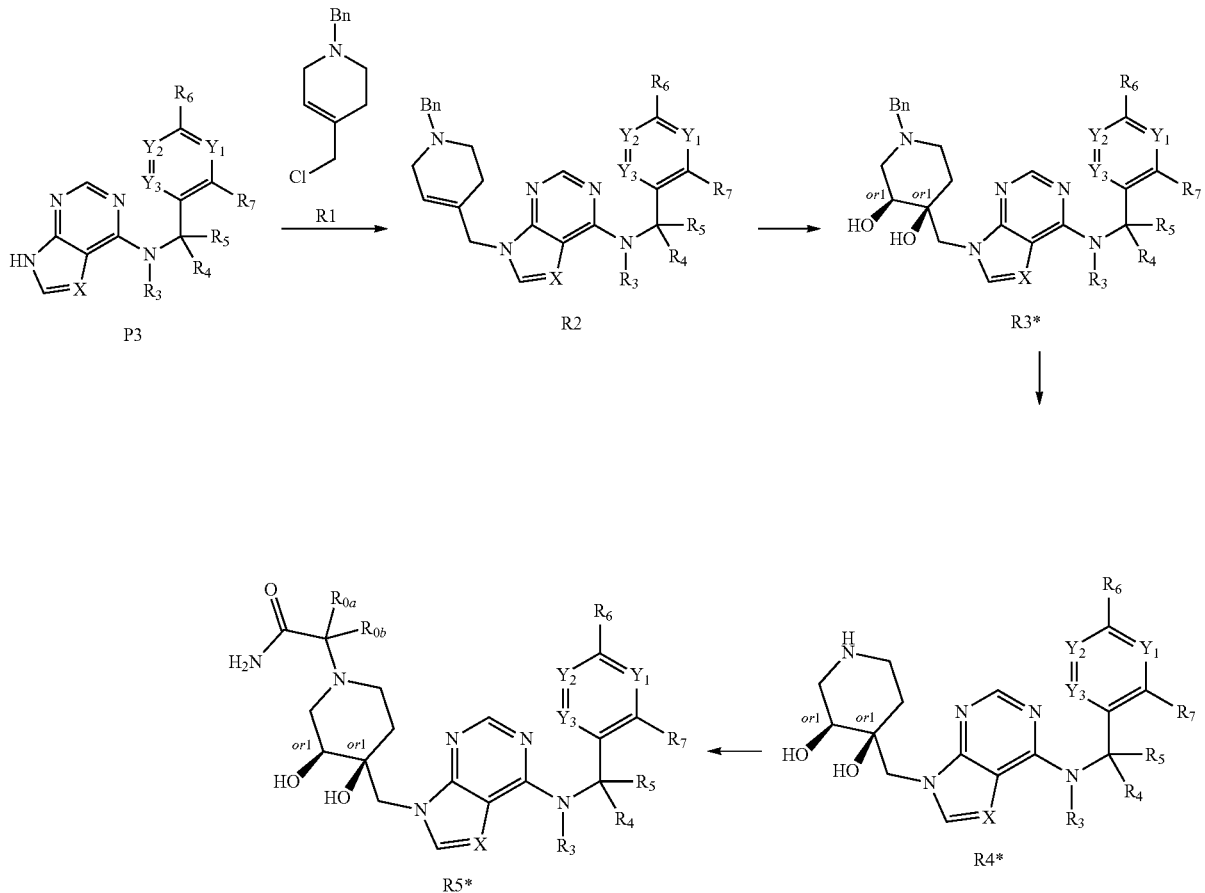

The intermediate P3 was alkylated with the benzyl-protected piperidine R1 and a base as outlined above. Sharpless dihydroxylation was then carried out on R2 to yield the diol R3". These were in turn deprotected with hydrogen and Pd/C in a suitable solvent at room temperature. The formed R4" was then alkylated with the corresponding 2-haloacetamides and a suitable base, such as DIEA, TEA, $Cs_2CO_3$ or $K_2CO_3$ to yield R5". R5" were first purified by chromatographic methods (to ensure pure products and to isolate possible diastereomers). In addition, the enantiomerically enriched R5" products were often subjected (but not always) to chiral resolution (by chromatography) to obtain the pure stereoisomers as the end products.

Example R5-1"
Synthesis of enantiomerically enriched rel-2-((3R,4R)-4-((4-((4-(1H-pyrazol-1-yl)benzyl)(ethyl)amino)-7H-pyrrolo[2,3-d]pyrimidin-7-yl)methyl)-3,4-dihydroxypiperidin-1-yl)acetamide, R5-1"

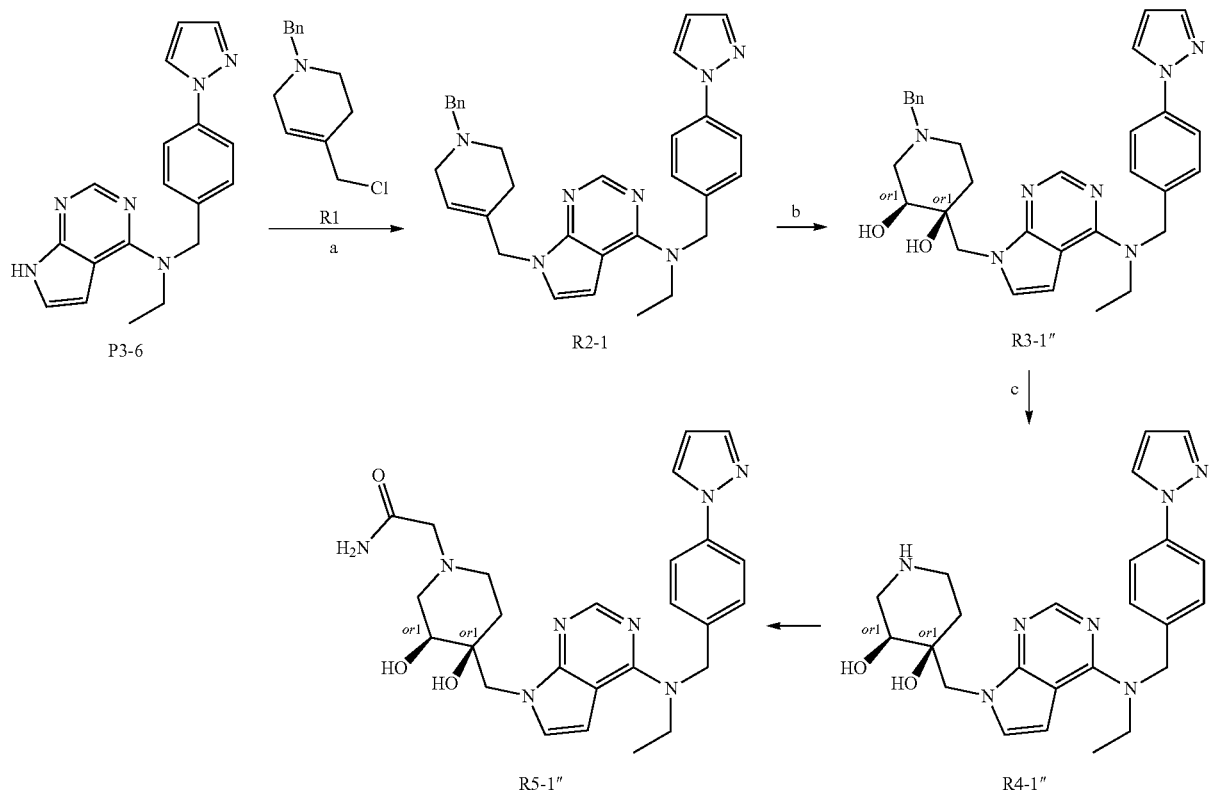

1-Benzyl-4-(chloromethyl)-1,2,3,6-tetrahydropyridine hydrochloride, R1

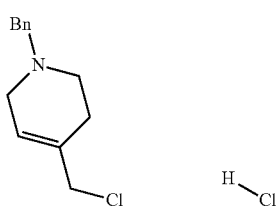

SOCl$_2$ (250 µL, 3.45 mmol) was added to a solution of (1-Benzyl-1,2,3,6-tetrahydropyridin-4-yl)methanol (500 mg, 2.46 mmol) in DCM (10 mL) and the reaction mixture was stirred at rt for 3 h. The solvent was removed in vacuo to yield R1 that was used without further purification.

N-(4-(1H-Pyrazol-1-yl)benzyl)-7-((1-benzyl-1,2,3,6-tetrahydropyridin-4-yl)methyl)-N-ethyl-7H-pyrrolo[2,3-d]pyrimidin-4-amine, R2-1

Under a N$_2$ atm R$_1$ (715 mg, 2.77 mmol) was added to a solution of P3-6 (800 mg, 2.51 mmol) and Cs$_2$CO$_3$ (2.5 g, 7.67 mmol) in dry DMF (25 mL). The reaction mixture was heated at 60° C. on. Then water was added and the resulting mixture was extracted with EA (×3). The combined organic layer was washed with H$_2$O, brine, dried (MgSO$_4$), filtered and concentrated in vacuo. The remaining solid R$_2$-1 was used without further purification.
LCMS: MS Calcd.: 503.6; MS Found: 504 ([M+H]$^+$).

Enantiomerically enriched rel-(3R,4R)-4-((4-((4-(1H-pyrazol-1-yl)benzyl)(ethyl)amino)-7H-pyrrolo[2,3-d]pyrimidin-7-yl)methyl)-1-benzylpiperidine-3,4-diol, R3-1"

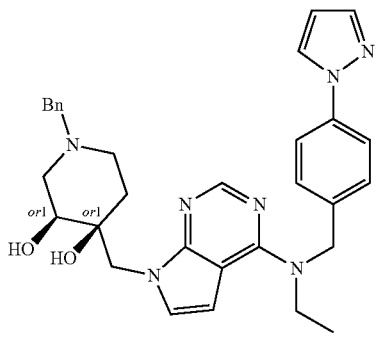 [SMILES: CCN(Cc1ccc(-n2cccn2)cc1)c1ncnc2c1ccn2C[C@@]1(O)CCN(Cc2ccccc2)C[C@@H]1O]

R2-1 (1.2 g, 2.38 mmol) was mixed with tBuOH (20 mL)/H₂O (20 mL) at 0° C. and then the following reagents were added: potassium hexacyanoferrate(III) (2.4 g, 7.29 mmol), potassium carbonate (990 mg, 7.16 mmol), (DHQ)₂PHAL (186 mg, 0.24 mmol), osmium(VI) dipotassium oxide dehydrate (88 mg, 0.24 mmol) and methanesulfonamide (272 mg, 2.86 mmol). The reaction was then stirred at rt for 2 days. The reaction was thereafter quenched by the addition of NaNO₂ (1.64 g) and water (3 mL), and the mixture was stirred at rt for 1 h. More water was added, and the mixture was extracted with DCM (×3). The combined organic layer was washed with water, brine, dried (MgSO₄) and concentrated in vacuo. The residue was then purified by Flash CC (MeOH:DCM=1:9) to yield R3-1".

LCMS: MS Calcd.: 537.7; MS Found: 538 ([M+H]⁺).

Enantiomerically enriched rel-(3R,4R)-4-((4-((4-(1H-pyrazol-1-yl)benzyl)(ethyl)amino)-7H-pyrrolo[2,3-d]pyrimidin-7-yl)methyl)piperidine-3,4-diol, R4-1"

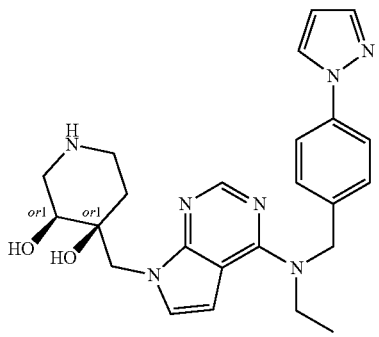 [SMILES: CCN(Cc1ccc(-n2cccn2)cc1)c1ncnc2c1ccn2C[C@@]1(O)CCNC[C@@H]1O]

Pd/C (10%, 30 mg) was added to a solution of R3-1" (288 mg, 0.54 mmol) in MeOH (10 mL) and the reaction was stirred under H₂ (18 psi) in a Parr reactor. Additional 10% Pd/C (30 mg, 0.28 mmol) was added and the reaction was again stirred under H₂ (18 psi) for 2 more days. The mixture was the filtered through celite and the solvent was removed in vacuo. The remaining solid R4-2" was used without further purification.

LCMS: MS Calcd.: 447.5; MS Found: 448 ([M+H]⁺).

Enantiomerically enriched rel-2-((3R,4R)-4-((4-((4-(1H-pyrazol-1-yl)benzyl)(ethyl)amino)-7H-pyrrolo[2,3-d]pyrimidin-7-yl)methyl)-3,4-dihydroxypiperidin-1-yl)acetamide, R5-1"

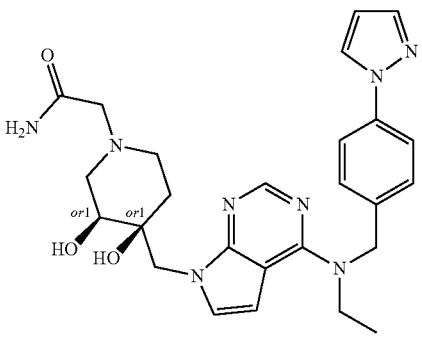 [SMILES: CCN(Cc1ccc(-n2cccn2)cc1)c1ncnc2c1ccn2C[C@@]1(O)CCN(CC(N)=O)C[C@@H]1O]

K₂CO₃ (372 mg, 2.69 mmol) and 2-bromoacetamide (136 mg, 0.99 mmol) were in turn added to a solution of R₄-1 (402 mg, 0, 0.90 mmol) in DMF (6 mL) and the reaction was stirred on at rt. Thereafter H₂O was added, and the mixture was extracted with AcOEt (×3). The combined organic layer was washed with H₂O, brine, dried (MgSO₄), filtered and concentrated in vacuo. The residue was purified by Flash CC (MeOH:DCM=1:9) to yield R5-1.

LCMS: MS Calcd.: 504.6; MS Found: 505 ([M+H]⁺).

The following compounds were synthesized according to Method R:

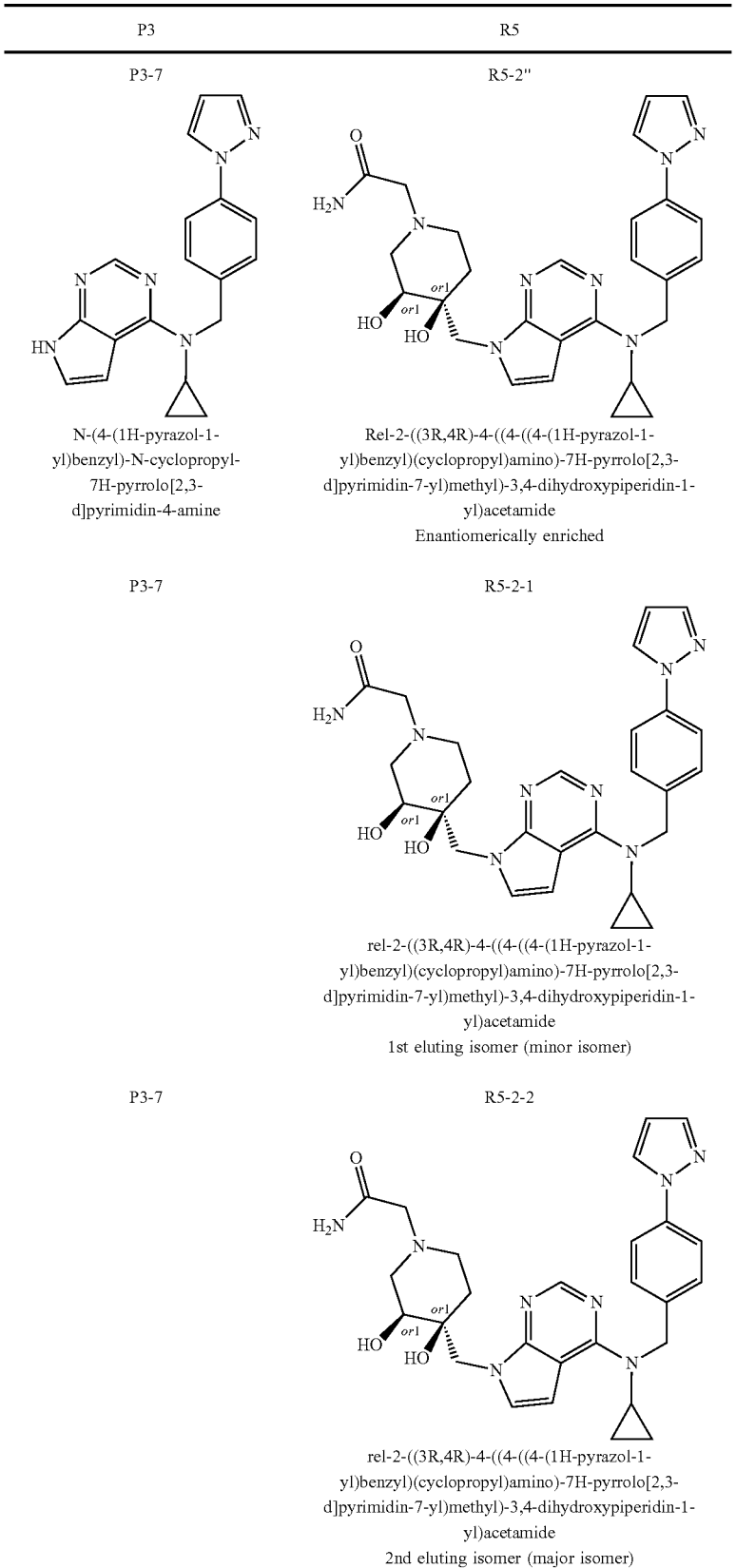

| P3 | R5 |
|---|---|
| P3-7 | R5-2" |
| N-(4-(1H-pyrazol-1-yl)benzyl)-N-cyclopropyl-7H-pyrrolo[2,3-d]pyrimidin-4-amine | Rel-2-((3R,4R)-4-((4-((4-(1H-pyrazol-1-yl)benzyl)(cyclopropyl)amino)-7H-pyrrolo[2,3-d]pyrimidin-7-yl)methyl)-3,4-dihydroxypiperidin-1-yl)acetamide<br>Enantiomerically enriched |
| P3-7 | R5-2-1 |
| | rel-2-((3R,4R)-4-((4-((4-(1H-pyrazol-1-yl)benzyl)(cyclopropyl)amino)-7H-pyrrolo[2,3-d]pyrimidin-7-yl)methyl)-3,4-dihydroxypiperidin-1-yl)acetamide<br>1st eluting isomer (minor isomer) |
| P3-7 | R5-2-2 |
| | rel-2-((3R,4R)-4-((4-((4-(1H-pyrazol-1-yl)benzyl)(cyclopropyl)amino)-7H-pyrrolo[2,3-d]pyrimidin-7-yl)methyl)-3,4-dihydroxypiperidin-1-yl)acetamide<br>2nd eluting isomer (major isomer) |

| P3 | R5 |
|---|---|
| P3-8 | R5-3 |
| 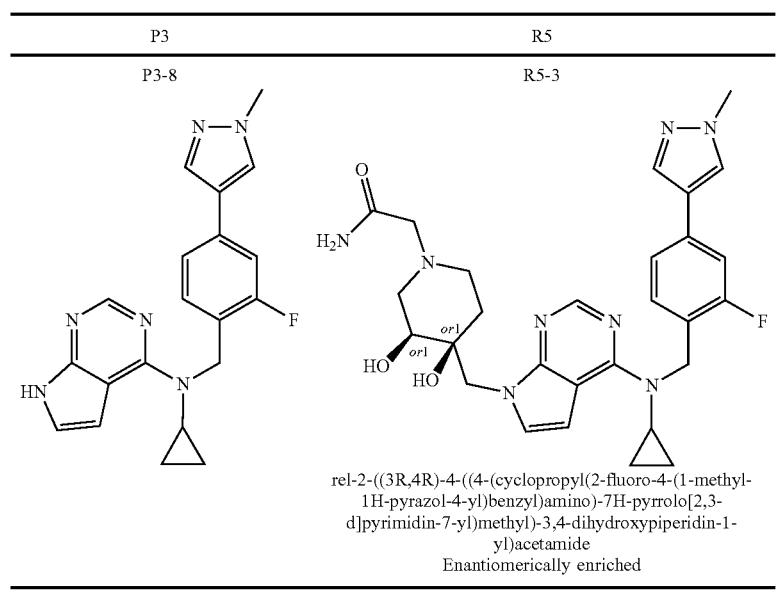 | rel-2-((3R,4R)-4-((4-(cyclopropyl(2-fluoro-4-(1-methyl-1H-pyrazol-4-yl)benzyl)amino)-7H-pyrrolo[2,3-d]pyrimidin-7-yl)methyl)-3,4-dihydroxypiperidin-1-yl)acetamide<br>Enantiomerically enriched |

General Method 2R

In some cases when R6 was a heterocyclic ring general the General Method 2R was used.

General Scheme 2R

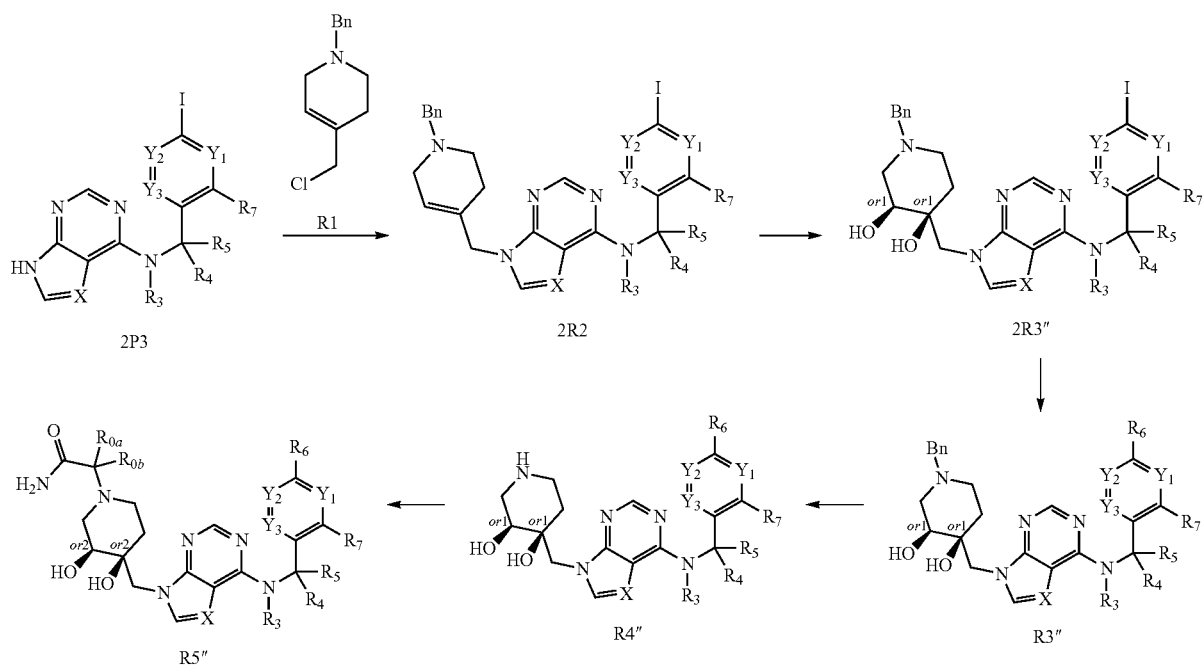

2P3 was obtained from the corresponding iodophenyl derivative as described above and then was reacted with the benzyl-protected piperidine R1 t alkylated with R1 to yield 2R2. The Sharpless dihydroxylation was performed to give enantiomerically enriched diol 2R3. Thereafter, 2R3″ underwent standard Buchwald coupling (together with Cu and a nitrogen containing heterocyclic ring) to give R3. Thereafter, R₃″ transformed into R₅, via deprotection to R₄ and subsequent alkylation with 2-bormo-acetamide, as described above.

Example R5-4"
Synthesis of enatiomerically enriched rel-2-((3R,4R)-4-((4-(cyclopropyl(2-fluoro-4-(1H-pyrazol-1-yl)benzyl)amino)-7H-pyrrolo[2,3-d]pyrimidin-7-yl)methyl)-3,4-dihydroxypiperidin-1-yl)acetamide, R5-4"2

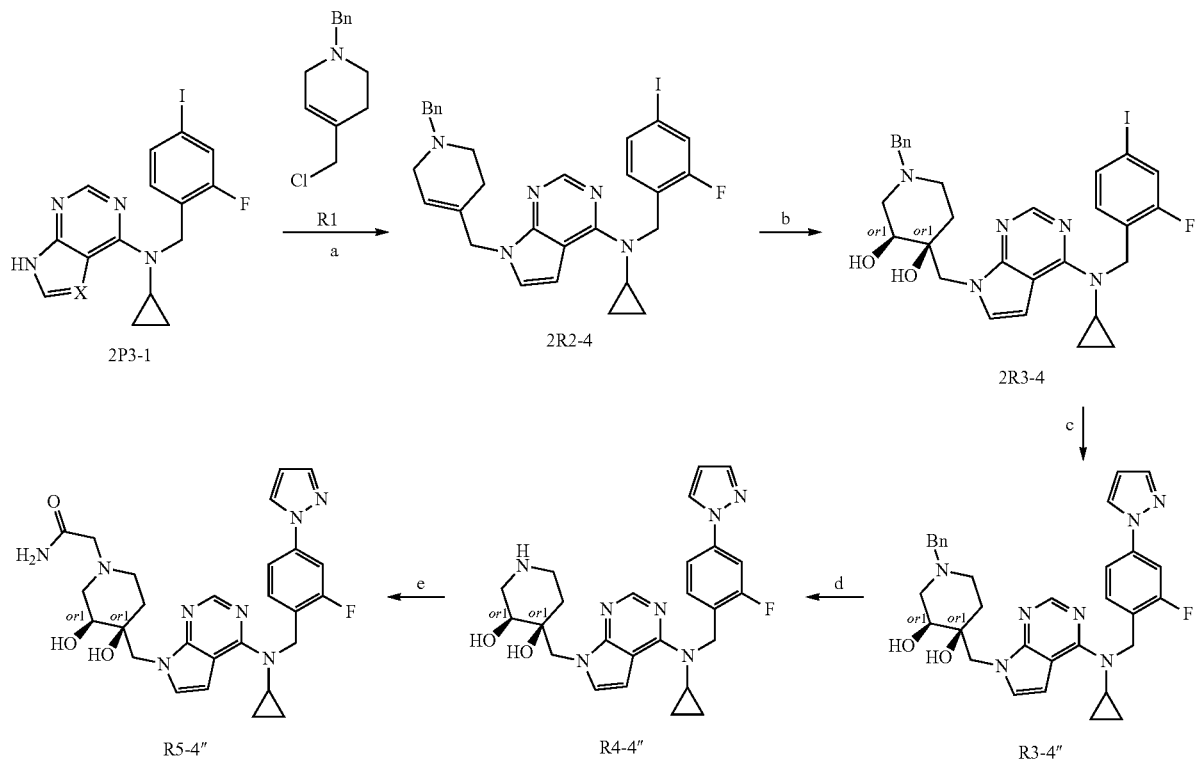

Scheme R5-4"

a) Cs$_2$CO$_3$, DMF. b) Sharpless dihydroxylation. c) CuI, 1H-pyrazole, (1R,2R)-cyclohexane-1,2-diamine, NMP.
d) Pd/C, H$_2$, MeOH. e) K$_2$CO$_3$, 2-boromoacetamide, DMF.

7-((1-Benzyl-1,2,3,6-tetrahydropyridin-4-yl)methyl)-N-cyclopropyl-N-(2-fluoro-4-iodobenzyl)-7H-pyrrolo[2,3-d]pyrimidin-4-amine, 2R2-4

Enantiomerically enriched rel-(3R,4R)-1-benzyl-4-((4-(cyclopropyl(2-fluoro-4-iodobenzyl)amino)-7H-pyrrolo[2,3-d]pyrimidin-7-yl)methyl)piperidine-3,4-diol, 2R3-4"

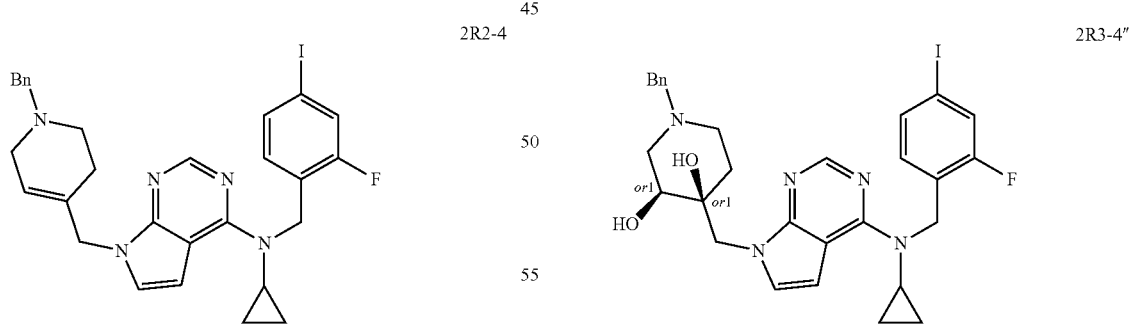

Under N$_2$ atm 2P3-1 (437 mg, 1.69 mmol) was added to a solution of R1 (628 mg, 1.54 mmol) and Cs$_2$CO$_3$ (1.5 g, 4.6 mmol) in dry DMF (15 mL). The reaction mixture was heated to 60° C. for 2 days. Water was added and the resulting mixture was extracted with EA (×3). The combined organic layer was washed with H$_2$O, brine, dried (MgSO$_4$), filtered and concentrated in vacuo. The residue was then purified by Flash CC (MeOH:DCM=1:9) to yield 2R2-4.
LCMS: MS Calcd.: 593.5; MS Found: 594 ([M+H]$^+$).

2R2-4 (430 mg, 0.72 mmol) was mixed with tBuOH (8 mL) and water (8 mL) at 0° C. Thereafter, the following reagents were added: potassium hexacyanoferrate(III) (715 mg, 2.17 mmol), K$_2$CO$_3$ (300 mg, 2.17 mmol), (DHQ)$_2$PHAL (56 mg, 0.072 mmol), osmium(VI) dipotassium oxide dehydrate (27 mg, 0.073 mmol) and methanesulfonamide (83 mg, 0.87 mmol). The reaction was then stirred at rt for 2 days. The reaction was thereafter quenched by the addition of NaNO$_2$ (500 mg) and H$_2$O (1 mL), and the mixture was stirred at rt for 2 h. The mixture was diluted with water and extracted with DCM (×3), the combined organic layer was washed with water and brine, dried (MgSO$_4$) and concentrated in vacuo. The residue was then purified by Flash CC (MeOH:DCM=1:9) to yield 2R3-4".

LCMS: MS Calcd.: 627.5; MS Found: 628 ([M+H]$^+$).

Enantiomerically enriched rel-(3R,4R)-1-benzyl-4-((4-(cyclopropyl(2-fluoro-4-(1H-pyrazol-1-yl)benzyl)amino)-7H-pyrrolo[2,3-d]pyrimidin-7-yl)methyl)piperidine-3,4-diol, R3-4"

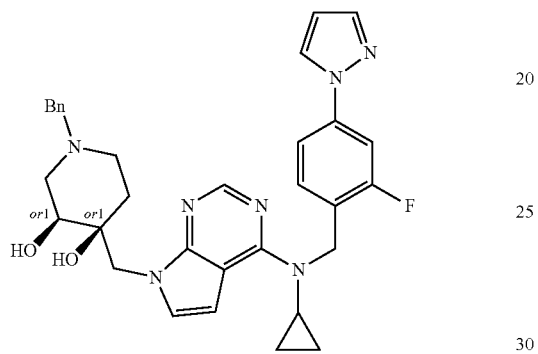

Under N$_2$ atm 1H-pyrazole (47 mg, 0.70 mmol), K$_2$CO$_3$ (96 mg, 0.69 mmol), (1R,2R)-cyclohexane-1,2-diamine (17 mg, 0.15 mmol) and CuI (6.6 mg, 0.035 mmol) were added to a solution of 2R3-4" in NMP (5 mL). The reaction mixture was stirred on at 120° C. Water was added and the product was extracted with AcOEt (×3). The combined organic layer was washed with H$_2$O, brine, dried (MgSO$_4$), filtered and concentrated in vacuo. The residue was then purified by Flash CC (MeOH:DCM=1:9) to yield R$_3$-4'.

LCMS: MS Calcd.: 567.7; MS Found: 568 ([M+H]$^+$).

Enantiomerically enriched rel-(3R,4R)-4-((4-(cyclopropyl(2-fluoro-4-(1H-pyrazol-1-yl)benzyl)amino)-7H-pyrrolo[2,3-d]pyrimidin-7-yl)methyl)piperidine-3,4-diol, R4-4"

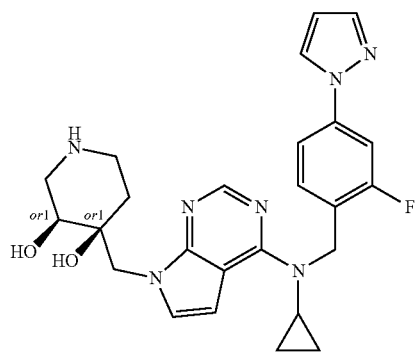 [SMILES: O[C@H]1CNCC[C@]1(O)Cn1ccc2c(N(Cc3ccc(-n4cccn4)cc3F)C3CC3)ncnc21]

Pd/C (10%, 14 mg) was added to a solution of R$_3$-4" (137 mg, 0.24 mmol) in MeOH (5 mL) and the reaction was stirred on under H$_2$ (1 atm). Then additional Pd/C (10%, 14 mg, 13) was added and reaction was again stirred under H$_2$ (1 atm) 2 more days. The mixture was filtered through Celite® and the filtrate was concentrated in vacuo. The solid R4-4" was used without further purification.

LCMS: MS Calcd.: 477.5; MS Found: 478 ([M+H]$^+$).

Enantiomerically enriched rel-2-((3R,4R)-4-((4-(cyclopropyl(2-fluoro-4-(1H-pyrazol-1-yl)benzyl)amino)-7H-pyrrolo[2,3-d]pyrimidin-7-yl)methyl)-3,4-dihydroxypiperidin-1-yl)acetamide, R5-4"

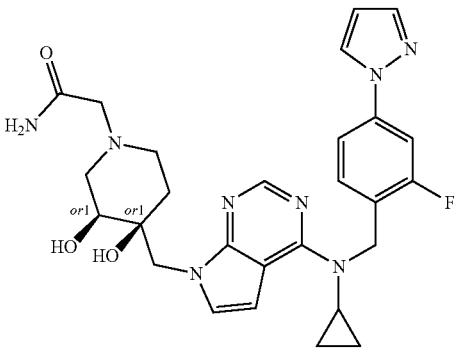 [SMILES: NC(=O)CN1CC[C@](O)(Cn2ccc3c(N(Cc4ccc(-n5cccn5)cc4F)C4CC4)ncnc32)[C@@H](O)C1]

R4-4" (103 mg, 0.21 mmol) was dissolved in DMF (3 mL) and K$_2$CO$_3$ (90 mg, 0.65 mmol) and 2-bromoacetamide (36 mg, 0.26 mmol) were added. The reaction was stirred on at rt. Water was added and the mixture was extracted with EA (×3). The combined organic layer was washed with water, brine, dried (MgSO$_4$), filtered and concentrated in vacuo. The residue was purified by Flash CC (MeOH:DCM=1:9) to yield R5-4". LCMS: MS Calcd.: 534.6; MS Found: 535 ([M+H]$^+$).

The following compounds were synthesized according to Method 2R:
| 2P3 | R5 |
|---|---|
| 2P3-2 | R5-5" |
| 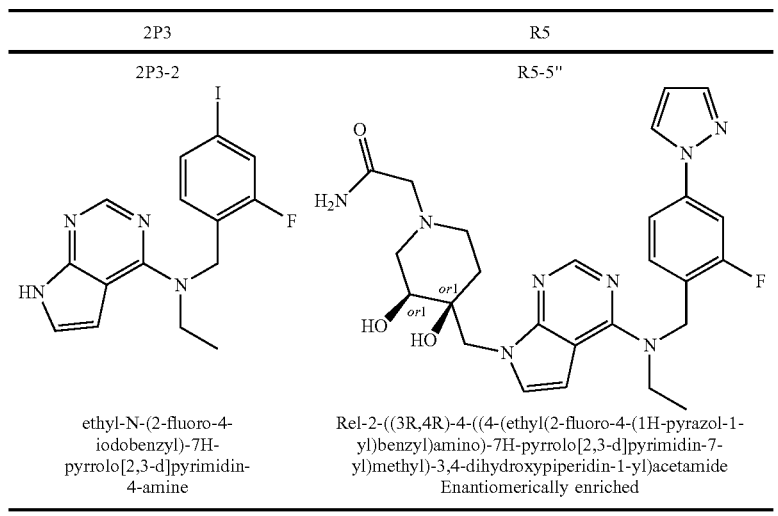 | |
| ethyl-N-(2-fluoro-4-iodobenzyl)-7H-pyrrolo[2,3-d]pyrimidin-4-amine | Rel-2-((3R,4R)-4-((4-(ethyl(2-fluoro-4-(1H-pyrazol-1-yl)benzyl)amino)-7H-pyrrolo[2,3-d]pyrimidin-7-yl)methyl)-3,4-dihydroxypiperidin-1-yl)acetamide Enantiomerically enriched |
General Method Q—from Left to Right
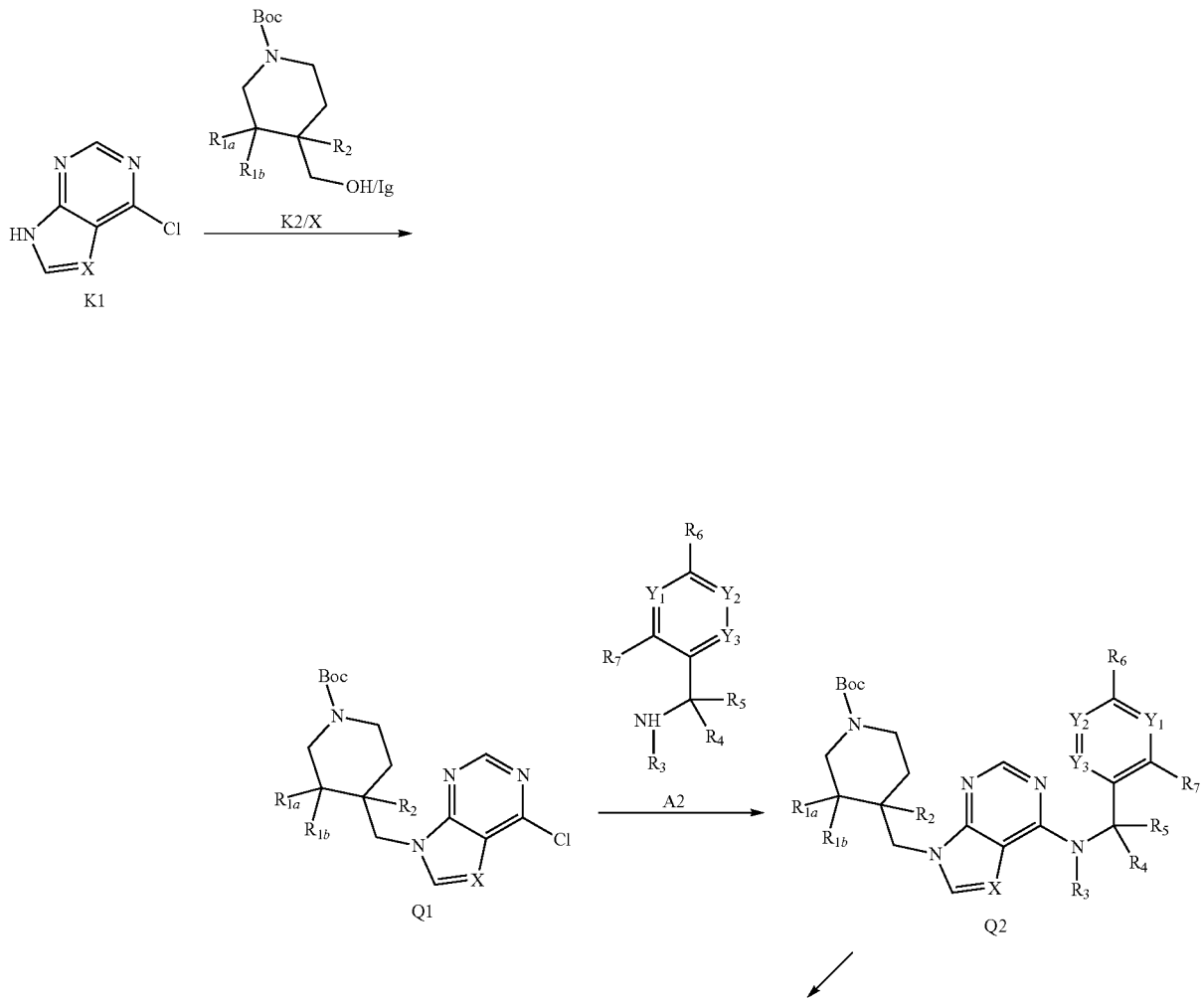

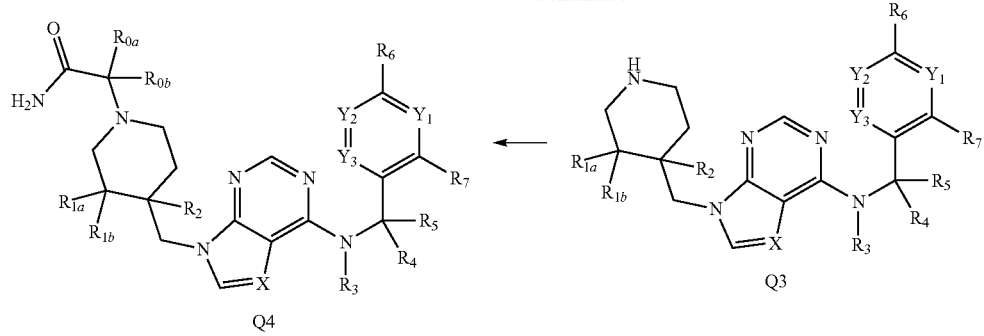

K1 was alkylated with the primary halide X and $Cs_2CO_3$, or via the hydroxy K2 (in a Mitsunobu reaction with $PPh_3$ and DIAD) to form Q1. Q1 was then subjected to a NAS reaction with A2, employing DIEA or TEA, to producing Q2. As described previously the intermediate, Q2, was then subjected to the Boc deprotection, to yield Q3, and subsequent alkylation with 2-bromoacetamide to give Q4. When Q4 contained mixtures of stereoisomers they were often (but not always) subjected to chiral chromatography to obtain the single stereoisomers.

Synthesis and isolation 2-((3R*,4R*)-3-fluoro-4-((4-((S)-3-(5-(trifluoromethyl)pyridin-2-yl)morpholino)-7H-pyrrolo[2,3-d]pyrimidin-7-yl)methyl)piperidin-1-yl)acetamide, Q4-1-1 and Q4-1-2, Scheme Q4-1

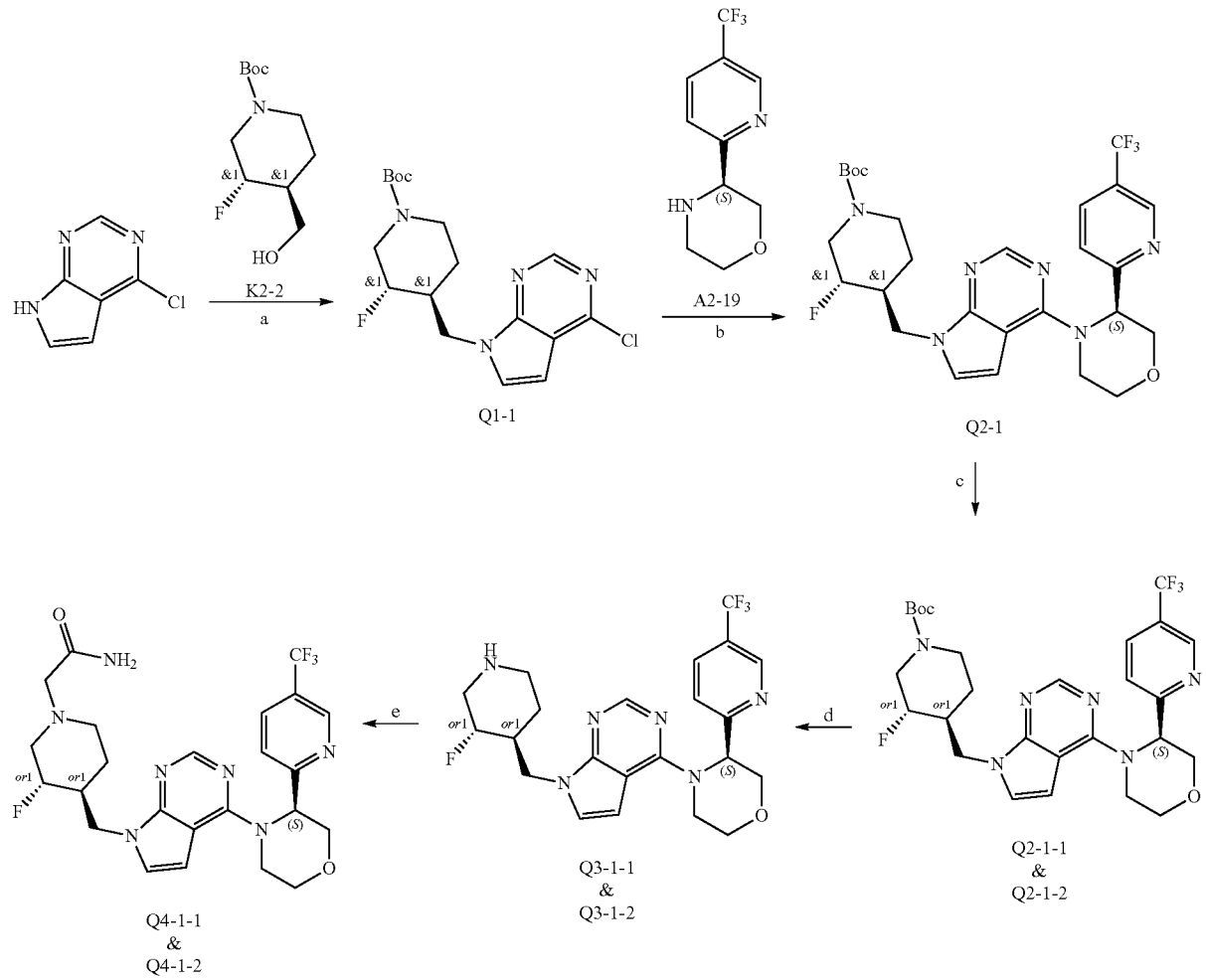

a) DIAD, PPh₃, DCM. b) Pd₂(dba)₃, Ruphos, Cs₂CO₃. c) Chiral separation. d) TFA, DCM. e) 2-bromoacetamide, f) K₂CO₃, DMF.

rac-tert-Butyl (3R,4R)-4-((4-chloro-7H-pyrrolo[2,3-d]pyrimidin-7-yl)methyl)-3-fluoropiperidine-1-carboxylate, Q1-1

Synthesis of the stereoisomers 2-((3R*,4R*)-3-fluoro-4-((4-((S)-3-(5-(trifluoromethyl)pyridin-2-yl)morpholino)-7H-pyrrolo[2,3-d]pyrimidin-7-yl)methyl)piperidin-1-yl)acetamide, Q4-1-1 and Q4-1-2

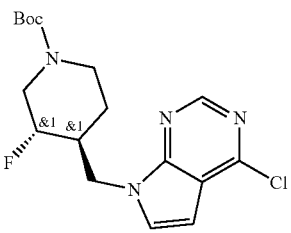

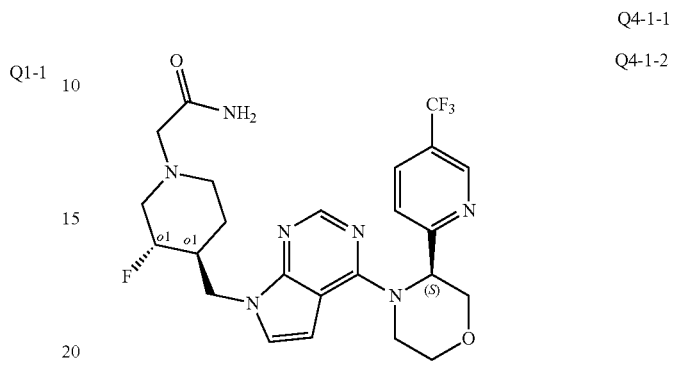

Under a $N_2$ atm DIAD (528 mg, 2.6 mmol) was added to an ice cooled mixture of; K1-1 (370 mg, 1.6 mmol), K2-2 (200 mg, 1.30 mmol) and $PPh_3$ (85 mg, 2.6 mmol) in DCM (15 mL). The reaction was allowed to reach rt and was then stirred at rt 16 h. $H_2O$ (100 mL) was added and the mixture was extracted with EA (3×50 mL). The combined organic phase was washed with brine (2×50 mL), dried ($Na_2SO_4$), filtered and concentrated in vacuo. The residue was purified by Flash CC (EA:PE=1:5) to yield Q1-1.

LCMS: MS Calcd.: 368; MS Found: 369 ([M+H]$^+$).

rac-tert-Butyl (3R,4R)-3-fluoro-4-((4-((S)-3-(5-(trifluoromethyl)pyridin-2-yl)morpholino)-7H-pyrrolo[2,3-d]pyrimidin-7-yl)methyl)piperidine-1-carboxylate, Q2-1

Example Q4-1-1

Q2-1-1 (6 mg, 11 μmol) was dissolved in DCM (3 mL) and then TFA (0.5 mL) was added. After stirring at rt for 2 h the solution was concentrated in vacuo to give a brown oil. This oil was added to a mixture of 2-bromoacetamide (1.5 mg, 16 μmol) and $K_2CO_3$ in DMF (3 mL) and the reaction was stirred at 50° C. for 16 h. Purification on preparative HLPC gave Q4-1-1.

Example Q4-1-2

Q2-1-2 (6 mg, 11 μmol) was dissolved in DCM (3 mL) and then TFA (0.5 mL) was added. After stirring at rt for 2 h the solution was concentrated in vacuo to give a brown oil. This oil was added to a mixture of 2-bromoacetamide (1.5 mg, 16 μmol) and $K_2CO_3$ in DMF (3 mL) and the reaction was stirred at 50° C. for 16 h. Purification on preparative HLPC gave Q4-1-2.

The following compounds were synthesized according to Method Q:

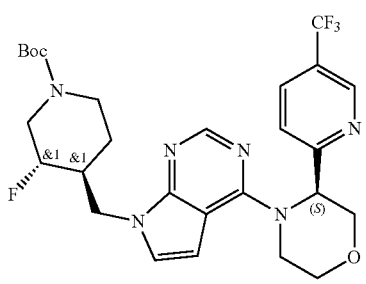

A vial was loaded with; Q1-1 (35 mg, 95 μmol), A2-19 (22 mg, 95 μmol), $Pd_2(dba)_3$ (8.7 mg, 10 μmol), Ruphos (8.8 mg, 20 μmol), $Cs_2CO_3$ (62 mg, 0.19 mmol) and dioxane (4 mL). The reaction was irradiated in a microwave reactor to 120° C. for 2 h. The reaction was concentrated and purified by Prep-HPLC to give Q2-1.

LCMS: MS Calcd.: 564; MS Found: 565 ([M+H]$^+$).

Subsequently, chiral Separation gave:

Q2-1-1, 1$^{st}$ eluting isomer

Q2-1-2, 2$^{nd}$ eluting isomer.

| K2/X | Q4 |
|---|---|
| X-2 | Q4-2 |

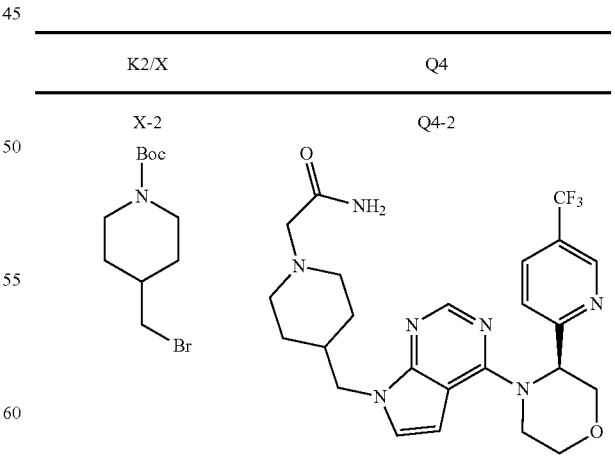

tert-butyl 4-(bromomethyl)piperidine-1-carboxylate (S)-2-(4-((4-(3-(5-(trifluoromethyl)pyridin-2-yl)morpholino)-7H-pyrrolo[2,3-d]pyrimidin-7-yl)methyl)piperidin-1-yl)acetamide Analytical Data.

| Ex. No. | ¹H-NMR | m/z (M + H)⁺ | Analytical Chiral Chromatography |
|---|---|---|---|
| K8-1-1 | ¹HNMR (400 MHz CD₃OD) δ 8.16 (s, 1H), 7.57 (d, J = 8 Hz , 2H), 7.40 (d, J = 8 Hz, 2H), 7.14 (d, J = 4 Hz, 1H), 6.95 (d, J = 4 Hz, 1H), 5.15 (s, 2H), 4.51-4.58 (m, 1H), 4.27-4.33 (m, 1H), 3.11-3.18 (m, 2H), 3.08 (s, 2H), 2.84-2.87 (m, 1H), 2.43-2.58 (m, 2H), 2.18-2.28 (m, 1H), 1.62-1.73 (m, 1H), 1.45-1.49 (m, 1H), 0.97-1.02 (m, 2H), 0.83-0.92 (m, 2H). | 523 | IC (CO₂:EtOH = 60:40) |
| K8-1-2 | ¹HNMR (400 MHz CD₃OD) δ 8.17 (s, 1H), 7.57 (d, J = 8 Hz, 2H), 7.41 (d, J = 8 Hz, 2H), 7.14 (d, J = 4 Hz, 1H), 6.94 (d, J = 4 Hz, 1H), 5.15 (s, 2H), 4.51-4.59 (m, 1H), 4.27-4.33 (m, 1H), 3.11-3.19 (m, 2H), 3.09 (s, 2H), 2.85-2.88 (m, 1H), 2.44-2.58 (m, 2H), 2.17-2.28 (m, 1H), 1.59-1.69 (m, 1H), 1.45-1.49 (m, 1H), 0.97-1.02 (m, 2H), 0.84-0.91 (m, 2H). | 523 | IC (CO2:EtOH = 60:40) |
| K8-2-1 | ¹H NMR (400 MHz, CD₃OD): δ 8.16 (s, 1H), 7.57 (d, J = 13.2 Hz, 2H), 7.42 (d, J = 4.8 Hz, 2H), 7.15-7.14 (m, 1H), 6.96-6.94 (m, 1H), 5.16 (s, 2H), 4.52-4.44 (m, 2H), 4.24-4.21 (m, 1H), 3.17-3.16 (m, 2H), 3.03 (s, 2H), 2.76-2.74 (m, 1H), 2.23-2.20 (m, 1H), 2.10-2.04 (m, 2H), 1.53-1.30 (m, 2H), 1.00-0.97 (m, 2H), 0.88-0.86 (m, 2H); | 505 | IE (Hex:EtOH = 60:40) |
| K8-2-2 | ¹H NMR (400 MHz, CD₃OD): δ8.20 (s, 1H), 7.61 (d, J = 8.4 Hz, 2H), 7.44 (d, J = 8.0 Hz, 2H), 7.18-7.17 (m, 1H), 6.99-6.98 (m, 1H), 5.19 (s, 2H), 4.88-4.52 (m, 2H), 4.30-4.24 (m, 1H), 3.21-3.19 (m, 2H), 3.06 (s, 2H), 2.80-2.77 (m, 1H), 2.30-2.25 (m, 1H), 2.13-2.10 (m, 2H), 1.52-1.42 (m, 2H), 1.04-1.03 (m, 2H), 0.91-0.90 (m, 2H); | 505 | IG (CO2:MeOH = 70:30) |
| K8-3-1 | ¹H NMR (400 MHz, CD₃OD) δ 8.77 (s, 1 H), 8.10 (s, 1 H), 8.00-7.98 (m, 1 H), 7.40 (d, J = 8.4 Hz, 1 H), 7.16 (d, J = 3.6 Hz, 1 H), 7.00 (d, J = 4.0 Hz, 1 H), 5.21 (s, 2 H), 4.56-4.51 (m, 1 H), 4.33-4.28 (m, 1 H), 3.36-3.32 (m, 1 H), 3.15-3.09 (m, 3 H), 2.87-2.85 (m, 1 H), 2.58-2.45 (m, 2 H), 2.28-2.22 (m, 1 H), 1.69-1.63 (m, 1 H), 1.50-1.45 (m, 1 H), 1.06-1.01 (m, 2 H), 0.93-0.89 (m, 2 H) | 524 | IC (CO2:EtOH:DEA = 65:35:0.3) |
| K8-3-2 | ¹H NMR (400 MHz, CD₃OD) δ 8.77 (s, 1 H), 8.10 (s, 1 H), 8.00-7.98 (m, 1 H), 7.40 (d, J = 8.4 Hz, 1 H), 7.16 (d, J = 3.6 Hz, 1 H), 7.00 (d, J = 4.0 Hz, 1 H), 5.21 (s, 2 H), 4.56-4.51 (m, 1 H), 4.33-4.28 (m, 1 H), 3.36-3.32 (m, 1 H), 3.15-3.09 (m, 3 H), 2.87-2.85 (m, 1 H), 2.58-2.45 (m, 2 H), 2.28-2.22 (m, 1 H), 1.69-1.63 (m, 1 H), 1.50-1.45 (m, 1 H), 1.06-1.01 (m, 2 H), 0.93-0.89 (m, 2 H) | 524 | IC (CO2:EtOH:DEA = 65:35:0.3) |
| P6-1-1 | ¹H NMR (400 MHz, CD₃OD-d4) δ 8.23 (s, 1H), 7.62 (s, 4H), 7.13 (d, J = 3.6 Hz, 1H), 6.54 (d, J = 3.2 Hz, 1H), 6.03 (s, 1H), 4.61-4.53 (m, 2H), 4.43-4.38 (m, 1H), 4.32-4.26 (m, 1H), 4.07-4.00 (m, 2H), 3.80 3.73 (m, 1H), 3.60-3.53 (m, 1H), 3.42-3.36 (m, 1H), 3.02-2.98 (m, 1H), 2.96 (s, 2H), 2.75 (d, J = 11.2 Hz, 1H), 2.04-1.98 (m, 2H), 1.76-1.68 (m, 1H), 1.48-1.44 (m, 1H), 1.39-1.28 (m, 1H). | 519 | AS-H (Hex:EtOH:DEA = 40:60:0.3) |
| P6-1-2 | ¹H NMR (400 MHz, CD₃OD-d4) δ 8.23 (s, 1H), 7.62 (s, 4H), 7.13 (d, J = 3.6 Hz, 1H), 6.54 (d, J = 3.2 Hz, 1H), 6.03 (s, 1H), 4.60-4.53 (m, 2H), 4.42-4.37 (m, 1H), 4.33-4.27 (m, 1H), 4.07-4.00 (m, 2H), 3.80-3.73 (m, 1H), 3.60-3.53 (m, 1H), 3.42-3.36 (m, 1H), 3.02-2.98 (m, 1H), 2.96 (s, 2H), 2.75 (d, J = 11.2 Hz, 1H), 2.04-1.98 (m, 2H), 1.76-1.68 (m, 1H), 1.49-1.44 (m, 1H), 1.39-1.28 (m, 1H). | 519 | AS-H (Hex:EtOH:DEA = 40:60:0.3) |

-continued

| Ex. No. | ¹H-NMR | m/z (M + H)⁺ | Analytical Chiral Chromatography |
|---|---|---|---|
| P6-2-1 | ¹H NMR (400 MHz, CD₃OD-d4) δ 8.22 (s, 1H), 7.63 (s, 4H), 7.13-7.12 (m, 1H), 6.52-6.51 (m, 1H), 6.03-6.02 (m, 1H), 4.60-4.54 (m, 2H), 4.09-4.00 (m, 4H), 3.80-3.74 (m, 1H), 3.60-3.54 (m, 1H), 2.95 (s, 2H), 2.88-2.86 (m, 2H), 2.10-2.02 (m, 2H), 1.89-1.84 (m, 1H), 1.54-1.50 (m, 2H), 1.45-1.35 (m, 2H). | 503 | AD (Hex:EtOH:DEA = 60:40:0.3) |
| P6-2-2 | ¹H NMR (400 MHz, CD₃OD-d4) δ 8.22 (s, 1H), 7.63 (s, 4H), 7.13-7.12 (m, 1H), 6.52-6.51 (m, 1H), 6.03-6.02 (m, 1H), 4.60-4.54 (m, 2H), 4.09-4.00 (m, 4H), 3.80-3.74 (m, 1H), 3.60-3.54 (m, 1H), 2.95 (s, 2H), 2.88-2.86 (m, 2H), 2.10-2.02 (m, 2H), 1.89-1.84 (m, 1H), 1.54-1.50 (m, 2H), 1.45-1.35 (m, 2H). | 503 | AD (Hex:EtOH:DEA = 60:40:0.3) |
| P6-3-1 | ¹H NMR (400 MHz, CD₃OD-d4) δ 8.24 (s, 1H), 7.75 (s, 1H), 7.72 (d, J = 8.0 Hz, 1H), 7.56-7.49 (m, 2H), 7.14 (d, J = 3.6 Hz, 1H), 6.56 (d, J = 3.6 Hz, 1H), 6.05 (s, 1H), 4.56-4.52 (m, 2H), 4.43-4.39 (m, 1H), 4.33-4.27 (m, 1H), 4.08-4.02 (m, 2H), 3.80 3.74 (m, 1H), 3.58-3.50 (m, 1H), 3.43-3.37 (m, 1H), 3.02-2.98 (m, 1H), 2.96 (s, 2H), 2.75 (d, J = 11.6 Hz, 1H), 2.04-1.99 (m, 2H), 1.76-1.69 (m, 1H), 1.47-1.43 (m, 1H), 1.38-1.28 (m, 1H). | 519 | IG (Hex:EtOH:DEA = 50:50:0.3) |
| P6-3-2 | ¹H NMR (400 MHz, CD₃OD-d4) δ 8.24 (s, 1H), 7.76 (s, 1H), 7.71 (d, J = 7.6 Hz, 1H), 7.56-7.48 (m, 2H), 7.14 (d, J = 4.0 Hz, 1H), 6.56 (d, J = 4.0 Hz, 1H), 6.04 (s, 1H), 4.57-4.51 (m, 2H), 4.43-4.38 (m, 1H), 4.33-4.28 (m, 1H), 4.08-4.02 (m, 2H), 3.80-3.74 (m, 1H), 3.57-3.50 (m, 1H), 3.42-3.36 (m, 1H), 3.02-2.99 (m, 1H), 2.96 (s, 2H), 2.75 (d, J = 11.2 Hz, 1H), 2.04-1.99 (m, 2H), 1.76-1.69 (m, 1H), 1.47-1.43 (m, 1H), 1.38-1.28 (m, 1H). | 519 | IG (Hex:EtOH:DEA = 50:50:0.3) |
| P6-4-1 | ¹H NMR (400 MHz, CD₃OD-d4) δ 8.24 (s, 1H), 7.76 (s, 1H), 7.71 (d, J = 7.2 Hz, 1H), 7.56-7.48 (m, 2H), 7.14 (d, J = 3.6 Hz, 1H), 6.56 (d, J = 3.6 Hz, 1H), 6.04 (s, 1H), 4.56-4.51 (m, 2H), 4.43-4.38 (m, 1H), 4.33-4.28 (m, 1H), 4.08-4.02 (m, 2H), 3.80-3.74 (m, 1H), 3.57-3.50 (m, 1H), 3.42-3.36 (m, 1H), 3.02-2.98 (m, 1H), 2.96 (s, 2H), 2.75 (d, J = 11.2 Hz, 1H), 2.04-1.99 (m, 2H), 1.76-1.69 (m, 1H), 1.47-1.43 (m, 1H), 1.38-1.27 (m, 1H). | 519 | IG (Hex:EtOH:DEA = 60:40:0.3) |
| P6-4-2 | ¹H NMR (400 MHz, CD₃OD-d4) δ 8.24 (s, 1H), 7.75 (s, 1H), 7.72 (d, J = 7.6 Hz, 1H), 7.56-7.48 (m, 2H), 7.14 (d, J = 3.6 Hz, 1H), 6.56 (d, J = 3.6 Hz, 1H), 6.04 (s, 1H), 4.56-4.51 (m, 2H), 4.43-4.39 (m, 1H), 4.33-4.27 (m, 1H), 4.08-4.02 (m, 2H), 3.80-3.74 (m, 1H), 3.57-3.50 (m, 1H), 3.43-3.37 (m, 1H), 3.02-2.99 (m, 1H), 2.96 (s, 2H), 2.75 (d, J = 11.6 Hz, 1H), 2.04-1.99 (m, 2H), 1.77-1.68 (m, 1H), 1.47-1.43 (m, 1H), 1.38-1.28 (m, 1H). | 519 | IG (Hex:EtOH:DEA = 60:40:0.3) |
| P6-5 | ¹H NMR (400 MHz, CDCl₃) δ 0.70 (s, 2H), 0.90 (q, J = 6.5 Hz, 2H), 1.19-1.49 (m, 4H), 1.89 (s, 1H), 2.04-2.26 (m, 2H), 2.89 (d, J = 10.9 Hz, 2H), 2.99 (s, 2H), 3.09 (dd, J = 6.6, 3.6 Hz, 1H), 4.06 (d, J = 7.3 Hz, 2H), 5.09 (s, 2H), 5.41 (s, 1H), 6.74 (d, J = 2.1 Hz, 1H), 7.05 (s, 1H), 7.38 (d, J = 8.0 Hz, 2H), 7.55 (d, J = 8.1 Hz, 2H), 8.28 (s, 1H). | 505 | |
| P6-6 | ¹H NMR (400 MHz, CDCl₃) δ 0.68-0.84 (m, 2H), 0.92-1.05 (m, 2H), 1.38-1.49 (m, 2H), 1.64-1.72 (m, 2H), 2.00 (s, 1H), 2.19 (s, 2H), 2.82-3.25 (m, 4H), 4.10 (d, J = 7.3 Hz, 2H), 5.38 (s, 1H), 5.43 (s, 1H), 7.07 (s, 1H), 7.37 (d, J = 8.0 Hz, 2H), 7.53 | 488 | |

| Ex. No. | ¹H-NMR | m/z (M + H)⁺ | Analytical Chiral Chromatography |
|---|---|---|---|
| | (d, J = 8.1 Hz, 2H), 7.71 (s, 1H), 8.45 (s, 1H). | | |
| P6-7 | ¹H NMR (400 MHz, CDCl₃) δ 0.62-0.81 (m, 2H), 1.04-1.18 (m, 2H), 1.20-1.50 (m, 3H), 1.64 (s, 1H), 1.83-2.06 (m, 1H), 2.06-2.26 (m, 2H), 2.90 (d, J = 11.7 Hz, 2H), 2.99 (s, 2H), 3.33-3.51 (m, 1H), 4.14 (d, J = 7.3 Hz, 2H), 5.09 (s, 2H), 5.40 (s, 1H), 6.90-7.07 (m, 1H), 7.43 (d, J = 8.1 Hz, 2H), 7.57 (d, J = 4.0 Hz, 2H), 8.35 (s, 1H). | 512 | |
| P6-8 | ¹H NMR (400 MHz, CDCl₃) δ 0.71-0.83 (m, 2H), 0.92-1.04 (m, 2H), 1.21 (d, J = 7.0 Hz, 3H), 1.29-1.45 (m, 3H), 1.66 (s, 1H), 1.92-2.04 (m, 1H), 2.11 (t, J = 10.6 Hz, 1H), 2.32 (t, J = 10.7 Hz, 1H), 2.82 (t, J = 10.1 Hz, 2H), 3.01-3.25 (m, 2H), 4.10 (d, J = 7.3 Hz, 2H), 5.38 (s, 3H), 7.06 (s, 1H), 7.37 (d, J = 8.0 Hz, 2H), 7.53 (d, J = 8.1 Hz, 2H), 7.72 (s, 1H), 8.46 (s, 1H). | 502 | |
| P6-9 | ¹H NMR (400 MHz, CDCl₃) δ 0.78 (s, 2H), 0.98 (q, J = 6.9 Hz, 2H), 1.23-1.36 (m, 8H), 1.86-2.05 (m, 1H), 2.04-2.23 (m, 2H), 2.85 (d, J = 11.2 Hz, 2H), 3.16 (s, 1H), 4.09 (d, J = 7.2 Hz, 2H), 5.16 (s, 1H), 5.38 (s, 2H), 7.08 (s, 1H), 7.37 (d, J = 8.1 Hz, 2H), 7.53 (d, J = 8.1 Hz, 2H), 7.71 (s, 1H), 8.46 (s, 1H). | 516 | |
| P6-10 | ¹H NMR (400 MHz, CDCl₃) δ 0.63-0.80 (m, 2H), 0.86-1.05 (m, 2H), 1.29-1.48 (m, 2H), 1.88 (ddd, J = 11.5, 7.7, 3.9 Hz, 1H), 2.14 (t, J = 10.7 Hz, 2H), 2.89 (d, J = 11.7 Hz, 2H), 2.98 (s, 2H), 3.14 (dd, J = 6.6, 3.7 Hz, 1H), 4.06 (d, J = 7.3 Hz, 2H), 5.11 (s, 2H), 5.39 (s, 1H), 6.75 (d, J = 2.2 Hz, 1H), 7.05 (s, 1H), 7.61 (d, J = 8.0 Hz, 1H), 7.79 (dd, J = 8.1, 1.5 Hz, 1H), 8.26 (s, 1H), 8.68 (d, J = 1.7 Hz, 1H). | 506 | |
| P6-11 | ¹H NMR (400 MHz, CDCl₃) δ 0.61-0.76 (m, 2H), 0.85-0.98 (m, 2H), 1.77-1.89 (m, 3H), 2.43-2.63 (m, 2H), 2.84-3.19 (m, 5H), 4.40 (s, 2H), 5.10 (s, 2H), 5.42 (s, 1H), 6.86 (s, 1H), 7.09 (d, J = 2.2 Hz, 1H), 7.38 (d, J = 8.0 Hz, 2H), 7.56 (d, J = 8.1 Hz, 2H), 8.25 (s, 1H). | 530 | |
| P6-12 | ¹H NMR (400 MHz, CDCl₃) δ 1.35-1.56 (m, 1H), 1.69-1.81 (m, 2H), 2.06-2.31 (m, 2H), 2.84 (d, J = 11.3 Hz, 1H), 3.01 (dd, J = 18.7, 2.1 Hz, 4H), 3.30 (d, J = 3.4 Hz, 3H), 3.70 (dd, J = 14.7, 2.3 Hz, 1H), 4.90 (dd, J = 14.7, 2.6 Hz, 1H), 5.09 (d, J = 3.0 Hz, 2H), 5.40 (s, 1H), 6.04 (s, 1H), 6.69 (d, J = 2.2 Hz, 1H), 6.77 (s, 1H), 7.40 (d, J = 8.0 Hz, 2H), 7.59 (d, J = 8.1 Hz, 2H), 8.26 (s, 1H). | 495 | |
| P6-13 | ¹H NMR (400 MHz, CDCl₃) δ 0.92 (ddd, J = 8.2, 6.6, 3.7 Hz, 2H), 0.98 (t, J = 6.6 Hz, 2H), 1.37-1.53 (m, 1H), 1.64-1.71 (m, 1H), 1.77 (dd, J = 12.9, 3.2 Hz, 1H), 2.09-2.30 (m, 2H), 2.85 (d, J = 11.2 Hz, 1H), 2.93-3.19 (m, 4H), 3.81 (dd, J = 14.6, 2.3 Hz, 1H), 4.90 (dd, J = 14.6, 3.5 Hz, 1H), 5.05-5.23 (m, 2H), 5.32 (s, 1H), 6.35 (s, 1H), 6.76 (s, 1H), 6.81-6.89 (m, 2H), 7.37 (d, J = 8.0 Hz, 2H), 7.54 (d, J = 8.1 Hz, 2H), 8.29 (s, 1H). | 503 | |
| P6-13-1 | ND | 503 | Lux C2 (Hept:EtOH:NH₃ = 40:60:0.2) First eluting isomer |
| P6-13-2 | ND | 503 | Lux C2 (Hept:EtOH:NH₃ = 40:60:0.2) Second eluting isomer |

-continued

| Ex. No. | ¹H-NMR | m/z (M + H)⁺ | Analytical Chiral Chromatography |
|---|---|---|---|
| P6-14 | ¹H NMR (400 MHz, CDCl₃) δ 0.67-0.78 (m, 2H), 0.89-0.98 (m, 2H), 1.19-1.55 (m, 4H), 1.75 (dd, J = 12.8, 3.0 Hz, 1H), 2.10-2.27 (m, 2H), 2.86 (d, J = 11.1 Hz, 1H), 2.93-3.20 (m, 3H), 3.71 (dd, J = 14.7, 2.3 Hz, 1H), 4.89 (dd, J = 14.7, 2.9 Hz, 1H), 5.00-5.24 (m, 2H), 5.38 (s, 1H), 6.00 (s, 1H), 6.71 (d, J = 2.3 Hz, 1H), 6.77 (s, 1H), 7.39 (d, J = 8.0 Hz, 2H), 7.56 (d, J = 8.1 Hz, 2H), 8.24 (s, 1H). | 521 | |
| P6-14-1 | ND | 521 | Lux C2 (Hept:EtOH:NH₃ = 40:60:0.2) First eluting isomer |
| P6-14-2 | ND | 521 | Lux C2 (Hept:EtOH:NH₃ = 40:60:0.2) Second eluting isomer |
| P6-15 | ¹H NMR (400 MHz, CDCl₃) δ 0.64-0.80 (m, 2H), 0.91-1.06 (m, 2H), 1.37-1.55 (m, 1H), 1.64-1.82 (m, 1H), 2.07-2.30 (m, 3H), 2.86 (d, J = 11.4 Hz, 1H), 2.93-3.11 (m, 3H), 3.11-3.22 (m, 1H), 3.71 (dd, J = 14.7, 2.3 Hz, 1H), 4.89 (dd, J = 14.7, 2.8 Hz, 1H), 5.05 (d, J = 15.7 Hz, 1H), 5.22 (d, J = 15.8 Hz, 1H), 5.34 (s, 1H), 5.90 (s, 1H), 6.73 (d, J = 2.3 Hz, 1H), 6.77 (s, 1H), 7.63 (d, J = 8.0 Hz, 1H), 7.80 (dd, J = 8.1, 1.6 Hz, 1H), 8.23 (s, 1H), 8.68 (d, J = 1.7 Hz, 1H). | 522 | |
| P6-16 | ¹H NMR (400 MHz, CDCl₃) δ 0.93 (dd, J = 6.7, 3.3 Hz, 2H), 1.05 (dd, J = 6.6, 2.7 Hz, 2H), 1.36-1.51 (m, 1H), 1.62-1.72 (m, 1H), 1.72-1.84 (m, 1H), 2.17 (s, 3H), 2.85 (d, J = 11.6 Hz, 1H), 2.95-3.08 (m, 3H), 3.08-3.21 (m, 1H), 3.82 (dd, J = 14.6, 2.3 Hz, 1H), 4.90 (dd, J = 14.6, 3.4 Hz, 1H), 5.05-5.26 (m, 2H), 5.30 (s, 1H), 6.25 (s, 1H), 6.75 (s, 1H), 6.81-6.95 (m, 2H), 7.61 (d, J = 8.1 Hz, 1H), 7.79 (d, J = 8.1 Hz, 1H), 8.27 (s, 1H), 8.66 (s, 1H). | 504 | |
| P6-17 | ¹H NMR (400 MHz, CDCl₃) δ 0.68-0.83 (m, 2H), 1.04 (d, J = 6.7 Hz, 2H), 1.72-1.82 (m, 1H), 2.10-2.28 (m, 2H), 2.86 (d, J = 11.4 Hz, 1H), 2.92-3.13 (m, 3H), 3.23 (dd, J = 6.6, 3.7 Hz, 1H), 3.73 (dd, J = 14.7, 2.3 Hz, 1H), 4.88 (dd, J = 14.8, 2.9 Hz, 1H), 4.97-5.27 (m, 2H), 5.41 (s, 1H), 5.78 (s, 1H), 6.75 (d, J = 2.3 Hz, 1H), 6.76 (s, 1H), 8.22 (s, 1H), 8.86 (s, 2H). | 523 | |
| P6-18 | ¹H NMR (400 MHz, CDCl₃) δ 0.65-0.84 (m, 2H), 0.84-1.06 (m, 2H), 2.14 (d, J = 53.0 Hz, 2H), 2.76-3.21 (m, 4H), 3.27 (dd, J = 6.5, 3.6 Hz, 1H), 3.72 (d, J = 14.0 Hz, 1H), 4.87 (d, J = 14.1 Hz, 1H), 5.11-5.33 (m, 2H), 5.36 (s, 1H), 6.01 (s, 1H), 6.72 (d, J = 1.9 Hz, 1H), 6.80 (s, 1H), 7.33 (d, J = 8.2 Hz, 1H), 7.84 (dd, J = 8.3, 2.0 Hz, 1H), 8.19 (s, 1H), 8.81 (s, 1H). | 522 | |
| P6-19 | ¹H NMR (400 MHz, CDCl₃) δ 1.27 (d, J = 6.6 Hz, 6H), 1.36-1.54 (m, 1H), 1.57-1.68 (m, 2H), 2.08-2.30 (m, 2H), 2.84 (d, J = 11.2 Hz, 1H), 2.90-3.14 (m, 4H), 3.67 (dd, J = 14.7, 2.2 Hz, 1H), 4.80-5.09 (m, 4H), 5.45 (s, 1H), 6.05 (s, 1H), 6.67 (d, J = 2.2 Hz, 1H), 6.77 (s, 1H), 7.37 (d, J = 8.1 Hz, 2H), 7.53 (d, J = 8.2 Hz, 2H), 8.19 (s, 1H). | 523 | |
| P6-20 | ¹H NMR (400 MHz, CDCl₃) δ 0.75-0.85 (m, 2H), 0.97-1.09 (m, 2H), 1.21-1.47 (m, 2H), 1.65-1.84 (m, 2H), 2.11-2.27 (m, 2H), 2.85 (d, J = 11.0 Hz, 1H), 2.94-3.24 (m, 4H), 3.97 (d, J = 14.5 Hz, 1H), | 504 | |

| Ex. No. | ¹H-NMR | m/z (M + H)⁺ | Analytical Chiral Chromatography |
|---|---|---|---|
| | 4.80 (dd, J = 14.5, 3.4 Hz, 1H), 5.30 (d, J = 14.6 Hz, 2H), 5.43 (s, 1H), 5.87 (s, 1H), 6.71 (s, 1H), 7.35-7.61 (m, 3H), 7.68 (s, 1H), 8.42 (s, 1H). | | |
| P6-21 | ¹H NMR (400 MHz, CDCl₃) δ 1.21-1.37 (m, 3H), 1.38-1.54 (m, 1H), 1.62-1.69 (m, 1H), 1.74 (dd, J = 12.8, 3.0 Hz, 1H), 2.08-2.30 (m, 2H), 2.85 (d, J = 11.4 Hz, 1H), 2.93-3.13 (m, 4H), 3.57-3.87 (m, 3H), 4.91 (dd, J = 14.8, 2.6 Hz, 1H), 4.99-5.21 (m, 2H), 5.29 (s, 1H), 6.09 (s, 1H), 6.68 (d, J = 2.2 Hz, 1H), 6.76 (s, 1H), 7.40 (d, J = 8.1 Hz, 2H), 7.57 (d, J = 8.1 Hz, 2H), 8.24 (s, 1H). | 509 | |
| P6-22 | ¹H NMR (400 MHz, CDCl₃) δ 1.26 (d, J = 6.6 Hz, 6H), 1.32-1.45 (m, 1H), 1.70-1.81 (m, 1H), 2.08-2.32 (m, 2H), 2.85 (d, J = 11.2 Hz, 1H), 2.93-3.14 (m, 4H), 3.96 (d, J = 14.4 Hz, 1H), 4.77 (dd, J = 14.6, 3.2 Hz, 1H), 5.05 (s, 1H), 5.41 (s, 1H), 5.98 (s, 1H), 6.72 (s, 1H), 7.37 (d, J = 8.1 Hz, 2H), 7.53 (d, J = 8.2 Hz, 2H), 7.65 (s, 1H), 8.30 (s, 1H). | 506 | |
| P6-23 | ¹H NMR (400 MHz, CDCl₃) δ 0.94 (m, 2H), 1.00 (m, 2H), 1.43 (qd, J = 12.5, 4.1 Hz, 1H), 1.65 (m, 1H), 1.75 (m, 1H), 2.04-2.32 (m, 2H), 2.83 (d, J = 11.2 Hz, 1H), 2.89-3.14 (m, 4H), 3.27 (tt, J = 6.7, 3.9 Hz, 1H), 3.82 (dd, J = 14.6, 2.3 Hz, 1H), 4.86 (dd, J = 14.6, 3.6 Hz, 1H), 5.21 (s, 2H), 5.61 (m, 1H), 6.29 (brs, 1H), 6.76 (m, 1H), 6.87 (s, 2H), 7.30 (d, J = 8.2 Hz, 1H), 7.81 (dd, J = 8.3, 1.9 Hz, 1H), 8.21 (s, 1H), 8.79 (m, 1H). | 504.0 | |
| P6-23-1 | ND | 504 | IB (Hept:EtOH:DEA = 90:10:0.2) First eluting isomer |
| P6-23-2 | ND | 504 | IB (Hept:EtOH:DEA = 90:10:0.2) Second eluting isomer |
| P6-24 | ¹H NMR (400 MHz, CDCl₃) δ 1.34 (t, J = 7.1Hz, 3H), 1.70-1.82 (m, 1H), 2.11-2.33 (m, 2H), 2.76-2.93 (m, 2H), 2.97-3.08 (m, 2H), 3.61-3.97 (m, 4H), 4.89 (dd, J = 14.5, 3.3 Hz, 1H), 5.01-5.18 (m, 2H), 5.30 (s, 2H), 6.35 (s, 1H), 6.81 (d, J = 3.6 Hz, 1H), 7.42 (d, J = 8.0 Hz, 2H), 7.59 (d, J = 8.1 Hz, 2H), 8.30 (s, 1H). | 491 | |
| P6-24-1 | ND | 491 | Reprosil AMS (MeOH:CO₂:NH₃ = 40:60:0.2) First eluting isomer |
| P6-24-2 | ND | 491 | Reprosil AMS (MeOH:CO₂:NH₃ = 40:60:0.2) Second eluting isomer |
| P6-25 | ND | 505 | |
| P6-25-1 | ND | 505 | Reprosil AMS (MeOH:CO₂:NH₃ = 35:65:0.2) First eluting isomer |
| P6-25-2 | ND | 505 | Reprosil AMS (MeOH:CO₂:NH₃ = 35:65:0.2) Second eluting isomer |
| P6-26" | ¹H NMR (400 MHz, CDCl₃) δ 0.80 (m, 2H), 1.01 (d, J = 7.1 Hz, 2H), 1.40 (d, J = 7.4 Hz, 1H), 1.76 (d, J = 11.5 Hz, 2H), 2.22 (s, 3H), 2.85 (s, 1H), 2.96-3.15 (m, 3H), 3.20 (s, 1H), 3.98 (d, J = 14.4 Hz, 1H), | 504 | |

| Ex. No. | ¹H-NMR | m/z (M + H)⁺ | Analytical Chiral Chromatography |
|---|---|---|---|
| | 4.78 (dd, J = 14.6, 3.5 Hz, 1H), 5.23-5.40 (m, 2H), 5.47 (s, 1H), 5.87 (s, 1H), 6.72 (s, 1H), 7.38 (d, J = 8.0 Hz, 2H), 7.55 (d, J = 8.1 Hz, 2H), 7.67 (s, 1H), 8.41 (s, 1H). | | |
| P6-26-1 | ND | 504 | IC (Hept:EtOH:DEA = 80:20:0.2) First (minor) isomer eluted |
| P6-26-2 | ND | 504 | IC (Hept:EtOH:DEA = 80:20:0.2) Second (minor) isomer eluted |
| P6-27" | ¹H NMR (400 MHz, CDCl₃) δ 1.39 (q, J = 6.8 Hz, 3H), 1.74 (dd, J = 12.9, 3.1 Hz, 1H), 2.10-2.27 (m, 2H), 2.83 (d, J = 11.3 Hz, 1H), 2.94-3.11 (m, 3H), 3.78 (dd, J = 14.6, 2.3 Hz, 1H), 3.81-4.02 (m, 2H), 4.89 (dd, J = 14.6, 3.4 Hz, 1H), 5.17 (q, J = 17.0 Hz, 2H), 5.30 (s, 1H), 6.36 (s, 2H), 6.75 (s, 1H), 6.82 (d, J = 3.5 Hz, 1H), 7.44 (d, J = 8.2 Hz, 1H), 7.85 (dd, J = 8.3, 1.9 Hz, 1H), 8.28 (s, 1H), 8.85 (s, 1H). | 492 | |
| P6-28" | ¹H NMR (400 MHz, CDCl₃) δ 1.32 (t, J = 6.8 Hz, 3H), 1.39-1.51 (m, 1H), 1.73 (dd, J = 12.8, 3.1Hz, 1H), 2.08-2.32 (m, 2H), 2.84 (d, J = 11.4 Hz, 1H), 2.93-3.12 (m, 3H), 3.67 (dd, J = 14.7, 2.3 Hz, 1H), 3.73-3.98 (m, 2H), 4.91 (dd, J = 14.7, 2.5 Hz, 1H), 5.02-5.26 (m, 2H), 5.30 (s, 1H), 6.04 (s, 1H), 6.68 (d, J = 2.2 Hz, 1H), 6.76 (s, 1H), 7.40 (d, J = 8.2 Hz, 1H), 7.85 (dd, J = 8.3, 1.9 Hz, 1H), 8.22 (s, 1H), 8.77-8.92 (m, 1H). | 510 | |
| P6-29" | ¹H NMR (400 MHz, CDCl₃) δ 1.34 (t, J = 7.1 Hz, 3H), 1.61-1.71 (m, 1H), 1.71-1.83 (m, 1H), 2.06-2.27 (m, 2H), 2.83 (d, J = 11.3 Hz, 1H), 2.92-3.14 (m, 3H), 3.64-3.94 (m, 3H), 4.90 (dd, J = 14.6, 3.4 Hz, 1H), 5.08 (s, 2H), 5.26 (s, 1H), 6.20-6.50 (m, 2H), 6.74 (s, 1H), 6.83 (d, J = 3.6 Hz, 1H), 7.41 (d, J = 8.5 Hz, 2H), 7.62 (d, J = 8.4 Hz, 2H), 8.28 (s, 1H). | 448 | |
| P6-30" | ¹H NMR (400 MHz, CDCl₃) δ 1.32 (t, J = 7.0 Hz, 3H), 1.71 (t, J = 13.4 Hz, 2H), 2.23 (q, J = 10.4, 9.6 Hz, 2H), 2.86 (d, J = 10.5 Hz, 1H), 2.98-3.10 (m, 3H), 3.69-3.92 (m, 3H), 4.80 (d, J = 14.1 Hz, 1H), 4.96-5.15 (m, 2H), 5.85 (s, 1H), 6.35 (d, J = 3.2 Hz, 1H), 6.45 (t, J = 2.0 Hz, 1H), 6.81 (d, J = 3.5 Hz, 1H), 6.89 (s, 1H), 7.39 (d, J = 8.5 Hz, 2H), 7.65 (d, J = 8.5 Hz, 2H), 7.70 (d, J = 1.7 Hz, 1H), 7.91 (d, J = 2.4 Hz, 1H), 8.30 (s, 1H). | 489 | |
| P6-31" | ND | 509 | |
| P6-32" | ¹H NMR (400 MHz, CDCl₃) δ 1.37 (t, J = 7.1Hz, 3H), 1.54-1.84 (m, 4H), 2.10-2.31 (m, 2H), 2.83 (d, J = 11.2 Hz, 1H), 2.92-3.13 (m, 4H), 3.67-4.00 (m, 3H), 4.88 (dd, J = 14.6, 3.4 Hz, 1H), 4.98-5.24 (m, 2H), 5.44 (s, 1H), 6.35 (d, J = 3.1 Hz, 1H), 6.76 (s, 1H), 6.83 (d, J = 3.6 Hz, 1H), 7.28-7.53 (m, 3H), 8.29 (s, 1H). | 509 | |
| P6-33" | ¹H NMR (400 MHz, CDCl₃) δ 8.32 (s, 1H), 7.88 (d, J = 2.3 Hz, 1H), 7.70 (d, J = 1.5 Hz, 1H), 7.61 (d, J = 8.5 Hz, 2H), 7.36 (d, J = 8.6 Hz, 2H), 6.82 (dd, J = 14.1, 3.5 Hz, 2H), 6.47-6.43 (m, 1H), 5.13 (d, J = 3.2 Hz, 2H), 4.90 (d, J = 11.3 Hz, 1H), 3.81 (d, J = 14.7 Hz, 1H), 3.16-2.95 (m, 6H), 2.86 (s, 2H), 2.17 (s, 3H), 1.75 (s, 2H), 1.01-0.95 (m, 2H), 0.95-0.88 (m, 2H). | 501.0 | |
| P6-34" | ¹H NMR (400 MHz, CDCl₃) δ 8.31 (s, 1H), 7.74 (s, 1H), 7.59 (s, 1H), 7.43 (d, J = 8.2 Hz, 2H), 7.30 (d, J = 8.2 Hz, 2H), 6.77 (d, | 503.0 | |

| Ex. No. | ¹H-NMR | m/z (M + H)⁺ | Analytical Chiral Chromatography |
|---|---|---|---|
| | J = 3.5 Hz, 2H), 6.50 (s, 1H), 6.36 (d, J = 3.4 Hz, 1H), 5.26 (s, 1H), 5.11-4.93 (m, 2H), 4.90 (dd, J = 14.6, 3.3 Hz, 1H), 3.94 (s, 3H), 3.91-3.68 (m, 4H), 3.49 (d, J = 5.0 Hz, 1H), 3.08-2.96 (m, 4H), 2.82 (d, J = 10.7 Hz, 1H), 2.25-2.12 (m, 2H), 1.73 (dd, J = 13.0, 2.9 Hz, 1H), 1.67-1.61 (m, 1H), 1.40 (dd, J = 12.6, 4.2 Hz, 1H), 1.32 (t, J = 7.0 Hz, 3H). | | |
| P6-35″ | ¹H NMR (400 MHz, CDCl₃) δ 8.24 (s, 1H), 7.65 (s, 1H), 7.52 (s, 1H), 7.22 (d, J = 8.0 Hz, 1H), 7.15-7.06 (m, 2H), 6.72 (d, J = 3.5 Hz, 1H), 6.28 (d, J = 3.0 Hz, 1H), 5.23 (s, 1H), 5.08-4.89 (m, 2H), 4.81 (dd, J = 14.6, 3.3 Hz, 1H), 3.87 (s, 3H), 3.80 (dd, J = 14.5, 7.2 Hz, 1H), 3.70 (dd, J = 14.5, 6.5 Hz, 2H), 3.02-2.86 (m, 4H), 2.76 (d, J = 10.3 Hz, 1H), 2.12 (q, J = 11.5, 10.3 Hz, 2H), 1.66 (d, J = 12.8 Hz, 2H), 1.37-1.31 (m, 1H), 1.28 (t, J = 7.0 Hz, 3H). | 521.0 | |
| P6-36″ | ¹H NMR (400 MHz, CDCl₃) δ 8.31 (s, 1H), 7.89 (d, J = 2.4 Hz, 1H), 7.72 (d, J = 1.6 Hz, 1H), 7.57-7.50 (m, 1H), 7.40-7.34 (m, 2H), 6.79 (dd, J = 7.2, 3.6 Hz, 2H), 6.50-6.45 (m, 1H), 6.42 (s, 1H), 6.37-6.30 (m, 1H), 5.30 (s, 1H), 5.16-5.01 (m, 2H), 4.89 (dd, J = 14.6, 3.3 Hz, 1H), 3.89-3.73 (m, 4H), 3.04-2.95 (m, 4H), 2.82 (d, J = 11.0 Hz, 1H), 2.25-2.12 (m, 3H), 1.73 (d, J = 12.9 Hz, 2H), 1.36 (t, J = 7.1 Hz, 3H). | 507.0 | |
| P6-37 | ¹H NMR (400 MHz, CDCl₃) δ 8.28 (d, J = 2.8 Hz, 1H), 7.54 (d, J = 8.1 Hz, 2H), 7.36 (d, J = 8.1 Hz, 2H), 6.92 (dd, J = 15.3, 4.5 Hz, 1H), 6.86 (t, J = 3.5 Hz, 1H), 6.82 (dd, J = 3.5, 1.8 Hz, 1H), 5.87 (s, 1H), 5.24-5.04 (m, 2H), 4.82 (ddd, J = 14.6, 5.7, 3.9 Hz, 1H), 3.99-3.77 (m, 3H), 3.18-2.94 (m, 5H), 2.89-2.79 (m, 1H), 2.63-2.52 (m, 1H), 2.41-2.20 (m, 2H), 1.80-1.63 (m, 2H), 1.02-0.94 (m, 2H), 0.93-0.85 (m, 2H). | 533.0 | |
| 3P6-1 | ¹H NMR (400 MHz, CDCl₃) δ 0.71 (s, 2H), 0.85-0.98 (m, 2H), 1.62-1.76 (m, 3H), 2.49-2.76 (m, 4H), 3.06 (s, 2H), 3.08-3.16 (m, 1H), 4.15 (s, 2H), 4.92 (s, 1H), 5.10 (s, 2H), 5.39 (s, 1H), 6.78 (d, J = 2.3 Hz, 1H), 7.07 (s, 1H), 7.38 (d, J = 8.1 Hz, 2H), 7.56 (d, J = 8.1 Hz, 2H), 8.22 (s, 1H). | 521 | |
| 3P6-2 | ¹H NMR (400 MHz, CDCl₃) δ 0.90 (m, 2H), 0.92-1.04 (m, 2H), 1.62-1.75 (m, 3H), 2.65 (s, 4H), 2.95-3.16 (m, 3H), 4.22 (s, 2H), 5.14 (s, 2H), 5.39 (s, 1H), 6.80 (d, J = 3.6 Hz, 1H), 6.90 (d, J = 3.6 Hz, 1H), 7.09 (s, 1H), 7.35 (d, J = 8.0 Hz, 2H), 7.54 (d, J = 8.1 Hz, 2H), 8.26 (s, 1H). | 503 | |
| 3P6-3 | ¹H NMR (400 MHz, CDCl₃) δ 0.79 (s, 2H), 0.99 (d, J = 6.2 Hz, 2H), 1.55 (d, J = 12.6 Hz, 2H), 1.70 (dd, J = 16.7, 7.5 Hz, 2H), 2.17 (s, 2H), 2.49-2.78 (m, 4H), 3.04 (s, 2H), 3.18 (s, 1H), 4.23 (s, 2H), 4.75 (s, 1H), 5.36 (s, 2H), 5.60 (s, 1H), 7.03 (s, 1H), 7.37 (d, J = 7.9 Hz, 2H), 7.54 (d, J = 8.0 Hz, 2H), 7.76 (s, 1H), 8.39 (s, 1H). | 504 | |
| 3P6-4 | ¹H NMR (400 MHz, CDCl₃) δ 0.67-0.80 (m, 2H), 1.05-1.18 (m, 2H), 1.52 (d, J = 12.5 Hz, 2H), 1.69-1.76 (m, 2H), 2.50-2.64 (m, 2H), 2.70 (d, J = 11.7 Hz, 2H), 3.05 (s, 2H), 3.40-3.48 (m, 1H), 4.19 (s, 1H), 4.27 (s, 2H), 5.10 (s, 2H), 5.45 (s, 1H), 7.00 (s, 1H), 7.42 (d, J = 8.0 Hz, 2H), 7.58 (d, J = 8.1 Hz, 2H), 7.67 (s, 1H), 8.30 (s, 1H). | 528 | |
| 3P6-5 | ¹H NMR (400 MHz, CDCl₃) δ 1.49-1.59 (m, 2H), 2.49-2.75 (m, 4H), 3.04 (s, 2H), 3.28 (d, J = 3.4 Hz, 3H), 4.15 (s, 2H), 5.03 | 495 | |

| Ex. No. | ¹H-NMR | m/z (M + H)⁺ | Analytical Chiral Chromatography |
|---|---|---|---|
| | (s, 1H), 5.08 (s, 2H), 5.44 (s, 1H), 6.76 (d, J = 2.2 Hz, 1H), 7.06 (s, 1H), 7.38 (d, J = 8.0 Hz, 2H), 7.58 (d, J = 8.1 Hz, 2H), 8.24 (s, 1H). | | |
| L5-1-1-1 | ¹H NMR (400 MHz, CDCl₃): δ8.26 (s, 1H), 7.54 (d, J = 8.0 Hz, 2H), 7.36 (d, J = 8.4 Hz, 2H), 6.88 (br s, 1H), 6.84 (br s, 1H), 6.77 (br s, 1H), 5.93 (br s, 1H), 5.62 (br s, 1H), 5.15 (dd, J = 26.4, 16.0 Hz, 2H), 4.50 (d, J = 14.4 Hz, 1H), 3.84 (d, J = 14.4 Hz, 1H), 3.41 (br s, 1H), 3.34-3.31 (m, 1H), 3.12-3.09 (m, 1H), 3.00 (s, 2H), 2.76-2.72 (m, 1H), 2.60-2.57 (m, 2H), 2.47 (t, J = 10.8 Hz, 1H), 1.78-1.67 (m, 4H), 1.00-0.88 (m, 4H). | MS Calcd.: 518; MS Found: 519 | IF (Hex:EtOH = 50:50) |
| L5-1-1-2 | ¹H NMR (400 MHz, CDCl₃): δ8.27 (s, 1H), 7.55 (d, J = 8.4 Hz, 2H), 7.36 (d, J = 7.2 Hz, 2H), 6.88 (br s, 1H), 6.84 (br s, 1H), 6.77 (br s, 1H), 5.92 (br s, 1H), 5.58 (br s, 1H), 5.15 (dd, J = 26.4, 16.0 Hz, 2H), 4.50 (d, J = 14.4 Hz, 1H), 3.84 (d, J = 14.0 Hz, 1H), 3.39 (br s, 1H), 3.33-3.31 (m, 1H), 3.12-3.08 (m, 1H), 3.00 (s, 2H), 2.75-2.71 (m, 1H), 2.60-2.56 (m, 2H), 2.46 (t, J = 10.8 Hz, 1H), 1.77-1.66 (m, 4H), 1.00-0.88 (m, 4H). | MS Calcd.: 518; MS Found: 519 | IF (Hex:EtOH = 50:50) |
| L5-2-1-1 | ¹H NMR (400 MHz, CD₃OD) δ 8.17 (s, 1H), 7.62 (d, J = 8.4 Hz, 2H), 7.48 (d, J = 8.4 Hz, 2H), 7.16 (d, J = 3.6 Hz, 1H), 6.46 (d, J = 3.6 Hz, 1H), 5.12 (s, 2H), 4.44 (d, J = 14.4 Hz, 1H), 4.18 (d, J = 14.4 Hz, 1H), 3.85 (q, J = 6.8 Hz, 2H), 3.55 (dd, J = 10.0 Hz, 4.4 Hz, 1H), 2.97 (s, 2H), 2.74-2.70 (m, 1H), 2.54-2.51 (m, 1H), 2.44-2.34 (m, 2H), 1.68-1.60 (m, 1H), 1.43-1.39 (m, 1H), 1.34 (t, J = 7.2 Hz, 3H). | MS Calcd.: 506; MS Found: 507 | IF (Hex:EtOH:DEA = 50:50:0.3) |
| L5-2-1-2 | ¹H NMR (400 MHz, CD₃OD) δ 8.17 (s, 1H), 7.62 (d, J = 8.0 Hz, 2H), 7.48 (d, J = 8.0 Hz, 2H), 7.16 (d, J = 3.6 Hz, 1H), 6.46 (d, J = 3.6 Hz, 1H), 5.12 (s, 2H), 4.44 (d, J = 14.4 Hz, 1H), 4.18 (d, J = 14.4 Hz, 1H), 3.85 (q, J = 7.2 Hz, 2H), 3.55 (dd, J = 10.4 Hz, 3.6 Hz, 1H), 2.97 (s, 2H), 2.74-2.70 (m, 1H), 2.54-2.49 (m, 1H), 2.45-2.35 (m, 2H), 1.68-1.60 (m, 1H), 1.43-1.39 (m, 1H), 1.32 (t, J = 7.2 Hz, 3H). | MS Calcd.: 506; MS Found: 507 | IF (Hex:EtOH:DEA = 50:50:0.3) |
| L5-3-1 | ¹H NMR (400 MHz, CD₃OD) δ 8.06 (s, 1H), 7.39 (d, J = 10.4 Hz, 1H), 7.30-7.27 (m, 2H), 7.05 (d, J = 3.6 Hz, 1H), 6.38 (d, J = 3.6 Hz, 1H), 5.03 (s, 2H), 4.34 (d, J = 14.4 Hz, 1H), 3.98 (d, J = 14.4 Hz, 1H), 3.81 (q, J = 6.8 Hz, 2H), 3.08 (s, 1H), 2.87 (d, J = 2.4 Hz, 2H), 2.61-2.52 (m, 3H), 2.36 (t, J = 7.2 Hz, 1H), 2.00-1.92 (m, 1H), 1.31-1.18 (m, 4H). | MS Calcd.: 524; MS Found: 525 | racemate |
| L5-3-1-1 | ¹H NMR (400 MHz, CD₃OD) δ 8.16 (s, 1H), 7.49 (d, J = 10.0 Hz, 1H), 7.40-7.37 (m, 2H), 7.19 (d, J = 3.6 Hz, 1H), 6.49 (d, J = 3.6 Hz, 1H), 5.13 (s, 2H), 4.44 (d, J = 14.4 Hz, 1H), 4.20 (d, J = 14.4 Hz, 1H), 3.90 (q, J = 7.2 Hz, 2H), 3.55 (dd, J = 10.0 Hz, 4.4 Hz, 1H), 2.96 (s, 2H), 2.74-2.70 (m, 1H), 2.53-2.51 (m, 1H), 2.44-2.35 (m, 2H), 1.68-1.60 (m, 1H), 1.43-1.40 (m, 1H), 1.35 (t, J = 7.2 Hz, 3H). | MS Calcd.: 524; MS Found: 525 | IG (Hex:EtOH:DEA = 40:60:0.3) |
| L5-3-1-2 | ¹H NMR (400 MHz, CD₃OD) δ 8.16 (s, 1H), 7.49 (d, J = 10.4Hz, 1H), 7.40-7.37 (m, 2H), 7.19 (d, J = 3.6 Hz, 1H), 6.49 (d, J = 3.6 Hz, 1H), 5.13 (s, 2H), 4.44 (d, J = 14.4 Hz, 1H), 4.20 (d, J = 14.4 Hz, 1H), 3.90 (q, J = 7.2 Hz, 2H), 3.55 (dd, J = 10.4Hz, 4.8Hz, 1H), 2.96 (s, 2H), 2.74-2.70 (m, 1H), 2.53-2.51 (m, 1H), 2.44-2.35 (m, 2H), 1.68-1.60 (m, 1H), 1.43-1.40 (m, 1H), 1.35 (t, J = 7.2 Hz, 3H). | MS Calcd.: 524; MS Found: 525 | IG (Hex:EtOH:DEA = 40:60:0.3) |

-continued

| Ex. No. | ¹H-NMR | m/z (M + H)⁺ | Analytical Chiral Chromatography |
|---|---|---|---|
| R5-1" | ¹H NMR (400 MHz, CDCl₃) δ 1.33 (t, J = 7.1 Hz, 3H), 1.68-1.73 (m, 2H), 2.41-2.84 (m, 4H), 2.98-3.03 (m, 2H), 3.27-3.32 (m, 2H), 3.81 (tt, J = 14.7, 7.3 Hz, 3H), 4.48 (d, J = 14.5 Hz, 1H), 5.05 (d, J = 8.3 Hz, 1H), 5.33 (s, 1H), 6.36 (s, 1H), 6.44-6.50 (m, 1H), 6.81 (d, J = 3.6 Hz, 1H), 7.39 (d, J = 8.6 Hz, 2H), 7.66 (d, J = 8.6 Hz, 2H), 7.72 (d, J = 1.4 Hz, 1H), 7.90 (d, J = 2.0 Hz, 1H), 8.30 (s, 1H). | 505.0 | |
| R5-2" | ¹H NMR (400 MHz, CDCl₃) δ 8.30 (s, 1H), 7.88 (d, J = 2.0 Hz, 1H), 7.71 (d, J = 1.4 Hz, 1H), 7.61 (d, J = 8.6 Hz, 2H), 7.36 (d, J = 8.6 Hz, 2H), 6.84 (dd, J = 16.2, 3.6 Hz, 2H), 6.77 (s, 1H), 6.46-6.44 (m, 1H), 5.34 (s, 1H), 5.13 (s, 2H), 4.50 (d, J = 14.5 Hz, 1H), 3.84 (d, J = 14.5 Hz, 1H), 3.32 (dd, J = 10.5, 5.0 Hz, 1H), 3.08 (dt, J = 6.6, 2.9 Hz, 1H), 3.00 (s, 2H), 2.74 (dd, J = 10.7, 4.8 Hz, 1H), 2.62-2.56 (m, 2H), 2.46 (t, J = 10.6 Hz, 1H), 1.77-1.69 (m, 2H), 1.02-0.97 (m, 2H), 0.96-0.90 (m, 2H). | 517.0 | |
| R5-2-1 | ¹H NMR (400 MHz, DMSO-d6) δ 8.41 (d, J = 2.1 Hz, 1H), 8.18 (s, 1H), 7.77-7.69 (m, 3H), 7.33 (d, J = 8.6 Hz, 2H), 7.27 (d, J = 3.6 Hz, 1H), 7.15 (s, 1H), 7.02 (s, 1H), 6.89 (d, J = 3.6 Hz, 1H), 6.51 (dd, J = 2.4, 1.8 Hz, 1H), 5.14 (d, J = 6.0 Hz, 1H), 5.06 (d, J = 5.1 Hz, 1H), 4.47 (d, 1H), 4.30 (d, J = 14.0 Hz, 1H), 4.17 (d, J = 14.0 Hz, 1H), 3.45 (dt, J = 10.5, 5.3 Hz, 1H), 3.11 (dq, J = 6.8, 3.4 Hz, 1H), 2.78 (s, 2H), 2.59 (dd, J = 10.1, 4.2 Hz, 1H), 2.37 (d, J = 10.5 Hz, 1H), 2.29-2.14 (m, 2H), 1.54-1.40 (m, 1H), 1.20 (d, J = 13.7 Hz, 1H), 1.05-0.94 (m, 2H), 0.92-0.77 (m, 2H). | 517.0 | Lux C4 (MeOH:DEA = 100:0.2) First (major) Eluting Isomer |
| R5-2-2 | ¹H NMR (400 MHz, DMSO-h6) δ 8.43-8.40 (m, 1H), 8.18 (s, 1H), 7.77-7.69 (m, 3H), 7.33 (d, J = 8.6 Hz, 2H), 7.27 (d, J = 3.6 Hz, 1H), 7.14 (s, 1H), 7.02 (s, 1H), 6.89 (d, J = 3.6 Hz, 1H), 6.51 (dd, J = 2.4, 1.8 Hz, 1H), 5.15 (s, 1H), 5.06 (d, J = 5.2 Hz, 1H), 4.47 (s, 1H), 4.30 (d, J = 14.0 Hz, 1H), 4.17 (d, J = 14.0 Hz, 1H), 3.49-3.41 (m, 1H), 3.12 (tt, J = 6.8, 3.8 Hz, 1H), 2.78 (s, 2H), 2.59 (dd, J = 10.2, 4.3 Hz, 1H), 2.41-2.31 (m, 1H), 2.29-2.14 (m, 2H), 1.46 (td, J = 13.2, 4.6 Hz, 1H), 1.20 (d, J = 13.7 Hz, 1H), 1.02-0.95 (m, 2H), 0.87-0.81 (m, 2H). | 517.0 | Lux C4 (MeOH:DEA = 100:0.2) Second (minor) Eluting Isomer |
| R5-3" | ¹H NMR (400 MHz, CDCl₃) δ 8.29 (s, 1H), 7.70 (d, J = 0.6 Hz, 1H), 7.57 (s, 1H), 7.22-7.11 (m, 2H), 6.87-6.80 (m, 2H), 6.76 (s, 1H), 5.91 (s, 1H), 5.27 (s, 1H), 5.13 (s, 2H), 4.49 (d, J = 14.5 Hz, 1H), 3.93 (s, 3H), 3.83 (d, J = 14.5 Hz, 1H), 3.33 (dd, J = 10.5, 4.9 Hz, 1H), 3.11 (tt, J = 6.7, 4.0 Hz, 1H), 2.74 (dd, J = 10.7, 4.9 Hz, 1H), 2.62-2.56 (m, 2H), 2.46 (t, J = 10.6 Hz, 1H), 1.79-1.66 (m, 2H), 1.04-0.96 (m, 2H), 0.96-0.89 (m, 2H). | 549.0 | |
| R5-4" | ¹H NMR (400 MHz, DMSO-d₆) δ 0.82-0.88 (m, 2H), 0.96-1.02 (m, 2H), 1.41-1.52 (m, 2H), 2.10-2.35 (m, 5H), 2.78 (s, 2H), 3.17 (d, J = 5.1 Hz, 2H), 4.09 (d, J = 5.1 Hz, 1H), 4.18 (d, J = 13.9 Hz, 1H), 4.30 (d, J = 14.0 Hz, 1H), 6.51-6.57 (m, 1H), 6.90 (d, J = 3.6 Hz, 1H), 7.02 (s, 1H), 7.15 (s, 1H), 7.24-7.32 (m, 2H), 7.59 (dd, J = 8.4, 2.0 Hz, 1H), 7.71 (dd, J = 11.6, 2.1 Hz, 1H), 7.74 (d, J = 1.5 Hz, 1H), 8.18 (s, 1H), 8.49 (d, J = 2.6 Hz, 1H). | 535.0 | |
| R5-5" | ¹H NMR (400 MHz, CDCl₃) δ 1.36 (t, J = 7.1 Hz, 3H), 1.67-1.75 (m, 2H), 2.46 (t, J = 10.4 Hz, 2H), 2.57 (d, J = 7.0 Hz, 2H), 2.70-2.75 (m, 1H), 2.99 (s, 2H), 3.30 (d, | 523.0 | |

-continued

| Ex. No. | $^1$H-NMR | m/z (M + H)$^+$ | Analytical Chiral Chromatography |
|---|---|---|---|
| | J = 5.5 Hz, 1H), 3.76-3.92 (m, 3H), 4.48 (d, J = 14.5 Hz, 1H), 5.08 (d, J = 8.3 Hz, 2H), 5.34 (s, 1H), 6.36 (s, 1H), 6.47 (dd, J = 2.5, 1.8 Hz, 1H), 6.77 (s, 1H), 6.82 (d, J = 3.6 Hz, 1H), 7.34-7.39 (m, 2H), 7.54 (d, J = 12.7 Hz, 1H), 7.72 (d, J = 1.5 Hz, 1H), 7.89 (d, J = 2.1 Hz, 1H), 8.30 (s, 1H). | | |
| Q4-1-1 | $^1$H NMR (400 MHz, DMSO-d$_6$): δ 8.779 (s, 1H), 8.096 (s, 1H), 7.916-7.941 (dd, 1H, J = 8), 7.402-7.423 (d, 1H, J = 8.4), 7.049-7.058 (d, 1H, J = 3.6), 6.457-6.466 (d, 1H, J = 3.6), 5.891 (s, 1H), 4.550-4.575 (d, 1H, J = 10), 4.379-4.391 (d, 1H, J = 4.8), 4.114-4.149 (m, 1H), 3.928-3.996 (m, 1H), 3.685-3.708 (m, 1H), 3.071 (s, 1H), 2.929 (s, 1H), 2.633-2.648 (d, 1H, J = 6), 2.081-2.124 (m, 2H), 1.930-1.995 (m, 3H), 1.205-1.503(m, 2H). | MS Calcd.: 521; MS Found: 522 | IC (Hex:EtOH = 70:30) |
| Q4-1-2 | $^1$H NMR (400 MHz, DMSO-d$_6$): δ 8.895 (s, 1H), 8.215 (s, 1H), 8.038-8.058 (dd, 1H, J = 8), 7.521-7.541 (d, 1H, J = 8), 7.169-7.178 (d, 1H, J = 3.6), 6.579-6.586 (d, 1H, J = 2.8), 6.008 (s, 1H), 4.667-4.692 (d, 1H, J = 10), 4.483-4.496 (d, 1H, J = 5.2), 4.260-4.279 (d, 1H, J = 7.6), 4.046-4.112 (m, 3H), 3.802-3.824 (d, 2H, J = 8.8), 3.188 (s, 1H), 3.046 (s, 1H), 2.743-2.781 (d, 1H, J = 15.2), 2.218-2.242 (m, 2H), 2.051-2.109 (m, 3H), 1.372-1.629(m, 2H). | MS Calcd.: 521; MS Found: 522 | IC (Hex:EtOH = 70:30) |
| Q4-2 | $^1$H NMR (400 MHz, CD$_3$OD): δ 8.866 (s, 1H), 8.178 (s, 1H), 8.000-8.025 (dd, J = 8, 1H), 7.485-7.506 (d, J = 8.4, 1H), 7.126-7.135 (d, J = 3.6, 1H), 6.529-6.536 (d, J = 2.8, 1H), 5.982 (s, 1H), 4.783-4.813 (d, J = 12, 1H), 4.643-4.669 (d, J = 10.4, 1H), 4.075-4.093 (d, J = 7.2, 2H), 4.013-4.049 (t, 2H), 3.769-3.791 (t, 2H), 2.969 (s, 2H), 2.871-2.899 (d, J = 11.2, 2H), 2.062-2.117 (t, 2H), 1.864-1.873 (d, J = 3.6, 1H), 1.511-1.539 (d, J = 11.2, 2H), 1.385-1.450 (m, 2H). | MS Calcd.: 503; MS Found: 504 | |

Biological Evaluation

The activity of the compounds was evaluated using a RORγReporter assay (also referred to as Gal4 assay). The Gal4 and the Th17 assays (another suitable assay) are both cell-based assays monitoring functional activity of the compound assayed.

The activity of the compounds disclosed was also evaluated using the IL-17A secretion in activated PBMCs assay.

Compounds disclosed herein have also been evaluated in a mouse in vivo pharmacodynamic model (anti-CD3-induced plasma IL-17A).

In addition, the compounds disclosed herein may be evaluated in various mouse disease models, e.g. Collagen-induced Arthritis (CIA) model (an animal model for rheumatoid arthritis) and Experimental Autoimmune Encephalomyelitis (EAE) model (an animal model for multiple sclerosis).

RORγ Reporter Assay (Gal4)

The HEK293 cell line is co-transfected transiently with two plasmids, one with the RORγ ligand-binding domain fused to galactose-responsive transcription factor (Gal4), and the other with the luciferase reporter gene and Gal binding sites (UAS). This construction allows to determine the RORT activity in a cellular system through the measurement of luminescence.

A suspension of RORγ reporter cells was dispensed into plates and cultured 2 h at 37° C. and 5% CO2. Media formulation consisted in DMEM/F-12 medium (Gibco) supplemented with 10% heat inactivated FBS (Sigma-Aldrich), non-essential aminoacids (Sigma-Aldrich), 2 mM Glutamax (Gibco) and 100 U/mL penicillin (Sigma-Aldrich). Dose-response curves with compounds were prepared in 100% DMSO and further diluted 100-fold in culture medium. Compound solutions were added to the plate containing cells (final DMSO concentration of 0.1%) and incubated for 24 h at 37° C. and 5% CO2. Luciferase detection reagent was added to each well, and relative light units (RLUs) were quantified from each assay well using a plate reading luminometer.

Values of average RLU±S.D. were computed for all treatment sets, followed by the calculations of percent-reduction of RORT activity in response to respective test compound. The following formula was used: activity=100*[1−[×test compound/average vehicle] where the theoretical minimum reduction (0% reduction). For all experiments, the activity values were plotted versus compound concentrations in one single plot and adjusted to a four-parameter logistic curve to obtain the absolute IC50 value along with the 95% confidence interval. These calculations were performed in excel-fit software using X-204 model curve.

The results of RORγ Reporter (Gal4) Assay are shown in the Table 2 below.

TABLE 2

RORγ Reporter Assay (Gal4)

| Patent example | IC$_{50}$ (nM) |
|---|---|
| 3P6-1 | 6.9 |
| 3P6-2 | 4.2 |
| 3P6-3 | 72 |
| 3P6-4 | 297 |
| 3P6-5 | 87 |
| K8-1-1 | 9.0 |
| K8-1-2 | 4.0 |
| K8-2-1 | 6.1 |
| K8-2-2 | 3.1 |
| K8-3-1 | 76 |
| K8-3-2 | 22 |
| L5-1-1-1 | 2.2 |
| L5-1-1-2 | 2.0 |
| L5-2-1-1 | 1.4 |
| L5-2-1-2 | 2.0 |
| L5-3-1 | 63 |
| L5-3-1-1 | 3 |
| L5-3-1-2 | 4.4 |
| P6-01-1 | 12 |
| P6-01-2 | 25 |
| P6-02-1 | ND |
| P6-02-2 | 30 |
| P6-03-1 | 13 |
| P6-03-2 | 26 |
| P6-04-1 | 47 |
| P6-04-2 | ND |
| P6-05 | 62 |
| P6-06 | 85 |
| P6-07 | 279 |
| P6-08 | 231 |
| P6-09 | >1000 |
| P6-10 | 93 |
| P6-11 | 16 |
| P6-12 | 5.2 |
| P6-13 | 0.9 |
| P6-13-1 | 1.6 |
| P6-13-2 | 2.0 |
| P6-14 | 1.0 |
| P6-14-1 | 3.8 |
| P6-14-2 | 1.0 |
| P6-15 | 10 |
| P6-16 | 5.0 |
| P6-17 | 43 |
| P6-18 | 4.6 |
| P6-19 | 9.8 |
| P6-20 | >1000 |
| P6-21 | 6.6 |
| P6-22 | 77 |
| P6-23 | 5.3 |
| P6-23-1 | 9.9 |
| P6-23-2 | 15 |
| P6-24 | 4.6 |
| P6-24-1 | 4.9 |
| P6-24-2 | 9.1 |
| P6-25 | 15 |
| P6-25-1 | 12 |
| P6-25-2 | 30 |
| P6-26" | 5.1 |
| P6-26-1 | 65 |
| P6-26-2 | 5 |
| P6-27" | 12 |
| P6-28" | 8.6 |
| P6-29" | >1000 |
| P6-30" | 6.5 |
| P6-31" | 1.9 |
| P6-32" | 2.0 |
| P6-33" | 8.5 |
| P6-34" | 12 |
| P6-35" | 24 |
| P6-36" | 14 |
| P6-37 | 2 |
| Q4-1-1 | 170 |
| Q4-1-2 | 250 |
| Q4-2 | 330 |
| R5-1" | 13 |
| R5-2" | 8.1 |
| R5-2-1 | 4.9 |
| R5-2-2 | 6.5 |
| R5-3" | 4 |
| R5-4" | 4.3 |
| R5-5" | 15 |

As can be seen from the Table 2 above, the compounds of the present disclosure were found to show beneficial activity across the RORγ Reporter (Gal4) Assay.

According to an embodiment, compounds having IC$_{50}$<500 nM values in the RORyReporter Assay (Gal4) are disclosed herein.

According to another preferred embodiment compounds having IC$_{50}$<100 nM values in the RORγ Reporter Assay (Gal4) are disclosed herein.

Th17 Assay (Another Suitable Assay)

Human peripheral blood mononuclear cells (PBMCs) were isolated from buffy coats of healthy human volunteers using the Ficoll paque PLUS kit (GE Healthcare, cat no 17-1440-02), as instructed by the manufacturer. Naive CD4+ T cells were isolated with Naive CD4+ T cell kit, human (Milteny Biotec, cat no 130-094-131). The following modifications were made to the manufacturer's protocol: 1) Incubation with Biotin-Antibody Cocktail and Anti-Biotin MicroBeads was prolonged to 30 minutes, and 2) Cells were washed with 40 mL of Miltenyi buffer. Differentiation of Th17 cells in anti-CD3 (BD Pharmingen, 5 μg/ml) coated 96-well plates (400,000 cells/well, 160 μl RPMI 1640+10% Fetal Bovine Serum) containing 5 μg/ml anti-CD28 (BD Pharmingen), 10 ng/ml IL-2 (R&D Systems), 2.5 ng/ml TGFβ-1 (R&D Systems), 20 ng/ml IL-10 (R&D Systems), 20 ng/ml IL-6 (R&D Systems), 30 ng/ml IL-23 (R&D Systems), 2.5 μg/ml anti-IL-4 (R&D Systems) and 1 μg/ml anti-IFNγ (R&D Systems) and with test compound during the entire differentiation (or vehicle, 0.1% DMSO for control). Test compounds were tested in triplicates, diluted 1000-fold in medium (final DMSO concentration is 0.1%). Incubated for seven days at 37° C., 5% CO$_2$, 95% humidity, and 2-fluoro-4'-[[4-(4-pyridinylmethyl)-1-piperazinyl]methyl]-α,α-bis(trifluoromethyl)-[1,1'-biphenyl]-4-methanol (SR2211 Calbiochem, Cat. No. 557353) was used as positive control. As negative control, cells were differentiated into Th0 using 5 μg/ml anti-CD28 (BD Pharmingen), 10 ng/ml IL-2 (R&D Systems), 2 μg/ml anti-IL4 (R&D Systems) and 2 μg/ml anti-IFN7 (R&D Systems) are negative control. IL-17 levels in supernatants were measured with ELISA (R&D Systems).

TABLE 3

| Example | IC$_{50}$ (nM) |
|---|---|
| P6-02-2 | 124 nM |

IL-17A Secretion in Activated PBMCs

Heparin-treated whole blood from healthy human volunteers was supplied from Hospital de Sant Pau (Barcelona) under the approval of the local ethical review board for human studies (Hospital de Sant Pau, Barcelona, Spain). Human peripheral blood mononuclear cells (PBMCs) were isolated from healthy human volunteers by density gradient centrifugation using the Ficoll-Paque (GE Healthcare).

PBMCs were suspended in cell culture medium which consisted on RPMI 1640 medium (Sigma-Aldrich) containing 10% heat inactivated fetal bovine serum (Sigma-Aldrich), 2 mM L-Glutamine (Gibco), 20 mM Hepes (Gibco) and 100 U/mL penicillin (Sigma-Aldrich). Cells were seeded in 384-well plate (DiscoverX), at 40,000 cells per well and cultured 2 h at 37° C. and 5% CO2.

Dose-response curves with compounds were prepared using a 5-fold serial dilution (10 concentrations) in 100% DMSO and further diluted 100-fold in culture medium. Compound solutions (5 μL) were added to the plate containing cells (final DMSO concentration of 0.1%) and incubated for 30 min. Then, cells were stimulated with CD3/CD28 Dynabeads (ThermoFisher, at a bead-to-cell ratio of 1:1) for 48 h at 37° C. and 5% CO2.

IL-17A levels in supernatant were determined by immunoassay using hIL17A QBeads (Intellicyt) and by fluorescence analysis in iQue flow cytometer following the manufacturer's instructions. Inhibition of IL-17A secretion was calculated using the following formula: inhibition=100*[1−[(x−mean basal condition)/(mean top condition—mean basal condition)]]. Activated DMSO-treated cells were used as top condition and activated GNE09461 (10 μM)-treated cells as basal condition. Inhibition values were plotted versus compound concentrations and adjusted to a four-parameter logistic curve to obtain the absolute IC50 value along with the 95% confidence interval.

TABLE 4

IL-17A secretion in activated PBMCs

| Patent example | IC$_{50}$ (nM) |
|---|---|
| 3P6-1 | 21 |
| 3P6-2 | 2.2 |
| L5-1-1-1 | 3.6 |
| L5-1-1-2 | 2.3 |
| L5-2-1-1 | 2.7 |
| L5-2-1-2 | 3.1 |
| L5-3-1-1 | 9.8 |
| L5-3-1-2 | 10 |
| P6-05 | 20 |
| P6-06 | 48 |
| P6-11 | 23 |
| P6-12 | 30 |
| P6-13 | 1.5 |
| P6-13-1 | 1.1 |
| P6-13-2 | 1.3 |
| P6-14 | 2.2 |
| P6-14-1 | 18 |
| P6-14-2 | 1.7 |
| P6-15 | 18 |
| P6-16 | 17 |
| P6-18 | 14 |
| P6-19 | 15 |
| P6-21 | 11 |
| P6-23 | 12 |
| P6-23-1 | 59 |
| P6-23-2 | 98 |
| P6-24 | 22 |
| P6-24-1 | 9.9 |
| P6-24-2 | 170 |
| P6-25 | 35 |
| P6-25-1 | 110 |
| P6-25-2 | 130 |
| P6-26" | 21 |
| P6-26-2 | 65 |
| P6-27" | 70 |
| P6-28" | 53 |
| P6-30" | 100 |
| P6-31" | 6 |
| P6-32" | 8.4 |
| P6-33" | 9.9 |
| P6-37 | 7 |

TABLE 4-continued

IL-17A secretion in activated PBMCs

| Patent example | IC$_{50}$ (nM) |
|---|---|
| R5-1" | 80 |
| R5-2" | 7.4 |
| R5-2-1 | 29 |
| R5-2-2 | 7.4 |
| R5-3" | 11 |
| R5-4" | 22 |

As can be seen from the Table 4 above, the compounds of the present disclosure were found to show beneficial activity across the IL-17A secretion in activated PBMCs Assay.

According to an embodiment, compounds having IC$_{50}$<500 nM values in the IL-17A secretion in activated PBMCs Assay are disclosed herein.

According to another preferred embodiment, compounds having IC$_{50}$<200 nM values in the IL-17A secretion in activated PBMCs Assay are disclosed herein.

According to another more preferred embodiment, compounds having IC$_{50}$<100 nM values in the IL-17A secretion in activated PBMCs Assay are disclosed herein.

According to another still more preferred embodiment, compounds having IC$_{50}$<50 nM values in the IL-17A secretion in activated PBMCs Assay are disclosed herein.

In Vivo IL-17A Induction in Anti-CD3 Model in Mice

Male $C_{57}BL/6JRj$ mice (7 week old) were purchased from Janvier Labs and housed at the animal facilities of Almirall throughout the study. Animals were allowed to condition for 5 days in their new environment at 22° C.±2° C., 55%±10% relative humidity and 12 h:12 h light:dark cycles. Animals were housed in polycarbonate cages, with free access to water and non-purified stock diet (2014 Teklad Global 14% Protein Rodent Maintenance Diet, Envigo) during the full course of the studies. Care of animals was undertaken in compliance with the European Committee Directive 2010/63/EU, and the Catalan and Spanish law. All procedures were performed according to the ARRIVE guidelines (Animal Research: Reporting of In Vivo Experiments) and with approval from the Animal Experimentation Ethical Committee of Almirall (Barcelona, Spain).

Mice were injected intraperitoneally with 7.5 μg of anti-CD3e (Clone 145-2C$_{11}$ from Pharmingen BD) at 0 h (day 0) and 48 h (day 3) time-points. The non-induced-group were injected with PBS instead of anti-CD3e. At study completion (4 h after anti-CD3e injection), animals were anaesthetized with isofluorane (Baxter) and 0.5-1 mL blood samples were drawn by intracardiac puncture in heparinized tubes. Plasma samples were stored at −80° C. for subsequent analysis.

Test compounds were freshly suspended in sterile 0.5% methylcellulose 0.1% tween-80 solution (10 mL/kg body weight). Compounds administered by oral gavage according to the selected dosing and body weight; control animals received an equivalent volume of vehicle. Treatments were given twice daily from day 0 to day 3, last administration was done 1 h before anti-CD3e injection.

Plasma levels of IL-17A were measured by ELISA (R&D Systems) according to the manufacturer's instruction. Results were calculated as the percentage of reduction of plasma IL-17A versus the difference between non-induced and anti-CD3e induced groups through the formula: inhibition=100*[1−[(x−mean non-induced)/(mean control vehicle−mean non-induced)]]. The IL-17A inhibition for each treatment can be expressed as the mean for each treatment group±S.E.M. Statistical analysis of data were conducted with one-way ANOVA followed by Dunnett's multiple comparisons test when appropriate. Differences were considered significant when $p \leq 0.05$.

Results:

| Compound | Inhibition of IL-17A (%) at 3 mg/kg |
| --- | --- |
| L5-1-1-1 | 94% |

In summary, compounds disclosed herein have been found to at least modulate the activity of RORγ. Compounds disclosed herein are active, e.g. having a Gal4<1000 nM, such as <500 nM, such as <100 nM and. Additionally, in a property comparison study they have shown an improved lipophilicity manifested by a decrease in Log P and/or Log D compared to previously described high potent compounds, see e.g. Tables 5 a-b. In these tables, all numbers (except Gal4 activity) are calculated; methods are indicated in column titles.

TABLE 5 a

| Examples | RORγ Gal4 assay | Number of compounds | ALogP Canvas[1] | LipE Canvas[1] |
| --- | --- | --- | --- | --- |
| Compounds disclosed herein | $IC_{50} < 100$ nM[1] | 61 | 2.21 | 5.83 |
| Compounds disclosed in WO2016020288 and WO2016020295 | $IC_{50} < 100$ nM[1] | 6[2] | 3.94 | 4.01 |

TABLE 5 b

| Examples | RORγ Gal4 assay (based on % inhibition at 0.1 and/or 1 uM)) | Number of compounds | ALogP Canvas[1] |
| --- | --- | --- | --- |
| Compounds disclosed in WO2016020288 and WO2016020295 | $IC_{50} < 100$ nM | 13[3] | 4.39 |

[1] average value based on "number of compounds"

[2] Gal4 of Examples: 252, 290, 326, 328 disclosed in WO2016020295, and Example I1, and A56 disclosed in WO2016020288.

[3] Gal4 of Examples in <100 range: 67, 69, 85, 195, 196, 252, 265, 284, 290, 326, and 328 disclosed in WO2016020295, and Example I1, and A56 in WO2016020288.

The RORγ Gal4 data used to generate the comparisons in Table 5 a is based on generated Gal4 data for the listed compounds (data not available in WO2016020288 or WO2016020295), LipE has not been reported in Table 5 b as Gal4 data existed as % inhibition only.

In connection with the above Tables 5 a-b, Tables 6 and 7 show a comparison between compounds of the present disclosure and known compounds of structural similarity and considered relevant.

TABLE 6

ALogP numbers are calculated by Canvas.

| Structure | | | |
| --- | --- | --- | --- |
| Ex. No | P6-13-1 | L5-1-1-1 | Example I1[1] |
| Gal4 assay | $IC_{50} < 100$ nM (Table 2 herein) | $IC_{50} < 100$ nM (Table 2 herein) | $IC_{50} < 100$ nM Compound from [1] |
| ALogP Canvas | 2.70 | 1.82 | 4.74 |

[1] WO2016020288

TABLE 7

ALogP numbers are calculated by Canvas.

| Structure | | | |
|---|---|---|---|
| Ex. No | Q4-2 | Q4-1-1 | Example 328[1] |
| Gal4 assay | IC$_{50}$ < 500 nM (Table 2 herein) | IC$_{50}$ < 500 nM (Table 2 herein) | IC$_{50}$ < 100 nM Compound from [1] |
| ALogP Canvas | 2.06 | 2.04 | 3.13 |

[1] WO2016020295

The ALogP and LipE are calculated using Canvas, a part of the Schradinger software suite, Release 2019-1.

As mentioned, the compounds disclosed herein may thus be improved modulators of RORγ, e.g. having an attractive interaction (e.g. high binding ability) to the hydrophobic binding sites of the ligand binding domain (LBD) of the RORγ receptor and improved physical chemical properties as discussed above.

Additionally it has been found that compounds disclosed herein have in vivo usefulness, and could consequently be useful in treating inflammatory, metabolic and autoimmune diseases or symptoms thereof.

The invention claimed is:

1. A compound according to Formula (I)

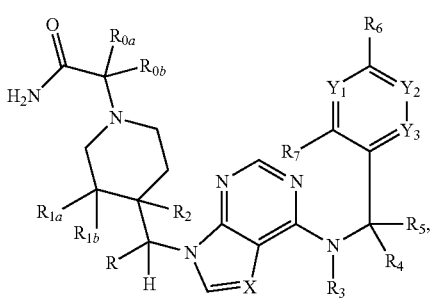

(I)

a stereoisomer thereof, or a pharmaceutically acceptable salt of the compound or stereoisomer, wherein:

$Y_1$, $Y_2$ and $Y_3$ are independently —N— or —C$R_8$—;

X is —C$R_9$—, or —N—;

$R_{0a}$ and $R_{0b}$ independently are selected from the group consisting of hydrogen, $C_{1-4}$ alkyl, $C_{1-4}$ hydroxyalkyl, and $C_{1-4}$ haloalkyl;

R is selected from the group consisting of hydrogen, $C_{1-8}$ alkyl and $C_{1-4}$ hydroxyalkyl;

$R_{1a}$ and $R_{1b}$ are independently selected from the group consisting of hydrogen, hydroxyl, halogen, amino, $C_{1-4}$ alkyl, $C_{1-4}$ hydroxyalkyl, and $C_{1-4}$ haloalkyl;

$R_2$ is selected from the group consisting of hydrogen, hydroxyl, amino, cyano, halogen, $C_{1-4}$ alkyl, $C_{1-4}$ haloalkyl, $C_{1-4}$ hydroxyalkyl, —C(=O)NH$_2$, —C(=O)OH, —C(=O)O—$C_{1-4}$ alkyl, and substituted or unsubstituted heteroaryl;

$R_3$ is selected from the group consisting of $C_{1-4}$ alkyl, $C_{1-4}$ alkenyl, $C_{1-4}$ haloalkyl, $C_{1-4}$ hydroxyalkyl, $C_{3-7}$ cycloalkyl, and $C_{3-7}$ cycloalkenyl; or $R_3$ and $R_4$ are taken together with the atoms to which they are attached to form a 4-6 membered heteroalicyclic ring system optionally substituted with one to three substituents selected from halogen, hydroxyl, and $C_{1-4}$ alkyl;

$R_4$ is hydrogen or $C_{1-4}$ alkyl, provided $R_3$ and $R_4$ are not taken together with the atoms to which they are attached to form a 4-6 membered heteroalicyclic ring system; or $R_4$ and $R_5$ are taken together with the carbon atom to which they are attached to form a $C_{3-4}$ cycloalkyl;

$R_5$ is absent, hydrogen or $C_{1-4}$ alkyl, provided that $R_4$ and $R_5$ are not taken together with the carbon atom to which they are attached to form a $C_{3-4}$ cycloalkyl;

$R_6$ is selected from the group consisting of hydrogen, —CN, halogen, $C_{1-4}$ alkyl, $C_{1-4}$ hydroxyalkyl, $C_{1-4}$ haloalkyl, $C_{1-6}$ hydroxyhaloalkyl, $C_{1-4}$ alkoxy, $C_{1-4}$ haloalkoxy, and 5-6 membered heteroaryl, wherein 5-6 membered heteroaryl is optionally substituted with $C_{1-4}$ alkyl;

$R_7$ is selected from the group consisting of hydrogen, hydroxyl, —CN, halogen, $C_{1-4}$ alkyl, $C_{1-4}$ haloalkyl, $C_{1-4}$ hydroxyalkyl, $C_{1-4}$ alkoxy, and $C_{1-4}$ haloalkoxy;

each $R_8$ is independently selected from the group consisting of hydrogen, hydroxyl, —CN, halogen, $C_{1-4}$ alkyl, $C_{1-4}$ haloalkyl, $C_{1-4}$ alkoxy, and $C_{1-4}$ haloalkoxy; and whenever $R_7$ is hydrogen and each $R_8$ present is hydrogen, then $R_6$ is selected from the group consisting of —CN, halogen, $C_{1-4}$ alkyl, $C_{1-4}$ haloalkyl, $C_{1-6}$ hydroxyhaloalkyl, $C_{1-4}$ hydroxyalkyl, $C_{1-4}$ alkoxy, $C_{1-4}$ haloalkoxy, and 5-6 membered heteroaryl, wherein 5-6 membered heteroaryl is optionally substituted with $C_{1-4}$ alkyl;

$R_9$ is selected from the group consisting of hydrogen, halogen, cyano, and $C_{1-4}$ alkyl.

2. The compound, stereoisomer thereof, or pharmaceutically acceptable salt of the compound or stereoisomer thereof according to claim 1, wherein R is hydrogen.

3. The compound, stereoisomer thereof, or pharmaceutically acceptable salt of the compound or stereoisomer thereof according to claim 1, wherein $R_{0a}$ is selected from the group consisting of hydrogen, methyl, —CH$_2$OH, —CH$_2$CH$_2$OH, —CH$_2$F, and —CHF$_2$; and $R_{0b}$ is selected from the group consisting of hydrogen, C$_{1-4}$ alkyl, C$_{1-4}$ hydroxyalkyl, and C$_{1-4}$ haloalkyl.

4. The compound, stereoisomer thereof, or pharmaceutically acceptable salt of the compound or stereoisomer thereof according to claim 1, wherein at least one of $R_{1a}$, $R_{1b}$ and $R_2$ is not hydrogen.

5. The compound, stereoisomer thereof, or pharmaceutically acceptable salt of the compound or stereoisomer thereof according to claim 1, wherein $R_{1a}$ is selected from the group consisting of hydroxyl, fluoro and —CF$_3$ and $R_{1b}$ is selected from the group consisting of hydrogen, fluoro, and methyl.

6. The compound, stereoisomer thereof, or pharmaceutically acceptable salt of the compound or stereoisomer thereof according to claim 1, wherein $R_2$ is selected from the group consisting of hydrogen, halogen, hydroxyl, cyano, methyl, ethyl, —CH$_2$OH, —CH$_2$CH$_2$OH and —C(═O)O—C$_{1-2}$ alkyl.

7. The compound, stereoisomer thereof, or pharmaceutically acceptable salt of the compound or stereoisomer thereof according to claim 1, wherein $R_3$ is selected from the group consisting of methyl, ethyl, n-propyl, isopropyl, n-butyl, iso-butyl, tert-butyl, cyclopropyl and cyclobutyl.

8. The compound, stereoisomer thereof, or pharmaceutically acceptable salt of the compound or stereoisomer thereof according to claim 1, wherein $R_4$ and $R_5$ independently are hydrogen or methyl.

9. The compound, stereoisomer thereof, or pharmaceutically acceptable salt of the compound or stereoisomer thereof according to claim 1, wherein $R^3$ and $R^4$, taken together with the atoms to which they are attached, form a 4-6 membered heteroalicyclic ring; and further wherein the heteroalicyclic ring system comprising $R_3$ and $R_4$ is selected from the group consisting of 4 membered heteroalicyclyl, 5 membered heteroalicyclyl, and 6 membered heteroalicyclyl; and further wherein the heteroalicyclic ring system is optionally substituted with one or two substituents selected from halogen, hydroxyl and C$_{1-4}$ alkyl.

10. The compound, stereoisomer thereof, or pharmaceutically acceptable salt of the compound or stereoisomer thereof according to claim 1, wherein $R_6$ is selected from the group consisting of hydrogen, halogen, C$_{1-4}$ haloalkyl, C$_{1-6}$ hydroxyhaloalkyl, C$_{1-4}$ haloalkoxy, C$_{1-4}$ hydroxyalkyl, and 5 membered heteroaryl optionally substituted with C$_{1-4}$ alkyl.

11. The compound, stereoisomer thereof, or pharmaceutically acceptable salt of the compound or stereoisomer thereof according to claim 1, wherein $R_7$ is selected from the group consisting of hydrogen, halogen, hydroxyl, cyano, —CF$_3$, —OCHF$_2$, —CHF$_2$ and —OCF$_3$.

12. The compound, stereoisomer thereof, or pharmaceutically acceptable salt of the compound or stereoisomer thereof according to claim 1, wherein
$Y_1$, $Y_2$ and $Y_3$ are —CH—; or
$Y_1$ is —N— and $Y_2$ and $Y_3$ are —CH—; or
$Y_2$ is —N— and $Y_1$ and $Y_3$ are —CH—; or
$Y_3$ is —N— and $Y_1$ and $Y_2$ are —CH—;
or $Y_3$ is —CH— and $Y_1$ and $Y_2$ are —N—.

13. The compound, stereoisomer thereof, or pharmaceutically acceptable salt of the compound or stereoisomer thereof according to claim 1, wherein
$Y_1$ is —CH—, and $Y_2$ and $Y_3$ are —CR$_8$— wherein each $R_8$ independently is selected from the group consisting of hydrogen, methyl, fluoro, hydroxyl and —CF$_3$.

14. The compound, stereoisomer thereof, or pharmaceutically acceptable salt of the compound or stereoisomer thereof according to claim 1, wherein
$Y_2$ is —N— and $Y_1$ and $Y_3$ are —CH— or
$Y_3$ is —N— and $Y_1$ and $Y_2$ are —CH—.

15. The compound, stereoisomer thereof, or pharmaceutically acceptable salt of the compound or stereoisomer thereof according to claim 1, wherein X is —CR$_9$— and $R_9$ is hydrogen, cyano or fluoro.

16. The compound, stereoisomer thereof, or pharmaceutically acceptable salt of the compound or stereoisomer thereof according to claim 1, wherein:
(i) $Y_2$ and $Y_3$ are independently —CH— or —CF; or
(ii) $Y_2$ is —CH— and $Y_3$ is —N—.

17. The compound, stereoisomer thereof, or pharmaceutically acceptable salt of the compound or stereoisomer thereof according to claim 1 wherein:
$R_{0a}$ and $R_{0b}$ are independently selected from the group consisting of hydrogen, methyl and —CH$_2$OH;
$R_{1a}$ and $R_{1b}$ are independently selected from the group consisting of hydrogen, fluoro, and hydroxyl;
$R_2$ is selected from the group consisting of hydrogen, cyano and hydroxyl;
R is hydrogen;
X is —CR$_9$— or —N—, wherein $R_9$ is selected from the group consisting of hydrogen, cyano, and fluoro;
$R_3$ is selected from the group consisting of methyl, ethyl, isopropyl and cyclopropyl, and
$R_4$ and $R_5$ independently are hydrogen, or
$R_3$ and $R_4$ are taken together with the atoms to which they are attached to form an unsubstituted morpholinyl, and $R_5$ is H;
$R_6$ is selected from the group consisting of hydrogen, —CF$_3$ and pyrazole, wherein the pyrazole is optionally substituted by methyl;
$R_7$ is hydrogen; and
$Y_1$, $Y_2$ and $Y_3$ are —CH—; or
$Y_1$ is —CH—, $Y_2$ is —CF— and $Y_3$ is —CH—; or
$Y_1$ is —CH—, $Y_2$ is —CH— and $Y_3$ is —CF—; or
$Y_1$ is —CH—, $Y_2$ is —CH— and $Y_3$ is —N—; or
$Y_1$ is —CH—, $Y_2$ is —N— and $Y_3$ is —CH—; or
$Y_1$ is —N—, $Y_2$ is —N— and $Y_3$ is —CH—; or
$Y_1$ is —CH—, $Y_2$ is —C(CF$_3$)— and $Y_3$ is —CH—.

18. The compound, stereoisomer thereof, or pharmaceutically acceptable salt of the compound or stereoisomer thereof according to claim 1 selected from the group consisting of:
2-(4-((4-(cyclopropyl(4-(trifluoromethyl)benzyl)amino)-5-fluoro-7H-pyrrolo[2,3-d]pyrimidin-7-yl)methyl)-4-hydroxypiperidin-1-yl)acetamide,
2-(4-((4-(cyclopropyl(4-(trifluoromethyl)benzyl)amino)-7H-pyrrolo[2,3-d]pyrimidin-7-yl)methyl)-4-hydroxypiperidin-1-yl)acetamide,
2-(4-((6-(cyclopropyl(4-(trifluoromethyl)benzyl)amino)-9H-purin-9-yl)methyl)-4-hydroxypiperidin-1-yl)acetamide,
2-(4-((5-cyano-4-(cyclopropyl(4-(trifluoromethyl)benzyl)amino)-7H-pyrrolo[2,3-d]pyrimidin-7-yl)methyl)-4-hydroxypiperidin-1-yl)acetamide,
2-(4-((5-fluoro-4-(methyl(4-(trifluoromethyl)benzyl)amino)-7H-pyrrolo[2,3-d]pyrimidin-7-yl)methyl)-4-hydroxypiperidin-1-yl)acetamide, 2-(4-((4-(cyclopropyl(4-(trifluoromethyl)benzyl)amino)-7H-pyrrolo[2,3-d]pyrimidin-7-yl)methyl)-3,3-difluoropiperidin-1-yl)acetamide, 2-(4-((4-(cyclopropyl(4-(trifluoromethyl)benzyl)amino)-7H-pyrrolo[2,3-d]pyrimidin-7-yl)methyl)-3-fluoropiperidin-1-yl)acetamide, 2-(4-((4-(cyclopropyl((5-(trifluoromethyl)pyridin-2-yl)methyl)amino)-7H-pyrrolo[2,3-d]pyrimidin-7-yl)methyl)-3-fluoropiperidin-1-yl)acetamide, 2-(4-((4-(cyclopropyl(4-(trifluoromethyl)benzyl)amino)-7H-pyrrolo[2,3-d]pyrimidin-7-yl)methyl)-3,4-dihydroxypiperidin-1-yl)acetamide, 2-(4-((4-(ethyl(4-(trifluoromethyl)benzyl)amino)-7H-pyrrolo[2,3-d]pyrimidin-7-yl)methyl)-3,4-dihydroxypiperidin-1-yl)acetamide, 2-(4-((4-(ethyl(2-fluoro-4-(trifluoromethyl)benzyl)amino)-7H-pyrrolo[2,3-d]pyrimidin-7-yl)methyl)-3,4-dihydroxypiperidin-1-yl)acetamide, 2-(3-hydroxy-4-((4-(3-(4-(trifluoromethyl)phenyl)morpholino)-7H-pyrrolo[2,3-d]pyrimidin-7-yl)methyl)piperidin-1-yl)acetamide 2-(4-((4-(3-(4-(trifluoromethyl)phenyl)morpholino)-7H-pyrrolo[2,3-d]pyrimidin-7-yl)methyl)piperidin-1-yl)acetamide, 2-(3-hydroxy-4-((4-(3-(3-(trifluoromethyl)phenyl)morpholino)-7H-pyrrolo[2,3-d]pyrimidin-7-yl)methyl)piperidin-1-yl)acetamide, 2-(4-((4-(cyclopropyl(4-(trifluoromethyl)benzyl)amino)-5-fluoro-7H-pyrrolo[2,3-d]pyrimidin-7-yl)methyl)piperidin-1-yl)acetamide, 2-(4-((6-(cyclopropyl(4-(trifluoromethyl)benzyl)amino)-9H-purin-9-yl)methyl)piperidin-1-yl)acetamide, 2-(4-((5-cyano-4-(cyclopropyl(4-(trifluoromethyl)benzyl)amino)-7H-pyrrolo[2,3-d]pyrimidin-7-yl)methyl)piperidin-1-yl)acetamide, 2-(4-((6-(cyclopropyl(4-(trifluoromethyl)benzyl)amino)-9H-purin-9-yl)methyl)piperidin-1-yl)propanamide, 2-(4-((6-(cyclopropyl(4-(trifluoromethyl)benzyl)amino)-9H-purin-9-yl)methyl)piperidin-1-yl)-2-methylpropanamide, 2-(4-((4-(cyclopropyl((6-(trifluoromethyl)pyridin-3-yl)methyl)amino)-5-fluoro-7H-pyrrolo[2,3-d]pyrimidin-7-yl)methyl)piperidin-1-yl)acetamide, 2-(4-cyano-4-((4-(cyclopropyl(4-(trifluoromethyl)benzyl)amino)-5-fluoro-7H-pyrrolo[2,3-d]pyrimidin-7-yl)methyl)piperidin-1-yl)acetamide, 2-(4-((5-fluoro-4-(methyl(4-(trifluoromethyl)benzyl)amino)-7H-pyrrolo[2,3-d]pyrimidin-7-yl)methyl)-3-hydroxypiperidin-1-yl)acetamide, 2-(4-((4-(cyclopropyl(4-(trifluoromethyl)benzyl)amino)-7H-pyrrolo[2,3-d]pyrimidin-7-yl)methyl)-3-hydroxypiperidin-1-yl)acetamide, 2-(4-((4-(cyclopropyl(4-(trifluoromethyl)benzyl)amino)-5-fluoro-7H-pyrrolo[2,3-d]pyrimidin-7-yl)methyl)-3-hydroxypiperidin-1-yl)acetamide, 2-(4-((4-(cyclopropyl((6-(trifluoromethyl)pyridin-3-yl)methyl)amino)-5-fluoro-7H-pyrrolo[2,3-d]pyrimidin-7-yl)methyl)-3-hydroxypiperidin-1-yl)acetamide, 2-(4-((4-(cyclopropyl((6-(trifluoromethyl)pyridin-3-yl)methyl)amino)-7H-pyrrolo[2,3-d]pyrimidin-7-yl)methyl)-3-hydroxypiperidin-1-yl)acetamide, 2-(4-((4-(cyclopropyl((2-(trifluoromethyl)pyrimidin-5-yl)methyl)amino)-5-fluoro-7H-pyrrolo[2,3-d]pyrimidin-7-yl)methyl)-3-hydroxypiperidin-1-yl)acetamide, 2-(4-((4-(cyclopropyl((5-(trifluoromethyl)pyridin-2-yl)methyl)amino)-5-fluoro-7H-pyrrolo[2,3-d]pyrimidin-7-yl)methyl)-3-hydroxypiperidin-1-yl)acetamide, 2-(4-((5-fluoro-4-(isopropyl(4-(trifluoromethyl)benzyl)amino)-7H-pyrrolo[2,3-d]pyrimidin-7-yl)methyl)-3-hydroxypiperidin-1-yl)acetamide, 2-(4-((6-(cyclopropyl(3-(trifluoromethyl)benzyl)amino)-9H-purin-9-yl)methyl)-3-hydroxypiperidin-1-yl)acetamide, 2-(4-((4-(ethyl(4-(trifluoromethyl)benzyl)amino)-5-fluoro-7H-pyrrolo[2,3-d]pyrimidin-7-yl)methyl)-3-hydroxypiperidin-1-yl)acetamide, 2-(3-hydroxy-4-((6-(isopropyl(4-(trifluoromethyl)benzyl)amino)-9H-purin-9-yl)methyl)piperidin-1-yl)acetamide, 2-(4-((4-(cyclopropyl((5-(trifluoromethyl)pyridin-2-yl)methyl)amino)-7H-pyrrolo[2,3-d]pyrimidin-7-yl)methyl)-3-hydroxypiperidin-1-yl)acetamide, 2-(4-((4-(ethyl(4-(trifluoromethyl)benzyl)amino)-7H-pyrrolo[2,3-d]pyrimidin-7-yl)methyl)-3-hydroxypiperidin-1-yl)acetamide, 2-(3-hydroxy-4-((4-(isopropyl(4-(trifluoromethyl)benzyl)amino)-7H-pyrrolo[2,3-d]pyrimidin-7-yl)methyl)piperidin-1-yl)acetamide 2-(4-((6-(cyclopropyl(4-(trifluoromethyl)benzyl)amino)-9H-purin-9-yl)methyl)-3-hydroxypiperidin-1-yl)acetamide, 2-(4-((4-(ethyl((5-(trifluoromethyl)pyridin-2-yl)methyl)amino)-7H-pyrrolo[2,3-d]pyrimidin-7-yl)methyl)-3-hydroxypiperidin-1-yl)acetamide, 2-(4-((4-(ethyl((5-(trifluoromethyl)pyridin-2-yl)methyl)amino)-5-fluoro-7H-pyrrolo[2,3-d]pyrimidin-7-yl)methyl)-3-hydroxypiperidin-1-yl)acetamide, 2-(4-((4-((4-cyanobenzyl)(ethyl)amino)-7H-pyrrolo[2,3-d]pyrimidin-7-yl)methyl)-3-hydroxypiperidin-1-yl)acetamide, 2-(4-((4-((4-(1H-pyrazol-1-yl)benzyl)(ethyl)amino)-7H-pyrrolo[2,3-d]pyrimidin-7-yl)methyl)-3-hydroxypiperidin-1-yl)acetamide, 2-(4-((4-(ethyl(3-fluoro-4-(trifluoromethyl)benzyl)amino)-7H-pyrrolo[2,3-d]pyrimidin-7-yl)methyl)-3-hydroxypiperidin-1-yl)acetamide, 2-(4-((4-(ethyl(2-fluoro-4-(trifluoromethyl)benzyl)amino)-7H-pyrrolo[2,3-d]pyrimidin-7-yl)methyl)-3-hydroxypiperidin-1-yl)acetamide, 2-(4-((4-((4-(1H-pyrazol-1-yl)benzyl)(cyclopropyl)amino)-7H-pyrrolo[2,3-d]pyrimidin-7-yl)methyl)-3-hydroxypiperidin-1-yl)acetamide, 2-(4-((4-(ethyl(4-(1-methyl-1H-pyrazol-4-yl)benzyl)amino)-7H-pyrrolo[2,3-d]pyrimidin-7-yl)methyl)-3-hydroxypiperidin-1-yl)acetamide, 2-(4-((4-(ethyl(2-fluoro-4-(1-methyl-1H-pyrazol-4-yl)benzyl)amino)-7H-pyrrolo[2,3-d]pyrimidin-7-yl)methyl)-3-hydroxypiperidin-1-yl)acetamide, 2-(4-((4-(ethyl(2-fluoro-4-(1H-pyrazol-1-yl)benzyl)amino)-7H-pyrrolo[2,3-d]pyrimidin-7-yl)methyl)-3-hydroxypiperidin-1-yl)acetamide, 2-(4-((4-(cyclopropyl(4-(trifluoromethyl)benzyl)amino)-7H-pyrrolo[2,3-d]pyrimidin-7-yl)methyl)-3-hydroxypiperidin-1-yl)-3-hydroxypropanamide, 2-(3-fluoro-4-((4-(3-(5-(trifluoromethyl)pyridin-2-yl)morpholino)-7H-pyrrolo[2,3-d]pyrimidin-7-yl)methyl)piperidin-1-yl)acetamide, 2-(4-((4-(3-(5-(trifluoromethyl)pyridin-2-yl)morpholino)-7H-pyrrolo[2,3-d]pyrimidin-7-yl)methyl)piperidin-1-yl)acetamide, 2-(4-((4-((4-(1H-pyrazol-1-yl)benzyl)(ethyl)amino)-7H-pyrrolo[2,3-d]pyrimidin-7-yl)methyl)-3,4-dihydroxypiperidin-1-yl)acetamide, 2-(4-((4-((4-(1H-pyrazol-1-yl)benzyl)(cyclopropyl)amino)-7H-pyrrolo[2,3-d]pyrimidin-7-yl)methyl)-3,4-dihydroxypiperidin-1-yl)acetamide, 2-(4-((4-(cyclopropyl(2-fluoro-4-(1-methyl-1H-pyrazol-4-yl)benzyl)amino)-7H-pyrrolo[2,3-d]pyrimidin-7-yl)methyl)-3,4-dihydroxypiperidin-1-yl)acetamide, 2-(4-((4-(cyclopropyl(2-fluoro-4-(1H-pyrazol-1-yl)benzyl)amino)-7H-pyrrolo[2,3-d]pyrimidin-7-yl)methyl)-3,4-dihydroxypiperidin-1-yl)acetamide, and 2-(4-((4-(ethyl(2-fluoro-4-(1H-pyrazol-1-yl)benzyl)amino)-7H-pyrrolo[2,3-d]pyrimidin-7-yl)methyl)-3,4-dihydroxypiperidin-1-yl)acetamide.

19. The compound, stereoisomer thereof, or pharmaceutically acceptable salt of the compound or stereoisomer thereof according to claim 1 and at least one pharmaceutical acceptable excipient.

20. A method of treating a metabolic or autoimmune disease in a subject suffering therefrom, the method comprising: administering to the subject a compound, stereoisomer thereof, or pharmaceutically acceptable salt of the compound or stereoisomer thereof according claim 1.

\* \* \* \* \*

UNITED STATES PATENT AND TRADEMARK OFFICE
CERTIFICATE OF CORRECTION

PATENT NO. : 11,780,843 B2
APPLICATION NO. : 17/218543
DATED : October 10, 2023
INVENTOR(S) : Sanne Schrøder Glad et al.

It is certified that error appears in the above-identified patent and that said Letters Patent is hereby corrected as shown below:

In the Claims

At Column 233, Line 61, "$C_{1-8}$" should be -- $C_{1-6}$ --.

At Column 235, Line 59, "wherein" should be -- wherein: --.

At Column 235, Line 64, "or" should be at Line 63, after "—CH—;", as a continuation point.

At Column 235, Line 67, "wherein" should be -- wherein: --.

At Column 236, Line 6, "wherein" should be -- wherein: --.

At Column 236, Line 7, "—CH—or" should be -- -CH- --.

At Column 236, Line 33, "cyclopropyl, and" should be -- cyclopropyl; --.

At Column 236, Line 34, "hydrogen, or" should be -- hydrogen; or --.

At Column 237, Line 21, "acetamide" should be -- acetamide, --.

At Column 238, Line 22, "acetamide" should be -- acetamide, --.

At Column 239, Line 21, "according" should be -- according to --.

Signed and Sealed this
Twenty-first Day of May, 2024

Katherine Kelly Vidal
*Director of the United States Patent and Trademark Office*